US008865461B2

(12) United States Patent
Rupprecht et al.

(10) Patent No.: US 8,865,461 B2
(45) Date of Patent: Oct. 21, 2014

(54) RABIES VIRUS VECTOR SYSTEMS AND COMPOSITIONS AND METHODS THEREOF

(75) Inventors: Charles E. Rupprecht, Lawrenceville, GA (US); Xianfu Wu, Atlanta, GA (US)

(73) Assignee: The United States of America as represtented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 996 days.

(21) Appl. No.: 12/956,949

(22) Filed: Nov. 30, 2010

(65) Prior Publication Data

US 2011/0070264 A1 Mar. 24, 2011

Related U.S. Application Data

(62) Division of application No. 12/090,083, filed as application No. PCT/US2006/040134 on Oct. 13, 2006, now Pat. No. 7,863,041.

(60) Provisional application No. 60/727,038, filed on Oct. 14, 2005.

(51) Int. Cl.

| | |
|---|---|
| ***C12N 15/00*** | (2006.01) |
| ***A61K 39/205*** | (2006.01) |
| ***C12N 15/86*** | (2006.01) |
| ***C12N 7/00*** | (2006.01) |

(52) U.S. Cl.

CPC *C12N 7/00* (2013.01); *C12N 15/86* (2013.01); *A61K 39/205* (2013.01); *C12N 2760/20143* (2013.01); *C12N 2760/20161* (2013.01); *C12N 2760/20134* (2013.01)

USPC .................................... 435/320.1; 424/224.1

(58) Field of Classification Search

None

See application file for complete search history.

(56) References Cited

U.S. PATENT DOCUMENTS

| | | | |
|---|---|---|---|
| 4,040,904 | A | 8/1977 | Slater |
| 4,393,201 | A | 7/1983 | Curtis et al. |
| 5,695,757 | A | 12/1997 | Rupprecht et al. |
| 5,789,229 | A | 8/1998 | Wert et al. |
| 6,719,981 | B1 | 4/2004 | Mabatsion et al. |
| 2002/0131981 | A1 | 9/2002 | Dietzschold et al. |
| 2003/0113346 | A1 | 6/2003 | Dietzchold et al. |
| 2003/0224017 | A1 | 12/2003 | Samal et al. |
| 2004/0208900 | A1 | 10/2004 | Fu |

FOREIGN PATENT DOCUMENTS

| | | |
|---|---|---|
| EP | 0 702 085 A1 | 3/1996 |
| EP | 0 780 475 A1 | 6/1997 |
| EP | 1 253 197 A1 | 10/2002 |
| EP | 1 394 259 A2 | 3/2004 |
| WO | WO 95/09249 | 4/1995 |
| WO | WO 00/32755 | 6/2000 |
| WO | WO 02/36170 | 5/2002 |

OTHER PUBLICATIONS

Anilionis et al., "Structure of the glycoprotein gene in rabies virus," *Nature*, 294:275-278 (1981).

Bridgen et al., "Rescue of a segmented negative-strand RNA virus entirely from cloned complementary DNAs," *Proc. Natl. Acad. Sci. USA*, 93:15400-15404 (1996).

Conzelmann et al., "Molecular Cloning and Complete Nucleotide Sequence of the Attenuated Rabies Virus SAD B19," *Virology*, 175:485-499 (1990).

Dietzschold et al., "Characterization of an antigenic determinant of the glycoprotein that correlates with pathogenicity of rabies virus," *Proc. Natl. Acad. Sci., USA* 80:60-74 (1983).

Dietzschold et al., "New Approaches to the Development of Live Attenuated Rabies Vaccines," *Hybridoma and Hybridomics*, 21(2):129-134 (2002).

Dietzschold et al., "New approaches to the prevention and eradication of rabies," *Expert Rev. Vaccines*, 2(3):399-406 (2003).

Faber, et al., "Overexpression of the Rabies Virus Glycoprotein Results in Enhancement of Apoptosis and Antiviral Immune Response," *Journal of Virology*, 76(7):3374-3381 (2002).

Fu et al., "Inhibition of Rabies Virus Infection by an Oligodeoxynucleotide Complementary to Rabies Virus Genomic RNA," *Antisense & Nucleic Acid Drug Development*, 6:87-93 (1996).

Fodor et al., "Nucleotide and deduced amino acid sequences of the glycoprotein gene of rabies virus vaccine strain Vnukove-32," *Arch. Virol.*, 135:451-459 (1994).

Gaudin, Yves, "Rabies Virus-induced Membrane Fusion Pathway," *The Journal of Cell Biology*, 150(3):601-611 (2000).

Hemachudha et al., "Human rabies: a disease of complex neuropathogenetic mechanisms and diagnostic challenges," *Lancet Neurology*, 1:101-109 (2002).

Hiramatsu et al., "Comparative Sequence Analysis of the M Gene Among Rabies Virus Strains and its Expression by Recombinant Vaccinia Virus," *Virus Genes*, 7(1):83-88 (1993).

Inoue et al., "An improved method for recovering rabies virus from cloned cDNA," *J. Virol. Method.*, 107, 229-236 (2003).

Ito et al., "A unique mutation of glycoprotein gene of the attenuated RC-HL strain of rabies virus, a seed virus used for production of animal vaccine in Japan," *Microbiol. Immunol.*, 38:479-482 (1994).

(Continued)

*Primary Examiner* — Stacy B Chen

(74) *Attorney, Agent, or Firm* — Klarquist Sparkman, LLP

(57) ABSTRACT

Rabies Virus compositions and methods are provided. The full-length sequence of Rabies Virus strain Evelyn-Rokitnicki-Abelseth (ERA) is disclosed. A reverse genetics system for producing recombinant ERA virus and derivatives thereof is provided, along with compositions including ERA and/or ERA derivative strain viruses, nucleic acids and/or proteins. In some instances, the compositions are immunogenic compositions useful for the pre- or post-exposure treatment of Rabies Virus.

20 Claims, 10 Drawing Sheets

(56) References Cited

OTHER PUBLICATIONS

Ito et al., "Improved Recovery of Rabies Virus from Cloned cDNA Using a Vaccinia Virus-Free Reverse Genetics System," *Microbiol. Immunol.*, 47(8):613-617 (2003).

Ito et al., "Rescue of Rabies Virus from Cloned cDNA and Identification of the Pathogenicity-related gene: Glycoprotein Gene is Associated with Virulence for Adult Mice," *J. Virol.*, 75:9121-9128 (2001).

Lawson et al., "The ERA Strain of Rabies Vaccine," *Can. J. Comp. Med*, 36:339-344 (1972).

Martins et al., "Pathogenesis of rabies virus by ERA and PV strains administered orally in hamsters (*M. auratus*)," *Brazilian Journal of Veterinary Research and Animal Science*, 40:79-84 (2003).

McKenna et al., "Recombinant Rhabdoviruses as Potential Vaccines for HIV-1 and Other Diseases," *Current HIV Research*, 1:229-237 (2003).

Morimoto et al., "Structure and transcription of the glycoprotein gene of attenuated HEP-Flury strain of rabies virus," *Virol.*, 173:465-477 (1989).

Rupprecht et al., "The ascension of wildlife rabies: a cause for public health concern or intervention?" *Emerg. Infect. Dis.*, 1(4):107-114 (1995).

Rupprecht et al., "Oral vaccination of dogs with recombinant rabies virus vaccines," *Virus Research*, 111:101-105 (2005).

Rupprecht et al., "Rabies re-examined," *Lancet Infectious Diseases*, 2:327-343 (2002).

Schnell et al., "Infectious rabies virus from cloned cDNA," *The EMBO Journal*, 13:4195-4203 (1994).

Schnell et al., "Polymerase activity of in vitro mutated rabies virus L protein," *Virol.*, 214:522-530 (1995).

Schnell et al., "The application of reverse genetics technology in the studies of rabies virus (RV) pathogenesis and for the development of novel RV vaccines," *Journal of NeuroVirology*, 11:76-81 (2005).

Tordo et al., "Completion of the Rabies Virus Genome Sequence Determination: Highly Conserved Domains among the L (polymerase) Proteins of Unsegmented Negative-Strand RNA Viruses," *Virology*, 165:565-576 (1988).

Tuffereau et al., "Arginine or lysine in position 333 of ERA and CVS glycoprotein is necessary for rabies virulence in adult mice," *Virology* 172:206-212 (1989).

Wandeler et al., "Oral immunization of wildlife against rabies: concept and first field experiments," *Rev. Infect. Dis.*, 10 suppl.4:649-653 (1988).

Wojczyk et al., "The role of site-specific N-glycosylation in secretion of soluble forms of rabies virus glycoprotein," *Glycobiology*, 8(2) 121-130 (1998).

Wu et al., "Both Viral Transcription and Replication Are Reduced when the Rabies Virus Nucleoprotein is Not Phosphorylated," *Journal of Virology*, 76(9):4153-4161 (2002).

Wu et al., "Glycoprotein Gene Relocation in Rabies Virus," *Virus Res*, 131:95-99 (2008).

Yamada et al., "Multigenic Relation to the Attenuation of Rabies Virus," *Microbiol. Immunol.*, 50(1):25-32 (2006).

Larson and Wunner, "Nucleotide and deduced amino acid sequences of the nominal nonstructural phosphoprotein of the ERA, PM and CVS-11 strains of rabies virus," *Nucleic Acids Res* 18(23):7172, 1990.

Finke and Conzelmann, "Replication strategies of rabies virus," *Virus Res*, 111(2):120-131, 2005.

GenBank Accession No. AAP81753, Jul. 3, 2003.

Sato et al., "A unique substitution at position 333 on the glycoprotein of rabies virus street strains isolated from non-hematophagous bats in Brazil," *Virus Genes*, vol. 38:74-79, 2009.

Préhaud et al., "Glycoprotein of Nonpathogenic Rabies Viruses is a Key Determinant of Human Cell Apoptosis," *J. Virol.*, vol. 77 (19):10537-10547, 2003.

Construction of transcription plasmid for ERA +cDNA pTMF construct for virus recovery ERAgreen2 (trans2) ERAgreen1 (trans1)

Survival rates of hamster against Alabama Bat Rabies Virus infection treated with PEP and live attenuated ERA-R333 mutant Survival rates of hamster against Thai Street Dog Rabies Virus infection treated with PEP and live attenuated ERA-R333 mutant

RABIES VIRUS VECTOR SYSTEMS AND COMPOSITIONS AND METHODS THEREOF

CROSS REFERENCE TO RELATED APPLICATIONS

This is a divisional of U.S. application Ser. No. 12/090,083, filed Apr. 11, 2008, issued as U.S. Pat. No. 7,863,041 on Jan. 4, 2011, which is the U.S. National Stage of International Application No. PCT/US2006/040134, filed Oct. 13, 2006, which was published in English under PCT Article 21(2), and which claims the benefit of U.S. Provisional Application No. 60/727,038, filed Oct. 14, 2005. All of the above-referenced applications are incorporated herein by reference in their entirety.

STATEMENT OF GOVERNMENT SUPPORT

This invention was made by the Centers for Disease Control and Prevention, an agency of the United States Government. Therefore, the United States Government has certain rights in this invention.

FIELD

This disclosure relates to the field of virology. More specifically, this disclosure relates to compositions and methods that are useful for the production of immunogenic compositions for protecting mammals from infection by rabies virus.

BACKGROUND OF THE DISCLOSURE

Rabies remains one of the most dreadful infectious diseases affecting human and animals, despite significant scientific advances in its prevention and control. Rabies presents as a distinct problem in different parts of the world. In the Americas, reservoirs of rabies exist in many wild animal species, including raccoons, skunks, foxes, and bats (Rupprecht et al., *Emerg. Infect. Dis.* 1(4):107-114, 1995). Outbreaks of rabies infections in these terrestrial mammals are found in broad geographic areas across the United States. For example, raccoon rabies affects an area of more than 1 million square kilometers from Florida to Maine. Although wildlife rabies still exists in developed countries, progress has been made in control and elimination of wildlife rabies using oral immunization of wild animals.

Nonetheless, rabies remains a major threat to public health and persists to cause between 50,000 and 60,000 human deaths each year (World Health Organization, April 2003). Humans get infected with the rabies virus mostly through bites from rabid domestic and wildlife animals. In developing countries, dogs are responsible for about 94% of human rabies deaths. Dog rabies is still epizootic in most countries of Africa, Asia and South America and in these countries dogs are responsible for most human deaths from the disease. Controlling rabies virus infection in domestic and wildlife animals, therefore, not only reduces the mortality in these animals but also reduces the risks of human exposure.

The rabies virus is transmitted through broken skin by the bite or scratch of an infected animal. Exposure to rabies virus results in its penetration of peripheral, unmyelineated nerve endings, followed by spreading through retrograde axonal transport, replication occurring exclusively in the neurons, and finally arrival in the central nervous system (CNS). Infection of the CNS causes cellular dysfunction and death (Rupprecht & Dietzschold, *Lab Invest.* 57:603, 1987). Since rabies virus spreads directly from cell to cell, it largely evades immune recognition (Clark & Prabhakar, *Rabies*, In: Olson et al., eds., Comparative Pathology of Viral Disease, 2:165, Boca Raton, Fla., CRC Press, 1985).

The rabies virus (RV) is a rhabdovirus—a nonsegmented RNA virus with negative sense polarity. Within the Rhabdoviridae family, rabies virus is the prototype of the Lyssavirus genus. RV is composed of two major structural components: a nucleocapsid or ribonucleoprotein (RNP), and an envelope in the form of a bilayer membrane surrounding the RNP core. The infectious component of all rhabdoviruses is the RNP core, which consists of the negative strand RNA genome encapsidated by nucleoprotein (N) in combination with RNA-dependent RNA-polymerase (L) and phosphoprotein (P). The membrane surrounding the RNP contains two proteins: the trans-membrane glycoprotein (G) and the matrix (M) protein, located at the inner site of the membrane. Thus, the viral genome codes for these five proteins: the three proteins in the RNP (N, L and P), the matrix protein (M), and the glycoprotein (G).

The molecular determinants of pathogenicity of various rabies virus strains have not been fully elucidated. RV pathogenicity was attributed to multigenic events (Yamada et al., *Microbiol. Immunol.* 50:25-32, 2006). For example, some positions in the RV genome if mutated, affect viral transcription or replication, reducing virulence. Mutations at serine residue 389 of the phosphorylation site in the N gene (Wu et al., *J. Virol.* 76:4153-4161, 2002) or GDN core sequence of the highly conserved C motif in the L gene (Schnell and Conzelmann, *Virol.* 214:522-530, 1995) dramatically reduced RV transcription and replication.

The G protein, also referred to as spike protein, is involved in cell attachment and membrane fusion of RV. The amino acid region at position 330 to 340 (referred to as antigenic site III) of the G protein has been identified as important for virulence of certain strains of RV. Several studies support the concept that the pathogenicity of fixed RV strains is determined by the presence of arginine or lysine at amino acid residue 333 of the glycoprotein (Dietzschold et al., *Proc. Natl. Acad. Sci. USA* 80: 70-74, 1983; Tuffereau et al., *Virol.* 172: 206-212, 1989).

This phenomenon seems to apply at least to fixed rabies viruses such as CVS, ERA, PV, SAD-B19 and HEP-Flury strains (Anilionis et al., *Nature* 294:275-278, 1981; Morimoto et al., *Virol.* 173:465-477, 1989). For example, rabies vaccine viruses possessing an amino acid differing from Arg at position 333 of the glycoprotein are described, for instance, in WO 00/32755 (describing RV mutants in which all three nucleotides in the G protein $Arg_{333}$ codon are altered compared to the parent virus, such that the Arg at position 333 is substituted with another amino acid); European Patent 350398 (describing an avirulent RV mutant SAG1 derived from the Bern SAD strain of RV, in which the Arg at position 333 of the glycoprotein has been substituted to Ser); and European patent application 583998 (describing an attenuated RV mutant, SAG2, in which the Arg at position 333 in the G protein has been substituted by Glu).

Other strains, such as the RC-HL strain, possess an arginine residue at position 333 of the G, but does not cause lethal infection in adult mice (Ito et al., *Microbiol. Immunol.* 38:479-482, 1994; Ito et al., *J. Virol.* 75:9121-9128, 2001). As such, the entire G may contribute to the virulence of RV, although the determinants or regions have not previously been identified. The G gene encodes the only protein that induces viral neutralizing antibody. At least three states of RV glycoprotein are known: the native state (N) being responsible for receptor binding; an active hydrophobic state (A) necessary in the initial step in membrane fusion process (Gaudin, *J. Cell Biol.* 150:601-612, 2000), and a fusion inactive conformation (I). Correct folding and maturation of the G play important roles for immune recognition. The three potential glycosylated positions in ERA G extracellular domain occur at $Asn^{37}$, $Asn^{247}$ and $Asn^{319}$residues (Wojczyk et al., *Glycobiology.* 8: 121-130, 1998), respectively. Nonglycosylation of G not only affects conformation, but also inhibits presentation of the protein at the cell surface. Thus, elucidating the molecular determinants underlying pathogenicity of rabies virus presents a complex problem.

SUMMARY OF THE DISCLOSURE

The complete sequence of the virus strain corresponding to the fixed vaccine of Evelyn-Rokitnicki-Abelseth (ERA) for rabies virus is disclosed herein, along with methods for sequencing this and other strains of lyssavirus.

A reverse genetics system for rabies virus is also described, in particular using the rabies virus strain ERA as an exemplar. Use of a T7 RNA polymerase, containing an eight amino acid nuclear localization signal (NLS) at the N terminal end facilitated virus recovery. Besides the parental ERA virus strain, several other derivative viruses are described, including ERA- (deletion of the psi-region), ERAgreen1 (green fluorescent protein gene inserted in psi region), ERAgreen2 (green fluorescent protein gene inserted at the phosphoprotein and matrix protein intergenic region), ERA2g (containing an extra copy of the glycoprotein in the psi-region), ERAg3 (with a mutation at amino acid 333 in glycoprotein), ERA2g3 (with an extra copy of altered glycoprotein at amino acid 333 in psi-region), ERA-G (from which the glycoprotein has been deleted) ERAgm (M and G genes switched in the genome), and ERAgmg (two copies of G in the rearranged ERAgm construct). The extra transcription unit was incorporated into ERA virus genome for efficient expression of Open Reading Frames (ORFs). By optimizing propagation conditions, which are described herein, rescued viruses reach titers in excess of $10^9$ ffu/ml in either bioreactors or stationary tissue flasks.

Also disclosed is a modified cell line that constitutively expresses the ERA glycoprotein. The cell line, designated BSR-G, is useful for the production of recombinant, including attenuated and/or replication deficient, rabies virus.

The foregoing and other objects, features, and advantages of the invention will become more apparent from the following detailed description.

SEQUENCE LISTING

Figure 1A:
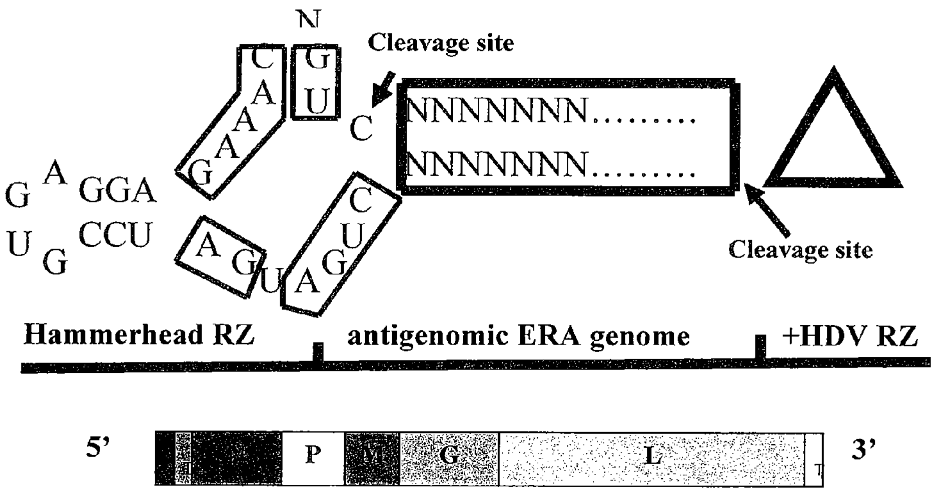
FIG. 1A. Schematic illustration of the ERA transcription plasmid. Positions of the hammerhead ribozymes and antigenomic ERA genome are indicated graphically. Relative positions of the N, P, M G and L proteins are shown in a 5' to 3' direction.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand unless the context makes it clear that only one strand is intended. As appropriate, it will be understood that a sequence presented as DNA can be converted to RNA by replacing thiamine residues with uracils. The Sequence Listing is submitted as an ASCII text file, created on Nov. 19, 2010, 285 KB, which is incorporated by reference herein. In the accompanying sequence listing:

SEQ ID NO: 1. ERA CDC wild type virus, 11,931 nucleotides 1-58 nucleotides, Leader region
71-1420 nucleotides, N gene
1514-2404 nucleotides, P gene
2496-3101 nucleotides, M gene
3317-4888 nucleotides, G gene
4964-5362 nucleotides, Psi-region
5417-11797 nucleotides, L gene
11862-11931 nucleotides, Trailer region SEQ ID NO: 2. ERACDC: 71 to 1420:450 aa, N protein.

SEQ ID NO: 3. ERACDC: 1514 to 2404:297 aa, P protein.

SEQ ID NO: 4. ERACDC: 2496 to 3101:202 aa, M protein.

SEQ ID NO: 5. ERACDC: 3317 to 4888:524 aa, G protein.

SEQ ID NO: 6. ERACDC: 5417 to 11797:2127 aa, L protein.

SEQ ID NO: 7. Recombinant ERA (rERA) recovered by reverse genetics system is 11,930 nucleotides. The specific poly ($A_8$) tract between G gene and psi-region in wild type ERA strain was mutated to a poly ($A_7$) tract in recombinant ERA reverse genetics system as a sequence marker. In light of this, rERA is one nucleotide shorter than wild type ERA. All the other sequence information is exactly the same.

SEQ ID NO: 8. ERAg3 strain (11,930 nucleotides), amino acid in the G protein (333Aa) has been altered; the corresponding nucleic acids are at positions 4370 to 4372.

SEQ ID NO: 9. ERA- (11,577 nucleotides), without the psi (pseudo-gene) region; an extra transcription unit has been introduced at nucleotide positions 4950 to 5008.

SEQ ID NO: 10. ERA-2G (13,150 nucleotides), this strain has two copies of the G gene; the second copy is inserted at positions 4988 to 6559.

SEQ ID NO: 11. ERAgreen (12,266 nucleotides), this strain contains the coding sequence for GFP at positions 4993 to 5673; it appears green under UV light after infection of cells or tissue.

SEQ ID NO: 12. ERA-G (10,288 nucleotides), this strain has no G gene.

SEQ ID NO: 13. ERA-2g3 (13,150 nucleotides); this strain has two copies of the G gene (the second of which is at positions 4988 to 6559), both of which are substituted at amino acid 333 (corresponding to nucleotide positions 4370-4372 and 6041-6043 in the shown sequence).

SEQ ID NO: 14. ERA-pt (11,976 nucleotides, with an extra transcription unit after the P gene, at positions 2469 to 2521).

SEQ ID NO: 15. ERA-pt-GFP (12,662 nucleotides, with GFP gene inserted after P gene at 2505 to 3185).

SEQ ID NO: 16. ERAgm (11,914 nucleotides) positions of G and M genes are switched with G at positions 2505-4076 and M at positions 4122-4727, respectively.

SEQ ID NO: 17. ERAg3m (11,914 nucleotides) positions of G and M genes are switched with G at positions 2505-4076 and M at positions 4122-4727, respectively. The G gene is mutated at amino acid position 333.

SEQ ID NO: 18. ERAgmg (13,556 nucleotides), this strain has two copies of the G gene at positions 2505-4076 and 4943-6514, flanking the M gene at positions 4122-4727.

SEQ ID NO: 19. First ten nucleotides of hammerhead ribozyme corresponding to 5' end of rabies virus ERA genome.

SEQ ID NO: 20. Nucleotide sequence encoding the SV40 T antigen nuclear localization signal (NLS).

SEQ ID NOs: 21-23. Artificial Kozak sequences.

SEQ ID NOs: 24-57. Synthetic oligonucleotides.

SEQ ID NO: 58. Amino acid sequence of G protein mutated at amino acid position 333 (from Arg to Glu).

SEQ ID NOs: 59-65. Synthetic oligonucleotides.

DETAILED DESCRIPTION

I. Introduction

Viral zoonoses are difficult to prevent. One major paradigm is the control of wildlife rabies by oral vaccination. All current licensed oral rabies vaccines are based on one common source. The fixed rabies virus (RV) of Evelyn-Rokitnicki-Abelseth (ERA) was derived from the Street-Alabama-Dufferin (SAD) strain, first isolated from a rabid dog in Alabama (USA) in 1935. The ERA strain was derived after multiple passages of SAD RV in mouse brains, baby hamster kidney (BHK) cells, and chicken embryos. Repeated cloning of ERA in BHK cells resulted eventually in a B-19 clone, which was named SAD-B 19 for vaccine studies. The first RV strain recovered by reverse genetics was SAD-B 19. Although SAD-B 19 and ERA RV derived from the same source, different outcomes have been observed in various animal oral vaccine studies. For example, ERA did not induce obvious neutralizing antibodies in either skunks or raccoons per os, while SAD-B 19 did. To elucidate potential differences between these two RV strains, a reverse genetics system for the ERA RV strain is required.

Reverse genetics presents a feasible way to modify RNA viruses in defined ways. A system for reverse genetics of an initial strain of rabies virus was successfully established in 1994 (Schnell et al., *The EMBO J.* 13, 4195-4203, 1994). In the intervening decade, improvements to the system have been made, resulting in increased efficiency of virus recovery. This increased efficiency has facilitated the elucidation of virus pathogenicity, protein-protein, and protein-RNA interactions.

Within the rabies virus genome, it has been proposed that some regions contain important signals, such as viral distal promoters region, nucleoprotein encapsidation, RNA dependent RNA polymerase L transcription initiation site, polyadenylation and termination sites. These signals are important for ensuring efficient recovery of virus and for designing an extra transcription unit for accepting an exogenous Open Reading Frame (ORF) into the rabies virus genome.

This disclosure provides an efficient reverse genetics system, and describes its use to produce variants of the ERA strain virus. Modifications described herein have resulted in strains that are suitable candidates for accepting ORF expression and vaccine development.

The reverse genetics system is composed of a set of plasmids. A first plasmid includes an ERA viral cRNA. In order to create authentic viral anti-genomic ends in transcribed viral cDNA, ERA genomic cDNA is flanked by a hammerhead ribozyme at the 3' end and a hepatitis delta virus ribozyme at the 5' end. The antigenomic cassette is fused to the bacteria phage T7 transcription initiation signal, which is optionally also under the control of cytomegalovirus (CMV) immediate-early promoter.

The system also includes a plurality of helper plasmids that encode proteins involved in viral encapsidation. For example, the system typically includes helper plasmids that encode the viral nucleoprotein (N), phosphoprotein (P), RNA dependent polymerase (L), and optionally the viral glycoprotein (G). The system also includes a plasmid that encodes the phage T7 RNA polymerase (T7), which can be modified by the addition of a nuclear localization signal (NLS) to increase expression of the T7 polymerase in the nucleus of transfected cells. The T7 RNA polymerase expression plasmid is constructed as an "autogene," which transcribes the whole length of viral anti-genomic cRNA for nucleoprotein encapsidation after transfection into cells.

The reverse genetics system is useful in the design and production of immunogenic compositions for the treatment (pre and/or post exposure) of rabies virus, and for producing rabies virus ERA vectors for expressing exogenous Open Reading Frames (ORFs). For example, an extra transcription unit can be designed, tested and incorporated into the ERA genome at either the Psi-region and/or at phosphoprotein (P)-matrix (M) protein intergenic region. Essentially any ORF of interest can be expressed in the context to the ERA vector, including ORFs encoding antigens of viruses and other pathogens, such as antigens of other lyssaviruses, as well as for expressing other proteins of therapeutic interest.

Thus, the methods and compositions disclosed herein are useful for the design and production of rabies virus immunogenic compositions, including compositions suitable as vaccines for the pre and/or post exposure treatment of rabies virus.

II. Abbreviations

ADE antibody-dependant enhancement
Ag-ELISA antigen-capture ELISA
DNA deoxyribonucleic acid
ERA Rabies virus strain Evelyn-Rokitnicki-Abelseth
ELISA enzyme-linked immunosorbent assay
G glycoprotein
i.c. intracerebral
IFA indirect immunofluorescence assay
i.m. intramuscular
L RNA-dependent RNA-polymerase
M matrix protein
mAb monoclonal antibody
N nucleoprotein
ORF open reading frame
P phosphoprotein
PCR polymerase chain reaction
RACE 5' rapid amplification of cDNA ends
RNA ribonucleic acid
RNP ribonucleoprotein
RT-PCR reverse transcription-polymerase chain reaction
RV rabies virus
trans 1 extra transcription unit 1
trans 2 extra transcription unit 2

III. Terms

Unless otherwise explained, all technical and scientific terms used herein have the same meaning as commonly understood by one of ordinary skill in the art to which this invention belongs. Similarly, unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

In order to facilitate review of the various embodiments of the invention, the following explanations of specific terms are provided:

Adjuvant: A substance that non-specifically enhances the immune response to an antigen. Development of vaccine adjuvants for use in humans is reviewed in Singh et al. (*Nat. Biotechnol.* 17:1075-1081, 1999), which discloses that, at the time of its publication, aluminum salts and the MF59 microemulsion are the only vaccine adjuvants approved for human use.

Amplification: Amplification of a nucleic acid molecule (e.g., a DNA or RNA molecule) refers to use of a laboratory technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by such techniques as electrophoresis, restriction endonuclease cleavage patterns, oligonucleotide hybridization or ligation, and/or nucleic acid sequencing.

Other examples of amplification methods include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320,308; gap filling ligase chain reaction amplification, as disclosed in U.S. Pat. No. 5,427,930; and NASBA™ RNA transcription-free amplification, as disclosed in U.S. Pat. No. 6,025,134. An amplification method can be modified, including for example by additional steps or coupling the amplification with another protocol.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and compositions of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antibody binding affinity: The strength of binding between a single antibody binding site and a ligand (e.g., an antigen or epitope). The affinity of an antibody binding site X for a ligand Y is represented by the dissociation constant ($K_d$), which is the concentration of Y that is required to occupy half of the binding sites of X present in a solution. A smaller ($K_d$) indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope.

In one example, antibody binding affinity is measured by end-point titration in an Ag-ELISA assay. Antibody binding affinity is substantially lowered (or measurably reduced) by the modification and/or substitution of one or more amino acids in the epitope recognized by the antibody paratope if the end-point titer of a specific antibody for the modified/substituted epitope differs by at least 4-fold, such as at least 10-fold, at least 100-fold or greater, as compared to the unaltered epitope.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a virus antigen.

Attenuated: In the context of a live virus, such as a rabies virus, the virus is attenuated if its ability to infect a cell or subject and/or its ability to produce disease is reduced (for example, eliminated). Typically, an attenuated virus retains at least some capacity to elicit an immune response following administration to an immunocompetent subject. In some cases, an attenuated virus is capable of eliciting a protective immune response without causing any signs or symptoms of infection.

Binding or Stable Binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including functional or physical binding assays. Binding can be detected functionally by determining whether binding has an observable effect upon a biosynthetic process such as expression of a gene, DNA replication, transcription, translation, and the like.

Physical methods of detecting the binding of complementary strands of DNA or RNA are well known in the art, and include such methods as DNase I or chemical footprinting, gel shift and affinity cleavage assays, Northern blotting, Southern blotting, dot blotting, and light absorption detection procedures. For example, a method which is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target dissociate or melt.

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Electrophoresis: Electrophoresis refers to the migration of charged solutes or particles in a liquid medium under the influence of an electric field. Electrophoretic separations are widely used for analysis of macromolecules. Of particular importance is the identification of proteins and nucleic acid sequences. Such separations can be based on differences in size and/or charge. Nucleotide sequences have a uniform charge and are therefore separated based on differences in size. Electrophoresis can be performed in an unsupported liquid medium (for example, capillary electrophoresis), but more commonly the liquid medium travels through a solid supporting medium. The most widely used supporting media are gels, for example, polyacrylamide and agarose gels.

Sieving gels (for example, agarose) impede the flow of molecules. The pore size of the gel determines the size of a molecule that can flow freely through the gel. The amount of time to travel through the gel increases as the size of the molecule increases. As a result, small molecules travel through the gel more quickly than large molecules and thus progress further from the sample application area than larger molecules, in a given time period. Such gels are used for size-based separations of nucleotide sequences.

Fragments of linear DNA migrate through agarose gels with a mobility that is inversely proportional to the $\log_{10}$ of their molecular weight. By using gels with different concentrations of agarose, different sizes of DNA fragments can be resolved. Higher concentrations of agarose facilitate separation of small DNAs, while low agarose concentrations allow resolution of larger DNAs.

Epitope: An antigenic determinant. These are particular chemical groups, such as contiguous or non-contiguous peptide sequences, on a molecule that are antigenic, that is, that elicit a specific immune response. An antibody binds a particular antigenic epitope based on the three dimensional structure of the antibody and the matching (or cognate) three dimensional structure of the epitope.

A "substituted epitope" comprises at least one structural substitution in the epitope, such as a substitution of one amino acid for another Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology*, $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

"Specific hybridization" refers to the binding, duplexing, or hybridizing of a molecule only or substantially only to a particular nucleotide sequence when that sequence is present in a complex mixture (for example, total cellular DNA or RNA). Specific hybridization may also occur under conditions of varying stringency.

Immune stimulatory composition: A term used herein to mean a composition useful for stimulating or eliciting a specific immune response (or immunogenic response) in a vertebrate. The immune stimulatory composition can be a protein antigen or a plasmid vector used to express a protein antigen. In some embodiments, the immunogenic response is protective or provides protective immunity, in that it enables the vertebrate animal to better resist infection with or disease progression from the organism against which the immune stimulatory composition is directed.

Without wishing to be bound by a specific theory, it is believed that an immunogenic response induced by an immune stimulatory composition may arise from the generation of an antibody specific to one or more of the epitopes provided in the immune stimulatory composition. Alternatively, the response may comprise a T-helper or cytotoxic cell-based response to one or more of the epitopes provided in the immune stimulatory composition. All three of these responses may originate from naïve or memory cells. One specific example of a type of immune stimulatory composition is a vaccine.

In some embodiments, an "effective amount" or "immune-stimulatory amount" of an immune stimulatory composition is an amount which, when administered to a subject, is sufficient to engender a detectable immune response. Such a response may comprise, for instance, generation of an antibody specific to one or more of the epitopes provided in the immune stimulatory composition. Alternatively, the response may comprise a T-helper or CTL-based response to one or more of the epitopes provided in the immune stimulatory composition. All three of these responses may originate from naïve or memory cells. In other embodiments, a "protective effective amount" of an immune stimulatory composition is an amount which, when administered to a subject, is sufficient to confer protective immunity upon the subject.

Inhibiting or treating a disease: Inhibiting the full development of a disease or condition, for example, in a subject who is at risk for a disease. A specific example of diseases is rabies. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" or "purified" biological component (such as a nucleic acid, peptide, protein, protein complex, or particle) has been substantially separated, produced apart from, or purified away from other biological components in the cell of the organism in which the component naturally occurs, that is, other chromosomal and extra-chromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Label: A detectable compound or composition that is conjugated directly or indirectly to another molecule to facilitate detection of that molecule. Specific, non-limiting examples of labels include fluorescent tags, enzymatic linkages, and radioactive isotopes.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Oligonucleotide: A nucleic acid molecule generally comprising a length of 300 bases or fewer. The term often refers to single-stranded deoxyribonucleotides, but it can refer as well to single- or double-stranded ribonucleotides, RNA:DNA hybrids and double-stranded DNAs, among others. The term "oligonucleotide" also includes oligonucleosides (that is, an oligonucleotide minus the phosphate) and any other organic base polymer.

In some examples, oligonucleotides are about 10 to about 90 bases in length, for example, 12, 13, 14, 15, 16, 17, 18, 19 or 20 bases in length. Other oligonucleotides are about 25, about 30, about 35, about 40, about 45, about 50, about 55, about 60 bases, about 65 bases, about 70 bases, about 75 bases or about 80 bases in length. Oligonucleotides may be single-stranded, for example, for use as probes or primers, or may be double-stranded, for example, for use in the construction of a mutant gene. Oligonucleotides can be either sense or anti-sense oligonucleotides. An oligonucleotide can be modified as discussed above in reference to nucleic acid molecules. Oligonucleotides can be obtained from existing nucleic acid sources (for example, genomic or cDNA), but can also be synthetic (for example, produced by laboratory or in vitro oligonucleotide synthesis).

Open Reading Frame (ORF): A series of nucleotide triplets (codons) coding for amino acids without any internal termination codons. These sequences are usually translatable into a peptide/polypeptide/protein/polyprotein.

It is recognized in the art that the following codons (shown for RNA) can be used interchangeably to code for each specific amino acid or termination: Alanine (Ala or A) GCU, GCG, GCA, or GCG; Arginine (Arg or R) CGU, CGC, CGA, CGG, AGA, or AGG; Asparagine (Asn or N) AAU or AAC; Aspartic Acid (Asp or D) GAU or GAC; Cysteine (Cys or C) UGU or UGC; Glutamic Acid (Glu or E) GAA or GAG; Glutamine (Gln or Q) CAA or CAG; Glycine (Gly or G) GGU, GGC, GGA, or GGG; Histidine (His or H) CAU or CAC; Isoleucine (Ile or I) AUU, AUC, or AUA; Leucine (Leu or L) UUA, UUG, CUU, CUC, CUA, or CUG; Lysine (Lys or K) AAA or AAG; Methionine (Met or M) AUG; Phenylalanine (Phe or F) UUU or UUC; Proline (Pro or P) CCU, CCC, CCA, or CCG; Serine (Ser or S) UCU, UCC, UCA, UCG, AGU, or AGC; Termination codon UAA (ochre) or UAG (amber) or UGA (opal); Threonine (Thr or T) ACU, ACC, ACA, or ACG; Tyrosine (Tyr or Y) UAU or UAC; Tryptophan (Trp or W) UGG; and Valine (Val or V) GUU, GUC, GUA, or GUG. The corresponding codons for DNA have T substituted for U in each instance.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence is the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Paratope: That portion of an antibody that is responsible for its binding to an antigenic determinant (epitope) on an antigen.

Pharmaceutically Acceptable Carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more SARS-CoV nucleic acid molecules, proteins or antibodies that bind these proteins, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues joined together through amide bonds. When the amino acids are alpha-amino acids, either the L-optical isomer or the D-optical isomer can be used, the L-isomers being preferred for many biological uses. The terms "polypeptide" or "protein" as used herein are intended to encompass any amino acid molecule and include modified amino acid molecules. The term "polypeptide" is specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan, and tyrosine are classified as both polar and aromatic amino acids. Additional amino acids that are classified in each of the above groups are known to those of ordinary skill in the art.

Substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Probes and primers: A probe comprises an isolated nucleic acid molecule attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual, 2nd* ed., vol. 1-3, Cold Spring Harbor Laboratory Press, Cold Spring Harbor, N.Y., 1989 and Ausubel et al. *Short Protocols in Molecular Biology, 4th* ed., John Wiley & Sons, Inc., 1999.

Primers are short nucleic acid molecules, for instance DNA oligonucleotides 6 nucleotides or more in length, for example that hybridize to contiguous complementary nucleotides or a sequence to be amplified. Longer DNA oligonucleotides may be about 10, 12, 15, 20, 25, 30, or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the polymerase chain reaction (PCR) or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033, 881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Methods for preparing and using nucleic acid probes and primers are described, for example, in Sambrook et al. (ed.), *Molecular Cloning: A Laboratory Manual,* 2nd ed., vol. 1-3, Cold Spring Harbor Laboratory Press, Cold Spring Harbor, N.Y., 1989; Ausubel et al. *Short Protocols in Molecular Biology,* 4th ed., John Wiley & Sons, Inc., 1999; and Innis et al. *PCR Protocols, A Guide to Methods and Applications*, Academic Press, Inc., San Diego, Calif., 1990. Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

Protein: A biological molecule, particularly a polypeptide, expressed by a gene and comprised of amino acids.

Purified: The term "purified" does not require absolute purity; rather, it is intended as a relative term. Thus, for example, a purified protein preparation is one in which the subject protein is more pure than in its natural environment within a cell. Generally, a protein preparation is purified such that the protein represents at least 50% of the total protein content of the preparation.

Recombinant nucleic acid: A nucleic acid molecule that is not naturally occurring or has a sequence that is made by an artificial combination of two otherwise separated segments of sequence. This artificial combination is accomplished by chemical synthesis or, more commonly, by the artificial manipulation of isolated segments of nucleic acids, e.g., by genetic engineering techniques such as those described in Sambrook et al. (ed.), *Molecular Cloning: A Laboratory Manual,* 2nd ed., vol. 1-3, Cold Spring Harbor Laboratory Press, Cold Spring Harbor, N.Y., 1989. The term recombinant includes nucleic acids that have been altered solely by addition, substitution, or deletion of a portion of a natural nucleic acid molecule.

Regulatory sequences or elements: These terms refer generally to a class of DNA sequences that influence or control expression of genes. Included in the term are promoters, enhancers, locus control regions (LCRs), insulators/boundary elements, silencers, matrix attachment regions (MARs, also referred to as scaffold attachment regions), repressor, transcriptional terminators, origins of replication, centromeres, and meiotic recombination hotspots. Promoters are sequences of DNA near the 5'-end of a gene that act as a binding site for DNA-dependent RNA polymerase, and from which transcription is initiated. Enhancers are control elements that elevate the level of transcription from a promoter, usually independently of the enhancer's orientation or distance from the promoter. LCRs confer tissue-specific and temporally regulated expression to genes to which they are linked. LCRs function independently of their position in relation to the gene, but are copy-number dependent. It is believed that they function to open the nucleosome structure, so other factors can bind to the DNA. LCRs may also affect replication timing and origin usage. Insulators (also know as boundary elements) are DNA sequences that prevent the activation (or inactivation) of transcription of a gene, by blocking effects of surrounding chromatin. Silencers and repressors are control elements that suppress gene expression; they act on a gene independently of their orientation or distance from the gene. MARs are sequences within DNA that bind to the nuclear scaffold; they can affect transcription, possibly by separating chromosomes into regulatory domains. It is believed that MARs mediate higher-order, looped structures within chromosomes. Transcriptional terminators are regions within the gene vicinity where RNA polymerase is released from the template. Origins of replication are regions of the genome that, during DNA synthesis or replication phases of cell division, begin the replication process of DNA. Meiotic recombination hotspots are regions of the genome that recombine more frequently than average during meiosis.

Replicon: Any genetic element (e.g., plasmid, chromosome, virus) that functions as an autonomous, self-replicating unit of DNA replication in vivo.

Sample: A portion, piece, or segment that is representative of a whole. This term encompasses any material, including for instance samples obtained from an animal, a plant, or the environment.

An "environmental sample" includes a sample obtained from inanimate objects or reservoirs within an indoor or outdoor environment. Environmental samples include, but are not limited to: soil, water, dust, and air samples; bulk samples, including building materials, furniture, and landfill contents; and other reservoir samples, such as animal refuse, harvested grains, and foodstuffs.

A "biological sample" is a sample obtained from a plant or animal subject. As used herein, biological samples include all samples useful for detection of viral infection in subjects, including, but not limited to: cells, tissues, and bodily fluids, such as blood; derivatives and fractions of blood (such as serum); extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; BAL; saliva; cervical swabs; vaginal swabs; and oropharyngeal wash.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.,* 2:482, 1981); Needleman and Wunsch (*J. Mol. Biol.,* 48:443, 1970); Pearson and Lipman (*Proc. Natl. Acad. Sci.,* 85:2444, 1988); Higgins and Sharp (*Gene,* 73:237-44, 1988); Higgins and Sharp (*CABIOS,* 5:151-53, 1989); Corpet et al. (*Nuc. Acids Res.,* 16:10881-90, 1988); Huang et al. (*Comp. Appls. Biosci.,* 8:155-65, 1992); and Pearson et al. (*Meth. Mol. Biol.,* 24:307-31, 1994). Altschul et al. (*Nature Genet.,* 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program © 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.,* 215:403-10, 1990; Gish and States, *Nature Genet.,* 3:266-72, 1993; Madden et al., *Meth. Enzymol.,* 266:131-41, 1996; Altschul et al., *Nucleic Acids Res.,* 25:3389-402, 1997; and Zhang and Madden, *Genome Res.,* 7:649-56, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, or at least 99% depending on their similarity to the reference sequence. Sequence identity over such short windows can be determined using LFASTA; methods are described at the NCSA website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specific binding agent: An agent that binds substantially only to a defined target. Thus a protein-specific binding agent binds substantially only the defined protein, or to a specific region within the protein. As used herein, protein-specific binding agents include antibodies and other agents that bind substantially to a specified polypeptide. The antibodies may be monoclonal or polyclonal antibodies that are specific for the polypeptide, as well as immunologically effective portions ("fragments") thereof.

The determination that a particular agent binds substantially only to a specific polypeptide may readily be made by using or adapting routine procedures. Examples of suitable in vitro assays which make use of the Western blotting procedure include IFA and Ag-ELISA, and are described in many standard texts, including Harlow and Lane, *Using Antibodies: A Laboratory Manual*, CSHL, New York, 1999.

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). A vector may also include one or more selectable marker genes and other genetic elements known in the art.

Virus: Microscopic infectious organism that reproduces inside living cells. A virus typically consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

IV. Overview of Several Embodiments

Provided herein in a first embodiment is a recombinant rabies virus genome comprising the nucleic acid as set forth in SEQ ID NO: 1 (full length ERA sequence). Also provided are isolated rabies virus proteins encoded by that genome, including specific proteins comprising an amino acid sequence as set forth in SEQ ID NO: 2 (N protein); SEQ ID NO: 3 (P protein); SEQ ID NO: 4 (M protein); SEQ ID NO: 5 (G protein); or SEQ ID NO: 6 (L protein); and isolated nucleic acid molecules that encode such proteins. By way of example, such isolated nucleic acid molecules comprise a nucleotide sequence as set forth in: nucleotides 71-1423 of SEQ ID NO: 1 (N protein); nucleotides 1511-2407 of SEQ ID NO: 1 (P protein); nucleotides 2491-3104 of SEQ ID NO: 1 (M protein); nucleotides 3318-4892 of SEQ ID NO: 1 (G protein); or nucleotides 5418-11,801 of SEQ ID NO: 1 (L protein).

Also provided is a recombinant virus genome with the nucleic acid sequence as set forth in SEQ ID NO: 7, which differs from SEQ ID NO: 1 by virtue of a deletion of one adenosine residue in the polyA tract between the G gene and the psi-region. SEQ ID NO: 7 also encodes the proteins shown as SEQ ID NOs: 2-6.

Also provided are genomes of derivatives of the ERA strain of virus, as shown in SEQ ID NOs: 8-18. In certain embodiments, the genomes are present in a vector, such as a plasmid. Yet another described embodiment is a system for sequencing full length rabies virus genome using a method as described herein. Viral vector systems for expression of heterologous proteins are also described.

Another embodiment provides compositions that comprise one or more nucleic acid molecules, or one or more proteins, provided herein. Optionally, such compositions contain a pharmaceutically acceptable carrier, an adjuvant, or a combination of two or more thereof.

Also provided is a method of eliciting an immune response against an antigenic epitope in a subject, comprising introducing into the subject a composition comprising a nucleotide, peptide, or polypeptide described herein, thereby eliciting an immune response in the subject.

Another aspect of the disclosure relates to a vector system for producing recombinant rabies virus. The vector system includes a first vector (transcription vector) containing a full-length rabies virus antigenomic DNA (or a derivative thereof) and a set of helper vectors containing nucleic acids that encode at least one rabies virus strain ERA protein. Expression of the vectors in a transfected host cell results in production of a live recombinant rabies virus. In certain embodiments, the antigenomic DNA is of the ERA strain (for example, SEQ ID NO: 1 or SEQ ID NO: 7) or a derivative thereof, such as one of SEQ ID NOs: 8-18. In certain embodiments, the vectors are plasmids.

To facilitate recovery of full length viral RNA, the transcription vector can include, in a 5' to 3' direction: a hammerhead ribozyme; a rabies virus antigenomic cDNA; and a hepatitis delta virus ribozyme. Nucleotides of the hammerhead ribozyme are selected to be complementary to the antisense genomic sequence of the rabies virus. Transcription of the antigenomic cDNA is under the transcription regulatory control of at least one of the CMV promoter and the phage T7 RNA polymerase promoter, and commonly under the control of both of these promoters.

The helper vectors typically include a vector comprising a polynucleotide sequence that encodes a rabies virus N protein; a vector comprising a polynucleotide sequence that encodes a rabies virus P protein; a vector comprising a polynucleotide sequence that encodes a rabies virus M protein; a vector comprising a polynucleotide sequence that encodes a rabies virus L protein; and a vector comprising a polynucleotide sequence that encodes a phage T7 RNA polymerase. In an embodiment, the T7 RNA polymerase comprises a nuclear localization signal (NLS). Optionally, the vector system also includes a vector comprising a polynucleotide sequence that encodes a rabies virus G protein.

Transcription of one or more of the polynucleotide sequences that encode the rabies virus P, M, L or G protein or the T7 polymerase is under the transcription regulatory control of both the CMV promoter and the T7 promoter. In contrast, transcription of the polynucleotide sequence that encodes the rabies virus N protein is under the transcription regulatory control of the T7 promoter, and transcription is cap-independent.

Yet more embodiments are live rabies vaccines, each comprising a recombinant rabies virus genome as provided herein. Examples of such recombinant rabies genomes comprise the sequence shown as ERA G333 (SEQ ID NO: 13); the sequence shown as ERA 2G (SEQ ID NO: 8); and the sequence shown herein as ERA 2G333 (SEQ ID NO: 10). Optionally, the rabies vaccine is attenuated.

Also provided is a method of producing a live rabies virus (for example, for use in an immunogenic composition, such as a vaccine) by introducing the vector system into a host cell. After transfection of vector system into a suitable host cell, live and optionally attenuated virus is recovered. Production and administration of a live rabies vaccine produced by such methods is also contemplated herein.

Also disclosed is a method of vaccinating a subject against rabies, which method comprises administering an effective amount of the live rabies vaccine according to the provided description to a subject, such that cells of the subject are infected with the rabies vaccine, wherein an anti-rabies immune response is produced in the subject. In one embodiment, the subject is a human. In another embodiment, the subject is a non-human animal. For instance, the non-human animal in some instances is a cat, dog, rat, mouse, bat, fox, raccoon, squirrel, opossum, coyote, or wolf.

In certain embodiments, the rabies vaccine is administered enterally. For instance, the enteral administration in some cases comprises oral administration. Oral administration includes administration through food-baits designed to vaccinate wild animal populations, for instance.

Pharmaceutical compositions that include the described live rabies vaccines (for instance, an attenuated live rabies vaccine) and a pharmaceutically acceptable carrier or excipient are also provided.

V. Method of Sequencing Entire Lyssavirus Genome

To facilitate sequencing of the full length ERA genome, a method for sequencing a full length negative strand RNA virus was developed. This method is applicable to the sequencing of a lyssavirus, such as a rabies virus, as well as other negative strand RNA viruses. Rabies virus is a single negative stranded RNA virus with a genome around 12 kb, with the range between 11,918 (Australian bat lyssavirus) and 11,940 (Mokola virus) bases. The available rabies viral nucleic acid sequences in GENBANK mainly focus on the sequences that encode proteins—nucleocapsid protein (N), glycoprotein (G), phosphoprotein (P) and matrix protein (M) genes, which are close to the 3' end of the genome. Prior phylogenetic analysis is mostly based on N and G genes. But, for remotely related rabies viral strains, RNA dependent RNA polymerase (L) gene is the most suitable candidate for phylogenetic analysis. Unfortunately, few L gene sequences are available in public gene databases. In addition, it has been proposed that both leader and trailer regions at rabies viral termini play very important roles for (regulation of) viral transcription and replication. These could be the conserved regions for nucleoprotein encapsidation or the binding sites for L/P proteins, for instance. Also the inter-genic regions among leader-N, N-P, P-M, M-G, pseudo-gene region and G-L serve as the signals for initiation of viral transcription. Thus, not only coding regions, but also non-coding regions within the viral genome, could be applied to phylogenetic analysis or evolution research. These sequences can all more readily be analyzed using the whole-genome sequencing methods provided herein.

The method includes a single step reverse transcription and a two step cloning into a suitable vector. This method produces a readily sequenced genome in the vector, without the need to perform error-prone repeated RT-PCR reactions. Exploiting the inverted repeat found at the ends of the rabies genome (and the genomes of other lyssaviruses), universal primers have been designed and are described herein for use in the rapid full-genome sequencing procedures described herein.

The leader and trailer regions in rabies virus contain signals for viral transcription and replication. Based on analysis the genome sequence available from GenBank, the terminal 11 nucleotides are strictly conserved in rabies viruses or rabies-related viruses, including Mokola virus. The rationale for the sequencing methods provided herein is based on the terminal 11 complementary nucleotides. Because these two 11 nucleotide sequences are complementary, they could are not used in the follow-up PCR reactions. It will be understood that other viruses with inverted repeats can similarly be amplified using primers corresponding to the sequences of those repeats. The 11 antigenome sense nucleotides were designed as reverse transcription primers for the purified ERA genome, whose integrity was verified by size comparison and Northern blots. The whole genome cDNA was also confirmed by Northern blot with N, P, M, G, L gene probes and 11 nucleotides as an oligonucleotide probe, which only bound genomic RNA, not viral mRNA.

It is reasonably feasible to reverse transcribe rabies viral whole genome in one reaction, using carefully designed conserved terminal sequence-corresponding primes, provided the quality of the viral genome preparation is high.

The sequence of the ERA is closely related to that of SAD, which is one of its derivatives. This is not surprising, because ERA was sent from CDC in the 1970s to Switzerland, where researchers adapted it to grow in cells, before sending it to Germany, where it was further derived, and the derivative fully sequenced in ~1990. Until now, rabies and rabies-related viruses have been classified into seven different types: classic rabies virus type1 (ERA is included), type2 (Lagos bat), type3 (Mokola), type4 (Duvenhage), type5 (European bat lyssavirus [EBL] I, type6 (EBL II) and type7 (Australian bat virus) according to serum cross protection and genetic studies. Sequence analysis plays an important role in phylogenetics, evolution research, gene function predictive studies and other related areas, including locating viral transcription and replication regulatory regions, and hence bioinformatics towards potential therapeutic drugs.

With the development of techniques in reverse transcriptional polymerase chain reaction (RT-PCR), which are known to those of ordinary skill in the art, now it is relatively easy to reverse transcribe as much as 12 kb or more of RNA to cDNA in one reaction. Under optimized conditions, PCR can amplify targets of more than 30 kb in one reaction.

With the provision herein of methods for generating full-length virus genome sequences, in particularly rabies genome sequences, it now becomes practical to analyze differ strains of virus. Effective design of attenuated virus, for instance for use in immunization or production of immune stimulatory compositions and vaccines, is also enabled using the resultant full length genomes.

There is no "general" rabies virus genome, but these genomes are related. The similarities range from 60% to 100% in different types. Some regions, such as the L gene, seem more conserved, whereas others, such as the psi region, which does not code for a polypeptide, are more variable. Not only will rabies and rabies related viruses drift, but also any RNA viruses will change over time. How the viruses adapt and emerge, is an open question. For this reason, whole genome sequence analysis is important for evolutionary, pathogenicity and gene function studies.

This system described herein is the first for rabies virus as concerns whole genome sequencing. It is believed to be suitable for other RNA viruses, particularly in the lyssavirus genus. At present, for rabies virus phylogenetic studies, scientists only make use of the N, P, or G genes, which are most abundant in the infected cells or tissues. It is known that for remote strain comparison, the L gene comprising more than half of the genome may be an ideal candidate site, which should be used. Unfortunately, such evolutionary comparisons are not possible due to the very limited data available, let alone the whole genome sequence. Also for viral transcription and replication studies, it is supposed that the leader and trailer regions located at the 3' and 5' extremities of the genome play important roles. The inter-genic regions are also the signals for viral trans and cis studies. All these data are quite limited, because they are not included in the mRNA. Only the whole genome sequence can provide the necessary information at this level. Whole genome sequencing is useful not only for vaccine development, it is also applicable for basic virus transcription and replication studies. It is also applicable for development siRNA and gene therapy as well.

VI. ERA Genome Sequence

Using the method described herein, the unique sequence of the ERA rabies virus genome has been generated. This sequence is shown in SEQ ID NO: 1. The five proteins of the ERA rabies virus (SEQ ID NOs: 2-6) are encoded at the following positions of the genome: N, 71-1423; P, 1511-2407; M, 2491-3104; G, 3318-4892; and L, 5418-11801. The homology between ERA and SAD-B19 are: N 99.56%, P 98.65%, M 96.53%, G 99.05% and L 99.20%, respectively. One specific difference between ERA and SAD-B 19 is the intergenic region between G and the pseudo-gene, with the SAD-B19 G transcription stop/polyadenylation signal destroyed.

The ERA rabies virus whole genome sequence is the prerequisite for vaccine development and pathogenicity studies using reverse genetics

VII. Optimized System for Production of Virus

Examples 6 and 7 provide an optimized set of conditions for ERA virus production, in which titers reach as high as $10^{10}$ ffu per ml. In bioreactors, the recovered virus can grow to ~$10^9$ to $10^{10}$ ffu/ml. Such high levels of production are of paramount importance for oral vaccine development, so sufficient vaccine material can be produced in a reasonable amount of time with reasonable resource allocation.

The provided growth conditions can stably produce such high virus titer for both parental and recombinant ERA strains. These production data are very important for potential rabies oral vaccine development.

VIII. BSR-G Cell Line for Production of -G Virus

Although strains of RV with deletions of the G protein have been previously rescued from BHK cells, this was not possible with ERA strain virus lacking the G protein. After inoculation of mice intracerebrally or intramuscularly with ERA-G, no mice died or showed any rabies symptoms. The ERA-G (without glycoprotein) can only grow in cells with the supplementation of the glycoprotein. Otherwise, the mutated virus cannot spread. To help ERA-G grow, a BSR-G cell line was established, which constitutively expressed ERA glycoprotein. Production of this cell line is described in the Examples below. This cell line is useful for recovery of RV strains such as ERA-G that are refractory to recovery in the absence of G, as well as for optimizing recovery of other strains.

IX. Reverse Genetics System for Engineering Rabies Virus Vaccines and Expression of Heterologous Proteins RNA cannot readily be manipulated directly by molecular biological methods. Traditional RNA virus vaccines are from naturally attenuated isolates, which are difficult to control and provide unpredictable results. Reverse genetics technology makes it possible to manipulate RNA viruses as DNA, which can be mutated, deleted or reconstructed according to deliberate designs. Every gene function can be studied carefully, independently, and in concert, which benefits vaccine development. Reverse genetics involves reverse transcription of the RNA viral genome into cDNA, and cloning into a vector, such as a plasmid. After transfection of host cells, the vector is transcribed into RNA, to be encapsidated by structural proteins, which can also be supplied by plasmids. The encapsidated RNA forms a ribonucleoprotein complex, which results in virions that can be recovered.

Although three systems for rabies virus (RV) reverse genetics have been published (Schnell et al., *The EMBO J.* 13, 4195-4203, 1994; Inoue et al., *J. Virol. Method.* 107, 229-236, 2003; Ito et al., *Microbiol. Immunol.* 47, 613-617, 2003), these systems are not readily adaptable to other strains. At present, no rabies virus strain has been recovered with the aid of helper plasmids from a different strain, even when the strains are closely related. Thus, for any specific virus strain mutation or vaccine development, a specifically tailored system must be developed.

The ERA strain is a good candidate for rabies oral vaccine development, but its residual pathogenicity is obvious. During the 1970s, the ERA RV underwent extensive vaccine development (Black and Lawson, *Can. J. Comp. Med.* 44:169-176, 1980; Charlton, and Casey, *Can. J. Vet. Res.* 20:168-172, 1978; Lawson, and Crawley, *Can. J. Vet. Res.* 36: 339-344, 1972). Both ERA and SAD-B19 are derived from SAD. In primary oral vaccine trials, SAD-B 19 was effective in both raccoons and skunks, while ERA was not. Additionally, ERA kills two-week old mice administrated intra cerebrally (i.c.), as demonstrated in animal tests. These observations raise questions of the relationship between these two RV strains and the potential effects of subtle alterations. From full viral genome sequence comparison, ERA and SAD-B 19 share extremely high nucleotide identity and amino acid homologies. To clarify the genetic basis of immunogenicity and pathogenicity of these highly related strains of rabies virus, an efficient reverse genetics system was developed for ERA, which differs from reverse genetics systems previously reported for rabies virus.

The rabies reverse genetics system disclosed herein is useful for a variety of purposes, including: (1) to attenuate ERA virus in a defined manner for vaccine development; (2) to produce ERA virus vectors for expressing heterologous ORFs (e.g., in the context of therapeutic compositions, such as vaccines and gene therapy); (3) to define the genetic basis of ERA RV pathogenesis; and (4) to determine the biological effects of genetic differences between the ERA and SAD viruses.

The reverse genetics system has some or all of the following characteristics, illustrated schematically in FIG. 1A using the exemplary ERA strain antigenomic cDNA.

This system is based a full length transcription plasmid plus a plurality of helper plasmids (e.g., five helper plasmids). The helper plasmids encode the N, P, L proteins, and optionally the G protein, as well as the T7 polymerase. Although the G protein is not necessary for virus rescue, it improves virus recovery efficiency or virus budding when included in transfection.

Transcription involves both cellular RNA dependent RNA polymerase II, which is available in mammalian cells, and T7 RNA polymerase, which is supplied by pNLST7 plasmids. The dual polymerases result in virus recovery efficiency is both high and stable.

In the transcription plasmid, hammerhead and hepatitis delta virus ribozymes flank a rabies virus (e.g., ERA strain) antigenomic cDNA, enabling the production of authentic 5' and 3' ends of antigenomic vRNA by transcription. The first ten nucleotides of the hammerhead sequence are designed to be complementary to the first ten nucleotides of the antisense genomic sequence. For example, the first ten nucleotides of the hammerhead sequence for the ERA antigenomic cDNA are:

```
TGTTAAGCGT.          (SEQ ID NO: 19)
```

Two modified T7 RNA polymerase constructs have been established, which support virus recovery more efficiently than the wild type T7 RNA polymerase applied previously. One T7 RNA polymerase has been mutated from the first ATG to AT. The second T7 RNA polymerase has an eight amino acid nuclear localization signal (NLS) derived from the SV40 virus large T antigen fused after the first ATG from the parental T7: ATG <u>CCAAAAAAGAAGAGAAAGGTAGAA</u> (SEQ ID NO: 20). The NLS is underlined. Addition of the NLS results in the T7 RNA polymerase being present predominantly in the nucleus. Following transfection mechanism of the NLS modified plasmid, the DNA/transfection reagent complex binds to surface of the cell. Through endocytosis, the complex is taken into the endosome/lysosome, and the DNA is released into the cytosol. In the absence of the NLS, the majority of the transfected plasmids are retained in the cytosol and only a small percentage of the released DNA reaches the nucleus, where it is transcribed into RNA. After protein synthesis, the NLST7 RNA polymerase is transported back to the cell nucleus, and the helper plasmids (with T7/CMV promoters) in the nucleus will be transcribed by both NLST7 and cellular polymerase II. Thus, more mRNAs of the helper plasmids and cRNA of the full-length pTMF or its derivatives were synthesized and resulted in high efficiency of virus recovery.

Figure 2:
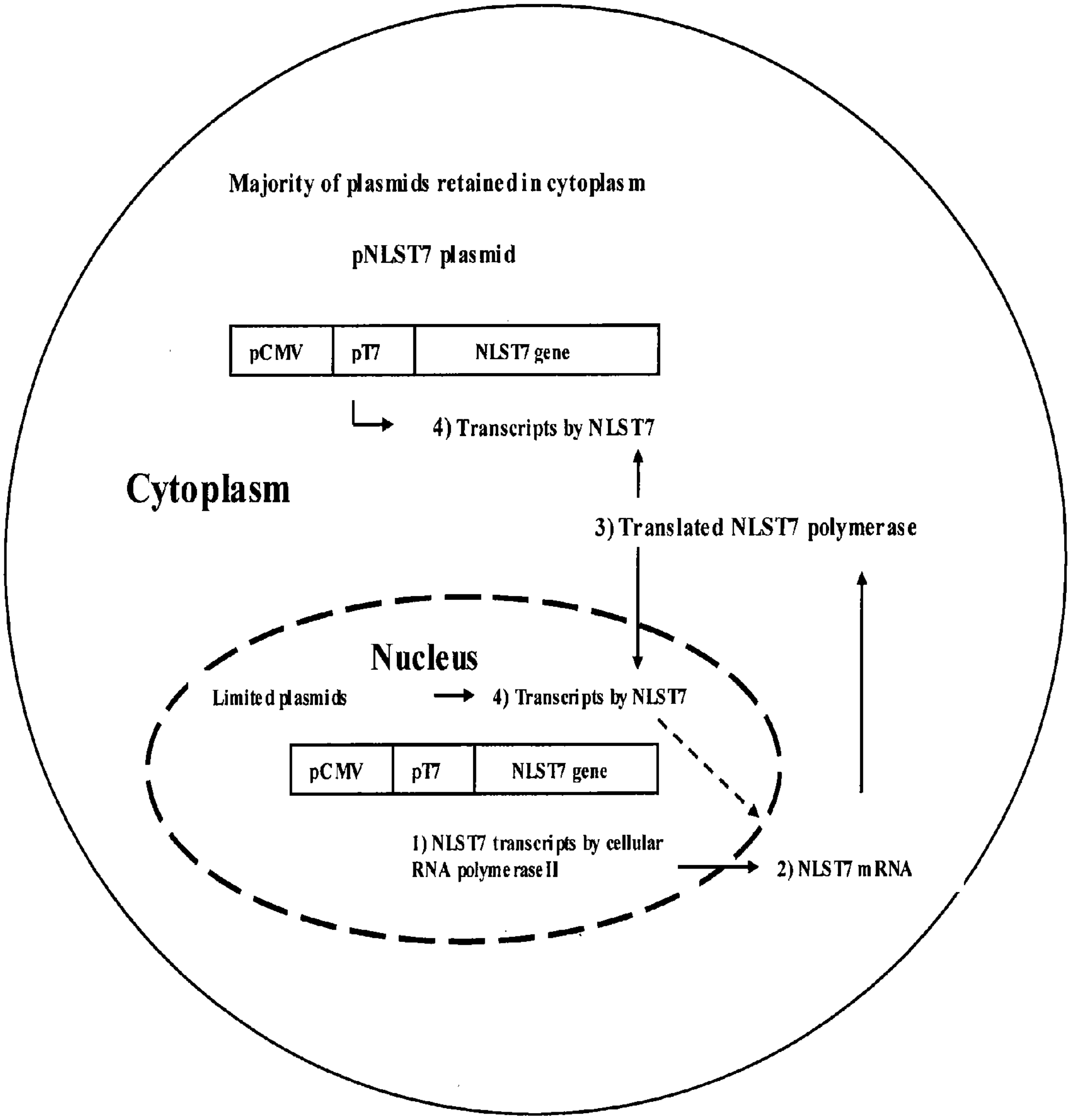
FIG. 2. Schematic illustration of the proposed mechanism of NLST7 RNA polymerase autogene action by pNLST7 plasmids. The DNA-transfection reagent complex is taken into cells by endocytosis. The majority of the DNA released from lysosomes and endosomes is retained in the cell cytoplasm. A limited amount of plasmids are transferred to the nucleus: 1) through a CMV immediate early promoter, the NLST7 gene is transcribed by cellular RNA polymerase II; 2) mature NLST7 mRNA is transported from the nucleus to the cytoplasm for NLST7 RNA polymerase synthesis; 3) Newly synthesized NLST7 RNA polymerase is trans-located to the nucleus, while a trace amount of NLST7 remains in the cytoplasm; 4) NLST7 RNA polymerase initiates transcription through a pT7 promoter. By posttranscriptional modifications, additional NLST7 mRNA is produced for protein synthesis, thus increasing virus recovery efficiency.

After the initial expression of NLST7 by CMV promoter, NLST7 polymerase binds to pT7 for transcription of NLST7 gene. Through modification of the transcripts in the nucleus, more NLST7 mRNA is synthesized, resulting in more expression of NLST7 polymerase. The pT7 of the NLST7 polymerase as well as of the full length antigenomic transcription unit is under the control of the NLST7 polymerase, which acts as an "autogene." The autogene mechanism of NLST7 RNA polymerase is illustrated in FIG. 2. After expression of T7 RNA polymerase in the nucleus, the transfected T7 constructs continue to transcribe full length RNA template for N protein encapsidation and/or L protein binding, enhancing virus recovery efficiency.

The T7 polymerase, and all other plasmids, except the N protein encoding plasmid pTN, are placed under control of both CMV and T7 transcriptional regulatory elements. The N protein encoding nucleic acid is under the control of a T7 promoter and is translated in cap-independent manner based on an IRES (Internal Ribosome Entry Site). Cellular RNA polymerase II alone can help the recovery of RV if all the plasmids were cloned under the control of the CMV promoter (19). In the ERA reverse genetics system disclosed herein, only pTN is under the control of the T7 promoter and was translated in a cap-independent manner. All other constructs are under control of both CMV and the T7 transcriptional regulatory elements. Typically, in RV, N synthesis is abundant and the ratio among N, P and L is approximately 50:25:1. To mimic the wild type viral transcription and assembly in RV reverse genetics, N expression should be the highest. With the aid of NLST7 polymerase and IRES translation mode, N protein was expressed efficiently after plasmid transfection. This reduces competition for transcription with house keeping genes in host cells, because the T7 transcription initiation signal does not exist in mammalian cells, and results in increased efficiency of T7 transcription.

To enhance production of viral proteins, the helper plasmids can be constructed to incorporate a Kozak sequence that has been optimized for the translation efficiency for each protein encoding sequence. Exemplary optimized Kozak sequences are shown in Table 2.

TABLE 2

Optimized Kozak sequences.

| constructs | promoters | Kozak context | SEQ ID NO: | Special characters |
|---|---|---|---|---|
| pTMF | CMV/T7 | n/a | n/a | HamRZ/HdvRZ at ends |
| pTN | T7/IRES | ACCACCATGG | SEQ ID NO: 21 | n/a |
| pMP | CMV/T7 | ACCACCATGA | SEQ ID NO: 22 | n/a |
| pMG | CMV/T7 | ACCACCATGG | SEQ ID NO: 21 | n/a |
| pML | CMV/T7 | ACCACCATGC | SEQ ID NO: 23 | n/a |
| pNLST7 | CMV/T7 | ACCACCATGA | SEQ ID NO: 22 | 8 amino acids NLS |

CMV/T7 symbolizes the CMV promoter ahead of a pT7 promoter. The HdRz indicates a hammerhead ribozyme and HDVRz is the hepatitis delta virus ribozyme. The pTMF is the full-length transcription plasmid, and the pTN, pMP, pMG, pML and pNLST7 are helper plasmids.

After five days post-transfection in the ERA reverse genetics system, the rescued virus reliably and repeatedly grew to $10^7$ ffu/ml without further amplification.

X. Derivative Viruses

The complete mechanism of Rabies virus pathogenicity has not been fully characterized, making rational vaccine design problematic. For example, the RV glycoprotein appears to play a role both in pathogenicity and immunogenicity of rabies virus. Mutations (such as at position 333 of the glycoprotein) result in virus that does not cause lethal infection in adult mice (Ito et al., *Microbiol. Immunol.* 38, 479-482, 1994; Ito et al., *J. Virol.* 75, 9121-9128, 2001). However, overexpression of RV glycoprotein has been shown to lead to the enhancement of apoptosis and antiviral immune response (Faber et al., *J. Virol.* 76, 3374-3381, 2002). Thus ERA strain virus with a modified (for example, deleted, amino acid substituted) G protein could be a particular strain for vaccine development.

Figure 3:
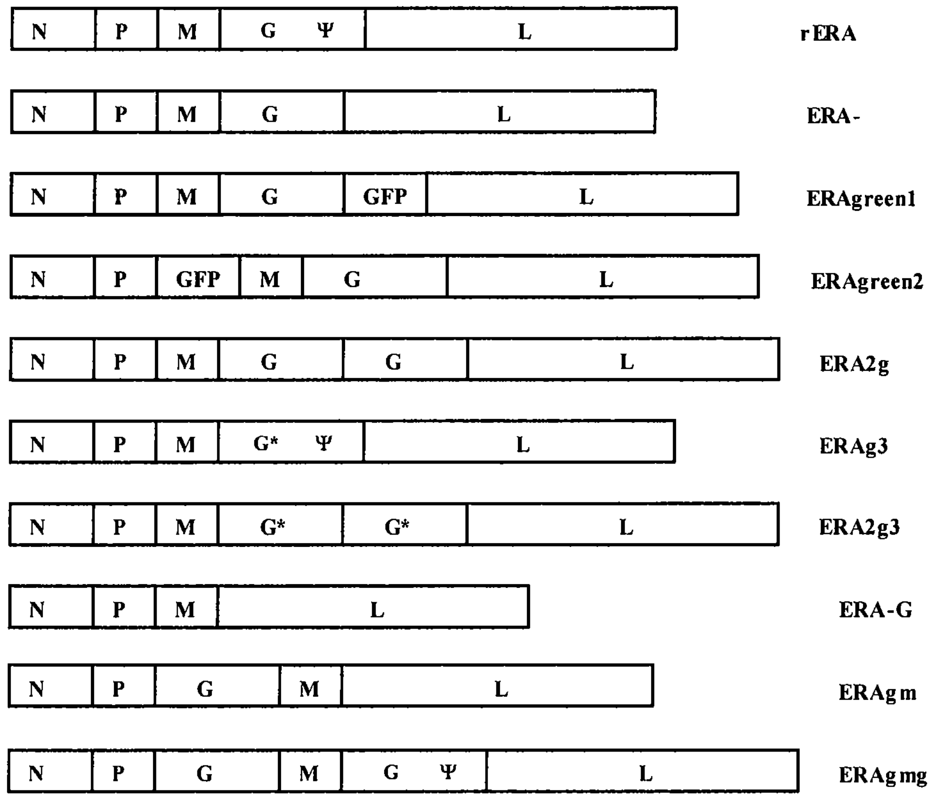
FIG. 3. Schematic diagram of the ten derivative ERA virus genomes. The size of each gene is not drawn to scale. Symbol "*" denotes mutations of G at the Aa333 residue and Ψ is the Psi-region.

Recombinant rabies viruses with favorable properties can be designed using the reverse genetics system disclosed herein. Exemplary recombinant viruses disclosed herein include, in addition to the parental ERA strain, ERA without Psi-region (ERA-), ERAgreen1 (green fluorescent gene inserted in the Psi-region), ERAgreen2 (green fluorescent gene cloned at P-M intergenic region), ERA2g (containing an extra copy of G in Psi-region), ERAg3 (G mutated at 333 amino acid), ERA2g3 (containing an extra copy of mutated G in Psi-region), ERAgm (M and G genes switched in the genome), and ERAgmg (two copies of G in the rearranged ERAgm construct). These exemplary strains are illustrated schematically in FIG. 3.

Modified strains having deleted and/or mutated glycoproteins are particularly suited for use as immunogenic compositions for pre and post exposure treatment of rabies virus because such viruses are incapable of spreading between cells and causing disease. Additionally, modified viruses such as ERA2g3, which overexpresses the G protein due to a duplication of sequences encoding a mutated glycoprotein is predicted enhance apoptosis and elicit an increased anti-viral immune response.

For example, after intracerebral and intramuscular inoculation of mice with a deletion of G (ERA-G), no adverse events were observed. Moreover, the ERA-G protected mice from lethal challenge by a street RV strain. Thus, ERA-G appears to be a safer strain that ERA for vaccine development.

Additionally, mutation of arginine at amino acid position 333 of the ERA G to glutamic acid (from nucleotides AGA to GAG, as in the ERAg3 and ERA2g3 strains) results in an attenuated virus. Attenuation was confirmed via animal inoculation tests. Because overexpression of RV G results in the enhancement of apoptosis and antiviral immune responses, attenuated viruses such as ERA2g3 that possess multiple copies of G are particularly favorable as vaccine candidates.

The system for rabies vaccine development described herein is not limited to modifications of the G gene, but is similarly applicable to each of the viral proteins. To facilitate a systematic approach to modifying the various protein components, detailed mapping of pathogenicity can be solved by reverse genetics based on the sequence data presented herein.

The reverse genetics system described herein also enables a rabies virus vector system for foreign (heterologous) gene expression. The described, non-limiting embodiment is based on the ERA virus. An extra transcription unit is shown herein to be functional in two different locations after incorporation into the ERA RV genome. In one embodiment, an extra transcription unit is incorporated in the position of the psi region (trans 1). In an alternative embodiment, an extra transcription unit is inserted into the RV P-M intergenic region.

In single stranded negative RNA viruses, the 3'-distal sequences of the genome serve mainly as a transcription promoter, while the 5'-terminal sequences of the genome serve as a replication promoter (Conzelmann and Schnell, *J. Virol.* 68:713-719, 1994; Finke et al., *J. Virol.* 71:7281-7288, 1997). Thus, trans2 occupies a position that results in stronger transcription for driving ORFs expression than trans1. Thus, the vectors disclosed herein can be used to modulate expression of a heterologous ORF to a desired level, simply by selecting the position into which the ORF is inserted in the vector. For example, when a high level of expression of a protein is desired, the trans 2 is typically an ideal position for the insertion of the heterologous ORF. Similarly, if more moderate levels of expression are desired, the heterologous ORF can be inserted into trans 1. Optimal expression levels for each ORF and for particular applications can be determined by one of skill in the art without undue experimentation.

Thus, the viral vectors provided herein are excellent construct for foreign gene insertion and expression, as is demonstrated herein with respect to expression of the green fluorescent protein gene. Although the utility and efficacy of the disclosed vectors is demonstrated with respect to GFP, it should be noted that the vectors are equally suitable for expressing any gene or ORF of interest.

As noted, the rabies-based heterologous expression system provided herein can be used to express any foreign (heterologous) protein(s). It is particularly contemplated, by way of example, that such heterologous genes are from another pathogenic organism, such as other pathogenic viruses, for instance SARS virus, Nipah virus, etc. In addition, the disclosed vectors can be used for delivery of other therapeutic genes, including for example, that encode proteins of therapeutic value or functional RNA molecules, such as siRNAs.

XI. Pharmaceutical and Immune Stimulatory Compositions and Uses Thereof

Pharmaceutical compositions including attenuated or fixed rescued viruses, virus nucleic acid sequences or virus polypeptides comprising at least one virus epitope are also encompassed by the present disclosure. These pharmaceutical compositions include a therapeutically effective amount of one or more active compounds, such as an attenuated or fixed virus, a virus polypeptides comprising at least one virus epitope, or one or more nucleic acid molecules encoding these polypeptides, in conjunction with a pharmaceutically acceptable carrier. It is contemplated that in certain embodiments, virus nucleic acid sequences or virus polypeptides comprising multiple virus epitopes will be useful in preparing the pharmaceutical compositions of the disclosure.

Disclosed herein are substances suitable for use as immune stimulatory compositions for the inhibition or treatment (either pre-exposure or post-exposure) of a virus infection, for example, a rabies virus infection.

In one embodiment, an immune stimulatory composition contains an attenuated or fixed rescued (recombinant) virus. In another embodiment, the composition contains an isolated or recombinant virus polypeptide including at least one virus epitope (such as a rabies virus G protein). In a further embodiment, the immune stimulatory composition contains a nucleic acid vector that includes at least one virus nucleic acid molecule described herein, or that includes a nucleic acid sequence encoding at least one virus epitope. In a specific, non-limiting example, a nucleic acid sequence encoding at least one virus epitope is expressed in a transcriptional unit, such as those described in published PCT Application Nos. PCT/US99/12298 and PCT/US02/10764 (both of which are incorporated herein in their entirety).

The immune stimulatory viruses, virus polypeptides, constructs or vectors encoding such polypeptides, are combined with a pharmaceutically acceptable carrier or vehicle for administration as an immune stimulatory composition to human or animal subjects.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immune stimulatory compositions, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on the route of administration. By way of example, intramuscular injections may range from about 0.1 ml to about 1.0 ml. Those of ordinary skill in the art will know appropriate volumes for different routes of administration.

A relatively recent development in the field of immune stimulatory compounds (for example, vaccines) is the direct injection of nucleic acid molecules encoding peptide antigens (broadly described in Janeway & Travers, *Immunobiology: The Immune System In Health and Disease*, page 13.25, Garland Publishing, Inc., New York, 1997; and McDonnell & Askari, *N. Engl. J. Med.* 334:42-45, 1996). Vectors that include nucleic acid molecules described herein, or that include a nucleic acid sequence encoding a virus polypeptide comprising at least one virus epitope may be utilized in such DNA vaccination methods.

Thus, the term "immune stimulatory composition" as used herein also includes nucleic acid vaccines in which a nucleic acid molecule encoding a virus polypeptide comprising at least one virus epitope is administered to a subject in a pharmaceutical composition. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264:16985, 1989), co-precipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992; Eisenbraun et al., *DNA Cell Biol.* 12:791, 1993), and in vivo infection using cloned retroviral vectors (Seeger et al., *Proc. Natl. Acad. Sci.* 81:5849, 1984). Similarly, nucleic acid vaccine preparations can be administered via viral carrier.

The amount of immunostimulatory compound in each dose of an immune stimulatory composition is selected as an amount that induces an immunostimulatory or immunoprotective response without significant, adverse side effects. Such amount will vary depending upon which specific immunogen is employed and how it is presented. Initial injections may range from about 1 μg to about 1 mg, with some embodiments having a range of about 10 μg to about 800 μg, and still other embodiments a range of from about 25 μg to about 500 μg. Following an initial administration of the immune stimulatory composition, subjects may receive one or several booster administrations, adequately spaced. Booster administrations may range from about 1 μg to about 1 mg, with other embodiments having a range of about 10 μg to about 750 μg, and still others a range of about 50 μg to about 500 μg. Periodic boosters at intervals of 1-5 years, for instance three years, may be desirable to maintain the desired levels of protective immunity.

It is also contemplated that the provided immunostimulatory molecules and compositions can be administered to a subject indirectly, by first stimulating a cell in vitro, which stimulated cell is thereafter administered to the subject to elicit an immune response. Additionally, the pharmaceutical or immune stimulatory compositions or methods of treatment may be administered in combination with other therapeutic treatments.

The preparation of food-baits containing immune stimulatory compositions is also within the ordinary skill of those in the art. For example, the preparation of food-baits containing live RV vaccines is disclosed in Wandeler et al. (*Rev. Infect. Dis.* 10 (suppl. 4):649-653, 1988), Aubert et al. (pp. 219-243, in *Lyssaviruses* (Rupprecht et al., eds.), Springer-Verlag, New York, 1994), and Fu et al. (pp. 607-617, in New Generation Vaccines (2$^{nd}$ Edit.) (Levine et al., eds.), Marcel Dekker, Inc., New York, 1997), the entire disclosures of each of which are incorporated by reference herein.

XII. Kits

Also provided herein are kits useful in the detection and/or diagnosis of virus infection, for instance infection with a rabies virus or other lyssavirus. An example of an assay kit provided herein is a recombinant virus polypeptide (or fragment thereof) as an antigen and an enzyme-conjugated anti-human antibody as a second antibody. Examples of such kits also can include one or more enzymatic substrates. Such kits can be used to test if a sample from a subject contains antibodies against a virus-specific protein. In such a kit, an appropriate amount of a virus polypeptide (or fragment thereof) is provided in one or more containers, or held on a substrate. A virus polypeptide can be provided in an aqueous solution or as a freeze-dried or lyophilized powder, for instance. The container(s) in which the virus polypeptide(s) are supplied can be any conventional container that is capable of holding the supplied form, for instance, microfuge tubes, ampoules, or bottles.

The amount of each polypeptide supplied in the kit can be any appropriate amount, and can depend on the market to which the product is directed. For instance, if the kit is adapted for research or clinical use, the amount of each polypeptide provided would likely be an amount sufficient for several assays. General guidelines for determining appropriate amounts can be found, for example, in Ausubel et al. (eds.), *Short Protocols in Molecular Biology*, John Wiley and Sons, New York, N.Y., 1999 and Harlow and Lane, *Using Antibodies: A Laboratory Manual*, CSHL, New York, 1999.

The following examples are provided to illustrate certain particular features and/or embodiments. These examples should not be construed to limit the invention to the particular features or embodiments described.

EXAMPLES

Example 1

Sequencing of ERA RV

This example provides a description of a method for sequencing the full length genome of a rhabdovirus, particularly in this case a rabies virus.

Rabies virus strain ERA was obtained from the CDC archive and was propagated in baby hamster kidney (BHK-21) cells. Virus was harvested after four days infection at 37° C., in a 5% $CO_2$ incubator and was purified. Briefly, the cell supernatant was collected and centrifuged at 2,000 rpm for 15 minutes to remove the cell debris. The clear supernatant was subjected to further centrifugation at 18,000 rpm for 1 hour. The pellet was resuspended in PBS and subjected to rabies genomic RNA extraction.

Total RNA from ERA-infected BHK-21 cells was extracted with Trizol™ reagent (GIBCO Invitrogen) according to the protocol recommended by the manufacturer. ERA genomic RNA was purified from the concentrated ERA virus supernatant with a high pure viral RNA kit from Roche.

Integrity of the purified ERA genomic RNA was verified by gel electrophoresis and Northern blot by N, P, G, and M hybridization probes. Briefly, 5 μg of genomic RNA was loaded in a denatured RNA gel and transferred to a nylon membrane for hybridization. The probe was labeled using the Dig DNA labeling kit from Roche, according to manufacturer's instructions.

The 11 conserved nucleotides from the rabies virus 5' antigenome were designed as a primer for reverse transcription. The RT reaction was carried out with a first-strand cDNA synthesis kit from Invitrogen. The complete cDNA from the ERA genome was confirmed by Northern blot using N, P, M, and G probe hybridization, as well as the 11 conserved nucleotides as oligonucleotide probes labeled by Digoxin.

Two sets of primers were chosen for PCR reactions, which amplify the whole ERA genome in two contiguous fragments. One set of primers is composed of the 11 nucleotides at 5' antigenome end, Le5: ACGCTTAACAA (SEQ ID NO: 24) and BLp3: GTCGCTTGCTAAGCACTCCTGGTA (SEQ ID NO: 25). Another set contains the 11 complementary nucleotides at the 5' genome end, Le3: TGCGAATTGTT (SEQ ID NO: 26) and BLp5 CCAG GAGTGCTTAG-CAAGCGACCT (SEQ ID NO: 27). The Blp3 and Blp5 primers are located in a relatively conserved region in the rabies virus genome.

PCR fragments were purified and cloned into the TOPO vector purchased from Invitrogen. Sequencing was conducted in an ABI 310 sequencer and the sequence was assembled by BioEdit™ software or SeqMerge™ software from Accelrys in the GCG environment.

The complete aligned sequence of the ERA genome is provided in SEQ ID NO: 1. The positions of individual protein encoding sequences are provided in Table 3, with reference to SEQ ID NO: 1. The amino acid sequences of the N, P, M, G and L proteins are provided in SEQ ID NOs: 2 through 6, respectively.

TABLE 3

| Gene/genome | NT | Positions in rERA sequence |
|---|---|---|
| ERA | 11930 | 1-11930 |
| N | 1412 | 71-1423 |
| P | 962 | 1511-2407 |
| M | 789 | 2491-3104 |
| G | 1647 | 3318-4892 |
| Psi-region | 398 | |
| L | 6445 | 5418-11801 |
| Leader | 58 | |
| Trailer | 70 | |

Positions of protein encoding sequences of rabies virus ERA strain

This method can be used for both rabies and rabies-related viruses. Rabies and rabies-related viruses have at least seven putative species types. The provided sequence method can be used also for other negative stranded RNA viruses. This is because almost all the negative-stranded RNA virus genomes have approximately 12 conserved nucleotides at both distal ends, which similarly can serve as primers for RT-PCR. The primers will of course be different for different viral species, and the sequence of specific primers can be determined by one of ordinary skill based on the teachings herein.

Example 2

Construction of Plasmids for a Reverse Genetics System for Rabies Virus

Figure 1B:
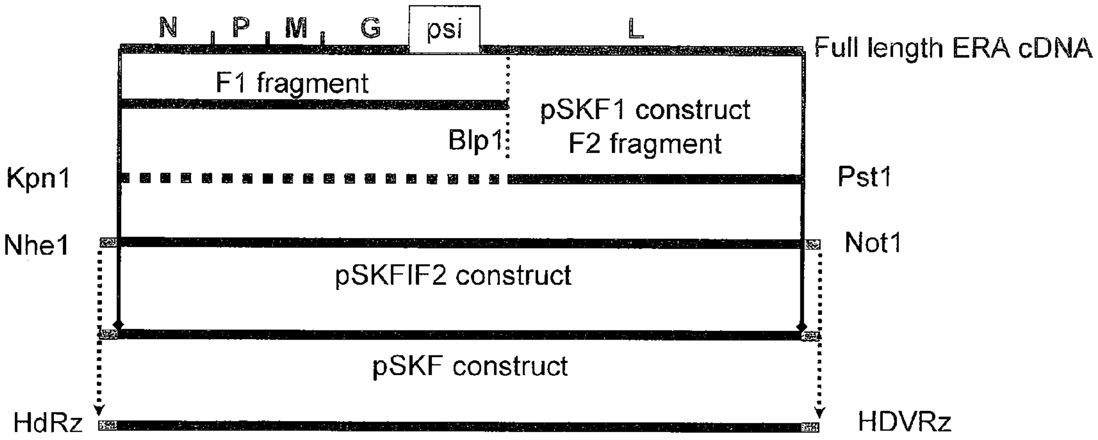
FIG. 1B. Schematic diagram of the construction of the full-length ERA rabies virus genomic cDNA plasmid pTMF. RT-PCR products F1, F2 fragments, and restriction enzyme recognition sites (Nhe1, Kpn1, Blp1, Pst1 and Not1) (not drawn to scale). The bar on the left indicates a RdRz-hammerhead ribozyme and the right bar indicates the HDVRz-hepatitis delta virus ribozyme. The symbol ♦ indicates that Kpn1 or Pst1 sites were deleted, and ↓ vertical arrow indicates that Nhe1 or Not1 sites were left intact.

This example describes the design and development of a Reverse Genetics System for Rabies Virus. Rabies virus strain ERA was obtained from the ATCC and was prepared as described (Wu et al., *J. Virol.* 76, 4153-4161, 2002). To obtain virus genome full-length virus cDNA, BSR cells (a clone of baby hamster kidney, BHK, cells) were infected with ERA strain virus and grown in Dulbecco's minimal essential medium supplemented with 10% of fetal bovine serum. Supernatants were recovered and subjected to centrifugation at 22,000 g for 1 hour. The virus pellets were collected for viral genomic RNA purification by use of a RNA virus extraction kit purchased from Qiagen (Valencia, Calif.) according to the manufacturer's instructions. The integrity of viral genomic RNA was confirmed by gel electrophoresis. Viral genomic cDNA was transcribed with the first-strand cDNA synthesis kit from Invitrogen (Carlsbad, Calif.). The reverse transcription (RT) reaction mixture was applied to amplification by the polymerase chain reaction (PCR) for the synthesis of full-length viral genomic cDNA, N, P, G and L genes, respectively. For assembling the full-length virus genomic cDNA, a pTMF plasmid was constructed in four sequential steps as illustrated schematically in FIG. 1B. Superscript III reverse transcriptase and proof reading platinum pfx polymerase (Invitrogen, Carlsbad, Calif.) were applied for cDNA transcript synthesis and consecutive PCR amplifications. For reverse transcription reactions, 1 μg of purified genomic RNA was used in the RT reaction mix and incubated at 50° C. for 80 min, followed by heating at 85° C. for 5 minutes to inactivate Superscript III. After the RT reaction, 1 unit of RNaseH was added to digest template RNA in the cDNA-RNA hybrids.

To generate full-length virus genomic cDNA, two overlapping fragments were amplified by RT-PCR as follows: Fragment1 (F1) was RT-PCR amplified with primers: Le5-Kpn (CCGGGTACCACGCTTAAC AACCAGATCAAAGA; SEQ ID NO: 28, Kpn1 recognition site underlined) and Le3-Blp (TAGGTCGCTTGCTAAGCACTCCTGGTAGGAC; SEQ ID NO: 29, Blp1 recognition site underlined). Fragment 2 (F2) was RT-PCR amplified with primers: Tr5-Blp (GTCCTACCAGGAGTGCTTAGCAAGCGACCTA; SEQ ID NO: 30, Blp1 recognition site underlined) and Tr3-Pst (AAAACTGCAGACGCTTAACAAATAAACAACAAAA; SEQ ID NO: 31, Pst1 recognition site underlined). After successful synthesis of the above two fragments, F1 digested by Kpn1 and Blp1 restriction enzymes was subjected to gel purification and cloned to pBluescriptIISK(+) phagemid (Stratagene, La Jolla, Calif.) to form the pSKF1 plasmid. The gel purified F2 fragment, cut by Blp1 and Pst1 was consecutively cloned to the pSKF1 plasmid to form the full-length viral antigenomic cDNA. Hammerhead ribozyme (oligo1, CAAG GCTAGCTGTTAAGCGTCTGATGAGTCCGTGAGGACG AAACTATAGGA AAGGAATTCCTATAGTC GGTACCACGCT; SEQ ID NO: 32, Nhe1 and Kpn1 recognition sites underlined; Oligo2, AGCGT GGTACCGACTATAGGAATTCCTTTCCTATAGTTTCGT CCTCACGGAC TCATCAGACGCTTAACA GCTAGCCTTG; SEQ ID NO: 33, Kpn1 and Nhe1 recognition sites underlined) was synthesized containing a Nhe1 recognition site at the 5' end and a Kpn1 site at the 3' end. This was fused ahead of the 5' end of the F1 fragment. A hepatitis delta virus ribozyme (oligo3, GAC CTGCAGGGGTCGGCATGGCATCTCCACCTCCTCGCG GTCCGACCTGGG CATCCGAAGGAGGACGCACGTCCACTCGGATGGCTAAGGGAGGGC GCGGCCGCACTC; SEQ ID NO: 34, Pst1 and Not1 recognition sites underlined; Oligo4, GAGT GCGGCCGCGCCCTCCCTTAGCCATCCGAGTGGACG TGCGTCCTCCTTC GGATGCCCAGGTCGGACCGCGAGGAGGTGGAGATGCCATGCCGACCC CTGCAGGTC; SEQ ID NO: 35, Not1 and Pst1 recognition sites underlined) (Symons, *Annu. Rev. Biochem.* 61: 641-671, 1992) was synthesized, having a Pst1 site at its 5' end and a Not1 site at its 3' end, and was fused to the 3' end of the F2 fragment. The connective Kpn1 recognition site, between the hammerhead ribozyme and the F1 fragment, and the Pst1 site between the F2 fragment and the hepatitis delta virus ribozyme, were deleted by site-directed mutagenesis. The full-length viral antigenomic cDNA was sandwiched by the hammerhead and hepatitis delta virus ribozymes. This was removed and cloned to the pBluescriptIISK(+) phagemid to make a pSKF construct. The full viral antigenomic cDNA with two ribozymes was fused downstream of the T7 transcription initiation site under control of the CMV immediate-early promoter in pcDNA3.1/Neo (+) plasmid (Invitrogen, Carlsbad, Calif.). This last step finished the construction of the pTMF plasmid.

The wild type ERA viral genome includes a polyA tract of eight residues (polyA$_8$) in the intergenic region between the G and Psi regions. To distinguish the rescued ERA (rERA) virus from the parental strain, a stretch of seven A (polyA$_7$) was introduced to the pTMF construct by deletion of one A instead of the original polyA$_8$. After rERA virus was recovered, RT-PCR was performed and subsequent sequence data confirmed the existence of the introduced poly A$_7$ sequence marker.

pTN plasmid: The N gene was amplified by RT-PCR with primers (5N: ACCACCATGGATGCCGACAAGATTG; SEQ ID NO: 36, Nco1 recognition site and start codon underlined; and 3N: GGC CCATGGTTATGAGTCACTCGAATATGTCTT; SEQ ID NO: 37, Nco1 recognition site and stop codon underlined) and cloned to the pCITE-2a(+) (Cap-Independent Translation Enhancer) plasmid (Novagen, Madison Wis.).

pMP plasmid: the P gene was amplified by RT-PCR with primers (5P: TTGGTACCACC ATGAGCAAGATCTTTGTCAATC; SEQ ID NO: 38, Kpn1 recognition site and start codon underlined; and 3P: GGAGAGGAATTCTTAGCAAGATGTATAGCGATTC; SEQ ID NO: 39, EcoR1 recognition site and stop codon underlined) and cloned to the pcDNA3.1/Neo (+) plasmid.

pMG plasmid: the G gene was amplified by RT-PCR with primers (5G: TTGGTACCACC ATGGTTCCTCAGGCTCTCCTG; SEQ ID NO: 40, Kpn1 recognition site and start codon underlined; and 3G: AAAA CTGCAGTCACAGTCTGGTCTCACCCCCAC; SEQ ID NO: 41, Pst1 recognition site and stop codon underlined) and cloned to the pcDNA3.1/Neo (+) plasmid.

pML plasmid: the L gene was amplified by RT-PCR with primers (5L: ACCGCTAGCACCACC ATGCTCGATCCTGGAGAGGTC; SEQ ID NO: 42, Nhe1 recognition site and start codon underlined; and 3L: AAAA CTGCAGTCACAGGCAACTGTAGTCTAGTAG; SEQ ID NO: 43, Pst1 recognition site and stop codon underlined) and cloned to the pcDNA3.1/Neo (+) plasmid.

pT7 plasmid: genomic DNA from bacteria BL-21 (Novagene, Madison, Wis.) was extracted with the DNeasy™ Tissue Kit (Qiagen, Valencia, Calif.) according to the manufacturer's instructions. The T7 RNA polymerase gene was amplified from the purified genomic DNA by PCR with primers (5T7: TC GCTAGCACCACCATGAACACGATTAACATCGCTAAG; SEQ ID NO: 44, Nhe1 recognition site and start codon underline; and 3T7: GAT GAATTCTTACGCGAACGCGAAGTCCGACTC; SEQ ID NO: 45, EcoR1 recognition site and stop codon underlined) and cloned to the pcDNA3.1/Neo (+) plasmid.

pNLST7 plasmid: an eight amino acid nuclear location signal (NLS), derived from SV40 large T antigen, was added to the N terminus of the T7 RNA polymerase by PCR amplification, using the pT7 plasmid as the template, with primers (5T7NLS: TCGCTAGCCACCATG CCAAAAAAGAAGAGAAAGGTAGAAAACACGATTAA CATCGCTAAGAAC; SEQ ID NO: 46, NLS underlined and 3T7 primer). The amplified fragment was designated NLST7, and was cloned to pcDNA3.1/Neo (+) to form the pNLST7 construct.

pGFP plasmid: Monster Green Fluorescent Protein (GFP) plasmid phMGFP was purchased from Promega (Madison, Wis.). The GFP gene was amplified by PCR with primers (GFP5: AAAACTGCAGGCCACC ATGGGCGTGATCAAG; SEQ ID NO: 47, Pst1 recognition site and start codon underlined; and GFP3: CCGCTC GGTACCTATTAGCCGGCCTGGCGGG; SEQ ID NO: 48, Kpn1 recognition site and stop codon underlined) and cloned to the pcDNA3.1/Neo (+) plasmid.

All plasmid constructs were sequenced at least three times to confirm the absence of unexpected mutations or deletions after cloning, site-directed mutagenesis, or gene deletion. Additionally, presence of a marker sequence consisting of a polyA tract having seven adenosine residues rather than the eight residues observed in the wild type ERA genome between the glycoprotein and Psi region was confirmed.

Example 3

T7 RNA Polymerase Expression in BSR Cells

This example demonstrates that addition of a nuclear localization signal to the phage T7 RNA polymerase directs expression of the polymerase in the nucleus of transfected cells. Transfection of BSR cells was performed as described by Wu, et al. (*J. Virol.* 76, 4153-4161, 2002). Briefly, BSR cells near 80% confluence in a six-well-plate were transfected with 0.5 μg of pT7 or pNLST7 plasmid per well, respectively. At 48 hours after transfection, cells were fixed with 80% chilled acetone for 1 h and dried at room temperature. Mouse monoclonal antibody against the T7 RNA polymerase and goat anti mouse IgG-FITC conjugate were successively added, and were washed in the two-step indirect fluorescent staining procedure. Results were recorded after UV microscopy. The T7 RNA polymerase expressed from pT7 without a nuclear localization signal was observed primarily in the cytosol, whereas NLST7 polymerase including a nuclear localization signal was present predominantly in the nucleus of cells. These results indicated that addition of an NLS effectively targeted the T7 RNA polymerase to the nucleus of transfected cells.

Example 4

Establishment of Constitutively Expressed ERA Glycoprotein BSR Cell Line

This example describes the design and production of a BHK cell line that constitutively expresses the ERA glycoprotein. A BHK cell line that expresses the ERA glycoprotein was constructed using the Flp-In™ system (Invitrogen, Carlsbad, Calif.). Briefly, Flp-In™-BHK cells (containing a single integrated Flp recombination target site) were grown to approximately 20% confluence in one six-well-plate and maintained in common DMEM medium, supplemented with 100 μg/ml of Zeocin, before transfection. The ERA G gene was amplified by PCR using pMG plasmid as template with primers EF5G5 (CACCATGGTTCCTCAGGCTCTCCTG; SEQ ID NO: 49) and EF5G3 (TCACAGTCTGGTCTCACCCCCAC; SEQ ID NO: 50), and cloned to a pEF5/FRT/V5-D-TOPO vector (Invitrogen, Carlsbad, Calif.) to create the pEFG construct. The pOG44 plasmid expressing Flp recombinase together with pEFG at the ratio of 10:1 was co-transfected to the Flp-In™-BHK cells. After transfection, the cells were kept in DMEM without Zeocin, but with hygromycin B at 400 μg/ml. After 48 hours, the cells were split so that no more than 20% confluency occurred the next day. The cells were grown in hygromycin B selective medium at 37° C. for approximately one week. The target ERA G expression was detected by indirect fluorescent staining with human anti-G monoclonal antibody and goat anti-human IgG-FITC conjugate. The cell line constitutively expressing the G was designated as BHK-G, and was used for the growth of ERA-G virus.

Example 5

Defined Modification of Rabies Virus Evelyn-Rokitnicki-Abelseth (ERA) Strain In addition to the parental ERA virus strain described above, derivative virus strains were developed using the reverse genetics system disclosed herein. Several exemplary modified viruses were produced, namely ERA- (deletion of the whole psi-region), ERAgreen1 (green florescent protein gene inserted in ERA viral genome psi region), ERAgreen2 (green florescent protein gene inserted in phosphoprotein and matrix protein intergenic region), ERA2g (containing an extra copy of glycoprotein in the psi-region), ERAg3 (with a mutation at amino acid 333 in glycoprotein), ERA2g3 (with an extra copy of mutated glycoprotein at Aa333 in psi-region), ERA-G (with glycoprotein deleted) ERAgm (M and G genes switched in the genome), and ERAgmg (two copies of G in the rearranged ERAgm construct) These derivatives are illustrated schematically in FIG. 3. By optimizing the growth conditions as described, all of the rescued viruses can be obtained at virus titers of $10^9$ to $10^{10}$ ffu/ml in both tissue culture flasks and bioreactors.

Gene Deletion and Site-Directed Mutagenesis in the Reverse Genetics System

Deletion of the Psi Region of the Rabies Virus ERA Genome

The complete Psi-region of the rabies virus ERA genome was deleted as follows: 3'Δψ fragment was amplified using pTMF as template by PCR with primers (5Δψ: CCCT CTGCAGTTT GGTACCGTCGAGAAAAAAACATTAGATCAGAAG; SEQ ID NO: 51, Pst1 and Kpn1 recognition sites underlined; and Le3-Blp primer) and was cloned to pCR-BluntII-TOPO vector (Invitrogen, Carlsbad, Calif.) for the construction of pPΔ5ψ plasmid. The 5'Δψ fragment was amplified using the same template by PCR with primers (SnaB5: ATGAACTTTCTACGTAAGATAGTG; SEQ ID NO: 52, SnaB1 recognition site underlined; and 3Δψ: CAAA CTGCAGAGGGGTGTTAGTTTTTTTCAAAAAGAACCC CCCAAG; SEQ ID NO: 53, Pst1 recognition site underlined) was successively cloned to the above pPΔ5ψ plasmid to finish the construction of the pPΔΨ plasmid. The fragment recovered by SnaB1 and Pst1 restriction enzyme digestion from the pPΔψ plasmid substituted the counterpart in the pSKF construct to make the pSKFΔψ plasmid. The whole DNA fragment containing the ERA genomic cDNA, digested by Nhe1 and Not1 from pSKFΔψ plasmid, was re-cloned to the pcDNA3.1/Neo (+) plasmid to finalize the construction of pTMFΔψ. For verification of the rescued strain lacking Psi, designated Era-, primers covering the Psi-region were applied in RT-PCR with total RNA from ERA-infected BSR cells. A 400 bp fragment corresponding to the Psi region was amplified only from rERA virus, but not from ERA. Sequence data verified the complete deletion of the Psi-region.

Deletion of the Glycoprotein Gene in the Rabies Virus ERA Genome:

The 5'gΔψ fragment was amplified using pSKF as template by PCR with primers (SnaB5 primer, and 3Δg: CAAACTGCAGAGGGGTGTTAGTTTTTTTCACATC-CAAGAGGATC; SEQ ID NO: 54). After digestion by SnaB1 and Pst1 restriction enzymes, this recovered fragment was cloned to replace its counterpart in the pSKFΔψ construct. The 3'gΔψ fragment was amplified using the same template by PCR with primers (5Δg: CCTCTGCAGTTTGGTACCT-TGAAAAAAACCTGGGTTCAATAG; SEQ ID NO: 55, and Le3-Blp primer), and was consecutively cloned to the modified pSKFΔψ, to replace its counterpart. The final fragment, recovered by SnaB1 and Blp1 restriction enzymes cut from this pSKFΔψ without the G gene, was re-cloned to pcDNA3.1/Neo (+) plasmid to form the pTMFΔg construct for virus recovery.

Glycoprotein Gene Site-Directed Mutagenesis:

Site directed mutagenesis to introduce a three nucleotide change from AGA to GAG at amino acid position 333 of the glycoprotein was performed as previously described (Wu et al., *J. Virol.* 76: 4153-4161, 2002). The primers in the mutagenesis reaction were M5G primer: CTCACTA-CAAGTCAGTCGAGACTTGGAATGAGATC (SEQ ID NO: 56, the three mutated nucleotides in bold) and M3G primer: GACTGACTTTGAGTGAGCATCGGCTTC-CATCAAGG (SEQ ID NO: 57). For the recovered strain (ERAg3), three nucleotide changes from AGA to GAG at amino acid position 333 (aa333) were confirmed by sequencing after RT-PCR with primers 5G and 3G. After confirmation by DNA sequencing, the mutated G was cloned back to the pTMF plasmid to make the pTMFg3 construct for virus recovery. The glycoprotein encoded by this mutated G gene is represented by SEQ ID NO: 58.

Incorporation of an Exogenous ORF into ERA Rabies Virus Genome

To express exogenous ORFs in RV, an extra transcription unit with Pst1 and Kpn1 recognition sites were created and incorporated at the Psi or P-M gene intergenic regions, respectively. In brief, for creation of an extra transcription unit at the Psi-region, the same steps were followed, except for the 5'Δψ fragment amplification step, the 3Δψ primer was changed to 3Δψcis: CCAAACTGCAGCGAAAG-GAGGGGTGTTAGTTTTTTTCATGATGAACCCCCC AAGGGGAGG (SEQ ID NO: 59). The final construct without the Psi-region, but with an extra transcription unit, was designated as pMTFΔψcis. The GFP, ERA G, or mutated G at amino acid residues 333 were cloned to this transcriptional unit to form pMTFgfp1, pMTF2g, pMTFg3, pMTF2g3 constructs, respectively, for virus rescue.

To incorporate an extra transcription unit to the P-M intergenic region, the cisp5 fragment was amplified using pMTF as template with primers cis55: GACTCACTATAGG-GAGACCCAAGCTGGCTAGCTGTTAAG (SEQ ID NO: 60), cis53: CCAAACTGCAGCGAAAGGAGGGGTGT-TAGTTTTTTTCATGTTGACTTTAGGA CATCTCGG (SEQ ID NO: 61), and was cloned in substitution of its counterpart in the pMTF plasmid. The cisp3 fragment was amplified and cloned in a similar way with primers cis35: CCTTTCGCTGCAGTTTGGTACCGTC-GAGAAAAAAACAGGCAACACCACTGA TAAAAT-GAAC (SEQ ID NO: 62) and cis33: CCTCCCCTTCAA-GAGGGCCCCTGGAATCAG (SEQ ID NO: 63). After assembling the cisp5 and cisp3 fragments together, the final construct was designated as pMTFcisp, for accepting ORFs. The recombinant construct containing the GFP gene was named pTMFgfp2 for virus recovery.

To produce an ERA derivative, designated ERAgm, in which the glycoprotein encoding sequence was reversed in order with the matrix protein encoding sequence, the glycoprotein gene was deleted as described above. The G gene (amplified as disclosed above) was then inserted between P and M genes, yielding a rabies virus genome in the order of N-P-G-M-L. Similarly, the same strategy was applied to produce the ERAg3m derivative, in which the glycoprotein has a triple nucleotide mutation at 333 amino acid residue (from AGA to GAG) by substituting the G gene produced by site directed mutagenesis as described above. To produce the ERAgmg construct, an extra copy of glycoprotein gene was inserted between P and M genes, and made the rabies virus genome in the order of N-P-G-M-G-L.

An extra transcription unit was modified and incorporated into two different regions of the ERA genome, namely psi-region and P-M intergenic region. When heterologous ORFs are incorporated into these transcription units, designated trans 1 and trans 2, respectively, efficient production of the encoded product results. Sequence of the transcription unit is: CTAACACCCCTCCTTTCGCTGCAGTTTG-GTACCGTCGAGAAAAAAA (SEQ ID NO: 64, Pst1 and Kpn1 were underlined).

Example 6

Recovery of Parental and Derivative Viruses

This example describes the recovery of parental ERA virus and exemplary derivatives using the reverse genetics system disclosed herein. BSR cells were transfected at near 80% confluence in six-well-plates with viral full length transcription plasmid pTMF (pTMFΔψ, pTMFg3, pTMF2g, pTMF2g3, pTMFgfp1, pTMFgfp2, pTMFΔg, pTMFgm, or pTMFgmg, respectively) at 3 μg/well, together with five helper plasmids: pTN (1 μg/well), pMP (0.5 μg/well), pML (0.5 μg/well), pMG (0.5 μg/well) and pNLST7 (1 μg/well) by TransIT-LT1 reagent (Mirus, Madison, Wis.) following the protocol recommended by the manufacturer. Four days after transfection, 1 ml of fresh BSR cell suspension (about $5\times10^5$ cells) was added to each well. Cells were incubated at 37° C., 5% $CO_2$ for 3 days. Cell supernatants were collected for virus titration.

To titrate the recovered virus, monolayers of BSR cells in LAB-TEK eight-well-plates (Naperville, Ill.) were infected with serial 10-fold dilutions of virus supernatant and incubated at 37° C., 0.5% $CO_2$ for 48 h. Cells were fixed in 80% chilled acetone at room temperature for 1 h and stained with FITC-labeled anti-rabies virus N monoclonal antibody at 37° C. for 30 minutes. After three rinses of the plates with PBS, stained foci were counted using direct fluorescent microscopy. Details for direct RV fluorescent assay (DFA) can be found on the World Wide Web at cdc.gov/ncidod/dvrd/rabies/professional/publications/DFA-diagnosis/DFA_protocol.htm.

All of the viruses except ERA-G were recovered at high titer from cultured BSR cells as indicated in Table 3. Surprisingly, rearrangement and switching of the G gene with the M gene did not hinder recovery of recombinant derivative ERA virus. Rearrangement of the G gene in the RV genomes was previously not believed feasible due to cell death from over-expression of G protein (Faber et al., *J. Virol.* 76:3374-3381, 2002). However, these results demonstrate that rearrangement is possible in the ERA strain. Accordingly, it is likely that RV gene shuffling is possible not only for the G gene, but also for other genes as well.

Figure 4A:
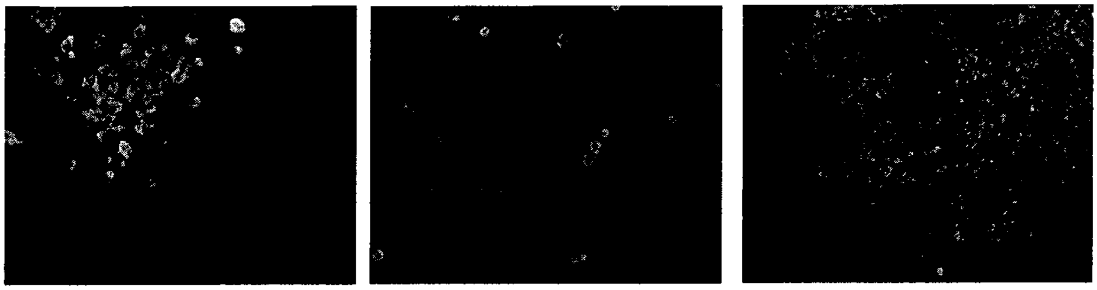
FIG. 4A. Analysis of recovered ERA-G virus in transfected cells, spread and growth in a BHK-G cell line. In A, the ERA-G viral foci were restrained even after seven-day post transfection with plasmids for virus recovery. In B, rescued ERA-G virus did not spread after passage in normal BSR cells. Only individual cells were stained by DFA. In C, the ERA-G virus grew well in the constitutive BHK-G cell line.
Figure 4B:
FIG. 4B. Analysis of G expression in a BHK-G cell line. By indirect fluorescent staining, the ERA rabies virus G was expressed in the cytoplasm in a stable cell line BHK-G.
Figure 4C:
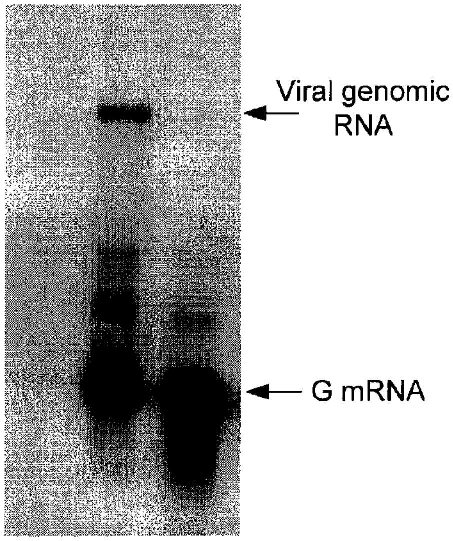
FIG. 4C. Analysis of G mRNA in ERA-G virus-infected cells by Northern blot with a G probe. Lane 2 shows that the G gene mRNA was detected in ERA-G virus infected BHK-G cells, while virus genomic RNA was not. Lane 1 was the control of total RNA from ERA-rabies virus-infected BHK-G cells, in which both G mRNA and viral genomic RNA were detected.

The ERA-G (without G) virus was recovered after plasmid transfection following the same procedure as for the other viral constructs rescue, but virus foci were very limited and restrained in local areas after the first round of transfection. The rescued virus was not capable of spreading further to the nearby healthy BSR cells (FIG. 4A) even after one week of incubation at 37° C., 5% $CO_2$. Infection of normal BSR cells with the above transfection supernatants presented single cell staining in the DFA test, which suggested the recovered virus was incapable of spread. To amplify the ERA-G virus, a BHK cell line constitutively expressing ERA G was established as described in Example 4 (designated BHK-G). By indirect fluorescent assay screening, a pool of BHK cells expressing G were selected and maintained for amplification of ERA-G virus (FIG. 4B). With the aid of the BHK-G cell line, ERA-G virus grew to $10^7$ ffu/ml. Total RNA from ERA-G virus-infected BHK-G cells was extracted for Northern blot analysis (FIG. 4C) with a G gene probe. The G gene was absent in the viral genomic RNA, however G mRNA was detected, which came from infected supportive BHK-G cells. In purified ERA-G viral genomic RNA, no hybridization signal was detected by G probe, indicating the deletion of the G gene in the ERA genome.

Example 7

Figure 5:
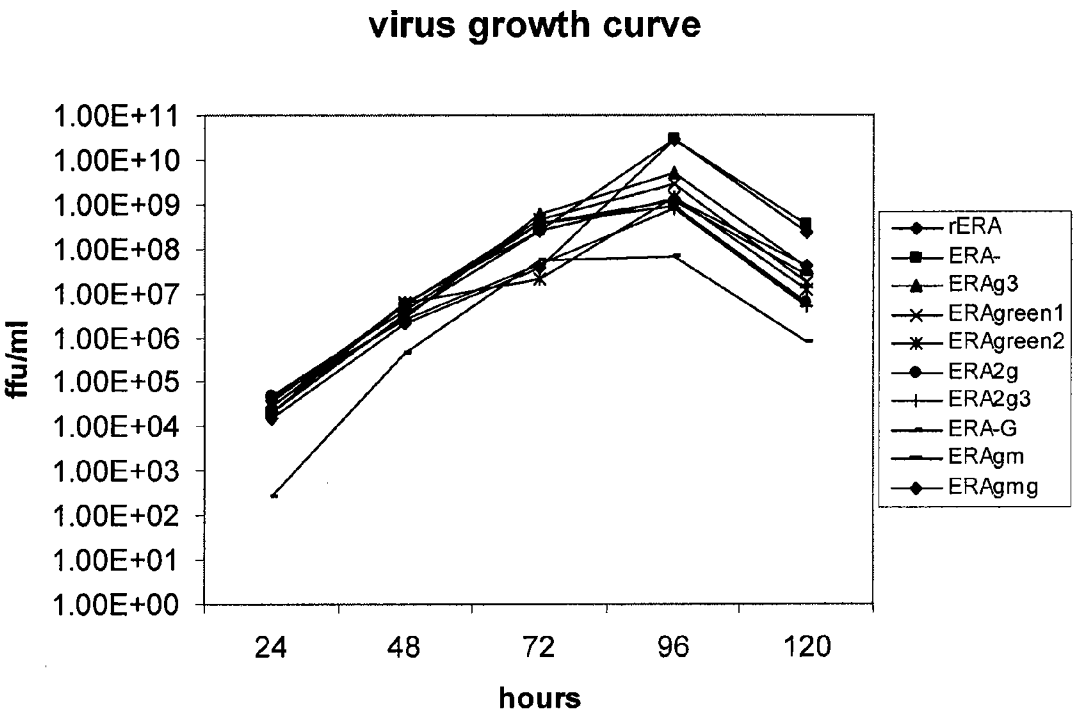
FIG. 5. Single-step virus growth curve. All recovered rabies virus ERA strains grew to $10^9$ or $10^{10}$ ffu/ml, but the ERA-G only reached $10^7$ ffu/ml.

Growth of Rescued ERA Virus and its Derivatives to High Titer in a Bioreactor In oral vaccine development, high virus titer is typically required to elicit reliable immunity after administration. This example demonstrates that the ERA virus and derivatives can be grown to high titer in a bioreactor at volumes applicable to commercial scale-up. All 10 rescued ERA viruses were amplified in a bioreactor, CELLine AD1000 (IBS Integra Bioscience, Chur, Switzerland) to titers ranging from $10^7$ to $10^{10}$ ffu/ml. In brief, BSR cells were transfected with the exemplary antigenome transcription vectors and helper vectors, as described above. Cells were inoculated at a multiplicity of infection of 1 virion per cell, at a concentration of $10^6$ cells/ml in one tenth the bioreactor vessel volume. Transfected cells were grown at 37° C., 5% $Co_2$ in DMEM supplemented with 10% fetal bovine serum. The supernatant was harvested every three to five days for between two and three harvests. The deficient ERA-G grew less well compared with other viruses, with only $10^8$ ffu/ml for the ERA-G (TABLE 3. and FIG. 5).

TABLE 3

Full-length plasmid constructs and corresponding rescued viruses

| Plasmid constructs | Rescued viruses | Titers ffu/ml from cultured cells | Titers ffu/ml in bioreactors |
|---|---|---|---|
| pTMF | rERA | $5 \times 10^7$ | $3 \times 10^{10}$ |
| pTMFΔψ | ERA- | $6.3 \times 10^7$ | $3.2 \times 10^{10}$ |
| pTMFg3 | ERAg3 | $3 \times 10^6$ | $1.8 \times 10^9$ |
| pTMFgfp1 | ERAgreen1 | $3.5 \times 10^6$ | $5.6 \times 10^9$ |
| pTMFgfp2 | ERAgreen2 | $2 \times 10^7$ | $6.2 \times 10^9$ |
| pTMF2g | ERA2g | $1.6 \times 10^6$ | $3.9 \times 10^9$ |
| pTMF2g3 | ERA2g3 | $8 \times 10^7$ | $4.6 \times 10^9$ |
| pTMFΔg | ERA-G | $1.2 \times 10^2$ | $1.5 \times 10^7$ |
| pTMFgm | ERAgm | $5.31 \times 10^6$ | $1.9 \times 10^9$ |
| pTMFgmg | ERAgmg | $3.1 \times 10^6$ | 1.2 × 109 |

Example 8

Expression of Exogenous Proteins from Extra Transcriptional Units in Rabies Virus This example demonstrates the expression of recombinant proteins from a heterologous ORF inserted into a rabies virus vector. In this example, the ERA virus vector is used as a prototype rabies virus vector. To construct ERA virus as a vector for accepting ORFs, a conservative RV transcriptional unit between the N and P genes was modified and introduced into the ERA genome at two different locations: 1) at the psi region (trans 1), and 2) at the P-M intergenic region (trans 2). The transcriptional unit was designed to possess two unique restriction enzyme recognition sites to facilitate introduction of heterologous polynucleotide sequences: (TTTTTTTGATTGTGGGGAGGAAAGCGACGTCAAA CCATGGCAGCTCTTTTTT T: SEQ ID NO: 65, Pst1 and Kpn1 sites underlined).

Figure 6:
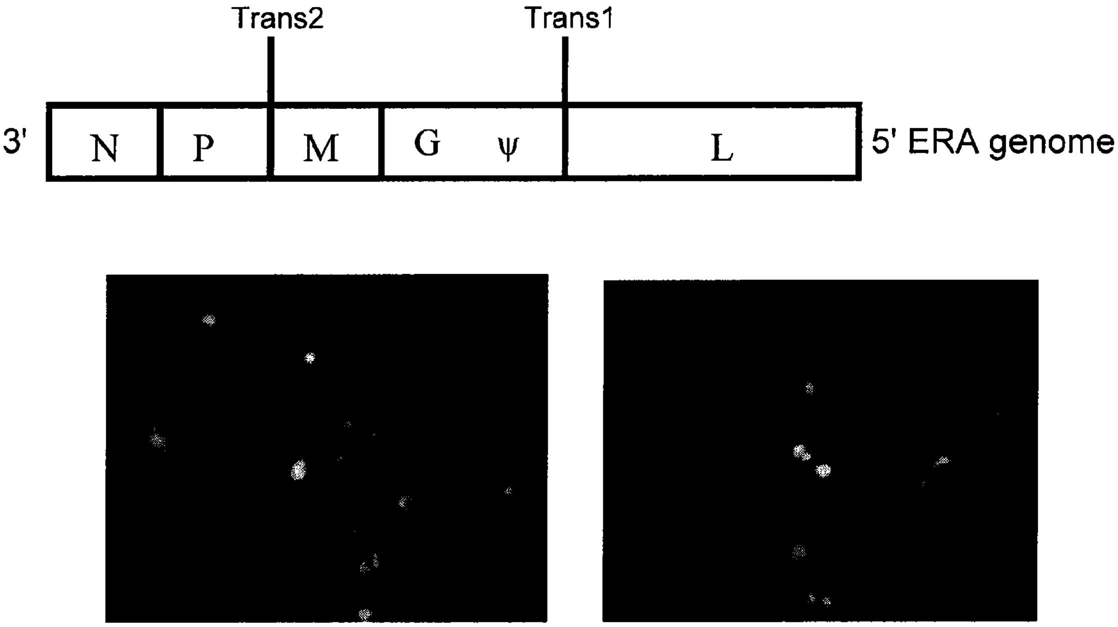
FIG. 6. Green foci in ERAgreen1/ERAgreen2 rabies virus-infected BSR cells. Trans 1 is the transcriptional unit incorporated at the Psi and L intergenic regions. Trans2 is the transcriptional unit at the P and M intergenic region. Both ERAgreen2 and ERAgreen1 expressed the GFP protein stably in virus-infected BSR cells, while the occurrence of the green foci of ERAgreen2 was 48 hours earlier after virus infection than in ERAgreen1.

In a first example, the GFP gene was cloned into this unit for virus recovery, since GFP expression could be observed directly under a UV microscope when the transfected BSR cells were still incubating. Expression of the GFP protein was directly visible by fluorescent microscopy with an excitation filter of 470±20 nm. The ERAgreen2 (GFP gene inserted after P gene in RV genome-trans 2)-infected cells showed clear green foci after three days of plasmid transfection, while ERAgreen1 (GFP gene inserted after G gene in the "traditional" Ψ region-trans 1) did not present obvious green foci until five days post-transfection (FIG. 6). The introduced transcriptional unit was functional in the RV genome at both locations, although expression and accumulation was apparent more rapidly when GFP was expressed from trans 2. Thus, these results also indicate that the level of expression from a heterologous ORF can be modulated by selecting the transcription unit into which the ORF is cloned.

Figure 7:
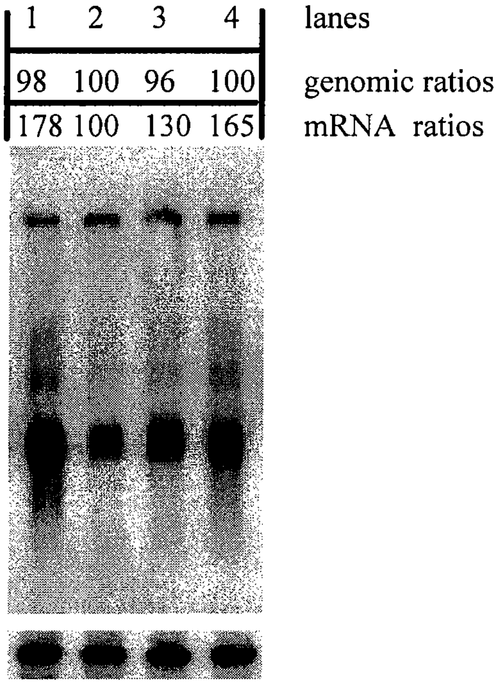
FIG. 7. Analysis of G mRNA expression in double G, and G, M rearranged ERA rabies viruses. In the Northern blot with a G probe, the measurement by density photometry of G mRNA in ERA2g (lane 1), ERAgm (lane 3) and ERA2g3 (lane 4) represented enhanced mRNA levels, compared with ERA-virus-infected cells (lane 2). The ratios were calculated by the use of ERA-virus as 100%.

In other examples, 1) an additional copy of ERA G; or 2) an additional copy of ERA G with an amino acid substitution at position 333, was incorporated into the ERA viral genome. The successfully rescued viruses were named ERA2g and ERA2g3, respectively. Since quantitation of viral G expression was not practical, the relative increase in expression levels of G in ERA2g and ERA2g3-infected cells was confirmed by Northern-blot with a G probe. In brief, the ERA G gene probe was labeled using the Dig DNA Labeling Kit (Roche, Indianapolis, Ind.) and imaged with Dig Nucleic Acid Detection Kit (Roche, Indianapolis, Ind.) and was measured by density spectrophotometry (FIG. 7). The tandem linked G genes in the recovered viruses were also confirmed by RT-PCR with 5G and 3G primers. A predominant band indicating a single G copy was observed at 1.5 kb. In addition, a second weaker band was observed at approximately 3.0 kb indicative of the two Gs in a tandem arrangement.

These results demonstrate that introduction of transcription units into the ERA genome can be used to express diverse heterologous proteins from introduced ORFs. Furthermore, expression of the protein encoded by the heterologous ORF is modulated by the position into which the ORF is inserted. Thus, ERA virus is a widely adaptable vector for the expression of recombinant proteins.

Example 9

In Vivo Immune Response to Engineered Viruses

This example demonstrates the in vivo effects of inoculation with the engineered ERA virus and exemplary derivatives. All animal care and experimental procedures were performed in compliance with the CDC Institutional Animal Care and Use Guidelines. Eighty three-week old mice were divided into 8 groups of 10 each for intramuscular (i.m) administration of recovered viruses ($10^6$ ffu of virus per mouse). Ten healthy mice were held as uninfected mock controls. For the ERA and ERAg3 constructs, additional intracerebral (i.c) injections of the same dose of viruses were applied to another group of ten three-week old mice. In two-day old suckling mice, only the ERAg3 and ERA-G viruses were inoculated intracerebrally, with the same dose. Animals were checked daily for illness. Ill animals were euthanized by $CO_2$ intoxication and brains were removed for rabies virus diagnosis. Ten days after infection, blood was collected by the retro orbital route and sera obtained for neutralizing antibody assays, following the standard rapid fluorescent focus inhibition test (RFFIT) (Smith et al., Bulletin of the World Health Organization. 48: 535-541, 1973). One month after infection, surviving animals were challenged with a lethal dose of street rabies virus (dog/coyote salivary gland homogenate) (Orciari et al., *Vaccine.* 19:4511-4518, 2001).

Mouse monoclonal antibody (Mab 523-11) against rabies virus G was maintained at CDC (Hamir et al., *Vet Rec.* 136, 295-296, 1995) and FITC-conjugated anti-N monoclonal antibody was purchased from Centocor (Horsham, Pa.). T7 RNA polymerase monoclonal antibody was from Novagen (Madison, Wis.). Goat anti-mouse IgG-FITC conjugate was purchased from Sigma-Aldrich (St. Louis, Mo.). Anti-rabies virus G monoclonal antibody (Mab 1-909) was maintained at CDC and goat anti-human IgG-FITC conjugate was purchased from Sigma-Aldrich (St. Louis, Mo.).

Figure 8A:
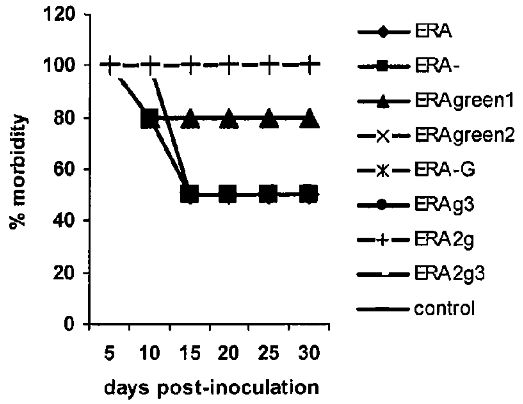
FIG. 8A. Morbidity induced by in vivo inoculation with recombinant ERA and derivatives. Three-week old mice were inoculated intramuscularly with the eight recovered viruses. At 10 days post inoculation, in ERA, ERA- and ERAgreen1 groups, 50%, 50% and 20% of mice showed compatible clinical signs of rabies, but no mortality, respectively. No adverse signs were observed in the other groups.
Figure 8B:
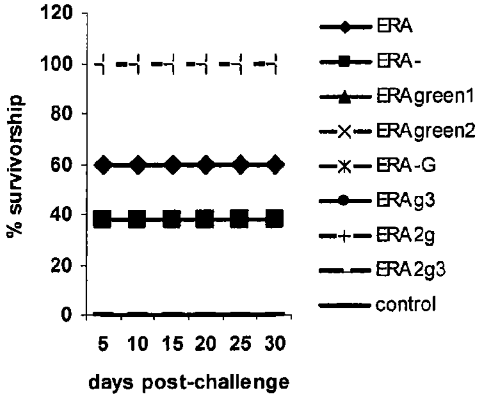
FIG. 8B. Post challenge survival in mice inoculated with recombinant ERA and derivatives. Mice surviving from the tests shown in FIG. 8A were challenged intramuscularly with a Texas dog/coyote rabies virus. At 5 days post challenge, in the ERA and ERA-groups, 40 and 62% of mice showed signs of rabies and were euthanized, respectively. In all other groups, no signs of rabies were observed.
Figure 8C:
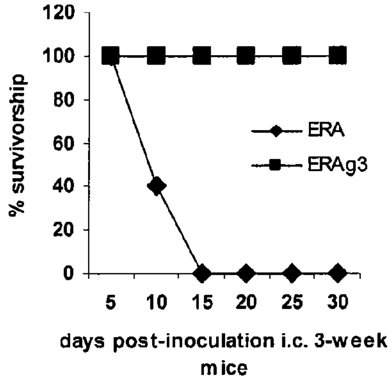
FIG. 8C. Survival following i.c. inoculation with recombinant ERA and ERAg3 viruses. Three-week old mice were inoculated intracerebrally with ERA and ERAg3 virus strains, respectively. All mice succumbed 15 days postinoculation in the ERA group, while in the ERAg3 group, all mice survived with no clinical signs.
Figure 8D:
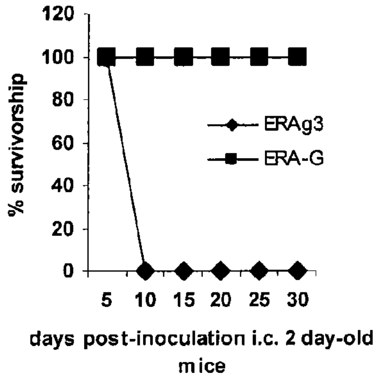
FIG. 8D. Survival following i.c. inoculation of suckling mice. Two-day old suckling mice were inoculated intracerebrally with ERAg3 and ERA-G virus constructs, respectively. All mice succumbed in the ERAg3 group, while no mice died in the ERA-G group.
Figure 8E:
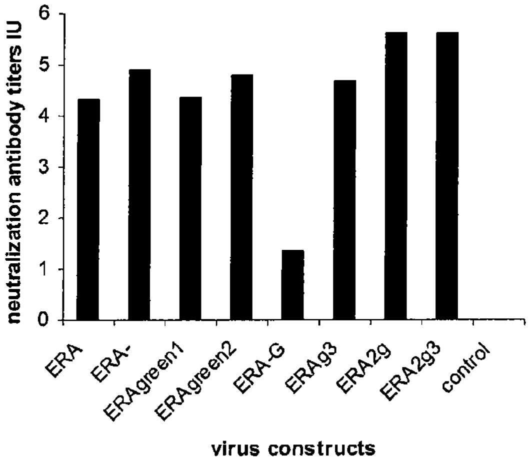
FIG. 8E. Neutralizing antibody titer in mice inoculated with recombinant ERA and derivative viruses. Mouse neutralization antibody titers were determined by the RFFIT, ranging from 1.36 to 5.61 IU per ml among the virus-inoculated groups.

Among the three-week old mice inoculated intramuscularly by the eight different virus constructs, 50% of mice inoculated with ERA (rERA) or ERA-, and 20% of mice inoculated with ERAgreen1 showed mild neurological signs at 10 days after inoculation. No other groups showed any sign suggestive of rabies virus infection (FIG. 8A). Sera were collected for neutralizing antibody titration before challenge. The ERA2g (5.60 IU) and ERA2g3 (5.61 IU) elicited higher titers than the single-copy G virus constructs (FIG. 8E). Mice surviving one month after inoculation were subjected to challenge with a lethal dog/coyote street virus (0.05 ml, maintained at CDC for standard animal challenge tests). In the ERA and ERA-groups, 40 to 62% of the mice showed mild rabies signs, respectively, and were euthanized. All other groups survived without any signs of rabies (FIG. 8B). In the i.c groups, three-week old mice survived after ERAg3 inoculation, but succumbed after ERA injection (FIG. 8C). The ERA-G construct did not kill 2-day old suckling mouse, however ERAg3 was virulent enough to kill all infected suckling mice (FIG. 8D). Exemplary antibody titers are shown in Table 4.

TABLE 4

Production of rabies specific antibodies

| Group | Average Titer |
|---|---|
| ERA | 433 |
| G333 | 468 |
| 2G | 560 |
| 2G333 | 561 |
| -PSI | 490 |
| GFP | 437 |
| G green | 833 |
| G minus | 136 |
| Controls | <1/5 |

These data demonstrate that all of the ERA based viruses were capable of eliciting an immune response following inoculation. As expected, the parental ERA virus was virulent, resulting in substantial morbidity and mortality in infected animals. In contrast, the various exemplary derivatives elicited a protective immune response when mice were inoculated prior to challenge.

Figure 9A:
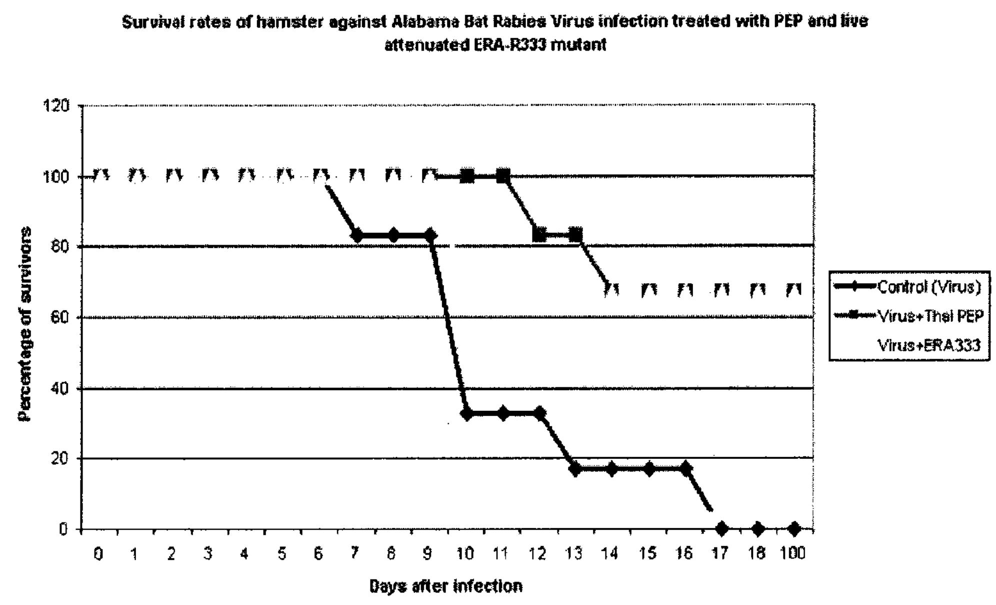
FIG. 9A. Survival following infection with Alabama Bat Rabies virus. Hamsters were inoculated with live Alabama Bat Rabies Virus, then treated post-exposure with either ERAg3 virus or with rabies immune globulin and commercially available inactivated RV vaccine. Survival was assessed over a more than three month period.
Figure 9B:
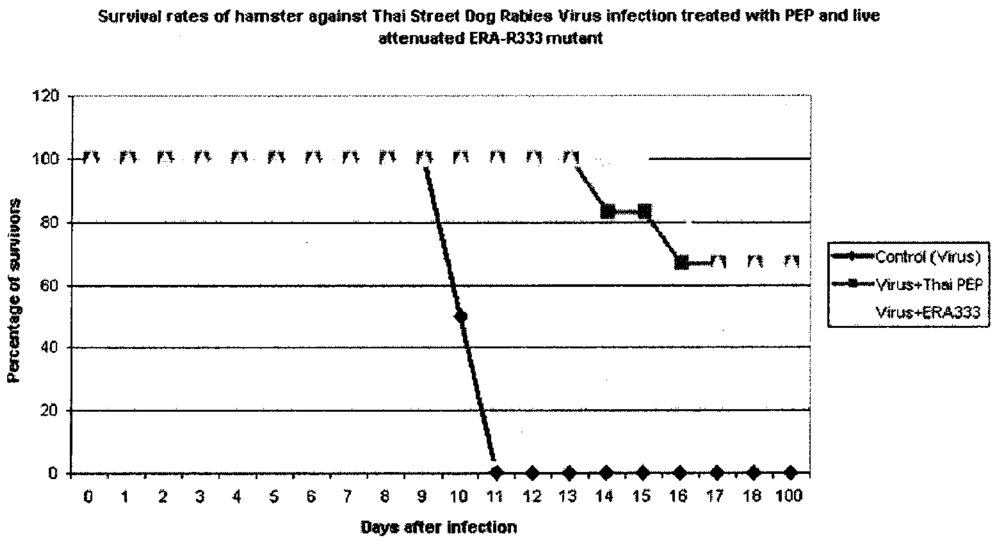
FIG. 9B. Survival following infection with Thai Street Dog Rabies virus. Hamsters were inoculated with live Alabama Bat Rabies Virus, then treated post-exposure with either ERAg3 virus or with rabies immune globulin and commercially available inactivated RV vaccine. Survival was assessed over a more than three month period.
Figure 9C:
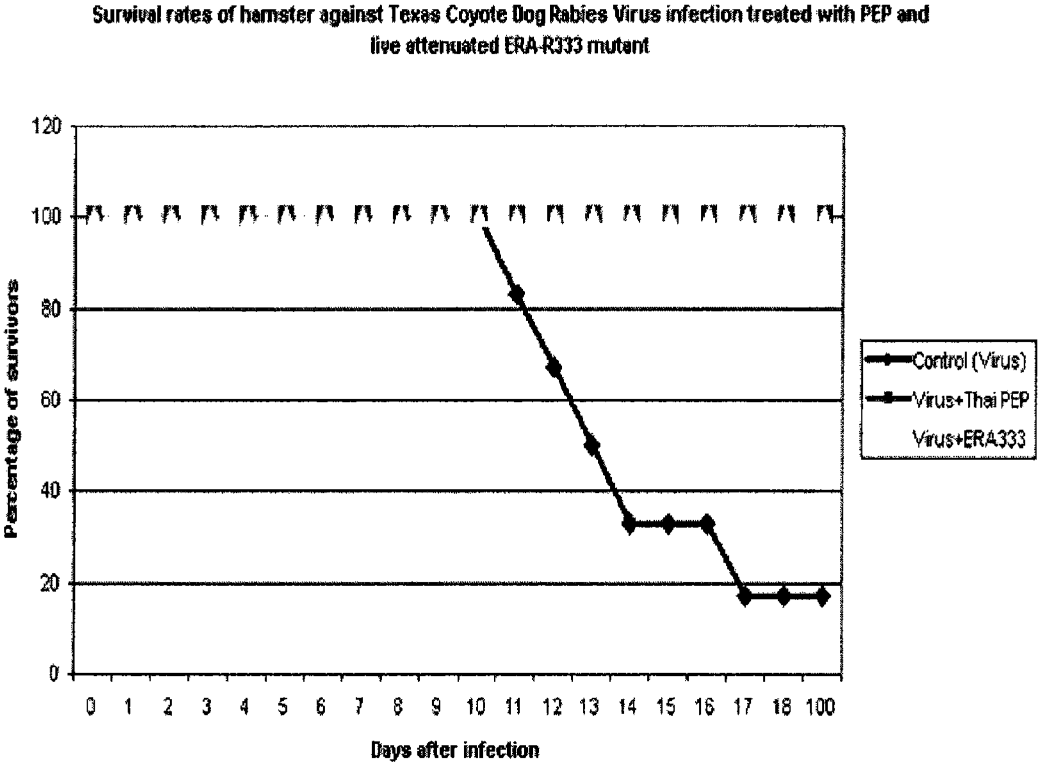
FIG. 9C. Survival following infection with Texas Coyote Dog Rabies virus. Hamsters were inoculated with live Alabama Bat Rabies Virus, then treated post-exposure with either ERAg3 virus or with rabies immune globulin and commercially available inactivated RV vaccine. Survival was assessed over a more than three month period.

In addition to the pre-exposure assessment described above, the ability of the ERA virus derivatives to elicit a protective immune response following infection with virulent rabies virus was determined. In brief, groups of hamsters were infected with one of three different strains of rabies virus (n=9 per group), and either given the recombinant vaccine (ERA-g333), or rabies immune globulin plus inactivated commercial rabies vaccines. Approximately 80-100% of control animals succumb, whereas approximately 60-100% of vaccinated animals survive as shown in FIGS. 9A-C. These results demonstrate that post-exposure administration of the derivative rabies virus confers substantial protection against different strains of rabies virus.

In view of the many possible embodiments to which the principles of the disclosed invention may be applied, it will be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A vector system comprising:

a first vector comprising a full-length rabies virus antigenomic DNA, wherein the full-length antigenomic DNA comprises the nucleic acid sequence of SEQ ID NO: 17; and, a plurality of helper vectors comprising nucleic acids that encode at least one rabies virus strain ERA protein, wherein expression of the plurality of vectors in a transfected host cell results in production of a recombinant rabies virus.

2. The vector system of claim 1, wherein the first vector comprises in a 5' to 3' direction: a hammerhead ribozyme; a rabies virus antigenomic DNA comprising the nucleic acid sequence of SEQ ID NO: 17; and a hepatitis delta virus ribozyme, wherein a plurality of nucleotides of the hammerhead ribozyme are complementary to the antisense genomic sequence of the rabies virus.

3. The vector system of claim 2, wherein transcription of the antigenomic DNA is under the transcription regulatory control of at least one of the CMV promoter and the phage T7 RNA polymerase promoter.

4. The vector system of claim 1, wherein the plurality of helper vectors comprises:

a vector comprising a polynucleotide sequence that encodes a rabies virus N protein;

a vector comprising a polynucleotide sequence that encodes a rabies virus P protein;

a vector comprising a polynucleotide sequence that encodes a rabies virus M protein;

a vector comprising a polynucleotide sequence that encodes a rabies virus L protein; and a vector comprising a polynucleotide sequence that encodes a phage T7 RNA polymerase.

5. The vector system of claim 4, further comprising a vector comprising a polynucleotide sequence that encodes a rabies virus G protein.

6. The vector system of claim 5, wherein transcription of one or more of the polynucleotide sequences that encode the rabies virus P, M, L or G protein or the T7 polymerase are under the transcription regulatory control of both the CMV promoter and the T7 promoter.

7. A recombinant virus genome comprising the nucleic acid sequence as set forth in SEQ ID NO: 17.

8. The recombinant virus genome of claim 7, further comprising a vector.

9. A recombinant virus comprising a genome as set forth in claim 7.

10. A live rabies virus vaccine comprising at least one recombinant rabies virus genome, wherein the at least one recombinant rabies virus genome comprises the sequence shown in SEQ ID NO: 17.

11. A method of producing a live rabies virus vaccine, comprising introducing the vector system of claim 4 into a host cell, and recovering live recombinant rabies virus.

12. A method of vaccinating a subject against rabies, comprising administering an effective amount of the live rabies virus vaccine produced according to the method of claim 11 to a subject, such that cells of the subject are infected with the rabies virus vaccine, wherein an anti-rabies immune response is produced in the subject.

13. The method of claim 12, wherein the subject is a human.

14. The method of claim 12, wherein the subject is a non-human animal.

15. The method of claim 12, wherein the administration comprises oral administration.

16. The method of claim 15, wherein the oral administration comprises administration through food-baits designed to vaccinate wild animal populations.

17. A pharmaceutical composition comprising the live rabies vaccine of claim 10 and a pharmaceutically acceptable carrier or excipient.

18. A method of eliciting an immune response against rabies in a subject, comprising administering an effective amount of the recombinant rabies virus of claim 9 to a subject, such that cells of the subject are infected with the rabies virus, wherein an anti-rabies immune response is produced in the subject.

19. A method of producing a recombinant rabies virus, comprising introducing the vector system of claim 4 into a host cell, and recovering recombinant rabies virus.

20. A method of producing a recombinant rabies virus, comprising introducing the vector system of claim 5 into a host cell, and recovering recombinant rabies virus.

* * * * *

SEQUENCE LISTING

```
<160> NUMBER OF SEQ ID NOS: 65

<210> SEQ ID NO 1
<211> LENGTH: 11931
<212> TYPE: DNA
<213> ORGANISM: rabies virus
<220> FEATURE:
<221> NAME/KEY: misc_feature
<222> LOCATION: (1)..(58)
<223> OTHER INFORMATION: Leader Region
<220> FEATURE:
<221> NAME/KEY: CDS
<222> LOCATION: (71)..(1420)
<223> OTHER INFORMATION: N gene
<220> FEATURE:
<221> NAME/KEY: CDS
<222> LOCATION: (1514)..(2404)
<223> OTHER INFORMATION: P gene
<220> FEATURE:
<221> NAME/KEY: CDS
<222> LOCATION: (2496)..(3101)
<223> OTHER INFORMATION: M gene
<220> FEATURE:
<221> NAME/KEY: CDS
<222> LOCATION: (3317)..(4888)
<223> OTHER INFORMATION: G gene
<220> FEATURE:
<221> NAME/KEY: misc_feature
<222> LOCATION: (4964)..(5362)
<223> OTHER INFORMATION: Psi region
<220> FEATURE:
<221> NAME/KEY: CDS
<222> LOCATION: (5417)..(11797)
<223> OTHER INFORMATION: L gene
<220> FEATURE:
<221> NAME/KEY: misc_feature
<222> LOCATION: (11862)..(11931)
<223> OTHER INFORMATION: Trailer region

<400> SEQUENCE: 1

acgcttaaca accagatcaa agaaaaaaca gacattgtca attgcaaagc aaaaatgtaa      60

cacccctaca atg gat gcc gac aag att gta ttc aaa gtc aat aat cag       109
           Met Asp Ala Asp Lys Ile Val Phe Lys Val Asn Asn Gln
           1               5                   10

gtg gtc tct ttg aag cct gag att atc gtg gat caa cat gag tac aag      157
Val Val Ser Leu Lys Pro Glu Ile Ile Val Asp Gln His Glu Tyr Lys
    15                  20                  25

tac cct gcc atc aaa gat ttg aaa aag ccc tgt ata acc cta gga aag      205
Tyr Pro Ala Ile Lys Asp Leu Lys Lys Pro Cys Ile Thr Leu Gly Lys
30                  35                  40                  45

gct ccc gat tta aat aaa gca tac aag tca gtt ttg tca ggc atg agc      253
Ala Pro Asp Leu Asn Lys Ala Tyr Lys Ser Val Leu Ser Gly Met Ser
                50                  55                  60

gcc gcc aaa ctt gat cct gac gat gta tgt tcc tat ttg gca gcg gca      301
Ala Ala Lys Leu Asp Pro Asp Asp Val Cys Ser Tyr Leu Ala Ala Ala
            65                  70                  75

atg cag ttt ttt gag ggg aca tgt ccg gaa gac tgg acc agc tat gga      349
Met Gln Phe Phe Glu Gly Thr Cys Pro Glu Asp Trp Thr Ser Tyr Gly
        80                  85                  90

atc gtg att gca cga aaa gga gat aag atc acc cca ggt tct ctg gtg      397
Ile Val Ile Ala Arg Lys Gly Asp Lys Ile Thr Pro Gly Ser Leu Val
    95                  100                 105

gag ata aaa cgt act gat gta gaa ggg aat tgg gct ctg aca gga ggc      445
Glu Ile Lys Arg Thr Asp Val Glu Gly Asn Trp Ala Leu Thr Gly Gly
110                 115                 120                 125

atg gaa ctg aca aga gac ccc act gtc cct gag cat gcg tcc tta gtc      493
Met Glu Leu Thr Arg Asp Pro Thr Val Pro Glu His Ala Ser Leu Val
                130                 135                 140
```

-continued

```
ggt ctt ctc ttg agt ctg tat agg ttg agc aaa ata tcc ggg caa aac      541
Gly Leu Leu Leu Ser Leu Tyr Arg Leu Ser Lys Ile Ser Gly Gln Asn
            145                 150                 155

act ggt aac tat aag aca aac att gca gac agg ata gag cag att ttt      589
Thr Gly Asn Tyr Lys Thr Asn Ile Ala Asp Arg Ile Glu Gln Ile Phe
        160                 165                 170

gag aca gcc cct ttt gtt aaa atc gtg gaa cac cat act cta atg aca      637
Glu Thr Ala Pro Phe Val Lys Ile Val Glu His His Thr Leu Met Thr
    175                 180                 185

act cac aaa atg tgt gct aat tgg agt act ata cca aac ttc aga ttt      685
Thr His Lys Met Cys Ala Asn Trp Ser Thr Ile Pro Asn Phe Arg Phe
190                 195                 200                 205

ttg gcc gga acc tat gac atg ttt ttc tcc cgg att gag cat cta tat      733
Leu Ala Gly Thr Tyr Asp Met Phe Phe Ser Arg Ile Glu His Leu Tyr
                210                 215                 220

tca gca atc aga gtg ggc aca gtt gtc act gct tat gaa gac tgt tca      781
Ser Ala Ile Arg Val Gly Thr Val Val Thr Ala Tyr Glu Asp Cys Ser
            225                 230                 235

gga ctg gta tca ttt act ggg ttc ata aaa caa atc aat ctc acc gct      829
Gly Leu Val Ser Phe Thr Gly Phe Ile Lys Gln Ile Asn Leu Thr Ala
        240                 245                 250

aga gag gca ata cta tat ttc ttc cac aag aac ttt gag gaa gag ata      877
Arg Glu Ala Ile Leu Tyr Phe Phe His Lys Asn Phe Glu Glu Glu Ile
    255                 260                 265

aga aga atg ttt gag cca ggg cag gag aca gct gtt cct cac tct tat      925
Arg Arg Met Phe Glu Pro Gly Gln Glu Thr Ala Val Pro His Ser Tyr
270                 275                 280                 285

ttc atc cac ttc cgt tca cta ggc ttg agt ggg aaa tct cct tat tca      973
Phe Ile His Phe Arg Ser Leu Gly Leu Ser Gly Lys Ser Pro Tyr Ser
                290                 295                 300

tca aat gct gtt ggt cac gtg ttc aat ctc att cac ttt gta gga tgc     1021
Ser Asn Ala Val Gly His Val Phe Asn Leu Ile His Phe Val Gly Cys
            305                 310                 315

tat atg ggt caa gtc aga tcc cta aat gca acg gtt att gct gca tgt     1069
Tyr Met Gly Gln Val Arg Ser Leu Asn Ala Thr Val Ile Ala Ala Cys
        320                 325                 330

gct cct cat gaa atg tct gtt cta ggg ggc tat ctg gga gag gaa ttc     1117
Ala Pro His Glu Met Ser Val Leu Gly Gly Tyr Leu Gly Glu Glu Phe
    335                 340                 345

ttc ggg aaa ggg aca ttt gaa aga aga ttc ttc aga gat gag aaa gaa     1165
Phe Gly Lys Gly Thr Phe Glu Arg Arg Phe Phe Arg Asp Glu Lys Glu
350                 355                 360                 365

ctt caa gaa tac gag gcg gct gaa ctg aca aag act gac gta gca ctg     1213
Leu Gln Glu Tyr Glu Ala Ala Glu Leu Thr Lys Thr Asp Val Ala Leu
                370                 375                 380

gca gat gat gga act gtc aac tct gac gac gag gac tac ttc tca ggt     1261
Ala Asp Asp Gly Thr Val Asn Ser Asp Asp Glu Asp Tyr Phe Ser Gly
            385                 390                 395

gaa acc aga agt ccg gag gct gtt tat act cga atc atg atg aat gga     1309
Glu Thr Arg Ser Pro Glu Ala Val Tyr Thr Arg Ile Met Met Asn Gly
        400                 405                 410

ggt cga cta aag aga tct cac ata cgg aga tat gtc tca gtc agt tcc     1357
Gly Arg Leu Lys Arg Ser His Ile Arg Arg Tyr Val Ser Val Ser Ser
    415                 420                 425

aat cat caa gcc cgt cca aac tca ttc gcc gag ttt cta aac aag aca     1405
Asn His Gln Ala Arg Pro Asn Ser Phe Ala Glu Phe Leu Asn Lys Thr
430                 435                 440                 445

tat tcg agt gac tca taagaagttg aacaacaaaa tgccggaaat ctacggattg     1460
Tyr Ser Ser Asp Ser
```

-continued

```
            450

tgtatatcca tcatgaaaaa aactaacacc cctcctttcg aaccatccca aac atg      1516
                                                           Met

agc aag atc ttt gtc aat cct agt gct att aga gcc ggt ctg gcc gat     1564
Ser Lys Ile Phe Val Asn Pro Ser Ala Ile Arg Ala Gly Leu Ala Asp
            455                 460                 465

ctt gag atg gct gaa gaa act gtt gat ctg atc aat aga aat atc gaa     1612
Leu Glu Met Ala Glu Glu Thr Val Asp Leu Ile Asn Arg Asn Ile Glu
        470                 475                 480

gac aat cag gct cat ctc caa ggg gaa ccc ata gaa gtg gac aat ctc     1660
Asp Asn Gln Ala His Leu Gln Gly Glu Pro Ile Glu Val Asp Asn Leu
    485                 490                 495

cct gag gat atg ggg cga ctt cac ctg gat gat gga aaa tcg ccc aac     1708
Pro Glu Asp Met Gly Arg Leu His Leu Asp Asp Gly Lys Ser Pro Asn
500                 505                 510                 515

cct ggt gag atg gcc aag gtg gga gaa ggc aag tat cga gag gac ttt     1756
Pro Gly Glu Met Ala Lys Val Gly Glu Gly Lys Tyr Arg Glu Asp Phe
                520                 525                 530

cag atg gat gaa gga gag gat ctt agc ttc ctg ttc cag tca tac ctg     1804
Gln Met Asp Glu Gly Glu Asp Leu Ser Phe Leu Phe Gln Ser Tyr Leu
            535                 540                 545

gaa aat gtt gga gtc caa ata gtc aga caa atg agg tca gga gag aga     1852
Glu Asn Val Gly Val Gln Ile Val Arg Gln Met Arg Ser Gly Glu Arg
        550                 555                 560

ttt ctc aag ata tgg tca cag acc gta gaa gag att ata tcc tat gtc     1900
Phe Leu Lys Ile Trp Ser Gln Thr Val Glu Glu Ile Ile Ser Tyr Val
    565                 570                 575

gcg gtc aac ttt ccc aac cct cca gga aag tct tca gag gat aaa tca     1948
Ala Val Asn Phe Pro Asn Pro Pro Gly Lys Ser Ser Glu Asp Lys Ser
580                 585                 590                 595

acc cag act act ggc cga gag ctc aag aag gag aca aca ccc act cct     1996
Thr Gln Thr Thr Gly Arg Glu Leu Lys Lys Glu Thr Thr Pro Thr Pro
                600                 605                 610

tct cag aga gaa agc caa tca tcg aaa gcc agg atg gcg gct caa att     2044
Ser Gln Arg Glu Ser Gln Ser Ser Lys Ala Arg Met Ala Ala Gln Ile
            615                 620                 625

gct tct ggc cct cca gcc ctt gaa tgg tcg gcc acc aat gaa gag gat     2092
Ala Ser Gly Pro Pro Ala Leu Glu Trp Ser Ala Thr Asn Glu Glu Asp
        630                 635                 640

gat cta tca gtg gag gct gag atc gct cac cag att gca gaa agt ttc     2140
Asp Leu Ser Val Glu Ala Glu Ile Ala His Gln Ile Ala Glu Ser Phe
    645                 650                 655

tcc aaa aaa tat aag ttt ccc tct cga tcc tca ggg ata ctc ttg tat     2188
Ser Lys Lys Tyr Lys Phe Pro Ser Arg Ser Ser Gly Ile Leu Leu Tyr
660                 665                 670                 675

aat ttt gag caa ttg aaa atg aac ctt gat gat ata gtt aaa gag gca     2236
Asn Phe Glu Gln Leu Lys Met Asn Leu Asp Asp Ile Val Lys Glu Ala
                680                 685                 690

aaa aat gta cca ggt gtg acc cgt tta gcc cat gac ggg tcc aaa ctc     2284
Lys Asn Val Pro Gly Val Thr Arg Leu Ala His Asp Gly Ser Lys Leu
            695                 700                 705

ccc cta aga tgt gta ctg gga tgg gtc gct ttg gcc aac cct aag aaa     2332
Pro Leu Arg Cys Val Leu Gly Trp Val Ala Leu Ala Asn Pro Lys Lys
        710                 715                 720

ttc cag ttg tta gtc gaa tcc gac aag ctg agt aaa atc atg caa gat     2380
Phe Gln Leu Leu Val Glu Ser Asp Lys Leu Ser Lys Ile Met Gln Asp
    725                 730                 735

gac ttg aat cgc tat aca tct tgc taaccgaacc tctccactca gtccctctag    2434
Asp Leu Asn Arg Tyr Thr Ser Cys
```

-continued

```
740                 745

acaataaagt ccgagatgtc ctaaagtcaa catgaaaaaa acaggcaaca ccactgataa   2494

a atg aac ttt cta cgt aag ata gtg aaa aat tgc agg gac gag gac act   2543
  Met Asn Phe Leu Arg Lys Ile Val Lys Asn Cys Arg Asp Glu Asp Thr
          750                 755                 760

caa aaa ccc tct ccc gtg tca gcc cct ctg gat gac gat gac ttg tgg     2591
Gln Lys Pro Ser Pro Val Ser Ala Pro Leu Asp Asp Asp Asp Leu Trp
    765                 770                 775

ctt cca ccc cct gaa tac gtc ccg ctg aaa gaa ctt aca agc aag aag     2639
Leu Pro Pro Pro Glu Tyr Val Pro Leu Lys Glu Leu Thr Ser Lys Lys
780                 785                 790                 795

aac atg agg aac ttt tgt atc aac gga ggg gtt aaa gtg tgt agc ccg     2687
Asn Met Arg Asn Phe Cys Ile Asn Gly Gly Val Lys Val Cys Ser Pro
                800                 805                 810

aat ggt tac tcg ttc agg atc ctg cgg cac att ctg aaa tca ttc gac     2735
Asn Gly Tyr Ser Phe Arg Ile Leu Arg His Ile Leu Lys Ser Phe Asp
            815                 820                 825

gag ata tat tct ggg aat cat agg atg atc ggg tta gcc aaa gta gtt     2783
Glu Ile Tyr Ser Gly Asn His Arg Met Ile Gly Leu Ala Lys Val Val
        830                 835                 840

att gga ctg gct ttg tca gga tct cca gtc cct gag ggc atg aac tgg     2831
Ile Gly Leu Ala Leu Ser Gly Ser Pro Val Pro Glu Gly Met Asn Trp
    845                 850                 855

gta tac aaa ttg agg aga acc ttt atc ttc cag tgg gct gat tcc agg     2879
Val Tyr Lys Leu Arg Arg Thr Phe Ile Phe Gln Trp Ala Asp Ser Arg
860                 865                 870                 875

ggc cct ctt gaa ggg gag gag ttg gaa tac tct cag gag atc act tgg     2927
Gly Pro Leu Glu Gly Glu Glu Leu Glu Tyr Ser Gln Glu Ile Thr Trp
                880                 885                 890

gat gat gat act gag ttc gtc gga ttg caa ata aga gtg att gca aaa     2975
Asp Asp Asp Thr Glu Phe Val Gly Leu Gln Ile Arg Val Ile Ala Lys
            895                 900                 905

cag tgt cat atc cag ggc aga atc tgg tgt atc aac atg aac ccg aga     3023
Gln Cys His Ile Gln Gly Arg Ile Trp Cys Ile Asn Met Asn Pro Arg
        910                 915                 920

gca tgt caa cta tgg tct gac atg tct ctt cag aca caa agg tcc gaa     3071
Ala Cys Gln Leu Trp Ser Asp Met Ser Leu Gln Thr Gln Arg Ser Glu
    925                 930                 935

gag gac aaa gat tcc tct ctg ctt cta gaa taatcagatt atatcccgca       3121
Glu Asp Lys Asp Ser Ser Leu Leu Leu Glu
940                 945

aatttatcac ttgtttacct ctggaggaga gaacatatgg gctcaactcc aacccttggg   3181

agcaatataa caaaaaacat gttatggtgc cattaaaccg ctgcatttca tcaaagtcaa   3241

gttgattacc tttacatttt gatcctcttg gatgtgaaaa aaactattaa catccctcaa   3301

aagactcaag gaaag atg gtt cct cag gct ctc ctg ttt gta ccc ctt ctg    3352
                 Met Val Pro Gln Ala Leu Leu Phe Val Pro Leu Leu
                 950                 955                 960

gtt ttt cca ttg tgt ttt ggg aaa ttc cct att tac acg ata cca gac     3400
Val Phe Pro Leu Cys Phe Gly Lys Phe Pro Ile Tyr Thr Ile Pro Asp
            965                 970                 975

aag ctt ggt ccc tgg agc ccg att gac ata cat cac ctc agc tgc cca     3448
Lys Leu Gly Pro Trp Ser Pro Ile Asp Ile His His Leu Ser Cys Pro
        980                 985                 990

aac aat ttg gta gtg gag gac  gaa gga tgc acc aac  ctg tca ggg ttc   3496
Asn Asn Leu Val Val Glu Asp  Glu Gly Cys Thr Asn  Leu Ser Gly Phe
    995                 1000                1005

tcc  tac atg gaa ctt aaa  gtt gga tac atc tta  gcc ata aaa atg      3541
```

-continued

```
Ser  Tyr Met Glu Leu Lys  Val Gly Tyr Ile Leu  Ala Ile Lys Met
1010                1015                1020

aac  ggg ttc act tgc aca  ggc gtt gtg acg gag  gct gaa acc tat      3586
Asn  Gly Phe Thr Cys Thr  Gly Val Val Thr Glu  Ala Glu Thr Tyr
1025                1030                1035

act  aac ttc gtt ggt tat  gtc aca acc acg ttc  aaa aga aag cat      3631
Thr  Asn Phe Val Gly Tyr  Val Thr Thr Thr Phe  Lys Arg Lys His
1040                1045                1050

ttc  cgc cca aca cca gat  gca tgt aga gcc gcg  tac aac tgg aag      3676
Phe  Arg Pro Thr Pro Asp  Ala Cys Arg Ala Ala  Tyr Asn Trp Lys
1055                1060                1065

atg  gcc ggt gac ccc aga  tat gaa gag tct cta  cac aat ccg tac      3721
Met  Ala Gly Asp Pro Arg  Tyr Glu Glu Ser Leu  His Asn Pro Tyr
1070                1075                1080

cct  gac tac cac tgg ctt  cga act gta aaa acc  acc aag gag tct      3766
Pro  Asp Tyr His Trp Leu  Arg Thr Val Lys Thr  Thr Lys Glu Ser
1085                1090                1095

ctc  gtt atc ata tct cca  agt gtg gca gat ttg  gac cca tat gac      3811
Leu  Val Ile Ile Ser Pro  Ser Val Ala Asp Leu  Asp Pro Tyr Asp
1100                1105                1110

aga  tcc ctt cac tcg agg  gtc ttc cct agc ggg  aag tgc tca gga      3856
Arg  Ser Leu His Ser Arg  Val Phe Pro Ser Gly  Lys Cys Ser Gly
1115                1120                1125

gta  gcg gtg tct tct acc  tac tgc tcc act aac  cac gat tac acc      3901
Val  Ala Val Ser Ser Thr  Tyr Cys Ser Thr Asn  His Asp Tyr Thr
1130                1135                1140

att  tgg atg ccc gag aat  ccg aga cta ggg atg  tct tgt gac att      3946
Ile  Trp Met Pro Glu Asn  Pro Arg Leu Gly Met  Ser Cys Asp Ile
1145                1150                1155

ttt  acc aat agt agg ggg  aag aga gca tcc aaa  ggg agt gag act      3991
Phe  Thr Asn Ser Arg Gly  Lys Arg Ala Ser Lys  Gly Ser Glu Thr
1160                1165                1170

tgc  ggc ttt gta gat gaa  aga ggc cta tat aag  tct tta aaa gga      4036
Cys  Gly Phe Val Asp Glu  Arg Gly Leu Tyr Lys  Ser Leu Lys Gly
1175                1180                1185

gca  tgc aaa ctc aag tta  tgt gga gtt cta gga  ctt aga ctt atg      4081
Ala  Cys Lys Leu Lys Leu  Cys Gly Val Leu Gly  Leu Arg Leu Met
1190                1195                1200

gat  gga aca tgg gtc gcg  atg caa aca tca aat  gaa acc aaa tgg      4126
Asp  Gly Thr Trp Val Ala  Met Gln Thr Ser Asn  Glu Thr Lys Trp
1205                1210                1215

tgc  ccc ccc gat cag ttg  gtg aac ctg cac gac  ttt cgc tca gac      4171
Cys  Pro Pro Asp Gln Leu  Val Asn Leu His Asp  Phe Arg Ser Asp
1220                1225                1230

gaa  att gag cac ctt gtt  gta gag gag ttg gtc  agg aag aga gag      4216
Glu  Ile Glu His Leu Val  Val Glu Glu Leu Val  Arg Lys Arg Glu
1235                1240                1245

gag  tgt ctg gat gca cta  gag tcc atc atg aca  acc aag tca gtg      4261
Glu  Cys Leu Asp Ala Leu  Glu Ser Ile Met Thr  Thr Lys Ser Val
1250                1255                1260

agt  ttc aga cgt ccc agt  cat tta aga aaa ctt  gtc cct ggg ttt      4306
Ser  Phe Arg Arg Pro Ser  His Leu Arg Lys Leu  Val Pro Gly Phe
1265                1270                1275

gga  aaa gca tat acc ata  ttc aac aag acc ttg  atg gaa gcc gat      4351
Gly  Lys Ala Tyr Thr Ile  Phe Asn Lys Thr Leu  Met Glu Ala Asp
1280                1285                1290

gct  cac tac aag tca gtc  aga act tgg aat gag  atc ctc cct tca      4396
Ala  His Tyr Lys Ser Val  Arg Thr Trp Asn Glu  Ile Leu Pro Ser
1295                1300                1305
```

-continued

```
aaa  ggg tgt tta aga gtt  ggg ggg agg tgt cat  cct cat gtg aac      4441
Lys  Gly Cys Leu Arg Val  Gly Gly Arg Cys His  Pro His Val Asn
1310                 1315                 1320

ggg  gtg ttt ttc aat ggt  ata ata tta gga cct  gac ggc aat gtc      4486
Gly  Val Phe Phe Asn Gly  Ile Ile Leu Gly Pro  Asp Gly Asn Val
1325                 1330                 1335

tta  atc cca gag atg caa  tca tcc ctc ctc cag  caa cat atg gag      4531
Leu  Ile Pro Glu Met Gln  Ser Ser Leu Leu Gln  Gln His Met Glu
1340                 1345                 1350

ttg  ttg gaa tcc tcg gtt  atc ccc ctt gtg cac  ccc ctg gca gac      4576
Leu  Leu Glu Ser Ser Val  Ile Pro Leu Val His  Pro Leu Ala Asp
1355                 1360                 1365

ccg  tct acc gtt ttc aag  gac ggt gac gag gct  gag gat ttt gtt      4621
Pro  Ser Thr Val Phe Lys  Asp Gly Asp Glu Ala  Glu Asp Phe Val
1370                 1375                 1380

gaa  gtt cac ctt ccc gat  gtg cac aat cag gtc  tca gga gtt gac      4666
Glu  Val His Leu Pro Asp  Val His Asn Gln Val  Ser Gly Val Asp
1385                 1390                 1395

ttg  ggt ctc ccg aac tgg  ggg aag tat gta tta  ctg agt gca ggg      4711
Leu  Gly Leu Pro Asn Trp  Gly Lys Tyr Val Leu  Leu Ser Ala Gly
1400                 1405                 1410

gcc  ctg act gcc ttg atg  ttg ata att ttc ctg  atg aca tgt tgt      4756
Ala  Leu Thr Ala Leu Met  Leu Ile Ile Phe Leu  Met Thr Cys Cys
1415                 1420                 1425

aga  aga gtc aat cga tca  gaa cct acg caa cac  aat ctc aga ggg      4801
Arg  Arg Val Asn Arg Ser  Glu Pro Thr Gln His  Asn Leu Arg Gly
1430                 1435                 1440

aca  ggg agg gag gtg tca  gtc act ccc caa agc  ggg aag atc ata      4846
Thr  Gly Arg Glu Val Ser  Val Thr Pro Gln Ser  Gly Lys Ile Ile
1445                 1450                 1455

tct  tca tgg gaa tca cac  aag agt ggg ggt gag  acc aga ctg          4888
Ser  Ser Trp Glu Ser His  Lys Ser Gly Gly Glu  Thr Arg Leu
1460                 1465                 1470

tgaggactgg ccgtcctttc aacgatccaa gtcctgaaga tcacctcccc ttgggggtt   4948

ctttttgaaa aaaaacctgg gttcaatagt cctcctcgaa ctccatgcaa ctgggtagat   5008

tcaagagtca tgagattttc attaatcctc tcagttgatc aagcaagatc atgtagattc   5068

tcataatagg ggagatcttc tagcagtttc agtgactaac ggtactttca ttctccagga   5128

actgacacca acagttgtag acaaaccacg gggtgtctcg ggtgactctg tgcttgggca   5188

cagacaaagg tcatggtgtg ttccatgata gcggactcag gatgagttaa ttgagagagg   5248

cagtcttcct cccgtgaagg acataagcag tagctcacaa tcatcccgcg tctcagcaaa   5308

gtgtgcataa ttataaagtg ctgggtcatc taagcttttc agtcgagaaa aaaacattag   5368

atcagaagaa caactggcaa cacttctcaa cctgagacct acttcaag atg ctc  gat   5425
                                                     Met Leu  Asp
                                                         1475

cct gga gag gtc  tat gat gac cct att  gac cca atc gag tta  gag      5470
Pro Gly Glu Val  Tyr Asp Asp Pro Ile  Asp Pro Ile Glu Leu  Glu
            1480                 1485                 1490

gat gaa ccc aga  gga acc ccc act gtc  ccc aac atc ttg agg  aac      5515
Asp Glu Pro Arg  Gly Thr Pro Thr Val  Pro Asn Ile Leu Arg  Asn
            1495                 1500                 1505

tct gac tac aat  ctc aac tct cct ttg  ata gaa gat cct gct  aga      5560
Ser Asp Tyr Asn  Leu Asn Ser Pro Leu  Ile Glu Asp Pro Ala  Arg
            1510                 1515                 1520

cta atg tta gaa  tgg tta aaa aca ggg  aat aga cct tat cgg  atg      5605
Leu Met Leu Glu  Trp Leu Lys Thr Gly  Asn Arg Pro Tyr Arg  Met
            1525                 1530                 1535
```

-continued

```
act cta aca gac  aat tgc tcc agg tct  ttc aga gtt ttg aaa  gat       5650
Thr Leu Thr Asp  Asn Cys Ser Arg Ser  Phe Arg Val Leu Lys  Asp
            1540                 1545                 1550

tat ttc aag aag  gta gat ttg ggt tct  ctc aag gtg ggc gga  atg       5695
Tyr Phe Lys Lys  Val Asp Leu Gly Ser  Leu Lys Val Gly Gly  Met
            1555                 1560                 1565

gct gca cag tca  atg att tct ctc tgg  tta tat ggt gcc cac  tct       5740
Ala Ala Gln Ser  Met Ile Ser Leu Trp  Leu Tyr Gly Ala His  Ser
            1570                 1575                 1580

gaa tcc aac agg  agc cgg aga tgt ata  aca gac ttg gcc cat  ttc       5785
Glu Ser Asn Arg  Ser Arg Arg Cys Ile  Thr Asp Leu Ala His  Phe
            1585                 1590                 1595

tat tcc aag tcg  tcc ccc ata gag aag  ctg ttg aat ctc acg  cta       5830
Tyr Ser Lys Ser  Ser Pro Ile Glu Lys  Leu Leu Asn Leu Thr  Leu
            1600                 1605                 1610

gga aat aga ggg  ctg aga atc ccc cca  gag gga gtg tta agt  tgc       5875
Gly Asn Arg Gly  Leu Arg Ile Pro Pro  Glu Gly Val Leu Ser  Cys
            1615                 1620                 1625

ctt gag agg gtt  gat tat gat aat gca  ttt gga agg tat ctt  gcc       5920
Leu Glu Arg Val  Asp Tyr Asp Asn Ala  Phe Gly Arg Tyr Leu  Ala
            1630                 1635                 1640

aac acg tat tcc  tct tac ttg ttc ttc  cat gta atc acc tta  tac       5965
Asn Thr Tyr Ser  Ser Tyr Leu Phe Phe  His Val Ile Thr Leu  Tyr
            1645                 1650                 1655

atg aac gcc cta  gac tgg gat gaa gaa  aag acc atc cta gca  tta       6010
Met Asn Ala Leu  Asp Trp Asp Glu Glu  Lys Thr Ile Leu Ala  Leu
            1660                 1665                 1670

tgg aaa gat tta  acc tca gtg gac atc  ggg aag gac ttg gta  aag       6055
Trp Lys Asp Leu  Thr Ser Val Asp Ile  Gly Lys Asp Leu Val  Lys
            1675                 1680                 1685

ttc aaa gac caa  ata tgg gga ctg ccg  atc gtg aca aag gac  ttt       6100
Phe Lys Asp Gln  Ile Trp Gly Leu Pro  Ile Val Thr Lys Asp  Phe
            1690                 1695                 1700

gtt tac tcc caa  agt tcc aat tgt ctt  ttt gac aga aac tac  aca       6145
Val Tyr Ser Gln  Ser Ser Asn Cys Leu  Phe Asp Arg Asn Tyr  Thr
            1705                 1710                 1715

ctt atg cta aaa  gaa ctt ttc ttg tct  cgc ttc aac tcc tta  atg       6190
Leu Met Leu Lys  Glu Leu Phe Leu Ser  Arg Phe Asn Ser Leu  Met
            1720                 1725                 1730

gtc ttg ctc tct  ccc cca gag ccc cga  tac tca gat gac ttg  ata       6235
Val Leu Leu Ser  Pro Pro Glu Pro Arg  Tyr Ser Asp Asp Leu  Ile
            1735                 1740                 1745

tct caa cta tgc  cag ctg tac att gct  ggg gat caa gtc ttg  tct       6280
Ser Gln Leu Cys  Gln Leu Tyr Ile Ala  Gly Asp Gln Val Leu  Ser
            1750                 1755                 1760

atg tgt gga aac  tcc ggc tat gaa gtc  atc aaa ata ttg gag  cca       6325
Met Cys Gly Asn  Ser Gly Tyr Glu Val  Ile Lys Ile Leu Glu  Pro
            1765                 1770                 1775

tat gtc gtg aat  agt tta gtc cag aga  gca gaa aag ttt agg  cct       6370
Tyr Val Val Asn  Ser Leu Val Gln Arg  Ala Glu Lys Phe Arg  Pro
            1780                 1785                 1790

ctc att cat tcc  ttg gga gac ttt cct  gta ttt ata aaa gac  aag       6415
Leu Ile His Ser  Leu Gly Asp Phe Pro  Val Phe Ile Lys Asp  Lys
            1795                 1800                 1805

gta agt caa ctt  gaa gag acg ttc ggt  ccc tgt gca aga agg  ttc       6460
Val Ser Gln Leu  Glu Glu Thr Phe Gly  Pro Cys Ala Arg Arg  Phe
            1810                 1815                 1820

ttt agg gct ctg  gat caa ttc gac aac  ata cat gac ttg gtt  ttt       6505
Phe Arg Ala Leu  Asp Gln Phe Asp Asn  Ile His Asp Leu Val  Phe
```

```
            1825                1830                1835

gtg tat ggc tgt  tac agg cat tgg ggg  cac cca tat ata gat  tat      6550
Val Tyr Gly Cys  Tyr Arg His Trp Gly  His Pro Tyr Ile Asp  Tyr
            1840                1845                1850

cga aag ggt ctg  tca aaa cta tat gat  cag gtt cac att aaa  aaa      6595
Arg Lys Gly Leu  Ser Lys Leu Tyr Asp  Gln Val His Ile Lys  Lys
            1855                1860                1865

gtg ata gat aag  tcc tac cag gag tgc  tta gca agc gac cta  gcc      6640
Val Ile Asp Lys  Ser Tyr Gln Glu Cys  Leu Ala Ser Asp Leu  Ala
            1870                1875                1880

agg agg atc ctt  aga tgg ggt ttt gat  aag tac tcc aag tgg  tat      6685
Arg Arg Ile Leu  Arg Trp Gly Phe Asp  Lys Tyr Ser Lys Trp  Tyr
            1885                1890                1895

ctg gat tca aga  ttc cta gcc cga gac  cac ccc ttg act ccc  tat      6730
Leu Asp Ser Arg  Phe Leu Ala Arg Asp  His Pro Leu Thr Pro  Tyr
            1900                1905                1910

atc aaa acc caa  aca tgg cca ccc aaa  cat att gta gac ttg  gtg      6775
Ile Lys Thr Gln  Thr Trp Pro Pro Lys  His Ile Val Asp Leu  Val
            1915                1920                1925

ggg gat aca tgg  cac aag ctc ccg atc  acg cag atc ttt gag  att      6820
Gly Asp Thr Trp  His Lys Leu Pro Ile  Thr Gln Ile Phe Glu  Ile
            1930                1935                1940

cct gaa tca atg  gat ccg tca gaa ata  ttg gat gac aaa tca  cat      6865
Pro Glu Ser Met  Asp Pro Ser Glu Ile  Leu Asp Asp Lys Ser  His
            1945                1950                1955

tct ttc acc aga  acg aga cta gct tct  tgg ctg tca gaa aac  cga      6910
Ser Phe Thr Arg  Thr Arg Leu Ala Ser  Trp Leu Ser Glu Asn  Arg
            1960                1965                1970

ggg gga cct gtt  cct agc gaa aaa gtt  att atc acg gcc ctg  tct      6955
Gly Gly Pro Val  Pro Ser Glu Lys Val  Ile Ile Thr Ala Leu  Ser
            1975                1980                1985

aag ccg cct gtc  aat ccc cga gag ttt  ctg agg tct ata gac  ctc      7000
Lys Pro Pro Val  Asn Pro Arg Glu Phe  Leu Arg Ser Ile Asp  Leu
            1990                1995                2000

gga gga ttg cca  gat gaa gac ttg ata  att ggc ctc aag cca  aag      7045
Gly Gly Leu Pro  Asp Glu Asp Leu Ile  Ile Gly Leu Lys Pro  Lys
            2005                2010                2015

gaa cgg gaa ttg  aag att gaa ggt cga  ttc ttt gct cta atg  tca      7090
Glu Arg Glu Leu  Lys Ile Glu Gly Arg  Phe Phe Ala Leu Met  Ser
            2020                2025                2030

tgg aat cta aga  ttg tat ttt gtc atc  act gaa aaa ctc ttg  gcc      7135
Trp Asn Leu Arg  Leu Tyr Phe Val Ile  Thr Glu Lys Leu Leu  Ala
            2035                2040                2045

aac tac atc ttg  cca ctt ttt gac gcg  ctg act atg aca gac  aac      7180
Asn Tyr Ile Leu  Pro Leu Phe Asp Ala  Leu Thr Met Thr Asp  Asn
            2050                2055                2060

ctg aac aag gtg  ttt aaa aag ctg atc  gac agg gtc acc ggg  caa      7225
Leu Asn Lys Val  Phe Lys Lys Leu Ile  Asp Arg Val Thr Gly  Gln
            2065                2070                2075

ggg ctt ttg gac  tat tca agg gtc aca  tat gca ttt cac ctg  gac      7270
Gly Leu Leu Asp  Tyr Ser Arg Val Thr  Tyr Ala Phe His Leu  Asp
            2080                2085                2090

tat gaa aag tgg  aac aac cat caa aga  tta gag tca aca gag  gat      7315
Tyr Glu Lys Trp  Asn Asn His Gln Arg  Leu Glu Ser Thr Glu  Asp
            2095                2100                2105

gta ttt tct gtc  cta gat caa gtg ttt  gga ttg aag aga gtg  ttt      7360
Val Phe Ser Val  Leu Asp Gln Val Phe  Gly Leu Lys Arg Val  Phe
            2110                2115                2120

tct aga aca cac  gag ttt ttt caa aag  gcc tgg atc tat tat  tca      7405
```

-continued

```
Ser Arg Thr His Glu Phe Phe Gln Lys Ala Trp Ile Tyr Tyr Ser
            2125                2130                2135

gac aga tca gac ctc atc ggg tta cgg gag gat caa ata tac tgc      7450
Asp Arg Ser Asp Leu Ile Gly Leu Arg Glu Asp Gln Ile Tyr Cys
            2140                2145                2150

tta gat gcg tcc aac ggc cca acc tgt tgg aat ggc cag gat ggc      7495
Leu Asp Ala Ser Asn Gly Pro Thr Cys Trp Asn Gly Gln Asp Gly
            2155                2160                2165

ggg cta gaa ggc tta cgg cag aag ggc tgg agt cta gtc agc tta      7540
Gly Leu Glu Gly Leu Arg Gln Lys Gly Trp Ser Leu Val Ser Leu
            2170                2175                2180

ttg atg ata gat aga gaa tct caa atc agg aac aca aga acc aaa      7585
Leu Met Ile Asp Arg Glu Ser Gln Ile Arg Asn Thr Arg Thr Lys
            2185                2190                2195

ata cta gct caa gga gac aac cag gtt tta tgt ccg aca tat atg      7630
Ile Leu Ala Gln Gly Asp Asn Gln Val Leu Cys Pro Thr Tyr Met
            2200                2205                2210

ttg tcg cca ggg cta tct caa gag ggg ctc ctc tat gaa ttg gag      7675
Leu Ser Pro Gly Leu Ser Gln Glu Gly Leu Leu Tyr Glu Leu Glu
            2215                2220                2225

aga ata tca agg aat gca ctt tcg ata tac aga gcc gtc gag gaa      7720
Arg Ile Ser Arg Asn Ala Leu Ser Ile Tyr Arg Ala Val Glu Glu
            2230                2235                2240

ggg gca tct aag cta ggg ctg atc acc aag aaa gaa gag acc atg      7765
Gly Ala Ser Lys Leu Gly Leu Ile Thr Lys Lys Glu Glu Thr Met
            2245                2250                2255

tgt agt tat gac ttc ctc atc tat gga aaa acc cct ttg ttt aga      7810
Cys Ser Tyr Asp Phe Leu Ile Tyr Gly Lys Thr Pro Leu Phe Arg
            2260                2265                2270

ggt aac ata ttg gtg cct gag tcc aaa aga tgg gcc aga gtc tct      7855
Gly Asn Ile Leu Val Pro Glu Ser Lys Arg Trp Ala Arg Val Ser
            2275                2280                2285

tgc gtc tct aat gac caa ata gtc aac ctc gcc aat ata atg tcg      7900
Cys Val Ser Asn Asp Gln Ile Val Asn Leu Ala Asn Ile Met Ser
            2290                2295                2300

aca gtg tcc acc aat gcg cta aca gtg gca caa cac tct caa tct      7945
Thr Val Ser Thr Asn Ala Leu Thr Val Ala Gln His Ser Gln Ser
            2305                2310                2315

ttg atc aaa ccg atg ggg gat ttt ctg ctc atg tca gta cag gca      7990
Leu Ile Lys Pro Met Gly Asp Phe Leu Leu Met Ser Val Gln Ala
            2320                2325                2330

gtc ttt cac tac ctg cta ttt agc cca atc tta aag gga aga gtt      8035
Val Phe His Tyr Leu Leu Phe Ser Pro Ile Leu Lys Gly Arg Val
            2335                2340                2345

tac aag att ctg agc gct gaa ggg gat agc ttt ctc cta gcc atg      8080
Tyr Lys Ile Leu Ser Ala Glu Gly Asp Ser Phe Leu Leu Ala Met
            2350                2355                2360

tca agg ata atc tat cta gat cct tct ttg gga ggg gta tct gga      8125
Ser Arg Ile Ile Tyr Leu Asp Pro Ser Leu Gly Gly Val Ser Gly
            2365                2370                2375

atg tcc ctc gga aga ttc cat ata cga cag ttc tca gac cct gtc      8170
Met Ser Leu Gly Arg Phe His Ile Arg Gln Phe Ser Asp Pro Val
            2380                2385                2390

tct gaa ggg tta tcc ttc tgg aga gag atc tgg tta agc tcc cac      8215
Ser Glu Gly Leu Ser Phe Trp Arg Glu Ile Trp Leu Ser Ser His
            2395                2400                2405

gag tcc tgg gtt cac gcg ttg tgt caa gag gct gga aac cca gat      8260
Glu Ser Trp Val His Ala Leu Cys Gln Glu Ala Gly Asn Pro Asp
            2410                2415                2420
```

-continued

```
ctt gga gag aga  aca ctc gag agc ttc  act cgc ctt cta gaa  gat      8305
Leu Gly Glu Arg  Thr Leu Glu Ser Phe  Thr Arg Leu Leu Glu  Asp
            2425                 2430                 2435

cct acc acc tta  aat atc aga gga ggg  gcc agt cct acc att  cta      8350
Pro Thr Thr Leu  Asn Ile Arg Gly Gly  Ala Ser Pro Thr Ile  Leu
            2440                 2445                 2450

ctc aag gat gca  atc aga aag gct tta  tat gac gag gtg gac  aag      8395
Leu Lys Asp Ala  Ile Arg Lys Ala Leu  Tyr Asp Glu Val Asp  Lys
            2455                 2460                 2465

gtg gag aat tca  gag ttt cga gag gca  atc ctg ttg tcc aag  acc      8440
Val Glu Asn Ser  Glu Phe Arg Glu Ala  Ile Leu Leu Ser Lys  Thr
            2470                 2475                 2480

cat aga gat aat  ttt ata ctc ttc tta  aca tct gtt gag cct  ctg      8485
His Arg Asp Asn  Phe Ile Leu Phe Leu  Thr Ser Val Glu Pro  Leu
            2485                 2490                 2495

ttt cct cga ttt  ctc agt gag cta ttc  agt tcg tct ttt ttg  gga      8530
Phe Pro Arg Phe  Leu Ser Glu Leu Phe  Ser Ser Ser Phe Leu  Gly
            2500                 2505                 2510

atc ccc gag tca  atc att gga ttg ata  caa aac tcc cga acg  ata      8575
Ile Pro Glu Ser  Ile Ile Gly Leu Ile  Gln Asn Ser Arg Thr  Ile
            2515                 2520                 2525

aga agg cag ttt  aga aag agt ctc tca  aaa act tta gaa gaa  tcc      8620
Arg Arg Gln Phe  Arg Lys Ser Leu Ser  Lys Thr Leu Glu Glu  Ser
            2530                 2535                 2540

ttc tac aac tca  gag atc cac ggg att  agt cgg atg acc cag  aca      8665
Phe Tyr Asn Ser  Glu Ile His Gly Ile  Ser Arg Met Thr Gln  Thr
            2545                 2550                 2555

cct cag agg gtt  ggg ggg gtg tgg cct  tgc tct tca gag agg  gca      8710
Pro Gln Arg Val  Gly Gly Val Trp Pro  Cys Ser Ser Glu Arg  Ala
            2560                 2565                 2570

gat cta ctt agg  gag atc tct tgg gga  aga aaa gtg gta ggc  acg      8755
Asp Leu Leu Arg  Glu Ile Ser Trp Gly  Arg Lys Val Val Gly  Thr
            2575                 2580                 2585

aca gtt cct cac  cct tct gag atg ttg  ggg tta ctt ccc aag  tcc      8800
Thr Val Pro His  Pro Ser Glu Met Leu  Gly Leu Leu Pro Lys  Ser
            2590                 2595                 2600

tct att tct tgc  act tgt gga gca aca  gga gga ggc aat cct  aga      8845
Ser Ile Ser Cys  Thr Cys Gly Ala Thr  Gly Gly Gly Asn Pro  Arg
            2605                 2610                 2615

gtt tct gta tca  gta ctc ccg tcc ttt  gat cag tca ttt ttt  tca      8890
Val Ser Val Ser  Val Leu Pro Ser Phe  Asp Gln Ser Phe Phe  Ser
            2620                 2625                 2630

cga ggc ccc cta  aag ggg tac ttg ggc  tcg tcc acc tct atg  tcg      8935
Arg Gly Pro Leu  Lys Gly Tyr Leu Gly  Ser Ser Thr Ser Met  Ser
            2635                 2640                 2645

acc cag cta ttc  cat gca tgg gaa aaa  gtc act aat gtt cat  gtg      8980
Thr Gln Leu Phe  His Ala Trp Glu Lys  Val Thr Asn Val His  Val
            2650                 2655                 2660

gtg aag aga gct  cta tcg tta aaa gaa  tct ata aac tgg ttc  att      9025
Val Lys Arg Ala  Leu Ser Leu Lys Glu  Ser Ile Asn Trp Phe  Ile
            2665                 2670                 2675

act aga gat tcc  aac ttg gct caa gct  cta att agg aac att  atg      9070
Thr Arg Asp Ser  Asn Leu Ala Gln Ala  Leu Ile Arg Asn Ile  Met
            2680                 2685                 2690

tct ctg aca ggc  cct gat ttc cct cta  gag gag gcc cct gtc  ttc      9115
Ser Leu Thr Gly  Pro Asp Phe Pro Leu  Glu Glu Ala Pro Val  Phe
            2695                 2700                 2705

aaa agg acg ggg  tca gcc ttg cat agg  ttc aag tct gcc aga  tac      9160
Lys Arg Thr Gly  Ser Ala Leu His Arg  Phe Lys Ser Ala Arg  Tyr
            2710                 2715                 2720
```

-continued

```
agc gaa gga ggg  tat tct tct gtc tgc  ccg aac ctc ctc tct  cat      9205
Ser Glu Gly Gly  Tyr Ser Ser Val Cys  Pro Asn Leu Leu Ser  His
            2725                 2730                 2735

att tct gtt agt  aca gac acc atg tct  gat ttg acc caa gac  ggg      9250
Ile Ser Val Ser  Thr Asp Thr Met Ser  Asp Leu Thr Gln Asp  Gly
            2740                 2745                 2750

aag aac tac gat  ttc atg ttc cag cca  ttg atg ctt tat gca  cag      9295
Lys Asn Tyr Asp  Phe Met Phe Gln Pro  Leu Met Leu Tyr Ala  Gln
            2755                 2760                 2765

aca tgg aca tca  gag ctg gta cag aga  gac aca agg cta aga  gac      9340
Thr Trp Thr Ser  Glu Leu Val Gln Arg  Asp Thr Arg Leu Arg  Asp
            2770                 2775                 2780

tct acg ttt cat  tgg cac ctc cga tgc  aac agg tgt gtg aga  ccc      9385
Ser Thr Phe His  Trp His Leu Arg Cys  Asn Arg Cys Val Arg  Pro
            2785                 2790                 2795

att gac gac gtg  acc ctg gag acc tct  cag atc ttc gag ttt  ccg      9430
Ile Asp Asp Val  Thr Leu Glu Thr Ser  Gln Ile Phe Glu Phe  Pro
            2800                 2805                 2810

gat gtg tcg aaa  aga ata tcc aga atg  gtt tct ggg gct gtg  cct      9475
Asp Val Ser Lys  Arg Ile Ser Arg Met  Val Ser Gly Ala Val  Pro
            2815                 2820                 2825

cac ttc cag agg  ctt ccc gat atc cgt  ctg aga cca gga gat  ttt      9520
His Phe Gln Arg  Leu Pro Asp Ile Arg  Leu Arg Pro Gly Asp  Phe
            2830                 2835                 2840

gaa tct cta agc  ggt aga gaa aag tct  cac cat atc gga tca  gct      9565
Glu Ser Leu Ser  Gly Arg Glu Lys Ser  His His Ile Gly Ser  Ala
            2845                 2850                 2855

cag ggg ctc tta  tac tca atc tta gtg  gca att cac gac tca  gga      9610
Gln Gly Leu Leu  Tyr Ser Ile Leu Val  Ala Ile His Asp Ser  Gly
            2860                 2865                 2870

tac aat gat gga  acc atc ttc cct gcc  aac ata tac ggc aag  gtt      9655
Tyr Asn Asp Gly  Thr Ile Phe Pro Ala  Asn Ile Tyr Gly Lys  Val
            2875                 2880                 2885

tcc cct aga gac  tat ttg aga ggg ctc  gca agg gga gta ttg  ata      9700
Ser Pro Arg Asp  Tyr Leu Arg Gly Leu  Ala Arg Gly Val Leu  Ile
            2890                 2895                 2900

gga tcc tcg att  tgc ttc ttg aca aga  atg aca aat atc aat  att      9745
Gly Ser Ser Ile  Cys Phe Leu Thr Arg  Met Thr Asn Ile Asn  Ile
            2905                 2910                 2915

aat aga cct ctt  gaa ttg atc tca ggg  gta atc tca tat att  ctc      9790
Asn Arg Pro Leu  Glu Leu Ile Ser Gly  Val Ile Ser Tyr Ile  Leu
            2920                 2925                 2930

ctg agg cta gat  aac cat ccc tcc ttg  tac ata atg ctc aga  gaa      9835
Leu Arg Leu Asp  Asn His Pro Ser Leu  Tyr Ile Met Leu Arg  Glu
            2935                 2940                 2945

ccg tct ctt aga  gga gag ata ttt tct  atc cct cag aaa atc  ccc      9880
Pro Ser Leu Arg  Gly Glu Ile Phe Ser  Ile Pro Gln Lys Ile  Pro
            2950                 2955                 2960

gcc gct tat cca  acc act atg aaa gaa  ggc aac aga tca atc  ttg      9925
Ala Ala Tyr Pro  Thr Thr Met Lys Glu  Gly Asn Arg Ser Ile  Leu
            2965                 2970                 2975

tgt tat ctc caa  cat gtg cta cgc tat  gag cga gag ata atc  acg      9970
Cys Tyr Leu Gln  His Val Leu Arg Tyr  Glu Arg Glu Ile Ile  Thr
            2980                 2985                 2990

gcg tct cca gag  aat gac tgg cta tgg  atc ttt tca gac ttt  aga     10015
Ala Ser Pro Glu  Asn Asp Trp Leu Trp  Ile Phe Ser Asp Phe  Arg
            2995                 3000                 3005

agt gcc aaa atg  acg tac cta acc ctc  att act tac cag tct  cat     10060
Ser Ala Lys Met  Thr Tyr Leu Thr Leu  Ile Thr Tyr Gln Ser  His
```

-continued

```
            3010                3015                3020

ctt cta ctc cag  agg gtt gag aga aac  cta tct aag agt atg  aga     10105
Leu Leu Leu Gln  Arg Val Glu Arg Asn  Leu Ser Lys Ser Met  Arg
            3025                3030                3035

gat aac ctg cga  caa ttg agt tcc ttg  atg agg cag gtg ctg  ggc     10150
Asp Asn Leu Arg  Gln Leu Ser Ser Leu  Met Arg Gln Val Leu  Gly
            3040                3045                3050

ggg cac gga gaa  gat acc tta gag tca  gac gac aac att caa  cga     10195
Gly His Gly Glu  Asp Thr Leu Glu Ser  Asp Asp Asn Ile Gln  Arg
            3055                3060                3065

ctg cta aaa gac  tct tta cga agg aca  aga tgg gtg gat caa  gag     10240
Leu Leu Lys Asp  Ser Leu Arg Arg Thr  Arg Trp Val Asp Gln  Glu
            3070                3075                3080

gtg cgc cat gca  gct aga acc atg act  gga gat tac agc ccc  aac     10285
Val Arg His Ala  Ala Arg Thr Met Thr  Gly Asp Tyr Ser Pro  Asn
            3085                3090                3095

aag aag gtg tcc  cgt aag gta gga tgt  tca gaa tgg gtc tgc  tct     10330
Lys Lys Val Ser  Arg Lys Val Gly Cys  Ser Glu Trp Val Cys  Ser
            3100                3105                3110

gct caa cag gtt  gca gtc tct acc tca  gca aac ccg gcc cct  gtc     10375
Ala Gln Gln Val  Ala Val Ser Thr Ser  Ala Asn Pro Ala Pro  Val
            3115                3120                3125

tcg gag ctt gac  ata agg gcc ctc tct  aag agg ttc cag aac  cct     10420
Ser Glu Leu Asp  Ile Arg Ala Leu Ser  Lys Arg Phe Gln Asn  Pro
            3130                3135                3140

ttg atc tcg ggc  ttg aga gtg gtt cag  tgg gca acc ggt gct  cat     10465
Leu Ile Ser Gly  Leu Arg Val Val Gln  Trp Ala Thr Gly Ala  His
            3145                3150                3155

tat aag ctt aag  cct att cta gat gat  ctc aat gtt ttc ccc  tct     10510
Tyr Lys Leu Lys  Pro Ile Leu Asp Asp  Leu Asn Val Phe Pro  Ser
            3160                3165                3170

ctc tgc ctt gta  gtt ggg gac ggg tca  ggg ggg ata tca agg  gca     10555
Leu Cys Leu Val  Val Gly Asp Gly Ser  Gly Gly Ile Ser Arg  Ala
            3175                3180                3185

gtc ctc aac atg  ttt cca gat gcc aag  ctt gtg ttc aac agt  ctc     10600
Val Leu Asn Met  Phe Pro Asp Ala Lys  Leu Val Phe Asn Ser  Leu
            3190                3195                3200

tta gag gtg aat  gac ctg atg gct tcc  gga aca cat cca ctg  cct     10645
Leu Glu Val Asn  Asp Leu Met Ala Ser  Gly Thr His Pro Leu  Pro
            3205                3210                3215

cct tca gca atc  atg agg gga gga aat  ggt atc gtc tcc aga  gtg     10690
Pro Ser Ala Ile  Met Arg Gly Gly Asn  Gly Ile Val Ser Arg  Val
            3220                3225                3230

ata gat ttt gac  tca atc tgg gaa aaa  ccg tcc gac ttg aga  aac     10735
Ile Asp Phe Asp  Ser Ile Trp Glu Lys  Pro Ser Asp Leu Arg  Asn
            3235                3240                3245

ttg gca acc tgg  aaa tac ttc cag tca  gtc caa aag cag gtc  aac     10780
Leu Ala Thr Trp  Lys Tyr Phe Gln Ser  Val Gln Lys Gln Val  Asn
            3250                3255                3260

atg tcc tat gac  ctc att att tgc gat  gca gaa gtt act gac  att     10825
Met Ser Tyr Asp  Leu Ile Ile Cys Asp  Ala Glu Val Thr Asp  Ile
            3265                3270                3275

gca tct atc aac  cgg ata acc ctg tta  atg tcc gat ttt gca  ttg     10870
Ala Ser Ile Asn  Arg Ile Thr Leu Leu  Met Ser Asp Phe Ala  Leu
            3280                3285                3290

tct ata gat gga  cca ctc tat ttg gtc  ttc aaa act tat ggg  act     10915
Ser Ile Asp Gly  Pro Leu Tyr Leu Val  Phe Lys Thr Tyr Gly  Thr
            3295                3300                3305

atg cta gta aat  cca aac tac aag gct  att caa cac ctg tca  aga     10960
```

-continued

```
Met Leu Val Asn  Pro Asn Tyr Lys Ala  Ile Gln His Leu Ser  Arg
            3310                 3315                 3320

gcg ttc ccc tcg  gtc aca ggg ttt atc  acc caa gta act tcg  tct     11005
Ala Phe Pro Ser  Val Thr Gly Phe Ile  Thr Gln Val Thr Ser  Ser
            3325                 3330                 3335

ttt tca tct gag  ctc tac ctc cga ttc  tcc aaa cga ggg aag  ctt     11050
Phe Ser Ser Glu  Leu Tyr Leu Arg Phe  Ser Lys Arg Gly Lys  Leu
            3340                 3345                 3350

ttc aga gat gct  gag tac ttg acc tct  tcc acc ctt cga gaa  atg     11095
Phe Arg Asp Ala  Glu Tyr Leu Thr Ser  Ser Thr Leu Arg Glu  Met
            3355                 3360                 3365

agc ctt gtg tta  ttc aat tgt agc agc  ccc aag agt gag atg  cag     11140
Ser Leu Val Leu  Phe Asn Cys Ser Ser  Pro Lys Ser Glu Met  Gln
            3370                 3375                 3380

aga gct cgt tcc  ttg aac tat cag gat  ctt gtg aga gga ttt  cct     11185
Arg Ala Arg Ser  Leu Asn Tyr Gln Asp  Leu Val Arg Gly Phe  Pro
            3385                 3390                 3395

gaa gaa atc ata  tca aat cct tac aat  gag atg atc ata act  ctg     11230
Glu Glu Ile Ile  Ser Asn Pro Tyr Asn  Glu Met Ile Ile Thr  Leu
            3400                 3405                 3410

att gac agt gat  gta gaa tct ttt cta  gtc cac aag atg gtt  gat     11275
Ile Asp Ser Asp  Val Glu Ser Phe Leu  Val His Lys Met Val  Asp
            3415                 3420                 3425

gat ctt gag tta  cag agg gga act ctg  tct aaa gtg gct atc  att     11320
Asp Leu Glu Leu  Gln Arg Gly Thr Leu  Ser Lys Val Ala Ile  Ile
            3430                 3435                 3440

ata gcc atc atg  ata gtt ttc tcc aac  aga gtc ttc aac gtt  tcc     11365
Ile Ala Ile Met  Ile Val Phe Ser Asn  Arg Val Phe Asn Val  Ser
            3445                 3450                 3455

aaa ccc cta act  gac ccc ttg ttc tat  cca ccg tct gat ccc  aaa     11410
Lys Pro Leu Thr  Asp Pro Leu Phe Tyr  Pro Pro Ser Asp Pro  Lys
            3460                 3465                 3470

atc ctg agg cac  ttc aac ata tgt cgc  agt act atg atg tat  cta     11455
Ile Leu Arg His  Phe Asn Ile Cys Arg  Ser Thr Met Met Tyr  Leu
            3475                 3480                 3485

tct act gct tta  ggt gac gtc cct agc  ttc gca aga ctt cac  gac     11500
Ser Thr Ala Leu  Gly Asp Val Pro Ser  Phe Ala Arg Leu His  Asp
            3490                 3495                 3500

ctg tat aac aga  cct ata act tat tac  ttc aga aag caa ttc  att     11545
Leu Tyr Asn Arg  Pro Ile Thr Tyr Tyr  Phe Arg Lys Gln Phe  Ile
            3505                 3510                 3515

cga ggg aac gtt  tat cta tct tgg agt  tgg tcc aac gac acc  tca     11590
Arg Gly Asn Val  Tyr Leu Ser Trp Ser  Trp Ser Asn Asp Thr  Ser
            3520                 3525                 3530

gtg ttc aaa agg  gta gcc tgt aat tct  agc ctg agt ctg tca  tct     11635
Val Phe Lys Arg  Val Ala Cys Asn Ser  Ser Leu Ser Leu Ser  Ser
            3535                 3540                 3545

cac tgg atc agg  ttg att tac aag ata  gtg aag gct acc aga  ctc     11680
His Trp Ile Arg  Leu Ile Tyr Lys Ile  Val Lys Ala Thr Arg  Leu
            3550                 3555                 3560

gtt ggc agc atc  aag gat cta tcc aga  gaa gtg gaa aga cac  ctt     11725
Val Gly Ser Ile  Lys Asp Leu Ser Arg  Glu Val Glu Arg His  Leu
            3565                 3570                 3575

cat agg tac aac  agg tgg atc acc cta  gag gat atc aga tct  aga     11770
His Arg Tyr Asn  Arg Trp Ile Thr Leu  Glu Asp Ile Arg Ser  Arg
            3580                 3585                 3590

tca tcc cta cta  gac tac agt tgc ctg  tgaaccggat actcctggaa        11817
Ser Ser Leu Leu  Asp Tyr Ser Cys Leu
            3595                 3600
```

```
gcctgcccat gctaagactc ttgtgtgatg tatcttgaaa aaaacaagat cctaaatctg  11877

aacctttggt tgtttgattg tttttctcat ttttgttgtt tatttgttaa gcgt        11931


<210> SEQ ID NO 2
<211> LENGTH: 450
<212> TYPE: PRT
<213> ORGANISM: rabies virus

<400> SEQUENCE: 2

Met Asp Ala Asp Lys Ile Val Phe Lys Val Asn Asn Gln Val Val Ser
1               5                   10                  15

Leu Lys Pro Glu Ile Ile Val Asp Gln His Glu Tyr Lys Tyr Pro Ala
            20                  25                  30

Ile Lys Asp Leu Lys Lys Pro Cys Ile Thr Leu Gly Lys Ala Pro Asp
        35                  40                  45

Leu Asn Lys Ala Tyr Lys Ser Val Leu Ser Gly Met Ser Ala Ala Lys
    50                  55                  60

Leu Asp Pro Asp Asp Val Cys Ser Tyr Leu Ala Ala Ala Met Gln Phe
65                  70                  75                  80

Phe Glu Gly Thr Cys Pro Glu Asp Trp Thr Ser Tyr Gly Ile Val Ile
                85                  90                  95

Ala Arg Lys Gly Asp Lys Ile Thr Pro Gly Ser Leu Val Glu Ile Lys
            100                 105                 110

Arg Thr Asp Val Glu Gly Asn Trp Ala Leu Thr Gly Gly Met Glu Leu
        115                 120                 125

Thr Arg Asp Pro Thr Val Pro Glu His Ala Ser Leu Val Gly Leu Leu
    130                 135                 140

Leu Ser Leu Tyr Arg Leu Ser Lys Ile Ser Gly Gln Asn Thr Gly Asn
145                 150                 155                 160

Tyr Lys Thr Asn Ile Ala Asp Arg Ile Glu Gln Ile Phe Glu Thr Ala
                165                 170                 175

Pro Phe Val Lys Ile Val Glu His His Thr Leu Met Thr Thr His Lys
            180                 185                 190

Met Cys Ala Asn Trp Ser Thr Ile Pro Asn Phe Arg Phe Leu Ala Gly
        195                 200                 205

Thr Tyr Asp Met Phe Phe Ser Arg Ile Glu His Leu Tyr Ser Ala Ile
    210                 215                 220

Arg Val Gly Thr Val Val Thr Ala Tyr Glu Asp Cys Ser Gly Leu Val
225                 230                 235                 240

Ser Phe Thr Gly Phe Ile Lys Gln Ile Asn Leu Thr Ala Arg Glu Ala
                245                 250                 255

Ile Leu Tyr Phe Phe His Lys Asn Phe Glu Glu Glu Ile Arg Arg Met
            260                 265                 270

Phe Glu Pro Gly Gln Glu Thr Ala Val Pro His Ser Tyr Phe Ile His
        275                 280                 285

Phe Arg Ser Leu Gly Leu Ser Gly Lys Ser Pro Tyr Ser Ser Asn Ala
    290                 295                 300

Val Gly His Val Phe Asn Leu Ile His Phe Val Gly Cys Tyr Met Gly
305                 310                 315                 320

Gln Val Arg Ser Leu Asn Ala Thr Val Ile Ala Ala Cys Ala Pro His
                325                 330                 335

Glu Met Ser Val Leu Gly Gly Tyr Leu Gly Glu Glu Phe Phe Gly Lys
            340                 345                 350

Gly Thr Phe Glu Arg Arg Phe Phe Arg Asp Glu Lys Glu Leu Gln Glu
```

```
        355                 360                 365

Tyr Glu Ala Ala Glu Leu Thr Lys Thr Asp Val Ala Leu Ala Asp Asp
    370                 375                 380

Gly Thr Val Asn Ser Asp Asp Glu Asp Tyr Phe Ser Gly Glu Thr Arg
385                 390                 395                 400

Ser Pro Glu Ala Val Tyr Thr Arg Ile Met Met Asn Gly Gly Arg Leu
                405                 410                 415

Lys Arg Ser His Ile Arg Arg Tyr Val Ser Val Ser Ser Asn His Gln
            420                 425                 430

Ala Arg Pro Asn Ser Phe Ala Glu Phe Leu Asn Lys Thr Tyr Ser Ser
        435                 440                 445

Asp Ser
    450


<210> SEQ ID NO 3
<211> LENGTH: 297
<212> TYPE: PRT
<213> ORGANISM: rabies virus

<400> SEQUENCE: 3

Met Ser Lys Ile Phe Val Asn Pro Ser Ala Ile Arg Ala Gly Leu Ala
1               5                   10                  15

Asp Leu Glu Met Ala Glu Glu Thr Val Asp Leu Ile Asn Arg Asn Ile
            20                  25                  30

Glu Asp Asn Gln Ala His Leu Gln Gly Glu Pro Ile Glu Val Asp Asn
        35                  40                  45

Leu Pro Glu Asp Met Gly Arg Leu His Leu Asp Asp Gly Lys Ser Pro
    50                  55                  60

Asn Pro Gly Glu Met Ala Lys Val Gly Glu Gly Lys Tyr Arg Glu Asp
65                  70                  75                  80

Phe Gln Met Asp Glu Gly Glu Asp Leu Ser Phe Leu Phe Gln Ser Tyr
                85                  90                  95

Leu Glu Asn Val Gly Val Gln Ile Val Arg Gln Met Arg Ser Gly Glu
            100                 105                 110

Arg Phe Leu Lys Ile Trp Ser Gln Thr Val Glu Glu Ile Ile Ser Tyr
        115                 120                 125

Val Ala Val Asn Phe Pro Asn Pro Pro Gly Lys Ser Ser Glu Asp Lys
    130                 135                 140

Ser Thr Gln Thr Thr Gly Arg Glu Leu Lys Lys Glu Thr Thr Pro Thr
145                 150                 155                 160

Pro Ser Gln Arg Glu Ser Gln Ser Ser Lys Ala Arg Met Ala Ala Gln
                165                 170                 175

Ile Ala Ser Gly Pro Pro Ala Leu Glu Trp Ser Ala Thr Asn Glu Glu
            180                 185                 190

Asp Asp Leu Ser Val Glu Ala Glu Ile Ala His Gln Ile Ala Glu Ser
        195                 200                 205

Phe Ser Lys Lys Tyr Lys Phe Pro Ser Arg Ser Ser Gly Ile Leu Leu
    210                 215                 220

Tyr Asn Phe Glu Gln Leu Lys Met Asn Leu Asp Asp Ile Val Lys Glu
225                 230                 235                 240

Ala Lys Asn Val Pro Gly Val Thr Arg Leu Ala His Asp Gly Ser Lys
                245                 250                 255

Leu Pro Leu Arg Cys Val Leu Gly Trp Val Ala Leu Ala Asn Pro Lys
            260                 265                 270
```

```
Lys Phe Gln Leu Leu Val Glu Ser Asp Lys Leu Ser Lys Ile Met Gln
        275                 280                 285

Asp Asp Leu Asn Arg Tyr Thr Ser Cys
    290                 295


<210> SEQ ID NO 4
<211> LENGTH: 202
<212> TYPE: PRT
<213> ORGANISM: rabies virus

<400> SEQUENCE: 4

Met Asn Phe Leu Arg Lys Ile Val Lys Asn Cys Arg Asp Glu Asp Thr
1               5                   10                  15

Gln Lys Pro Ser Pro Val Ser Ala Pro Leu Asp Asp Asp Asp Leu Trp
            20                  25                  30

Leu Pro Pro Pro Glu Tyr Val Pro Leu Lys Glu Leu Thr Ser Lys Lys
        35                  40                  45

Asn Met Arg Asn Phe Cys Ile Asn Gly Gly Val Lys Val Cys Ser Pro
    50                  55                  60

Asn Gly Tyr Ser Phe Arg Ile Leu Arg His Ile Leu Lys Ser Phe Asp
65                  70                  75                  80

Glu Ile Tyr Ser Gly Asn His Arg Met Ile Gly Leu Ala Lys Val Val
                85                  90                  95

Ile Gly Leu Ala Leu Ser Gly Ser Pro Val Pro Glu Gly Met Asn Trp
            100                 105                 110

Val Tyr Lys Leu Arg Arg Thr Phe Ile Phe Gln Trp Ala Asp Ser Arg
        115                 120                 125

Gly Pro Leu Glu Gly Glu Glu Leu Glu Tyr Ser Gln Glu Ile Thr Trp
    130                 135                 140

Asp Asp Asp Thr Glu Phe Val Gly Leu Gln Ile Arg Val Ile Ala Lys
145                 150                 155                 160

Gln Cys His Ile Gln Gly Arg Ile Trp Cys Ile Asn Met Asn Pro Arg
                165                 170                 175

Ala Cys Gln Leu Trp Ser Asp Met Ser Leu Gln Thr Gln Arg Ser Glu
            180                 185                 190

Glu Asp Lys Asp Ser Ser Leu Leu Leu Glu
        195                 200


<210> SEQ ID NO 5
<211> LENGTH: 524
<212> TYPE: PRT
<213> ORGANISM: rabies virus

<400> SEQUENCE: 5

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95
```

-continued

```
Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Pro
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
```

```
        515                 520


<210> SEQ ID NO 6
<211> LENGTH: 2127
<212> TYPE: PRT
<213> ORGANISM: rabies virus

<400> SEQUENCE: 6

Met Leu Asp Pro Gly Glu Val Tyr Asp Asp Pro Ile Asp Pro Ile Glu
1               5                   10                  15

Leu Glu Asp Glu Pro Arg Gly Thr Pro Thr Val Pro Asn Ile Leu Arg
            20                  25                  30

Asn Ser Asp Tyr Asn Leu Asn Ser Pro Leu Ile Glu Asp Pro Ala Arg
        35                  40                  45

Leu Met Leu Glu Trp Leu Lys Thr Gly Asn Arg Pro Tyr Arg Met Thr
    50                  55                  60

Leu Thr Asp Asn Cys Ser Arg Ser Phe Arg Val Leu Lys Asp Tyr Phe
65                  70                  75                  80

Lys Lys Val Asp Leu Gly Ser Leu Lys Val Gly Gly Met Ala Ala Gln
                85                  90                  95

Ser Met Ile Ser Leu Trp Leu Tyr Gly Ala His Ser Glu Ser Asn Arg
            100                 105                 110

Ser Arg Arg Cys Ile Thr Asp Leu Ala His Phe Tyr Ser Lys Ser Ser
        115                 120                 125

Pro Ile Glu Lys Leu Leu Asn Leu Thr Leu Gly Asn Arg Gly Leu Arg
    130                 135                 140

Ile Pro Pro Glu Gly Val Leu Ser Cys Leu Glu Arg Val Asp Tyr Asp
145                 150                 155                 160

Asn Ala Phe Gly Arg Tyr Leu Ala Asn Thr Tyr Ser Ser Tyr Leu Phe
                165                 170                 175

Phe His Val Ile Thr Leu Tyr Met Asn Ala Leu Asp Trp Asp Glu Glu
            180                 185                 190

Lys Thr Ile Leu Ala Leu Trp Lys Asp Leu Thr Ser Val Asp Ile Gly
        195                 200                 205

Lys Asp Leu Val Lys Phe Lys Asp Gln Ile Trp Gly Leu Pro Ile Val
    210                 215                 220

Thr Lys Asp Phe Val Tyr Ser Gln Ser Ser Asn Cys Leu Phe Asp Arg
225                 230                 235                 240

Asn Tyr Thr Leu Met Leu Lys Glu Leu Phe Leu Ser Arg Phe Asn Ser
                245                 250                 255

Leu Met Val Leu Leu Ser Pro Pro Glu Pro Arg Tyr Ser Asp Asp Leu
            260                 265                 270

Ile Ser Gln Leu Cys Gln Leu Tyr Ile Ala Gly Asp Gln Val Leu Ser
        275                 280                 285

Met Cys Gly Asn Ser Gly Tyr Glu Val Ile Lys Ile Leu Glu Pro Tyr
    290                 295                 300

Val Val Asn Ser Leu Val Gln Arg Ala Glu Lys Phe Arg Pro Leu Ile
305                 310                 315                 320

His Ser Leu Gly Asp Phe Pro Val Phe Ile Lys Asp Lys Val Ser Gln
                325                 330                 335

Leu Glu Glu Thr Phe Gly Pro Cys Ala Arg Arg Phe Phe Arg Ala Leu
            340                 345                 350

Asp Gln Phe Asp Asn Ile His Asp Leu Val Phe Val Tyr Gly Cys Tyr
        355                 360                 365
```

-continued

```
Arg His Trp Gly His Pro Tyr Ile Asp Tyr Arg Lys Gly Leu Ser Lys
    370                 375                 380

Leu Tyr Asp Gln Val His Ile Lys Lys Val Ile Asp Lys Ser Tyr Gln
385                 390                 395                 400

Glu Cys Leu Ala Ser Asp Leu Ala Arg Arg Ile Leu Arg Trp Gly Phe
                405                 410                 415

Asp Lys Tyr Ser Lys Trp Tyr Leu Asp Ser Arg Phe Leu Ala Arg Asp
            420                 425                 430

His Pro Leu Thr Pro Tyr Ile Lys Thr Gln Thr Trp Pro Pro Lys His
        435                 440                 445

Ile Val Asp Leu Val Gly Asp Thr Trp His Lys Leu Pro Ile Thr Gln
    450                 455                 460

Ile Phe Glu Ile Pro Glu Ser Met Asp Pro Ser Glu Ile Leu Asp Asp
465                 470                 475                 480

Lys Ser His Ser Phe Thr Arg Thr Arg Leu Ala Ser Trp Leu Ser Glu
                485                 490                 495

Asn Arg Gly Gly Pro Val Pro Ser Glu Lys Val Ile Ile Thr Ala Leu
            500                 505                 510

Ser Lys Pro Pro Val Asn Pro Arg Glu Phe Leu Arg Ser Ile Asp Leu
        515                 520                 525

Gly Gly Leu Pro Asp Glu Asp Leu Ile Ile Gly Leu Lys Pro Lys Glu
    530                 535                 540

Arg Glu Leu Lys Ile Glu Gly Arg Phe Phe Ala Leu Met Ser Trp Asn
545                 550                 555                 560

Leu Arg Leu Tyr Phe Val Ile Thr Glu Lys Leu Leu Ala Asn Tyr Ile
                565                 570                 575

Leu Pro Leu Phe Asp Ala Leu Thr Met Thr Asp Asn Leu Asn Lys Val
            580                 585                 590

Phe Lys Lys Leu Ile Asp Arg Val Thr Gly Gln Gly Leu Leu Asp Tyr
        595                 600                 605

Ser Arg Val Thr Tyr Ala Phe His Leu Asp Tyr Glu Lys Trp Asn Asn
    610                 615                 620

His Gln Arg Leu Glu Ser Thr Glu Asp Val Phe Ser Val Leu Asp Gln
625                 630                 635                 640

Val Phe Gly Leu Lys Arg Val Phe Ser Arg Thr His Glu Phe Phe Gln
                645                 650                 655

Lys Ala Trp Ile Tyr Tyr Ser Asp Arg Ser Asp Leu Ile Gly Leu Arg
            660                 665                 670

Glu Asp Gln Ile Tyr Cys Leu Asp Ala Ser Asn Gly Pro Thr Cys Trp
        675                 680                 685

Asn Gly Gln Asp Gly Gly Leu Glu Gly Leu Arg Gln Lys Gly Trp Ser
    690                 695                 700

Leu Val Ser Leu Leu Met Ile Asp Arg Glu Ser Gln Ile Arg Asn Thr
705                 710                 715                 720

Arg Thr Lys Ile Leu Ala Gln Gly Asp Asn Gln Val Leu Cys Pro Thr
                725                 730                 735

Tyr Met Leu Ser Pro Gly Leu Ser Gln Glu Gly Leu Leu Tyr Glu Leu
            740                 745                 750

Glu Arg Ile Ser Arg Asn Ala Leu Ser Ile Tyr Arg Ala Val Glu Glu
        755                 760                 765

Gly Ala Ser Lys Leu Gly Leu Ile Thr Lys Lys Glu Glu Thr Met Cys
    770                 775                 780

Ser Tyr Asp Phe Leu Ile Tyr Gly Lys Thr Pro Leu Phe Arg Gly Asn
```

-continued

```
785                 790                 795                 800

Ile Leu Val Pro Glu Ser Lys Arg Trp Ala Arg Val Ser Cys Val Ser
                805                 810                 815

Asn Asp Gln Ile Val Asn Leu Ala Asn Ile Met Ser Thr Val Ser Thr
            820                 825                 830

Asn Ala Leu Thr Val Ala Gln His Ser Gln Ser Leu Ile Lys Pro Met
        835                 840                 845

Gly Asp Phe Leu Leu Met Ser Val Gln Ala Val Phe His Tyr Leu Leu
    850                 855                 860

Phe Ser Pro Ile Leu Lys Gly Arg Val Tyr Lys Ile Leu Ser Ala Glu
865                 870                 875                 880

Gly Asp Ser Phe Leu Leu Ala Met Ser Arg Ile Ile Tyr Leu Asp Pro
                885                 890                 895

Ser Leu Gly Gly Val Ser Gly Met Ser Leu Gly Arg Phe His Ile Arg
            900                 905                 910

Gln Phe Ser Asp Pro Val Ser Glu Gly Leu Ser Phe Trp Arg Glu Ile
        915                 920                 925

Trp Leu Ser Ser His Glu Ser Trp Val His Ala Leu Cys Gln Glu Ala
    930                 935                 940

Gly Asn Pro Asp Leu Gly Glu Arg Thr Leu Glu Ser Phe Thr Arg Leu
945                 950                 955                 960

Leu Glu Asp Pro Thr Thr Leu Asn Ile Arg Gly Gly Ala Ser Pro Thr
                965                 970                 975

Ile Leu Leu Lys Asp Ala Ile Arg Lys Ala Leu Tyr Asp Glu Val Asp
            980                 985                 990

Lys Val Glu Asn Ser Glu Phe Arg  Glu Ala Ile Leu Leu  Ser Lys Thr
        995                 1000                1005

His Arg  Asp Asn Phe Ile Leu  Phe Leu Thr Ser Val  Glu Pro Leu
    1010                1015                1020

Phe Pro  Arg Phe Leu Ser Glu  Leu Phe Ser Ser Ser  Phe Leu Gly
    1025                1030                1035

Ile Pro  Glu Ser Ile Ile Gly  Leu Ile Gln Asn Ser  Arg Thr Ile
    1040                1045                1050

Arg Arg  Gln Phe Arg Lys Ser  Leu Ser Lys Thr Leu  Glu Glu Ser
    1055                1060                1065

Phe Tyr  Asn Ser Glu Ile His  Gly Ile Ser Arg Met  Thr Gln Thr
    1070                1075                1080

Pro Gln  Arg Val Gly Gly Val  Trp Pro Cys Ser Ser  Glu Arg Ala
    1085                1090                1095

Asp Leu  Leu Arg Glu Ile Ser  Trp Gly Arg Lys Val  Val Gly Thr
    1100                1105                1110

Thr Val  Pro His Pro Ser Glu  Met Leu Gly Leu Leu  Pro Lys Ser
    1115                1120                1125

Ser Ile  Ser Cys Thr Cys Gly  Ala Thr Gly Gly Gly  Asn Pro Arg
    1130                1135                1140

Val Ser  Val Ser Val Leu Pro  Ser Phe Asp Gln Ser  Phe Phe Ser
    1145                1150                1155

Arg Gly  Pro Leu Lys Gly Tyr  Leu Gly Ser Ser Thr  Ser Met Ser
    1160                1165                1170

Thr Gln  Leu Phe His Ala Trp  Glu Lys Val Thr Asn  Val His Val
    1175                1180                1185

Val Lys  Arg Ala Leu Ser Leu  Lys Glu Ser Ile Asn  Trp Phe Ile
    1190                1195                1200
```

-continued

```
Thr Arg  Asp Ser Asn Leu Ala  Gln Ala Leu Ile Arg  Asn Ile Met
    1205                 1210                 1215

Ser Leu  Thr Gly Pro Asp Phe  Pro Leu Glu Glu Ala  Pro Val Phe
    1220                 1225                 1230

Lys Arg  Thr Gly Ser Ala Leu  His Arg Phe Lys Ser  Ala Arg Tyr
    1235                 1240                 1245

Ser Glu  Gly Gly Tyr Ser Ser  Val Cys Pro Asn Leu  Leu Ser His
    1250                 1255                 1260

Ile Ser  Val Ser Thr Asp Thr  Met Ser Asp Leu Thr  Gln Asp Gly
    1265                 1270                 1275

Lys Asn  Tyr Asp Phe Met Phe  Gln Pro Leu Met Leu  Tyr Ala Gln
    1280                 1285                 1290

Thr Trp  Thr Ser Glu Leu Val  Gln Arg Asp Thr Arg  Leu Arg Asp
    1295                 1300                 1305

Ser Thr  Phe His Trp His Leu  Arg Cys Asn Arg Cys  Val Arg Pro
    1310                 1315                 1320

Ile Asp  Asp Val Thr Leu Glu  Thr Ser Gln Ile Phe  Glu Phe Pro
    1325                 1330                 1335

Asp Val  Ser Lys Arg Ile Ser  Arg Met Val Ser Gly  Ala Val Pro
    1340                 1345                 1350

His Phe  Gln Arg Leu Pro Asp  Ile Arg Leu Arg Pro  Gly Asp Phe
    1355                 1360                 1365

Glu Ser  Leu Ser Gly Arg Glu  Lys Ser His His Ile  Gly Ser Ala
    1370                 1375                 1380

Gln Gly  Leu Leu Tyr Ser Ile  Leu Val Ala Ile His  Asp Ser Gly
    1385                 1390                 1395

Tyr Asn  Asp Gly Thr Ile Phe  Pro Ala Asn Ile Tyr  Gly Lys Val
    1400                 1405                 1410

Ser Pro  Arg Asp Tyr Leu Arg  Gly Leu Ala Arg Gly  Val Leu Ile
    1415                 1420                 1425

Gly Ser  Ser Ile Cys Phe Leu  Thr Arg Met Thr Asn  Ile Asn Ile
    1430                 1435                 1440

Asn Arg  Pro Leu Glu Leu Ile  Ser Gly Val Ile Ser  Tyr Ile Leu
    1445                 1450                 1455

Leu Arg  Leu Asp Asn His Pro  Ser Leu Tyr Ile Met  Leu Arg Glu
    1460                 1465                 1470

Pro Ser  Leu Arg Gly Glu Ile  Phe Ser Ile Pro Gln  Lys Ile Pro
    1475                 1480                 1485

Ala Ala  Tyr Pro Thr Thr Met  Lys Glu Gly Asn Arg  Ser Ile Leu
    1490                 1495                 1500

Cys Tyr  Leu Gln His Val Leu  Arg Tyr Glu Arg Glu  Ile Ile Thr
    1505                 1510                 1515

Ala Ser  Pro Glu Asn Asp Trp  Leu Trp Ile Phe Ser  Asp Phe Arg
    1520                 1525                 1530

Ser Ala  Lys Met Thr Tyr Leu  Thr Leu Ile Thr Tyr  Gln Ser His
    1535                 1540                 1545

Leu Leu  Leu Gln Arg Val Glu  Arg Asn Leu Ser Lys  Ser Met Arg
    1550                 1555                 1560

Asp Asn  Leu Arg Gln Leu Ser  Ser Leu Met Arg Gln  Val Leu Gly
    1565                 1570                 1575

Gly His  Gly Glu Asp Thr Leu  Glu Ser Asp Asp Asn  Ile Gln Arg
    1580                 1585                 1590
```

```
Leu Leu  Lys Asp Ser Leu Arg  Arg Thr Arg Trp Val  Asp Gln Glu
    1595                 1600                 1605

Val Arg  His Ala Ala Arg Thr  Met Thr Gly Asp Tyr  Ser Pro Asn
    1610                 1615                 1620

Lys Lys  Val Ser Arg Lys Val  Gly Cys Ser Glu Trp  Val Cys Ser
    1625                 1630                 1635

Ala Gln  Gln Val Ala Val Ser  Thr Ser Ala Asn Pro  Ala Pro Val
    1640                 1645                 1650

Ser Glu  Leu Asp Ile Arg Ala  Leu Ser Lys Arg Phe  Gln Asn Pro
    1655                 1660                 1665

Leu Ile  Ser Gly Leu Arg Val  Val Gln Trp Ala Thr  Gly Ala His
    1670                 1675                 1680

Tyr Lys  Leu Lys Pro Ile Leu  Asp Asp Leu Asn Val  Phe Pro Ser
    1685                 1690                 1695

Leu Cys  Leu Val Val Gly Asp  Gly Ser Gly Gly Ile  Ser Arg Ala
    1700                 1705                 1710

Val Leu  Asn Met Phe Pro Asp  Ala Lys Leu Val Phe  Asn Ser Leu
    1715                 1720                 1725

Leu Glu  Val Asn Asp Leu Met  Ala Ser Gly Thr His  Pro Leu Pro
    1730                 1735                 1740

Pro Ser  Ala Ile Met Arg Gly  Gly Asn Gly Ile Val  Ser Arg Val
    1745                 1750                 1755

Ile Asp  Phe Asp Ser Ile Trp  Glu Lys Pro Ser Asp  Leu Arg Asn
    1760                 1765                 1770

Leu Ala  Thr Trp Lys Tyr Phe  Gln Ser Val Gln Lys  Gln Val Asn
    1775                 1780                 1785

Met Ser  Tyr Asp Leu Ile Ile  Cys Asp Ala Glu Val  Thr Asp Ile
    1790                 1795                 1800

Ala Ser  Ile Asn Arg Ile Thr  Leu Leu Met Ser Asp  Phe Ala Leu
    1805                 1810                 1815

Ser Ile  Asp Gly Pro Leu Tyr  Leu Val Phe Lys Thr  Tyr Gly Thr
    1820                 1825                 1830

Met Leu  Val Asn Pro Asn Tyr  Lys Ala Ile Gln His  Leu Ser Arg
    1835                 1840                 1845

Ala Phe  Pro Ser Val Thr Gly  Phe Ile Thr Gln Val  Thr Ser Ser
    1850                 1855                 1860

Phe Ser  Ser Glu Leu Tyr Leu  Arg Phe Ser Lys Arg  Gly Lys Leu
    1865                 1870                 1875

Phe Arg  Asp Ala Glu Tyr Leu  Thr Ser Ser Thr Leu  Arg Glu Met
    1880                 1885                 1890

Ser Leu  Val Leu Phe Asn Cys  Ser Ser Pro Lys Ser  Glu Met Gln
    1895                 1900                 1905

Arg Ala  Arg Ser Leu Asn Tyr  Gln Asp Leu Val Arg  Gly Phe Pro
    1910                 1915                 1920

Glu Glu  Ile Ile Ser Asn Pro  Tyr Asn Glu Met Ile  Ile Thr Leu
    1925                 1930                 1935

Ile Asp  Ser Asp Val Glu Ser  Phe Leu Val His Lys  Met Val Asp
    1940                 1945                 1950

Asp Leu  Glu Leu Gln Arg Gly  Thr Leu Ser Lys Val  Ala Ile Ile
    1955                 1960                 1965

Ile Ala  Ile Met Ile Val Phe  Ser Asn Arg Val Phe  Asn Val Ser
    1970                 1975                 1980

Lys Pro  Leu Thr Asp Pro Leu  Phe Tyr Pro Pro Ser  Asp Pro Lys
```

```
    1985                1990                1995

Ile Leu  Arg His Phe Asn Ile  Cys Arg Ser Thr Met  Met Tyr Leu
    2000                2005                2010

Ser Thr  Ala Leu Gly Asp Val  Pro Ser Phe Ala Arg  Leu His Asp
    2015                2020                2025

Leu Tyr  Asn Arg Pro Ile Thr  Tyr Tyr Phe Arg Lys  Gln Phe Ile
    2030                2035                2040

Arg Gly  Asn Val Tyr Leu Ser  Trp Ser Trp Ser Asn  Asp Thr Ser
    2045                2050                2055

Val Phe  Lys Arg Val Ala Cys  Asn Ser Ser Leu Ser  Leu Ser Ser
    2060                2065                2070

His Trp  Ile Arg Leu Ile Tyr  Lys Ile Val Lys Ala  Thr Arg Leu
    2075                2080                2085

Val Gly  Ser Ile Lys Asp Leu  Ser Arg Glu Val Glu  Arg His Leu
    2090                2095                2100

His Arg  Tyr Asn Arg Trp Ile  Thr Leu Glu Asp Ile  Arg Ser Arg
    2105                2110                2115

Ser Ser  Leu Leu Asp Tyr Ser  Cys Leu
    2120                2125

<210> SEQ ID NO 7
<211> LENGTH: 11930
<212> TYPE: DNA
<213> ORGANISM: artificial sequence
<220> FEATURE:
<223> OTHER INFORMATION: Recombinant ERA rabies virus genome
<220> FEATURE:
<221> NAME/KEY: misc_feature
<222> LOCATION: (1)..(58)
<223> OTHER INFORMATION: Leader region
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (4963)..(5361)
<223> OTHER INFORMATION: Psi region
<220> FEATURE:
<221> NAME/KEY: misc_feature
<222> LOCATION: (5416)..(11796)
<220> FEATURE:
<221> NAME/KEY: misc_feature
<222> LOCATION: (11861)..(11930)
<223> OTHER INFORMATION: Trailer region

<400> SEQUENCE: 7
acgcttaaca accagatcaa agaaaaaaca gacattgtca attgcaaagc aaaaatgtaa      60
cacccctaca atggatgccg acaagattgt attcaaagtc aataatcagg tggtctcttt     120
gaagcctgag attatcgtgg atcaacatga gtacaagtac cctgccatca aagatttgaa     180
aaagccctgt ataaccctag gaaaggctcc cgatttaaat aaagcataca agtcagtttt     240
gtcaggcatg agcgccgcca aacttgatcc tgacgatgta tgttcctatt tggcagcggc     300
aatgcagttt tttgagggga catgtccgga agactggacc agctatggaa tcgtgattgc     360
acgaaaagga gataagatca ccccaggttc tctggtggag ataaaacgta ctgatgtaga     420
```

-continued

```
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagatttttg agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttctcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aacaacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaagt ggacaatctc cctgaggata tggggcgact   1680
tcacctggat gatggaaaat cgcccaaccc tggtgagatg gccaaggtgg gagaaggcaa   1740
gtatcgagag gactttcaga tggatgaagg agaggatctt agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aaccctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaaacaggc aacaccactg ataaaatgaa ctttctacgt aagatagtga   2520
aaaattgcag ggacgaggac actcaaaaac cctctcccgt gtcagcccct ctggatgacg   2580
atgacttgtg gcttccaccc cctgaatacg tcccgctgaa agaacttaca agcaagaaga   2640
acatgaggaa cttttgtatc aacggagggg ttaaagtgtg tagcccgaat ggttactcgt   2700
tcaggatcct gcggcacatt ctgaaatcat tcgacgagat atattctggg aatcatagga   2760
```

-continued

```
tgatcgggtt agccaaagta gttattggac tggctttgtc aggatctcca gtccctgagg   2820
gcatgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagaatct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caaccccttgg  3180
gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagactcaa ggaaagatgg ttcctcaggc tctcctgttt gtaccccttc tggtttttcc   3360
attgtgtttt gggaaattcc ctatttacac gataccagac aagcttggtc cctggagccc   3420
gattgacata catcacctca gctgcccaaa caatttggta gtggaggacg aaggatgcac   3480
caacctgtca gggttctcct acatggaact taaagttgga tacatcttag ccataaaaat   3540
gaacgggttc acttgcacag gcgttgtgac ggaggctgaa acctatacta acttcgttgg   3600
ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cactggcttc gaactgtaaa aaccaccaag gagtctctcg ttatcatatc   3780
tccaagtgtg gcagatttgg acccatatga cagatccctt cactcgaggg tcttccctag   3840
cgggaagtgc tcaggagtag cggtgtcttc tacctactgc tccactaacc acgattacac   3900
catttggatg cccgagaatc cgagactagg gatgtcttgt gacattttta ccaatagtag   3960
ggggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtcgcga tgcaaacatc aaatgaaacc aaatggtgcc cccccgatca   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtcccagtc atttaagaaa acttgtccct gggtttggaa aagcatatac   4320
catattcaac aagaccttga tggaagccga tgctcactac aagtcagtca gaacttggaa   4380
tgagatcctc ccttcaaaag ggtgtttaag agttgggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tccccccttgt  4560
gcaccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataatttt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgtg aggactggcc gtcctttcaa cgatccaagt   4920
cctgaagatc acctcccctt ggggggttct ttttgaaaaa aacctgggtt caatagtcct   4980
cctcgaactc catgcaactg ggtagattca agagtcatga gattttcatt aatcctctca   5040
gttgatcaag caagatcatg tagattctca taatagggga gatcttctag cagtttcagt   5100
gactaacggt actttcattc tccaggaact gacaccaaca gttgtagaca aaccacgggg   5160
```

```
tgtctcgggt gactctgtgc ttgggcacag acaaaggtca tggtgtgttc catgatagcg   5220
gactcaggat gagttaattg agagaggcag tcttcctccc gtgaaggaca taagcagtag   5280
ctcacaatca tcccgcgtct cagcaaagtg tgcataatta taaagtgctg ggtcatctaa   5340
gcttttcagt cgagaaaaaa acattagatc agaagaacaa ctggcaacac ttctcaacct   5400
gagacctact tcaagatgct cgatcctgga gaggtctatg atgaccctat tgacccaatc   5460
gagttagagg atgaacccag aggaaccccc actgtcccca acatcttgag gaactctgac   5520
tacaatctca actctccttt gatagaagat cctgctagac taatgttaga atggttaaaa   5580
acagggaata gaccttatcg gatgactcta acagacaatt gctccaggtc tttcagagtt   5640
ttgaaagatt atttcaagaa ggtagatttg ggttctctca aggtgggcgg aatggctgca   5700
cagtcaatga tttctctctg gttatatggt gcccactctg aatccaacag gagccggaga   5760
tgtataacag acttggccca tttctattcc aagtcgtccc ccatagagaa gctgttgaat   5820
ctcacgctag gaaatagagg gctgagaatc cccccagagg gagtgttaag ttgccttgag   5880
agggttgatt atgataatgc atttggaagg tatcttgcca acacgtattc ctcttacttg   5940
ttcttccatg taatcacctt atacatgaac gccctagact gggatgaaga aaagaccatc   6000
ctagcattat ggaaagattt aacctcagtg gacatcggga aggacttggt aaagttcaaa   6060
gaccaaatat ggggactgcc gatcgtgaca aaggactttg tttactccca aagttccaat   6120
tgtctttttg acagaaacta cacacttatg ctaaaagaac ttttcttgtc tcgcttcaac   6180
tccttaatgg tcttgctctc tcccccagag ccccgatact cagatgactt gatatctcaa   6240
ctatgccagc tgtacattgc tggggatcaa gtcttgtcta tgtgtggaaa ctccggctat   6300
gaagtcatca aaatattgga gccatatgtc gtgaatagtt tagtccagag agcagaaaag   6360
tttaggcctc tcattcattc cttgggagac tttcctgtat ttataaaaga caaggtaagt   6420
caacttgaag agacgttcgg tccctgtgca agaaggttct ttagggctct ggatcaattc   6480
gacaacatac atgacttggt tttgtgtat ggctgttaca ggcattgggg gcacccatat   6540
atagattatc gaaagggtct gtcaaaacta tatgatcagg ttcacattaa aaaagtgata   6600
gataagtcct accaggagtg cttagcaagc gacctagcca ggaggatcct tagatggggt   6660
tttgataagt actccaagtg gtatctggat tcaagattcc tagcccgaga ccaccccttg   6720
actccctata tcaaaaccca aacatggcca cccaaacata ttgtagactt ggtgggggat   6780
acatggcaca agctcccgat cacgcagatc tttgagattc ctgaatcaat ggatccgtca   6840
gaaatattgg atgacaaatc acattctttc accagaacga gactagcttc ttggctgtca   6900
gaaaaccgag gggacctgt tcctagcgaa aaagttatta tcacggccct gtctaagccg   6960
cctgtcaatc cccgagagtt tctgaggtct atagacctcg gaggattgcc agatgaagac   7020
ttgataattg gcctcaagcc aaaggaacgg gaattgaaga ttgaaggtcg attctttgct   7080
ctaatgtcat ggaatctaag attgtatttt gtcatcactg aaaaactctt ggccaactac   7140
atcttgccac tttttgacgc gctgactatg acagacaacc tgaacaaggt gtttaaaaag   7200
ctgatcgaca gggtcaccgg gcaagggctt ttggactatt caagggtcac atatgcattt   7260
cacctggact atgaaaagtg gaacaaccat caaagattag agtcaacaga ggatgtattt   7320
tctgtcctag atcaagtgtt tggattgaag agagtgtttt ctagaacaca cgagtttttt   7380
caaaaggcct ggatctatta ttcagacaga tcagacctca tcgggttacg ggaggatcaa   7440
atatactgct tagatgcgtc caacggccca acctgttgga atggccagga tggcgggcta   7500
```

-continued

```
gaaggcttac ggcagaaggg ctggagtcta gtcagcttat tgatgataga tagagaatct   7560
caaatcagga acacaagaac caaaatacta gctcaaggag acaaccaggt tttatgtccg   7620
acatatatgt tgtcgccagg gctatctcaa gaggggctcc tctatgaatt ggagagaata   7680
tcaaggaatg cactttcgat atacagagcc gtcgaggaag gggcatctaa gctagggctg   7740
atcaccaaga aagaagagac catgtgtagt tatgacttcc tcatctatgg aaaaacccct   7800
ttgtttagag gtaacatatt ggtgcctgag tccaaaagat gggccagagt ctcttgcgtc   7860
tctaatgacc aaatagtcaa cctcgccaat ataatgtcga cagtgtccac caatgcgcta   7920
acagtggcac aacactctca atctttgatc aaaccgatgg gggattttct gctcatgtca   7980
gtacaggcag tctttcacta cctgctattt agcccaatct taaagggaag agtttacaag   8040
attctgagcg ctgaagggga tagctttctc ctagccatgt caaggataat ctatctagat   8100
ccttctttgg gaggggtatc tggaatgtcc ctcggaagat tccatatacg acagttctca   8160
gaccctgtct ctgaagggtt atccttctgg agagagatct ggttaagctc ccacgagtcc   8220
tgggttcacg cgttgtgtca agaggctgga aacccagatc ttggagagag aacactcgag   8280
agcttcactc gccttctaga agatcctacc accttaaata tcagaggagg ggccagtcct   8340
accattctac tcaaggatgc aatcagaaag gctttatatg acgaggtgga caaggtggag   8400
aattcagagt ttcgagaggc aatcctgttg tccaagaccc atagagataa ttttatactc   8460
ttcttaacat ctgttgagcc tctgtttcct cgatttctca gtgagctatt cagttcgtct   8520
tttttgggaa tccccgagtc aatcattgga ttgatacaaa actcccgaac gataagaagg   8580
cagtttagaa agagtctctc aaaaacttta gaagaatcct tctacaactc agagatccac   8640
gggattagtc ggatgaccca gacacctcag agggttgggg gggtgtggcc ttgctcttca   8700
gagagggcag atctacttag ggagatctct tggggaagaa aagtggtagg cacgacagtt   8760
cctcaccctt ctgagatgtt ggggttactt cccaagtcct ctatttcttg cacttgtgga   8820
gcaacaggag gaggcaatcc tagagtttct gtatcagtac tcccgtcctt tgatcagtca   8880
ttttttttcac gaggcccccct aaaggggtac ttgggctcgt ccacctctat gtcgacccag   8940
ctattccatg catgggaaaa agtcactaat gttcatgtgg tgaagagagc tctatcgtta   9000
aaagaatcta taaactggtt cattactaga gattccaact tggctcaagc tctaattagg   9060
aacattatgt ctctgacagg ccctgatttc cctctagagg aggcccctgt cttcaaaagg   9120
acggggtcag ccttgcatag gttcaagtct gccagataca gcgaaggagg gtattcttct   9180
gtctgcccga acctcctctc tcatatttct gttagtacag acaccatgtc tgatttgacc   9240
caagacggga agaactacga tttcatgttc cagccattga tgctttatgc acagacatgg   9300
acatcagagc tggtacagag agacacaagg ctaagagact ctacgtttca ttggcacctc   9360
cgatgcaaca ggtgtgtgag acccattgac gacgtgaccc tggagacctc tcagatcttc   9420
gagtttccgg atgtgtcgaa aagaatatcc agaatggttt ctggggctgt gcctcacttc   9480
cagaggcttc ccgatatccg tctgagacca ggagattttg aatctctaag cggtagagaa   9540
aagtctcacc atatcggatc agctcagggg ctcttatact caatcttagt ggcaattcac   9600
gactcaggat acaatgatgg aaccatcttc cctgccaaca tatacggcaa ggtttcccct   9660
agagactatt tgagagggct cgcaagggga gtattgatag gatcctcgat ttgcttcttg   9720
acaagaatga caaatatcaa tattaataga cctcttgaat tgatctcagg ggtaatctca   9780
tatattctcc tgaggctaga taaccatccc tccttgtaca taatgctcag agaaccgtct   9840
cttagaggag agatattttc tatccctcag aaaatccccg ccgcttatcc aaccactatg   9900
```

```
aaagaaggca acagatcaat cttgtgttat ctccaacatg tgctacgcta tgagcgagag   9960
ataatcacgg cgtctccaga gaatgactgg ctatggatct tttcagactt tagaagtgcc  10020
aaaatgacgt acctaaccct cattacttac cagtctcatc ttctactcca gagggttgag  10080
agaaacctat ctaagagtat gagagataac ctgcgacaat tgagttcctt gatgaggcag  10140
gtgctgggcg ggcacggaga agatacctta gagtcagacg acaacattca acgactgcta  10200
aaagactctt tacgaaggac aagatgggtg gatcaagagg tgcgccatgc agctagaacc  10260
atgactggag attacagccc caacaagaag gtgtcccgta aggtaggatg ttcagaatgg  10320
gtctgctctg ctcaacaggt tgcagtctct acctcagcaa acccggcccc tgtctcggag  10380
cttgacataa gggccctctc taagaggttc cagaaccctt tgatctcggg cttgagagtg  10440
gttcagtggg caaccggtgc tcattataag cttaagccta ttctagatga tctcaatgtt  10500
ttcccctctc tctgccttgt agttggggac gggtcagggg ggatatcaag ggcagtcctc  10560
aacatgtttc cagatgccaa gcttgtgttc aacagtctct tagaggtgaa tgacctgatg  10620
gcttccggaa cacatccact gcctccttca gcaatcatga ggggaggaaa tggtatcgtc  10680
tccagagtga tagattttga ctcaatctgg gaaaaaccgt ccgacttgag aaacttggca  10740
acctggaaat acttccagtc agtccaaaag caggtcaaca tgtcctatga cctcattatt  10800
tgcgatgcag aagttactga cattgcatct atcaaccgga taaccctgtt aatgtccgat  10860
tttgcattgt ctatagatgg accactctat ttggtcttca aaacttatgg gactatgcta  10920
gtaaatccaa actacaaggc tattcaacac ctgtcaagag cgttcccctc ggtcacaggg  10980
tttatcaccc aagtaacttc gtctttttca tctgagctct acctccgatt ctccaaacga  11040
gggaagcttt tcagagatgc tgagtacttg acctcttcca cccttcgaga aatgagcctt  11100
gtgttattca attgtagcag ccccaagagt gagatgcaga gagctcgttc cttgaactat  11160
caggatcttg tgagaggatt tcctgaagaa atcatatcaa atccttacaa tgagatgatc  11220
ataactctga ttgacagtga tgtagaatct tttctagtcc acaagatggt tgatgatctt  11280
gagttacaga ggggaactct gtctaaagtg gctatcatta tagccatcat gatagttttc  11340
tccaacagag tcttcaacgt ttccaaaccc ctaactgacc ccttgttcta tccaccgtct  11400
gatcccaaaa tcctgaggca cttcaacata tgtcgcagta ctatgatgta tctatctact  11460
gctttaggtg acgtccctag cttcgcaaga cttcacgacc tgtataacag acctataact  11520
tattacttca gaaagcaatt cattcgaggg aacgtttatc tatcttggag ttggtccaac  11580
gacacctcag tgttcaaaag ggtagcctgt aattctagcc tgagtctgtc atctcactgg  11640
atcaggttga tttacaagat agtgaaggct accagactcg ttggcagcat caaggatcta  11700
tccagagaag tggaaagaca ccttcatagg tacaacaggt ggatcaccct agaggatatc  11760
agatctagat catccctact agactacagt tgcctgtgaa ccggatactc ctggaagcct  11820
gcccatgcta agactcttgt gtgatgtatc ttgaaaaaaa caagatccta aatctgaacc  11880
tttggttgtt tgattgtttt tctcattttt gttgtttatt tgttaagcgt             11930
```

<210> SEQ ID NO 8
<211> LENGTH: 11930
<212> TYPE: DNA
<213> ORGANISM: artificial sequence
<220> FEATURE:
<223> OTHER INFORMATION: Recombinant ERAg3 rabies virus genome
<220> FEATURE:
<221> NAME/KEY: misc_feature
<222> LOCATION: (71)..(1420)

-continued

<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (5416)..(11796)

<400> SEQUENCE: 8

```
acgcttaaca accagatcaa agaaaaaaca gacattgtca attgcaaagc aaaaatgtaa     60

cacccctaca atggatgccg acaagattgt attcaaagtc aataatcagg tggtctcttt    120

gaagcctgag attatcgtgg atcaacatga gtacaagtac cctgccatca aagatttgaa    180

aaagccctgt ataaccctag gaaaggctcc cgatttaaat aaagcataca agtcagtttt    240

gtcaggcatg agcgccgcca aacttgatcc tgacgatgta tgttcctatt tggcagcggc    300

aatgcagttt tttgagggga catgtccgga agactggacc agctatggaa tcgtgattgc    360

acgaaaagga gataagatca ccccaggttc tctggtggag ataaaacgta ctgatgtaga    420

agggaattgg gctctgacag gaggcatgga actgacaaga gaccccactg tccctgagca    480

tgcgtcctta gtcggtcttc tcttgagtct gtataggttg agcaaaatat ccgggcaaaa    540

cactggtaac tataagacaa acattgcaga caggatagag cagatttttg agacagcccc    600

ttttgttaaa atcgtggaac accatactct aatgacaact cacaaaatgt gtgctaattg    660

gagtactata ccaaacttca gatttttggc cggaacctat gacatgtttt tctcccggat    720

tgagcatcta tattcagcaa tcagagtggg cacagttgtc actgcttatg aagactgttc    780

aggactggta tcatttactg ggttcataaa acaaatcaat ctcaccgcta gagaggcaat    840

actatatttc ttccacaaga actttgagga agagataaga agaatgtttg agccagggca    900

ggagacagct gttcctcact cttatttcat ccacttccgt tcactaggct tgagtgggaa    960

atctccttat tcatcaaatg ctgttggtca cgtgttcaat ctcattcact ttgtaggatg   1020

ctatatgggt caagtcagat ccctaaatgc aacggttatt gctgcatgtg ctcctcatga   1080

aatgtctgtt ctagggggct atctgggaga ggaattcttc gggaaaggga catttgaaag   1140

aagattcttc agagatgaga aagaacttca agaatacgag gcggctgaac tgacaaagac   1200

tgacgtagca ctggcagatg atggaactgt caactctgac gacgaggact acttctcagg   1260

tgaaaccaga agtccggagg ctgtttatac tcgaatcatg atgaatggag gtcgactaaa   1320

gagatctcac atacggagat atgtctcagt cagttccaat catcaagccc gtccaaactc   1380

attcgccgag tttctaaaca agacatattc gagtgactca taagaagttg aacaacaaaa   1440

tgccggaaat ctacggattg tgtatatcca tcatgaaaaa aactaacacc cctcctttcg   1500

aaccatccca aacatgagca agatctttgt caatcctagt gctattagag ccggtctggc   1560

cgatcttgag atggctgaag aaactgttga tctgatcaat agaaatatcg aagacaatca   1620

ggctcatctc caaggggaac ccatagaagt ggacaatctc cctgaggata tggggcgact   1680

tcacctggat gatggaaaat cgcccaaccc tggtgagatg gccaaggtgg gagaaggcaa   1740

gtatcgagag gactttcaga tggatgaagg agaggatctt agcttcctgt tccagtcata   1800

cctggaaaat gttggagtcc aaatagtcag acaaatgagg tcaggagaga gatttctcaa   1860

gatatggtca cagaccgtag aagagattat atcctatgtc gcggtcaact ttcccaaccc   1920
```

-continued

```
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aaccctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaaacaggc aacaccactg ataaaatgaa ctttctacgt aagatagtga   2520
aaaattgcag ggacgaggac actcaaaaac cctctcccgt gtcagcccct ctggatgacg   2580
atgacttgtg gcttccaccc cctgaatacg tcccgctgaa agaacttaca agcaagaaga   2640
acatgaggaa cttttgtatc aacggagggg ttaaagtgtg tagcccgaat ggttactcgt   2700
tcaggatcct gcggcacatt ctgaaatcat tcgacgagat atattctggg aatcatagga   2760
tgatcgggtt agccaaagta gttattggac tggctttgtc aggatctcca gtccctgagg   2820
gcatgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagaatct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagactcaa ggaaagatgg ttcctcaggc tctcctgttt gtaccccttc tggtttttcc   3360
attgtgtttt gggaaattcc ctatttacac gataccagac aagcttggtc cctggagccc   3420
gattgacata catcacctca gctgcccaaa caatttggta gtggaggacg aaggatgcac   3480
caacctgtca gggttctcct acatggaact taaagttgga tacatcttag ccataaaaat   3540
gaacgggttc acttgcacag gcgttgtgac ggaggctgaa acctatacta acttcgttgg   3600
ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cactggcttc gaactgtaaa aaccaccaag gagtctctcg ttatcatatc   3780
tccaagtgtg gcagatttgg acccatatga cagatccctt cactcgaggg tcttccctag   3840
cgggaagtgc tcaggagtag cggtgtcttc tacctactgc tccactaacc acgattacac   3900
catttggatg cccgagaatc cgagactagg gatgtcttgt gacattttta ccaatagtag   3960
ggggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtcgcga tgcaaacatc aaatgaaacc aaatggtgcc cccccgatca   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtcccagtc atttaagaaa acttgtccct gggtttggaa aagcatatac   4320
```

-continued

```
catattcaac aagaccttga tggaagccga tgctcactac aagtcagtcg agacttggaa   4380
tgagatcctc ccttcaaaag ggtgtttaag agttgggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tccccccttgt   4560
gcaccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataatttt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgtg aggactggcc gtcctttcaa ctatccaagt   4920
cctgaagatc acctcccctt ggggggttct ttttgaaaaa aacctgggtt caatagtcct   4980
cctcgaactc catgcaactg ggtagattca agagtcatga gattttcatt aatcctctca   5040
gttgatcaag caagatcatg tagattctca taatagggga gatcttctag cagtttcagt   5100
gactaacggt actttcattc tccaggaact gacaccaaca gttgtagaca aaccacgggg   5160
tgtctcgggt gactctgtgc ttgggcacag acaaaggtca tggtgtgttc catgatagcg   5220
gactcaggat gagttaattg agagaggcag tcttcctccc gtgaaggaca taagcagtag   5280
ctcacaatca tcccgcgtct cagcaaagtg tgcataatta taaagtgctg ggtcatctaa   5340
gcttttcagt cgagaaaaaa acattagatc agaagaacaa ctggcaacac ttctcaacct   5400
gagacctact tcaagatgct cgatcctgga gaggtctatg atgaccctat tgacccaatc   5460
gagttagagg atgaacccag aggaaccccc actgtcccca acatcttgag gaactctgac   5520
tacaatctca actctccttt gatagaagat cctgctagac taatgttaga atggttaaaa   5580
acagggaata gaccttatcg gatgactcta acagacaatt gctccaggtc tttcagagtt   5640
ttgaaagatt atttcaagaa ggtagatttg ggttctctca aggtgggcgg aatggctgca   5700
cagtcaatga tttctctctg gttatatggt gcccactctg aatccaacag gagccggaga   5760
tgtataacag acttggccca tttctattcc aagtcgtccc ccatagagaa gctgttgaat   5820
ctcacgctag gaaatagagg gctgagaatc cccccagagg gagtgttaag ttgccttgag   5880
agggttgatt atgataatgc atttggaagg tatcttgcca acacgtattc ctcttacttg   5940
ttcttccatg taatcacctt atacatgaac gccctagact gggatgaaga aaagaccatc   6000
ctagcattat ggaaagattt aacctcagtg gacatcggga aggacttggt aaagttcaaa   6060
gaccaaatat ggggactgcc gatcgtgaca aaggactttg tttactccca aagttccaat   6120
tgtctttttg acagaaacta cacacttatg ctaaaagaac ttttcttgtc tcgcttcaac   6180
tccttaatgg tcttgctctc tcccccagag ccccgatact cagatgactt gatatctcaa   6240
ctatgccagc tgtacattgc tggggatcaa gtcttgtcta tgtgtggaaa ctccggctat   6300
gaagtcatca aaatattgga gccatatgtc gtgaatagtt tagtccagag agcagaaaag   6360
tttaggcctc tcattcattc cttgggagac tttcctgtat ttataaaaga caaggtaagt   6420
caacttgaag agacgttcgg tccctgtgca agaaggttct ttagggctct ggatcaattc   6480
gacaacatac atgacttggt ttttgtgtat ggctgttaca ggcattgggg gcacccatat   6540
atagattatc gaaagggtct gtcaaaacta tatgatcagg ttcacattaa aaaagtgata   6600
gataagtcct accaggagtg cttagcaagc gacctagcca ggaggatcct tagatggggt   6660
```

-continued

```
tttgataagt actccaagtg gtatctggat tcaagattcc tagcccgaga ccaccccttg   6720
actccttata tcaaaaccca aacatggcca cccaaacata ttgtagactt ggtgggggat   6780
acatggcaca agctcccgat cacgcagatc tttgagattc ctgaatcaat ggatccgtca   6840
gaaatattgg atgacaaatc acattctttc accagaacga gactagcttc ttggctgtca   6900
gaaaaccgag ggggacctgt tcctagcgaa aaagttatta tcacggccct gtctaagccg   6960
cctgtcaatc cccgagagtt tctgaggtct atagacctcg gaggattgcc agatgaagac   7020
ttgataattg gcctcaagcc aaaggaacgg gaattgaaga ttgaaggtcg attctttgct   7080
ctaatgtcat ggaatctaag attgtatttt gtcatcactg aaaaactctt ggccaactac   7140
atcttgccac tttttgacgc gctgactatg acagacaacc tgaacaaggt gtttaaaaag   7200
ctgatcgaca gggtcaccgg gcaagggctt ttggactatt caagggtcac atatgcattt   7260
cacctggact atgaaaagtg gaacaaccat caaagattag agtcaacaga ggatgtattt   7320
tctgtcctag atcaagtgtt tggattgaag agagtgtttt ctagaacaca cgagtttttt   7380
caaaaggcct ggatctatta ttcagacaga tcagacctca tcgggttacg ggaggatcaa   7440
atatactgct tagatgcgtc caacggccca acctgttgga atggccagga tggcgggcta   7500
gaaggcttac ggcagaaggg ctggagtcta gtcagcttat tgatgataga tagagaatct   7560
caaatcagga acacaagaac caaaatacta gctcaaggag acaaccaggt tttatgtccg   7620
acatatatgt tgtcgccagg gctatctcaa gaggggctcc tctatgaatt ggagagaata   7680
tcaaggaatg cactttcgat atacagagcc gtcgaggaag ggcatctaa gctagggctg   7740
atcatcaaga aagaagagac catgtgtagt tatgacttcc tcatctatgg aaaaacccct   7800
ttgtttagag gtaacatatt ggtgcctgag tccaaaagat gggccagagt ctcttgcgtc   7860
tctaatgacc aaatagtcaa cctcgccaat ataatgtcga cagtgtccac caatgcgcta   7920
acagtggcac aacactctca atctttgatc aaaccgatga gggattttct gctcatgtca   7980
gtacaggcag tctttcacta cctgctattt agcccaatct taaagggaag agtttacaag   8040
attctgagcg ctgaaggggga tagctttctc ctagccatgt caaggataat ctatctagat   8100
ccttctttgg gaggggtatc tggaatgtcc ctcggaagat tccatatacg acagttctca   8160
gaccctgtct ctgaagggtt atccttctgg agagagatct ggttaagctc ccacgagtcc   8220
tggattcacg cgttgtgtca agaggctgga aacccagatc ttggagagag aacactcgag   8280
agcttcactc gccttctaga agatcctacc accttaaata tcagaggagg ggccagtcct   8340
accattctac tcaaggatgc aatcagaaag gctttatatg acgaggtgga caaggtggag   8400
aattcagagt ttcgagaggc aatcctgttg tccaagaccc atagagataa ttttatactc   8460
ttcttaacat ctgttgagcc tctgtttcct cgatttctca gtgagctatt cagttcgtct   8520
tttttgggaa tccccgagtc aatcattgga ttgatacaaa actcccgaac gataagaagg   8580
cagtttagaa agagtctctc aaaaacttta gaagaatcct tctacaactc agagatccac   8640
gggattagtc ggatgaccca gacacctcag agggttgggg gggtgtggcc ttgctcttca   8700
gagagggcag atctacttag ggagatctct tggggaagaa aagtggtagg cacgacagtt   8760
cctcaccctt ctgagatgtt ggggttactt cccaagtcct ctatttcttg cacttgtgga   8820
gcaacaggag gaggcaatcc tagagtttct gtatcagtac tcccgtcctt tgatcagtca   8880
ttttttcac gaggcccct aaaggggtac ttgggctcgt ccacctctat gtcgacccag   8940
ctattccatg catgggaaaa agtcactaat gttcatgtgg tgaagagagc tctatcgtta   9000
aaagaatcta taaactggtt cattactaga gattccaact tggctcaagc tctaattagg   9060
```

```
aacattatgt ctctgacagg ccctgatttc cctctagagg aggcccctgt cttcaaaagg   9120
acggggtcag ccttgcatag gttcaagtct gccagataca gcgaaggagg gtattcttct   9180
gtctgcccga acctcctctc tcatatttct gttagtacag acaccatgtc tgatttgacc   9240
caagacggga agaactacga tttcatgttc cagccattga tgctttatgc acagacatgg   9300
acatcagagc tggtacagag agacacaagg ctaagagact ctacgtttca ttggcacctc   9360
cgatgcaaca ggtgtgtgag acccattgac gacgtgaccc tggagacctc tcagatcttc   9420
gagtttccgg atgtgtcgaa aagaatatcc agaatggttt ctggggctgt gcctcacttc   9480
cagaggcttc ccgatatccg tctgagacca ggagattttg aatctctaag cggtagagaa   9540
aagtctcacc atatcggatc agctcagggg ctcttatact caatcttagt ggcaattcac   9600
gactcaggat acaatgatgg aaccatcttc cctgtcaaca tatacgacaa ggtttcccct   9660
agagactatt tgagagggct cgcaagggga gtattgatag gatcctcgat ttgcttcttg   9720
acaagaatga caaatatcaa tattaataga cctcttgaat tgatctcagg ggtaatctca   9780
tatattctcc tgaggctaga taaccatccc tccttgtaca taatgctcag agaaccgtct   9840
cttagaggag agatattttc tatccctcag aaaatccccg ccgcttatcc aaccactatg   9900
aaagaaggca acagatcaat cttgtgttat ctccaacatg tgctacgcta tgagcgagag   9960
ataatcacgg cgtctccaga gaatgactgg ctatggatct tttcagactt tagaagtgcc  10020
aaaatgacgt acctaaccct cattacttac cagtctcatc ttctactcca gagggttgag  10080
agaaacctat ctaagagtat gagagataac ctgcgacaat tgagttcctt gatgaggcag  10140
gtgctgggcg ggcacggaga agatacctta gagtcagacg acaacattca acgactgcta  10200
aaagactctt tacgaaggac aagatgggtg gatcaagagg tgcgccatgc agctagaacc  10260
atgactggag attacagccc caacaagaag gtgtcccgta aggtaggatg ttcagaatgg  10320
gtctgctctg ctcaacaggt tgcagtctct acctcagcaa acccggcccc tgtctcggag  10380
cttgacataa gggccctctc taagaggttc cagaaccctt tgatctcggg cttgagagtg  10440
gttcagtggg caaccggtgc tcattataag cttaagccta ttctagatga tctcaatgtt  10500
ttcccatctc tctgccttgt agttggggac gggtcagggg ggatatcaag ggcagtcctc  10560
aacatgtttc cagatgccaa gcttgtgttc aacagtctct tagaggtgaa tgacctgatg  10620
gcttccggaa cacatccact gcctccttca gcaatcatga ggggaggaaa tgatatcgtc  10680
tccagagtga tagattttga ctcaatctgg gaaaaaccgt ccgacttgag aaacttggca  10740
acctggaaat acttccagtc agtccaaaag caggtcaaca tgtcctatga cctcattatt  10800
tgcgatgcag aagttactga cattgcatct atcaaccgga taaccctgtt aatgtccgat  10860
tttgcattgt ctatagatgg accactctat ttggtcttca aaacttatgg gactatgcta  10920
gtaaatccaa actacaaggc tattcaacac ctgtcaagag cgttcccctc ggtcacaggg  10980
tttatcaccc aagtaacttc gtctttttca tctgagctct acctccgatt ctccaaacga  11040
gggaagtttt tcagagatgc tgagtacttg acctcttcca cccttcgaga aatgagcctt  11100
gtgttattca attgtagcag ccccaagagt gagatgcaga gagctcgttc cttgaactat  11160
caggatcttg tgagaggatt tcctgaagaa atcatatcaa atccttacaa tgagatgatc  11220
ataactctga ttgacagtga tgtagaatct tttctagtcc acaagatggt tgatgatctt  11280
gagttacaga ggggaactct gtctaaagtg gctatcatta tagccatcat gatagttttc  11340
tccaacagag tcttcaacgt ttccaaaccc ctaactgacc ccttgttcta tccaccgtct  11400
```

-continued gatcccaaaa tcctgaggca cttcaacata tgttgcagta ctatgatgta tctatctact 11460
gctttaggtg acgtccctag cttcgcaaga cttcacgacc tgtataacag acctataact 11520
tattacttca gaaagcaatt cattcgaggg aacgtttatc tatcttggag ttggtccaac 11580
gacacctcag tgttcaaaag ggtagcctgt aattctagcc tgagtctgtc atctcactgg 11640
atcaggttga tttacaagat agtgaagact accagactcg ttggcagcat caaggatcta 11700
tccagagaag tggaaagaca ccttcatagg tacaacaggt ggatcaccct agaggatatc 11760
agatctagat catccctact agactacagt tgcctgtgaa ccggatactc ctggaagcct 11820
gcccatgcta agactcttgt gtgatgtatc ttgaaaaaaa caagatccta aatctgaacc 11880
tttggttgtt tgattgtttt tctcattttt gttgtttatt tgttaagcgt 11930

<210> SEQ ID NO 9
<211> LENGTH: 11577
<212> TYPE: DNA
<213> ORGANISM: artificial sequence
<220> FEATURE:
<223> OTHER INFORMATION: recombinant ERA- rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (5063)..(11443)

<400> SEQUENCE: 9
acgcttaaca accagatcaa agaaaaaaca gacattgtca attgcaaagc aaaaatgtaa 60
cacccctaca atggatgccg acaagattgt attcaaagtc aataatcagg tggtctcttt 120
gaagcctgag attatcgtgg atcaacatga gtacaagtac cctgccatca aagatttgaa 180
aaagccctgt ataaccctag gaaaggctcc cgatttaaat aaagcataca agtcagtttt 240
gtcaggcatg agcgccgcca aacttgatcc tgacgatgta tgttcctatt tggcagcggc 300
aatgcagttt tttgagggga catgtccgga agactggacc agctatggaa tcgtgattgc 360
acgaaaagga gataagatca ccccaggttc tctggtggag ataaaacgta ctgatgtaga 420
agggaattgg gctctgacag gaggcatgga actgacaaga gaccccactg tccctgagca 480
tgcgtcctta gtcggtcttc tcttgagtct gtataggttg agcaaaatat ccgggcaaaa 540
cactggtaac tataagacaa acattgcaga caggatagag cagatttttg agacagcccc 600
ttttgttaaa atcgtggaac accatactct aatgacaact cacaaaatgt gtgctaattg 660
gagtactata ccaaacttca gatttttggc cggaacctat gacatgtttt tctcccggat 720
tgagcatcta tattcagcaa tcagagtggg cacagttgtc actgcttatg aagactgttc 780
aggactggta tcatttactg ggttcataaa acaaatcaat ctcaccgcta gagaggcaat 840
actatatttc ttccacaaga actttgagga agagataaga agaatgtttg agccagggca 900
ggagacagct gttcctcact cttatttcat ccacttccgt tcactaggct tgagtgggaa 960
atctccttat tcatcaaatg ctgttggtca cgtgttcaat ctcattcact ttgtaggatg 1020
ctatatgggt caagtcagat ccctaaatgc aacggttatt gctgcatgtg ctcctcatga 1080
aatgtctgtt ctagggggct atctgggaga ggaattcttc gggaaaggga catttgaaag 1140
aagattcttc agagatgaga aagaacttca agaatacgag gcggctgaac tgacaaagac 1200
tgacgtagca ctggcagatg atggaactgt caactctgac gacgaggact acttctcagg 1260
tgaaaccaga agtccggagg ctgtttatac tcgaatcatg atgaatggag gtcgactaaa 1320
gagatctcac atacggagat atgtctcagt cagttccaat catcaagccc gtccaaactc 1380
attcgccgag tttctaaaca agacatattc gagtgactca taagaagttg aataacaaaa 1440
tgccggaaat ctacggattg tgtatatcca tcatgaaaaa aactaacacc cctcctttcg 1500
aaccatccca aacatgagca agatctttgt caatcctagt gctattagag ccggtctggc 1560
cgatcttgag atggctgaag aaactgttga tctgatcaat agaaatatcg aagacaatca 1620
ggctcatctc caaggggaac ccatagaagt ggacaatctc cctgaggata tggggcgact 1680
tcacctggat gatggaaaat cgcccaaccc tggtgagatg gccaaggtgg gagaaggcaa 1740
gtatcgagag gactttcaga tggatgaagg agaggatcct agcttcctgt tccagtcata 1800
cctggaaaat gttggagtcc aaatagtcag acaaatgagg tcaggagaga gatttctcaa 1860
gatatggtca cagaccgtag aagagattat atcctatgtc gcggtcaact ttcccaaccc 1920
tccaggaaag tcttcagagg ataaatcaac ccagactact ggccgagagc tcaagaagga 1980
gacaacaccc actccttctc agagagaaag ccaatcatcg aaagccagga tggcggctca 2040
aattgcttct ggccctccag cccttgaatg gtcggccacc aatgaagagg atgatctatc 2100
agtggaggct gagatcgctc accagattgc agaaagtttc tccaaaaaat ataagtttcc 2160
ctctcgatcc tcagggatac tcttgtataa ttttgagcaa ttgaaaatga accttgatga 2220
tatagttaaa gaggcaaaaa atgtaccagg tgtgacccgt ttagcccatg acgggtccaa 2280
actcccccta agatgtgtac tgggatgggt cgctttggcc aactctaaga aattccagtt 2340
gttagtcgaa tccgacaagc tgagtaaaat catgcaagat gacttgaatc gctatacatc 2400
ttgctaaccg aacctctcca ctcagtccct ctagacaata aagtccgaga tgtcctaaag 2460
tcaacatgaa aaaaacaggc aacaccactg ataaaatgaa ctttctacgt aagatagtga 2520
aaaattgcag ggacgaggac actcaaaaac cctctcccgt gtcagcccct ctggatgacg 2580
atgacttgtg gcttccaccc cctgaatacg tcccgctgaa agaacttaca agcaagaaga 2640
acatgaggaa cttttgtatc aacggagggg ttaaagtgtg tagcccgaat ggttactcgt 2700
tcaggatcct gcggcacatt ctgaaatcat tcgacgagat atattctggg aatcatagga 2760
tgatcgggtt agtcaaagta gttattggac tggctttgtc aggatctcca gtccctgagg 2820
gcatgaactg ggtatacaaa ttgaggagaa cctttatctt ccagtgggct gattccaggg 2880
gccctcttga aggggaggag ttggaatact ctcaggagat cacttgggat gatgatactg 2940
agttcgtcgg attgcaaata agagtgattg caaaacagtg tcatatccag ggcagaatct 3000
ggtgtatcaa catgaacccg agagcatgtc aactatggtc tgacatgtct cttcagacac 3060
aaaggtccga agaggacaaa gattcctctc tgcttctaga ataatcagat tatatcccgc 3120
aaatttatca cttgtttacc tctggaggag agaacatatg ggctcaactc caacccttgg 3180
gagcaatata acaaaaaaca tgttatggtg ccattaaacc gctgcatttc atcaaagtca 3240
agttgattac ctttacattt tgatcctctt ggatgtgaaa aaaactatta acatccctca 3300
aaagactcaa ggaaagatgg ttcctcaggc tctcctgttt gtacccccttc tggtttttcc 3360
attgtgtttt gggaaattcc ctatttacac gataccagac aagcttggtc cctggagccc 3420
gattgacata catcacctca gctgcccaaa caatttggta gtggaggacg aaggatgcac 3480
caacctgtca gggttctcct acatggaact taaagttgga tacatcttag ccataaaaat 3540
gaacgggttc acttgcacag gcgttgtgac ggaggctgaa acctacacta acttcgttgg 3600
ttatgtcaca accacgttca aagaaagca tttccgccca acaccagatg catgtagagc 3660
cgcgtacaac tggaagatgg ccggtgaccc cagatatgaa gagtctctac acaatccgta 3720
ccctgactac cactggcttc gaactgtaaa aaccaccaag gagtctctcg ttatcatatc 3780
tccaagtgtg gcagatttgg acccatatga cagatccctt cactcgaggg tcttccctag 3840
cgggaagtgc tcaggagtag cggtgtcttc tacctactgc tccactaacc acgattacac 3900
catttggatg cccgagaatc cgagactagg gatgtcttgt gacattttta ccaatagtag 3960
agggaagaga gcatccaaag ggagtgagac ttgcggcttt gtagatgaaa gaggcctata 4020
taagtcttta aaaggagcat gcaaactcaa gttatgtgga gttctaggac ttagacttat 4080
ggatggaaca tgggtcgcga tgcaaacatc aaatgaaacc aaatggtgcc ctcccgatca 4140
gttggtgaac ctgcacgact ttcgctcaga cgaaattgag caccttgttg tagaggagtt 4200
ggtcaggaag agagaggagt gtctggatgc actagagtcc atcatgacaa ccaagtcagt 4260
gagtttcaga cgtctcagtc atttaagaaa acttgtccct gggtttggaa aagcatatac 4320
catattcaac aagaccttga tggaagccga tgctcactac aagtcagtca gaacttggaa 4380
tgagatcctc ccttcaaaag ggtgtttaag agttgggggg aggtgtcatc ctcatgtgaa 4440
cggggtgttt ttcaatggta taatattagg acctgacggc aatgtcttaa tcccagagat 4500
gcaatcatcc ctcctccagc aacatatgga gttgttggaa tcctcggtta tccccccttgt 4560
gcacccccctg gcagacccgt ctaccgtttt caaggacggt gacgaggctg aggattttgt 4620
tgaagttcac cttcccgatg tgcacaatca ggtctcagga gttgacttgg gtctcccgaa 4680
ctgggggaag tatgtattac tgagtgcagg ggccctgact gccttgatgt tgataatttt 4740
cctgatgaca tgttgtagaa gagtcaatcg atcagaacct acgcaacaca atctcagagg 4800
gacagggagg gaggtgtcag tcactcccca aagcgggaag atcatatctt catgggaatc 4860
acacaagagt gggggtgaga ccagactgtg aggactggcc gtcctttcaa ctatccaagt 4920
cctgaagatc acctcccctt ggggggttca tcatgaaaaa aactaacacc cctcctttcg 4980
ctgcagtttg gtaccgtcga gaaaaaaaca ttagatcaga agaacaactg gcaacacttc 5040
tcaacctgag acctacttca agatgctcga tcctggagag gtctatgatg accctattga 5100
cccaatcgag ttagaggatg aacccagagg aacccccact gtccccaaca tcttgaggaa 5160
ctctgactac aatctcaact ctcctttgat agaagatcct gctagactaa tgttagaatg 5220
gttaaaaaca gggaatagac cttatcggat gactctaaca gacaattgct ccaggtcttt 5280
cagagttttg aaagattatt tcaagaaggt agatttgggt tctctcaagg tgggcggaat 5340
ggctgcacag tcaatgattt ctctctggtt atatggtgcc cactctgaat ccaacaggag 5400
ccggagatgt ataacagact tggcccattt ctattccaag tcgtccccca tagagaagct 5460
gttgaatctc acgctaggaa atagagggct gagaatcccc ccagagggag tgttaagttg 5520
ccttgagagg gttgattatg ataatgcatt tggaaggtat cttgccaaca cgtattcctc 5580
ttacttgttc ttccatgtaa tcaccttata catgaacgcc ctagactggg atgaagaaaa 5640
gaccatccta gcattatgga aagatttaac ctcagtggac atcgggaagg acttggtaaa 5700
gttcaaagac caaatatggg gactgctgat cgtgacaaag gactttgttt actcccaaag 5760
ttccaattgt ctttttgaca gaaactacac acttatgcta aaagatcttt tcttgtctcg 5820

```
cttcaactcc ttaatggtct tgctctctcc cccagagccc cgatactcag atgacttgat   5880
atctcaacta tgccagctgt acattgctgg ggatcaagtc ttgtctatgt gtggaaactc   5940
cggctatgaa gtcatcaaaa tattggagcc atatgtcgtg aatagtttag tccagagagc   6000
agaaaagttt aggcctctca ttcattcctt gggagacttt cctgtattta taaaagacaa   6060
ggtaagtcaa cttgaagaga cgttcggtcc ctgtgcaaga aggttcttta gggctctgga   6120
tcaattcgac aacatacatg acttggtttt tgtgtatggc tgttacaggc attgggggca   6180
cccatatata gattatcgaa agggtctgtc aaaactatat gatcaggttc acattaaaaa   6240
agtgatagat aagtcctacc aggagtgctt agcaagcgac ctagccagga ggatccttag   6300
atggggtttt gataagtact ccaagtggta tctggattca agattcctag cccgagacca   6360
ccccttgact ccttatatca aaacccaaac atggccaccc aaacatattg tagacttggt   6420
gggggataca tggcacaagc tcccgatcac gcagatcttt gagattcctg aatcaatgga   6480
tccgtcagaa atattggatg acaaatcaca ttctttcacc agaacgagac tagcttcttg   6540
gctgtcagaa aaccgagggg gacctgttcc tagcgaaaaa gttattatca cggccctgtc   6600
taagccgcct gtcaatcccc gagagtttct gaggtctata gacctcggag gattgccaga   6660
tgaagacttg ataattggcc tcaagccaaa ggaacgggaa ttgaagattg aaggtcgatt   6720
ctttgctcta atgtcatgga atctaagatt gtattttgtc atcactgaaa aactcttggc   6780
caactacatc ttgccacttt ttgacgcgct gactatgaca gacaacctga acaaggtgtt   6840
taaaaagctg atcgacaggg tcaccgggca agggcttttg gactattcaa gggtcacata   6900
tgcatttcac ctggactatg aaaagtggaa caaccatcaa agattagagt caacagagga   6960
tgtattttct gtcctagatc aagtgtttgg attgaagaga gtgttttcta gaacacacga   7020
gtttttttcaa aaggcctgga tctattattc agacagatca gacctcatcg ggttacggga   7080
ggatcaaata tactgcttag atgcgtccaa cggcccaacc tgttggaatg gccaggatgg   7140
cgggctagaa ggcttacggc agaagggctg gagtctagtc agcttattga tgatagatag   7200
agaatctcaa atcaggaaca caagaaccaa aatactagct caaggagaca accaggtttt   7260
atgtccgaca tatatgttgt cgccagggct atctcaagag ggctcctct atgaattgga   7320
gagaatatca aggaatgcac tttcgatata cagagccgtc gaggaagggg catctaagct   7380
agggctgatc atcaagaaag aagagaccat gtgtagttat gacttcctca tctatggaaa   7440
aaccccttttg tttagaggta acatattggt gcctgagtcc aaaagatggg ccagagtctc   7500
ttgcgtctct aatgaccaaa tagtcaacct cgccaatata atgtcgacag tgtccaccaa   7560
tgcgctaaca gtggcacaac actctcaatc tttgatcaaa ccgatgaggg attttctgct   7620
catgtcagta caggcagtct ttcactacct gctatttagc ccaatcttaa agggaagagt   7680
ttacaagatt ctgagcgctg aaggggatag ctttctccta gccatgtcaa ggataatcta   7740
tctagatcct tctttgggag gggtatctgg aatgtccctc ggaagattcc atatacgaca   7800
gttctcagac cctgtctctg aagggttatc cttctggaga gagatctggt taagctccca   7860
cgagtcctgg attcacgcgt tgtgtcaaga ggctggaaac ccagatcttg gagagagaac   7920
actcgagagc ttcactcgcc ttctagaaga tcctaccacc ttaaatatca gaggaggggc   7980
cagtcctacc attctactca aggatgcaat cagaaaggct ttatatgacg aggtggacaa   8040
ggtggagaat tcagagtttc gagaggcaat cctgttgtcc aagacccata gagataattt   8100
tatactcttc ttaacatctg ttgagcctct gtttcctcga tttctcagtg agctattcag   8160
ttcgtctttt ttgggaatcc ccgagtcaat cattggattg atacaaaact cccgaacgat   8220
```

-continued

```
aagaaggcag tttagaaaga gtctctcaaa aactttagaa gaatccttct acaactcaga   8280
gatccacggg attagtcgga tgacccagac acctcagagg gttggggggg tgtggccttg   8340
ctcttcagag agggcagatc tacttaggga gatctcttgg ggaagaaaag tggtaggcac   8400
gacagttcct caccccttctg agatgttggg gttacttccc aagtcctcta tttcttgcac   8460
ttgtggagca acaggaggag gcaatcctag agtttctgta tcagtactcc cgtcctttga   8520
tcagtcattt ttttcacgag gccccctaaa ggggtacttg ggctcgtcca cctctatgtc   8580
gacccagcta ttccatgcat gggaaaaagt cactaatgtt catgtggtga agagagctct   8640
atcgttaaaa gaatctataa actggttcat tactagagat tccaacttgg ctcaagctct   8700
aattaggaac attatgtctc tgacaggccc tgatttccct ctagaggagg cccctgtctt   8760
caaaaggacg gggtcagcct tgcataggtt caagtctgcc agatacagcg aaggagggta   8820
ttcttctgtc tgcccgaacc tcctctctca tatttctgtt agtacagaca ccatgtctga   8880
tttgacccaa gacgggaaga actacgattt catgttccag ccattgatgc tttatgcaca   8940
gacatggaca tcagagctgg tacagagaga cacaaggcta agagactcta cgtttcattg   9000
gcacctccga tgcaacaggt gtgtgagacc cattgacgac gtgaccctgg agacctctca   9060
gatcttcgag tttccggatg tgtcgaaaag aatatccaga atggtttctg ggctgtgcc   9120
tcacttccag aggcttcccg atatccgtct gagaccagga gattttgaat ctctaagcgg   9180
tagagaaaag tctcaccata tcggatcagc tcaggggctc ttatactcaa tcttagtggc   9240
aattcacgac tcaggataca atgatggaac catcttccct gtcaacatat acgacaaggt   9300
ttcccctaga gactatttga gagggctcgc aaggggagta ttgataggat cctcgatttg   9360
cttcttgaca agaatgacaa atatcaatat taatagacct cttgaattga tctcaggggt   9420
aatctcatat attctcctga ggctagataa ccatccctcc ttgtacataa tgctcagaga   9480
accgtctctt agaggagaga tattttctat ccctcagaaa atccccgccg cttatccaac   9540
cactatgaaa gaaggcaaca gatcaatctt gtgttatctc caacatgtgc tacgctatga   9600
gcgagagata atcacggcgt ctccagagaa tgactggcta tggatctttt cagactttag   9660
aagtgccaaa atgacgtacc taaccctcat tacttaccag tctcatcttc tactccagag   9720
ggttgagaga aacctatcta agagtatgag agataacctg cgacaattga gttccttgat   9780
gaggcaggtg ctgggcgggc acggagaaga taccttagag tcagacgaca acattcaacg   9840
actgctaaaa gactctttac gaaggacaag atgggtggat caagaggtgc gccatgcagc   9900
tagaaccatg actggagatt acagccccaa caagaaggtg tcccgtaagg taggatgttc   9960
agaatgggtc tgctctgctc aacaggttgc agtctctacc tcagcaaacc cggcccctgt  10020
ctcggagctt gacataaggg ccctctctaa gaggttccag aaccctttga tctcgggctt  10080
gagagtggtt cagtgggcaa ccggtgctca ttataagctt aagcctattc tagatgatct  10140
caatgttttc ccatctctct gccttgtagt tggggacggg tcagggggga tatcaagggc  10200
agtcctcaac atgtttccag atgccaagct tgtgttcaac agtctcttag aggtgaatga  10260
cctgatggct tccggaacac atccactgcc tccttcagca atcatgaggg gaggaaatga  10320
tatcgtctcc agagtgatag attttgactc aatctgggaa aaaccgtccg acttgagaaa  10380
cttggcaacc tggaaatact tccagtcagt ccaaaagcag gtcaacatgt cctatgacct  10440
cattatttgc gatgcagaag ttactgacat tgcatctatc aaccggataa ccctgttaat  10500
gtccgatttt gcattgtcta tagatggacc actctatttg gtcttcaaaa cttatgggac  10560
```

```
tatgctagta aatccaaact acaaggctat tcaacacctg tcaagagcgt tcccctcggt  10620

cacagggttt atcacccaag taacttcgtc tttttcatct gagctctacc tccgattctc  10680

caaacgaggg aagtttttca gagatgctga gtacttgacc tcttccaccc ttcgagaaat  10740

gagccttgtg ttattcaatt gtagcagccc caagagtgag atgcagagag ctcgttcctt  10800

gaactatcag gatcttgtga gaggatttcc tgaagaaatc atatcaaatc cttacaatga  10860

gatgatcata actctgattg acagtgatgt agaatctttt ctagtccaca agatggttga  10920

tgatcttgag ttacagaggg gaactctgtc taaagtggct atcattatag ccatcatgat  10980

agttttctcc aacagagtct tcaacgtttc caaaccccta actgacccct tgttctatcc  11040

accgtctgat cccaaaatcc tgaggcactt caacatatgt tgcagtacta tgatgtatct  11100

atctactgct ttaggtgacg tccctagctt cgcaagactt cacgacctgt ataacagacc  11160

tataacttat tacttcagaa agcaattcat tcgagggaac gtttatctat cttggagttg  11220

gtccaacgac acctcagtgt tcaaaagggt agcctgtaat tctagcctga gtctgtcatc  11280

tcactggatc aggttgattt acaagatagt gaagactacc agactcgttg gcagcatcaa  11340

ggatctatcc agagaagtgg aaagacacct tcataggtac aacaggtgga tcaccctaga  11400

ggatatcaga tctagatcat ccctactaga ctacagttgc ctgtgatccg gatactcctg  11460

gaagcctgcc catgctaaga ctcttgtgtg atgtatcttg aaaaaaacaa gatcctaaat  11520

ctgaaccttt ggttgtttga ttgtttttct catttttgtt gtttatttgt taagcgt     11577
```

```
<210> SEQ ID NO 10
<211> LENGTH: 13150
<212> TYPE: DNA
<213> ORGANISM: artificial sequence
<220> FEATURE:
<223> OTHER INFORMATION: Recombinant ERA-2G rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (4988)..(6559)
<220> FEATURE:
<221> NAME/KEY: misc_feature
<222> LOCATION: (6636)..(13016)

<400> SEQUENCE: 10

acgcttaaca accagatcaa agaaaaaaca gacattgtca attgcaaagc aaaaatgtaa     60

cacccctaca atggatgccg acaagattgt attcaaagtc aataatcagg tggtctcttt    120

gaagcctgag attatcgtgg atcaacatga gtacaagtac cctgccatca aagatttgaa    180

aaagccctgt ataaccctag gaaaggctcc cgatttaaat aaagcataca agtcagtttt    240

gtcaggcatg agcgccgcca aacttgatcc tgacgatgta tgttcctatt tggcagcggc    300

aatgcagttt tttgagggga catgtccgga agactggacc agctatggaa tcgtgattgc    360

acgaaaagga gataagatca ccccaggttc tctggtggag ataaaacgta ctgatgtaga    420

agggaattgg gctctgacag gaggcatgga actgacaaga gaccccactg tccctgagca    480

tgcgtcctta gtcggtcttc tcttgagtct gtataggttg agcaaaatat ccgggcaaaa    540
```

```
cactggtaac tataagacaa acattgcaga caggatagag cagatttttg agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttctcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaagt ggacaatctc cctgaggata tggggcgact   1680
tcacctggat gatggaaaat cgcccaaccc tggtgagatg gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaaacaggc aacaccactg ataaaatgaa ctttctacgt aagatagtga   2520
aaaattgcag ggacgaggac actcaaaaac cctctcccgt gtcagcccct ctggatgacg   2580
atgacttgtg gcttccaccc cctgaatacg tcccgctgaa agaacttaca agcaagaaga   2640
acatgaggaa cttttgtatc aacggagggg ttaaagtgtg tagcccgaat ggttactcgt   2700
tcaggatcct gcggcacatt ctgaaatcat tcgacgagat atattctggg aatcatagga   2760
tgatcgggtt agtcaaagta gttattggac tggctttgtc aggatctcca gtccctgagg   2820
gcatgaactg ggtatacaaa ttgaggagaa cctttatctt ccagtgggct gattccaggg   2880
```

-continued

```
gccctcttga aggggaggag ttggaatact ctcaggagat cacttgggat gatgatactg   2940
agttcgtcgg attgcaaata agagtgattg caaaacagtg tcatatccag ggcagaatct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagactcaa ggaaagatgg ttcctcaggc tctcctgttt gtaccccttc tggtttttcc   3360
attgtgtttt gggaaattcc ctatttacac gataccagac aagcttggtc cctggagccc   3420
gattgacata catcacctca gctgcccaaa caatttggta gtggaggacg aaggatgcac   3480
caacctgtca gggttctcct acatggaact taaagttgga tacatcttag ccataaaaat   3540
gaacgggttc acttgcacag gcgttgtgac ggaggctgaa acctacacta acttcgttgg   3600
ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cactggcttc gaactgtaaa aaccaccaag gagtctctcg ttatcatatc   3780
tccaagtgtg gcagatttgg acccatatga cagatccctt cactcgaggg tcttccctag   3840
cgggaagtgc tcaggagtag cggtgtcttc tacctactgc tccactaacc acgattacac   3900
catttggatg cccgagaatc cgagactagg gatgtcttgt gacattttta ccaatagtag   3960
agggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtcgcga tgcaaacatc aaatgaaacc aaatggtgcc ctcccgatca   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtctcagtc atttaagaaa acttgtccct gggtttggaa aagcatatac   4320
catattcaac aagaccttga tggaagccga tgctcactac aagtcagtca gaacttggaa   4380
tgagatcctc ccttcaaaag ggtgtttaag agttgggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tccccttgt   4560
gcacccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataatttt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgtg aggactggcc gtcctttcaa ctatccaagt   4920
cctgaagatc acctcccctt ggggggttca tcatgaaaaa aactaacacc cctcctttcg   4980
ctgcaggatg gttcctcagg ctctcctgtt tgtacccctt ctggtttttc cattgtgttt   5040
tgggaaattc cctatttaca cgataccaga caagcttggt ccctggagcc cgattgacat   5100
acatcacctc agctgcccaa acaatttggt agtggaggac gaaggatgca ccaacctgtc   5160
agggttctcc tacatggaac ttaaagttgg atacatctta gccataaaaa tgaacgggtt   5220
cacttgcaca ggcgttgtga cggaggctga aacctacact aacttcgttg gttatgtcac   5280
```

-continued

```
aaccacgttc aaaagaaagc atttccgccc aacaccagat gcatgtagag ccgcgtacaa   5340
ctggaagatg gccggtgacc ccagatatga agagtctcta cacaatccgt accctgacta   5400
ccactggctt cgaactgtaa aaaccaccaa ggagtctctc gttatcatat ctccaagtgt   5460
ggcagatttg gacccatatg acagatccct tcactcgagg gtcttcccta gcgggaagtg   5520
ctcaggagta gcggtgtctt ctacctactg ctccactaac cacgattaca ccatttggat   5580
gcccgagaat ccgagactag ggatgtcttg tgacattttt accaatagta gagggaagag   5640
agcatccaaa gggagtgaga cttgcggctt tgtagatgaa agaggcctat ataagtcttt   5700
aaaaggagca tgcaaactca agttatgtgg agttctagga cttagactta tggatggaac   5760
atgggtcgcg atgcaaacat caaatgaaac caaatggtgc cctcccgatc agttggtgaa   5820
cctgcacgac tttcgctcag acgaaattga gcaccttgtt gtagaggagt tggtcaggaa   5880
gagagaggag tgtctggatg cactagagtc catcatgaca accaagtcag tgagtttcag   5940
acgtctcagt catttaagaa aacttgtccc tgggtttgga aaagcatata ccatattcaa   6000
caagaccttg atggaagccg atgctcacta caagtcagtc agaacttgga atgagatcct   6060
cccttcaaaa gggtgtttaa gagttggggg gaggtgtcat cctcatgtga acggggtgtt   6120
tttcaatggt ataatattag gacctgacgg caatgtctta atcccagaga tgcaatcatc   6180
cctcctccag caacatatgg agttgttgga atcctcggtt atcccccttg tgcaccccct   6240
ggcagacccg tctaccgttt tcaaggacgg tgacgaggct gaggattttg ttgaagttca   6300
ccttcccgat gtgcacaatc aggtctcagg agttgacttg ggtctcccga actgggggaa   6360
gtatgtatta ctgagtgcag gggccctgac tgccttgatg ttgataattt tcctgatgac   6420
atgttgtaga agagtcaatc gatcagaacc tacgcaacac aatctcagag ggacagggag   6480
ggaggtgtca gtcactcccc aaagcgggaa gatcatatct tcatgggaat cacacaagag   6540
tgggggtgag accagactgt gaggtaccgt cgagaaaaaa acattagatc agaagaacaa   6600
ctggcaacac ttctcaacct gagacctact tcaagatgct cgatcctgga gaggtctatg   6660
atgaccctat tgacccaatc gagttagagg atgaacccag aggaaccccc actgtcccca   6720
acatcttgag gaactctgac tacaatctca actctccttt gatagaagat cctgctagac   6780
taatgttaga atggttaaaa acagggaata gaccttatcg gatgactcta acagacaatt   6840
gctccaggtc tttcagagtt ttgaaagatt atttcaagaa ggtagatttg ggttctctca   6900
aggtgggcgg aatggctgca cagtcaatga tttctctctg gttatatggt gcccactctg   6960
aatccaacag gagccggaga tgtataacag acttggccca tttctattcc aagtcgtccc   7020
ccatagagaa gctgttgaat ctcacgctag gaaatagagg gctgagaatc cccccagagg   7080
gagtgttaag ttgccttgag agggttgatt atgataatgc atttggaagg tatcttgcca   7140
acacgtattc ctcttacttg ttcttccatg taatcacctt atacatgaac gccctagact   7200
gggatgaaga aaagaccatc ctagcattat ggaaagattt aacctcagtg gacatcggga   7260
aggacttggt aaagttcaaa gaccaaatat ggggactgct gatcgtgaca aaggactttg   7320
tttactccca aagttccaat tgtctttttg acagaaacta cacacttatg ctaaaagatc   7380
ttttcttgtc tcgcttcaac tccttaatgg tcttgctctc tcccccagag ccccgatact   7440
cagatgactt gatatctcaa ctatgccagc tgtacattgc tggggatcaa gtcttgtcta   7500
tgtgtggaaa ctccggctat gaagtcatca aaatattgga gccatatgtc gtgaatagtt   7560
tagtccagag agcagaaaag tttaggcctc tcattcattc cttgggagac tttcctgtat   7620
```

-continued

```
ttataaaaga caaggtaagt caacttgaag agacgttcgg tccctgtgca agaaggttct   7680
ttagggctct ggatcaattc gacaacatac atgacttggt ttttgtgtat ggctgttaca   7740
ggcattgggg gcacccatat atagattatc gaaagggtct gtcaaaacta tatgatcagg   7800
ttcacattaa aaaagtgata gataagtcct accaggagtg cttagcaagc gacctagcca   7860
ggaggatcct tagatggggt tttgataagt actccaagtg gtatctggat tcaagattcc   7920
tagcccgaga ccaccccttg actccttata tcaaaaccca aacatggcca cccaaacata   7980
ttgtagactt ggtgggggat acatggcaca agctcccgat cacgcagatc tttgagattc   8040
ctgaatcaat ggatccgtca gaaatattgg atgacaaatc acattctttc accagaacga   8100
gactagcttc ttggctgtca gaaaaccgag ggggacctgt tcctagcgaa aaagttatta   8160
tcacggccct gtctaagccg cctgtcaatc cccgagagtt tctgaggtct atagacctcg   8220
gaggattgcc agatgaagac ttgataattg gcctcaagcc aaaggaacgg gaattgaaga   8280
ttgaaggtcg attctttgct ctaatgtcat ggaatctaag attgtatttt gtcatcactg   8340
aaaaactctt ggccaactac atcttgccac tttttgacgc gctgactatg acagacaacc   8400
tgaacaaggt gtttaaaaag ctgatcgaca gggtcaccgg gcaagggctt ttggactatt   8460
caagggtcac atatgcattt cacctggact atgaaaagtg gaacaaccat caaagattag   8520
agtcaacaga ggatgtattt tctgtcctag atcaagtgtt tggattgaag agagtgtttt   8580
ctagaacaca cgagtttttt caaaaggcct ggatctatta ttcagacaga tcagacctca   8640
tcgggttacg ggaggatcaa atatactgct tagatgcgtc caacggccca acctgttgga   8700
atggccagga tggcgggcta gaaggcttac ggcagaaggg ctggagtcta gtcagcttat   8760
tgatgataga tagagaatct caaatcagga acacaagaac caaaatacta gctcaaggag   8820
acaaccaggt tttatgtccg acatatatgt tgtcgccagg gctatctcaa gaggggctcc   8880
tctatgaatt ggagagaata tcaaggaatg cactttcgat atacagagcc gtcgaggaag   8940
gggcatctaa gctagggctg atcatcaaga aagaagagac catgtgtagt tatgacttcc   9000
tcatctatgg aaaaacccct ttgtttagag gtaacatatt ggtgcctgag tccaaaagat   9060
gggccagagt ctcttgcgtc tctaatgacc aaatagtcaa cctcgccaat ataatgtcga   9120
cagtgtccac caatgcgcta acagtggcac aacactctca atctttgatc aaaccgatga   9180
gggatttctt gctcatgtca gtacaggcag tctttcacta cctgctattt agcccaatct   9240
taaagggaag agtttacaag attctgagcg ctgaagggga tagctttctc ctagccatgt   9300
caaggataat ctatctagat ccttctttgg gaggggtatc tggaatgtcc ctcggaagat   9360
tccatatacg acagttctca gaccctgtct ctgaagggtt atccttctgg agagagatct   9420
ggttaagctc ccacgagtcc tggattcacg cgttgtgtca agaggctgga aacccagatc   9480
ttggagagag aacactcgag agcttcactc gccttctaga agatcctacc accttaaata   9540
tcagaggagg ggccagtcct accattctac tcaaggatgc aatcagaaag gctttatatg   9600
acgaggtgga caaggtggag aattcagagt ttcgagaggc aatcctgttg tccaagaccc   9660
atagagataa ttttatactc ttcttaacat ctgttgagcc tctgtttcct cgatttctca   9720
gtgagctatt cagttcgtct tttttgggaa tccccgagtc aatcattgga ttgatacaaa   9780
actcccgaac gataagaagg cagtttagaa agagtctctc aaaaacttta gaagaatcct   9840
tctacaactc agagatccac gggattagtc ggatgaccca gacacctcag agggttgggg   9900
gggtgtggcc ttgctcttca gagagggcag atctacttag ggagatctct tggggaagaa   9960
aagtggtagg cacgacagtt cctcaccctt ctgagatgtt ggggttactt cccaagtcct  10020
```

-continued ctatttcttg cacttgtgga gcaacaggag gaggcaatcc tagagtttct gtatcagtac 10080
tcccgtcctt tgatcagtca ttttttcac gaggccccct aaaggggtac ttgggctcgt 10140
ccacctctat gtcgacccag ctattccatg catgggaaaa agtcactaat gttcatgtgg 10200
tgaagagagc tctatcgtta aaagaatcta taaactggtt cattactaga gattccaact 10260
tggctcaagc tctaattagg aacattatgt ctctgacagg ccctgatttc cctctagagg 10320
aggcccctgt cttcaaaagg acggggtcag ccttgcatag gttcaagtct gccagataca 10380
gcgaaggagg gtattcttct gtctgcccga acctcctctc tcatatttct gttagtacag 10440
acaccatgtc tgatttgacc caagacggga agaactacga tttcatgttc cagccattga 10500
tgctttatgc acagacatgg acatcagagc tggtacagag agacacaagg ctaagagact 10560
ctacgtttca ttggcacctc cgatgcaaca ggtgtgtgag acccattgac gacgtgaccc 10620
tggagacctc tcagatcttc gagtttccgg atgtgtcgaa aagaatatcc agaatggttt 10680
ctggggctgt gcctcacttc cagaggcttc ccgatatccg tctgagacca ggagattttg 10740
aatctctaag cggtagagaa aagtctcacc atatcggatc agctcagggg ctcttatact 10800
caatcttagt ggcaattcac gactcaggat acaatgatgg aaccatcttc cctgtcaaca 10860
tatacgacaa ggtttcccct agagactatt tgagagggct cgcaagggga gtattgatag 10920
gatcctcgat ttgcttcttg acaagaatga caaatatcaa tattaataga cctcttgaat 10980
tgatctcagg ggtaatctca tatattctcc tgaggctaga taaccatccc tccttgtaca 11040
taatgctcag agaaccgtct cttagaggag agatattttc tatccctcag aaaatccccg 11100
ccgcttatcc aaccactatg aaagaaggca acagatcaat cttgtgttat ctccaacatg 11160
tgctacgcta tgagcgagag ataatcacgg cgtctccaga gaatgactgg ctatggatct 11220
tttcagactt tagaagtgcc aaaatgacgt acctaaccct cattacttac cagtctcatc 11280
ttctactcca gagggttgag agaaacctat ctaagagtat gagagataac ctgcgacaat 11340
tgagttcctt gatgaggcag gtgctgggcg ggcacggaga agataccttta gagtcagacg 11400
acaacattca acgactgcta aaagactctt tacgaaggac aagatgggtg gatcaagagg 11460
tgcgccatgc agctagaacc atgactggag attacagccc caacaagaag gtgtcccgta 11520
aggtaggatg ttcagaatgg gtctgctctg ctcaacaggt tgcagtctct acctcagcaa 11580
acccggcccc tgtctcggag cttgacataa gggccctctc taagaggttc cagaaccctt 11640
tgatctcggg cttgagagtg gttcagtggg caaccggtgc tcattataag cttaagccta 11700
ttctagatga tctcaatgtt ttcccatctc tctgccttgt agttggggac gggtcagggg 11760
ggatatcaag ggcagtcctc aacatgtttc cagatgccaa gcttgtgttc aacagtctct 11820
tagaggtgaa tgacctgatg gcttccggaa cacatccact gcctccttca gcaatcatga 11880
ggggaggaaa tgatatcgtc tccagagtga tagattttga ctcaatctgg gaaaaaccgt 11940
ccgacttgag aaacttggca acctggaaat acttccagtc agtccaaaag caggtcaaca 12000
tgtcctatga cctcattatt tgcgatgcag aagttactga cattgcatct atcaaccgga 12060
taaccctgtt aatgtccgat tttgcattgt ctatagatgg accactctat ttggtcttca 12120
aaacttatgg gactatgcta gtaaatccaa actacaaggc tattcaacac ctgtcaagag 12180
cgttcccctc ggtcacaggg tttatcaccc aagtaacttc gtctttttca tctgagctct 12240
acctccgatt ctccaaacga gggaagtttt tcagagatgc tgagtacttg acctcttcca 12300
cccttcgaga aatgagcctt gtgttattca attgtagcag ccccaagagt gagatgcaga 12360

```
gagctcgttc cttgaactat caggatcttg tgagaggatt tcctgaagaa atcatatcaa  12420

atccttacaa tgagatgatc ataactctga ttgacagtga tgtagaatct tttctagtcc  12480

acaagatggt tgatgatctt gagttacaga ggggaactct gtctaaagtg gctatcatta  12540

tagccatcat gatagttttc tccaacagag tcttcaacgt ttccaaaccc ctaactgacc  12600

ccttgttcta tccaccgtct gatcccaaaa tcctgaggca cttcaacata tgttgcagta  12660

ctatgatgta tctatctact gctttaggtg acgtccctag cttcgcaaga cttcacgacc  12720

tgtataacag acctataact tattacttca gaaagcaatt cattcgaggg aacgtttatc  12780

tatcttggag ttggtccaac gacacctcag tgttcaaaag ggtagcctgt aattctagcc  12840

tgagtctgtc atctcactgg atcaggttga tttacaagat agtgaagact accagactcg  12900

ttggcagcat caaggatcta tccagagaag tggaaagaca ccttcatagg tacaacaggt  12960

ggatcaccct agaggatatc agatctagat catccctact agactacagt tgcctgtgat  13020

ccggatactc ctggaagcct gcccatgcta agactcttgt gtgatgtatc ttgaaaaaaa  13080

caagatccta aatctgaacc tttggttgtt tgattgtttt tctcattttt gttgtttatt  13140

tgttaagcgt                                                         13150


<210> SEQ ID NO 11
<211> LENGTH: 12266
<212> TYPE: DNA
<213> ORGANISM: artificial sequence
<220> FEATURE:
<223> OTHER INFORMATION: Recombinant ERAgreen rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (4993)..(5673)
<220> FEATURE:
<221> NAME/KEY: misc_feature
<222> LOCATION: (5752)..(12132)

<400> SEQUENCE: 11

acgcttaaca accagatcaa agaaaaaaca gacattgtca attgcaaagc aaaaatgtaa     60

caccccctaca atggatgccg acaagattgt attcaaagtc aataatcagg tggtctcttt    120

gaagcctgag attatcgtgg atcaacatga gtacaagtac cctgccatca aagatttgaa    180

aaagccctgt ataaccctag gaaaggctcc cgatttaaat aaagcataca agtcagtttt    240

gtcaggcatg agcgccgcca aacttgatcc tgacgatgta tgttcctatt tggcagcggc    300

aatgcagttt tttgagggga catgtccgga agactggacc agctatggaa tcgtgattgc    360

acgaaaagga gataagatca ccccaggttc tctggtggag ataaaacgta ctgatgtaga    420

agggaattgg gctctgacag gaggcatgga actgacaaga gaccccactg tccctgagca    480

tgcgtcctta gtcggtcttc tcttgagtct gtataggttg agcaaaatat ccgggcaaaa    540

cactggtaac tataagacaa acattgcaga caggatagag cagatttttg agacagcccc    600

ttttgttaaa atcgtggaac accatactct aatgacaact cacaaaatgt gtgctaattg    660

gagtactata ccaaacttca gatttttggc cggaacctat gacatgtttt tctcccggat    720
```

tgagcatcta tattcagcaa tcagagtggg cacagttgtc actgcttatg aagactgttc 780
aggactggta tcatttactg ggttcataaa acaaatcaat ctcaccgcta gagaggcaat 840
actatatttc ttccacaaga actttgagga agagataaga agaatgtttg agccagggca 900
ggagacagct gttcctcact cttatttcat ccacttccgt tcactaggct tgagtgggaa 960
atctccttat tcatcaaatg ctgttggtca cgtgttcaat ctcattcact ttgtaggatg 1020
ctatatgggt caagtcagat ccctaaatgc aacggttatt gctgcatgtg ctcctcatga 1080
aatgtctgtt ctagggggct atctgggaga ggaattcttc gggaaaggga catttgaaag 1140
aagattcttc agagatgaga aagaacttca agaatacgag gcggctgaac tgacaaagac 1200
tgacgtagca ctggcagatg atggaactgt caactctgac gacgaggact acttctcagg 1260
tgaaaccaga agtccggagg ctgtttatac tcgaatcatg atgaatggag gtcgactaaa 1320
gagatctcac atacggagat atgtctcagt cagttccaat catcaagccc gtccaaactc 1380
attcgccgag tttctaaaca agacatattc gagtgactca taagaagttg aataacaaaa 1440
tgccggaaat ctacggattg tgtatatcca tcatgaaaaa aactaacacc cctcctttcg 1500
aaccatccca aacatgagca agatctttgt caatcctagt gctattagag ccggtctggc 1560
cgatcttgag atggctgaag aaactgttga tctgatcaat agaaatatcg aagacaatca 1620
ggctcatctc caaggggaac ccatagaagt ggacaatctc cctgaggata tggggcgact 1680
tcacctggat gatggaaaat cgcccaaccc tggtgagatg gccaaggtgg gagaaggcaa 1740
gtatcgagag gactttcaga tggatgaagg agaggatcct agcttcctgt tccagtcata 1800
cctggaaaat gttggagtcc aaatagtcag acaaatgagg tcaggagaga gatttctcaa 1860
gatatggtca cagaccgtag aagagattat atcctatgtc gcggtcaact ttcccaaccc 1920
tccaggaaag tcttcagagg ataaatcaac ccagactact ggccgagagc tcaagaagga 1980
gacaacaccc actccttctc agagagaaag ccaatcatcg aaagccagga tggcggctca 2040
aattgcttct ggccctccag cccttgaatg gtcggccacc aatgaagagg atgatctatc 2100
agtggaggct gagatcgctc accagattgc agaaagtttc tccaaaaaat ataagtttcc 2160
ctctcgatcc tcagggatac tcttgtataa ttttgagcaa ttgaaaatga accttgatga 2220
tatagttaaa gaggcaaaaa atgtaccagg tgtgacccgt ttagcccatg acgggtccaa 2280
actcccccta agatgtgtac tgggatgggt cgctttggcc aactctaaga aattccagtt 2340
gttagtcgaa tccgacaagc tgagtaaaat catgcaagat gacttgaatc gctatacatc 2400
ttgctaaccg aacctctcca ctcagtccct ctagacaata aagtccgaga tgtcctaaag 2460
tcaacatgaa aaaaacaggc aacaccactg ataaaatgaa ctttctacgt aagatagtga 2520
aaaattgcag ggacgaggac actcaaaaac cctctcccgt gtcagcccct ctggatgacg 2580
atgacttgtg gcttccaccc cctgaatacg tcccgctgaa agaacttaca agcaagaaga 2640
acatgaggaa cttttgtatc aacggagggg ttaaagtgtg tagcccgaat ggttactcgt 2700
tcaggatcct gcggcacatt ctgaaatcat tcgacgagat atattctggg aatcatagga 2760
tgatcgggtt agtcaaagta gttattggac tggctttgtc aggatctcca gtccctgagg 2820
gcatgaactg ggtatacaaa ttgaggagaa cctttatctt ccagtgggct gattccaggg 2880
gccctcttga aggggaggag ttggaatact ctcaggagat cacttgggat gatgatactg 2940
agttcgtcgg attgcaaata agagtgattg caaaacagtg tcatatccag ggcagaatct 3000
ggtgtatcaa catgaacccg agagcatgtc aactatggtc tgacatgtct cttcagacac 3060

-continued

```
aaaggtccga agaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagactcaa ggaaagatgg ttcctcaggc tctcctgttt gtaccccttc tggtttttcc   3360
attgtgtttt gggaaattcc ctatttacac gataccagac aagcttggtc cctggagccc   3420
gattgacata catcacctca gctgcccaaa caatttggta gtggaggacg aaggatgcac   3480
caacctgtca gggttctcct acatggaact taaagttgga tacatcttag ccataaaaat   3540
gaacgggttc acttgcacag gcgttgtgac ggaggctgaa acctacacta acttcgttgg   3600
ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cactggcttc gaactgtaaa aaccaccaag gagtctctcg ttatcatatc   3780
tccaagtgtg gcagatttgg acccatatga cagatccctt cactcgaggg tcttccctag   3840
cgggaagtgc tcaggagtag cggtgtcttc tacctactgc tccactaacc acgattacac   3900
catttggatg cccgagaatc cgagactagg gatgtcttgt gacattttta ccaatagtag   3960
agggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtcgcga tgcaaacatc aaatgaaacc aaatggtgcc ctcccgatca   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtctcagtc atttaagaaa acttgtccct gggtttggaa aagcatatac   4320
catattcaac aagaccttga tggaagccga tgctcactac aagtcagtca gaacttggaa   4380
tgagatcctc ccttcaaaag ggtgtttaag agttgggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tcccccttgt   4560
gcacccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataatttt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgtg aggactggcc gtcctttcaa ctatccaagt   4920
cctgaagatc acctcccctt ggggggttca tcatgaaaaa aactaacacc cctcctttcg   4980
ctgcaggcca ccatgggcgt gatcaagccc gacatgaaga tcaagctgcg gatggagggc   5040
gccgtgaacg gccacaaatt cgtgatcgag ggcgacggga aaggcaagcc ctttgagggt   5100
aagcagacta tggacctgac cgtgatcgag ggcgcccccc tgcccttcgc ttatgacatt   5160
ctcaccaccg tgttcgacta cggtaaccgt gtcttcgcca agtaccccaa ggacatccct   5220
gactacttca agcagacctt ccccgagggc tactcgtggg agcgaagcat gacatacgag   5280
gaccagggaa tctgtatcgc tacaaacgac atcaccatga tgaagggtgt ggacgactgc   5340
ttcgtgtaca aaatccgctt cgacggggtc aacttccctg ctaatggccc ggtgatgcag   5400
cgcaagaccc taaagtggga gcccagtacc gagaagatgt acgtgcggga cggcgtactg   5460
```

-continued

```
aagggcgatg ttaatatggc actgctcttg gagggaggcg gccactaccg ctgcgacttc   5520
aagaccacct acaaagccaa gaaggtggtg cagcttcccg actaccactt cgtggaccac   5580
cgcatcgaga tcgtgagcca cgacaaggac tacaacaaag tcaagctgta cgagcacgcc   5640
gaagcccaca gcggactacc ccgccaggcc ggctaatagg taccgtcgag aaaaaaacat   5700
tagatcagaa gaacaactgg caacacttct caacctgaga cctacttcaa gatgctcgat   5760
cctggagagg tctatgatga ccctattgac ccaatcgagt tagaggatga acccagagga   5820
acccccactg tccccaacat cttgaggaac tctgactaca atctcaactc tcctttgata   5880
gaagatcctg ctagactaat gttagaatgg ttaaaaacag ggaatagacc ttatcggatg   5940
actctaacag acaattgctc caggtctttc agagttttga aagattattt caagaaggta   6000
gatttgggtt ctctcaaggt gggcggaatg gctgcacagt caatgatttc tctctggtta   6060
tatggtgccc actctgaatc caacaggagc cggagatgta taacagactt ggcccatttc   6120
tattccaagt cgtcccccat agagaagctg ttgaatctca cgctaggaaa tagagggctg   6180
agaatccccc cagagggagt gttaagttgc cttgagaggg ttgattatga taatgcattt   6240
ggaaggtatc ttgccaacac gtattcctct tacttgttct tccatgtaat caccttatac   6300
atgaacgccc tagactggga tgaagaaaag accatcctag cattatggaa agatttaacc   6360
tcagtggaca tcgggaagga cttggtaaag ttcaaagacc aaatatgggg actgctgatc   6420
gtgacaaagg actttgttta ctcccaaagt tccaattgtc tttttgacag aaactacaca   6480
cttatgctaa aagatctttt cttgtctcgc ttcaactcct taatggtctt gctctctccc   6540
ccagagcccc gatactcaga tgacttgata tctcaactat gccagctgta cattgctggg   6600
gatcaagtct tgtctatgtg tggaaactcc ggctatgaag tcatcaaaat attggagcca   6660
tatgtcgtga atagtttagt ccagagagca gaaaagttta ggcctctcat tcattccttg   6720
ggagactttc ctgtatttat aaaagacaag gtaagtcaac ttgaagagac gttcggtccc   6780
tgtgcaagaa ggttctttag ggctctggat caattcgaca acatacatga cttggttttt   6840
gtgtatggct gttacaggca ttgggggcac ccatatatag attatcgaaa gggtctgtca   6900
aaactatatg atcaggttca cattaaaaaa gtgatagata agtcctacca ggagtgctta   6960
gcaagcgacc tagccaggag gatccttaga tggggttttg ataagtactc caagtggtat   7020
ctggattcaa gattcctagc ccgagaccac cccttgactc cttatatcaa aacccaaaca   7080
tggccaccca aacatattgt agacttggtg gggdatacat ggcacaagct cccgatcacg   7140
cagatctttg agattcctga atcaatggat ccgtcagaaa tattggatga caaatcacat   7200
tctttcacca gaacgagact agcttcttgg ctgtcagaaa accgaggggg acctgttcct   7260
agcgaaaaag ttattatcac ggccctgtct aagccgcctg tcaatccccg agagtttctg   7320
aggtctatag acctcggagg attgccagat gaagacttga taattggcct caagccaaag   7380
gaacgggaat tgaagattga aggtcgattc tttgctctaa tgtcatggaa tctaagattg   7440
tattttgtca tcactgaaaa actcttggcc aactacatct tgccactttt tgacgcgctg   7500
actatgacag acaacctgaa caaggtgttt aaaaagctga tcgacagggt caccgggcaa   7560
gggcttttgg actattcaag ggtcacatat gcatttcacc tggactatga aaagtggaac   7620
aaccatcaaa gattagagtc aacagaggat gtattttctg tcctagatca agtgtttgga   7680
ttgaagagag tgttttctag aacacacgag ttttttcaaa aggcctggat ctattattca   7740
gacagatcag acctcatcgg gttacgggag gatcaaatat actgcttaga tgcgtccaac   7800
```

-continued

```
ggcccaacct gttggaatgg ccaggatggc gggctagaag gcttacggca gaagggctgg   7860
agtctagtca gcttattgat gatagataga gaatctcaaa tcaggaacac aagaaccaaa   7920
atactagctc aaggagacaa ccaggtttta tgtccgacat atatgttgtc gccagggcta   7980
tctcaagagg ggctcctcta tgaattggag agaatatcaa ggaatgcact ttcgatatac   8040
agagccgtcg aggaaggggc atctaagcta gggctgatca tcaagaaaga agagaccatg   8100
tgtagttatg acttcctcat ctatggaaaa accccttttgt ttagaggtaa catattggtg   8160
cctgagtcca aaagatgggc cagagtctct tgcgtctcta atgaccaaat agtcaacctc   8220
gccaatataa tgtcgacagt gtccaccaat gcgctaacag tggcacaaca ctctcaatct   8280
ttgatcaaac cgatgaggga ttttctgctc atgtcagtac aggcagtctt tcactacctg   8340
ctatttagcc caatcttaaa gggaagagtt tacaagattc tgagcgctga aggggatagc   8400
tttctcctag ccatgtcaag gataatctat ctagatcctt ctttgggagg ggtatctgga   8460
atgtccctcg gaagattcca tatacgacag ttctcagacc ctgtctctga agggttatcc   8520
ttctggagag agatctggtt aagctcccac gagtcctgga ttcacgcgtt gtgtcaagag   8580
gctggaaacc cagatcttgg agagagaaca ctcgagagct tcactcgcct tctagaagat   8640
cctaccacct taaatatcag aggaggggcc agtcctacca ttctactcaa ggatgcaatc   8700
agaaaggctt tatatgacga ggtggacaag gtggagaatt cagagtttcg agaggcaatc   8760
ctgttgtcca agacccatag agataatttt atactcttct taacatctgt tgagcctctg   8820
tttcctcgat ttctcagtga gctattcagt tcgtcttttt tgggaatccc cgagtcaatc   8880
attggattga tacaaaactc ccgaacgata agaaggcagt ttagaaagag tctctcaaaa   8940
actttagaag aatccttcta caactcagag atccacggga ttagtcggat gacccagaca   9000
cctcagaggg ttgggggggt gtggccttgc tcttcagaga gggcagatct acttagggag   9060
atctcttggg gaagaaaagt ggtaggcacg acagttcctc acccttctga gatgttgggg   9120
ttacttccca agtcctctat ttcttgcact tgtggagcaa caggaggagg caatcctaga   9180
gtttctgtat cagtactccc gtcctttgat cagtcatttt tttcacgagg cccccctaaag   9240
gggtacttgg gctcgtccac ctctatgtcg acccagctat tccatgcatg ggaaaaagtc   9300
actaatgttc atgtggtgaa gagagctcta tcgttaaaag aatctataaa ctggttcatt   9360
actagagatt ccaacttggc tcaagctcta attaggaaca ttatgtctct gacaggccct   9420
gatttccctc tagaggaggc ccctgtcttc aaaaggacgg ggtcagcctt gcataggttc   9480
aagtctgcca gatacagcga aggagggtat tcttctgtct gcccgaacct cctctctcat   9540
atttctgtta gtacagacac catgtctgat ttgacccaag acgggaagaa ctacgatttc   9600
atgttccagc cattgatgct ttatgcacag acatggacat cagagctggt acagagagac   9660
acaaggctaa gagactctac gtttcattgg cacctccgat gcaacaggtg tgtgagaccc   9720
attgacgacg tgaccctgga gacctctcag atcttcgagt ttccggatgt gtcgaaaaga   9780
atatccagaa tggtttctgg ggctgtgcct cacttccaga ggcttcccga tatccgtctg   9840
agaccaggag attttgaatc tctaagcggt agagaaaagt ctcaccatat cggatcagct   9900
caggggctct tatactcaat cttagtggca attcacgact caggatacaa tgatggaacc   9960
atcttccctg tcaacatata cgacaaggtt tcccctagag actatttgag agggctcgca  10020
aggggagtat tgataggatc ctcgatttgc ttcttgacaa gaatgacaaa tatcaatatt  10080
aatagacctc ttgaattgat ctcaggggta atctcatata ttctcctgag gctagataac  10140
catccctcct tgtacataat gctcagagaa ccgtctctta gaggagagat attttctatc  10200
```

```
cctcagaaaa tccccgccgc ttatccaacc actatgaaag aaggcaacag atcaatcttg  10260
tgttatctcc aacatgtgct acgctatgag cgagagataa tcacggcgtc tccagagaat  10320
gactggctat ggatcttttc agactttaga agtgccaaaa tgacgtacct aaccctcatt  10380
acttaccagt ctcatcttct actccagagg gttgagagaa acctatctaa gagtatgaga  10440
gataacctgc gacaattgag ttccttgatg aggcaggtgc tgggcgggca cggagaagat  10500
accttagagt cagacgacaa cattcaacga ctgctaaaag actctttacg aaggacaaga  10560
tgggtggatc aagaggtgcg ccatgcagct agaaccatga ctggagatta cagccccaac  10620
aagaaggtgt cccgtaaggt aggatgttca gaatgggtct gctctgctca acaggttgca  10680
gtctctacct cagcaaaccc ggcccctgtc tcggagcttg acataagggc cctctctaag  10740
aggttccaga accctttgat ctcgggcttg agagtggttc agtgggcaac cggtgctcat  10800
tataagctta agcctattct agatgatctc aatgttttcc catctctctg ccttgtagtt  10860
ggggacgggt caggggggat atcaagggca gtcctcaaca tgtttccaga tgccaagctt  10920
gtgttcaaca gtctcttaga ggtgaatgac ctgatggctt ccggaacaca tccactgcct  10980
ccttcagcaa tcatgagggg aggaaatgat atcgtctcca gagtgataga ttttgactca  11040
atctgggaaa aaccgtccga cttgagaaac ttggcaacct ggaaatactt ccagtcagtc  11100
caaaagcagg tcaacatgtc ctatgacctc attatttgcg atgcagaagt tactgacatt  11160
gcatctatca accggataac cctgttaatg tccgattttg cattgtctat agatggacca  11220
ctctatttgg tcttcaaaac ttatgggact atgctagtaa atccaaacta caaggctatt  11280
caacacctgt caagagcgtt cccctcggtc acagggttta tcacccaagt aacttcgtct  11340
ttttcatctg agctctacct ccgattctcc aaacgaggga agtttttcag agatgctgag  11400
tacttgacct cttccaccct tcgagaaatg agccttgtgt tattcaattg tagcagcccc  11460
aagagtgaga tgcagagagc tcgttccttg aactatcagg atcttgtgag aggatttcct  11520
gaagaaatca tatcaaatcc ttacaatgag atgatcataa ctctgattga cagtgatgta  11580
gaatcttttc tagtccacaa gatggttgat gatcttgagt tacagagggg aactctgtct  11640
aaagtggcta tcattatagc catcatgata gttttctcca acagagtctt caacgtttcc  11700
aaacccctaa ctgacccctt gttctatcca ccgtctgatc ccaaaatcct gaggcacttc  11760
aacatatgtt gcagtactat gatgtatcta tctactgctt taggtgacgt ccctagcttc  11820
gcaagacttc acgacctgta taacagacct ataacttatt acttcagaaa gcaattcatt  11880
cgagggaacg tttatctatc ttggagttgg tccaacgaca cctcagtgtt caaaagggta  11940
gcctgtaatt ctagcctgag tctgtcatct cactggatca ggttgattta caagatagtg  12000
aagactacca gactcgttgg cagcatcaag gatctatcca gagaagtgga aagacacctt  12060
cataggtaca acaggtggat caccctagag gatatcagat ctagatcatc cctactagac  12120
tacagttgcc tgtgatccgg atactcctgg aagcctgccc atgctaagac tcttgtgtga  12180
tgtatcttga aaaaaacaag atcctaaatc tgaacctttg gttgtttgat tgtttttctc  12240
atttttgttg tttatttgtt aagcgt                                       12266
```

<210> SEQ ID NO 12
<211> LENGTH: 10288
<212> TYPE: DNA
<213> ORGANISM: artificial sequence
<220> FEATURE:
<223> OTHER INFORMATION: Recombinant ERA-G rabies virus
<220> FEATURE:

<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3774)..(10154)

<400> SEQUENCE: 12
acgcttaaca accagatcaa agaaaaaaca gacattgtca attgcaaagc aaaaatgtaa 60 caccccctaca atggatgccg acaagattgt attcaaagtc aataatcagg tggtctcttt 120
gaagcctgag attatcgtgg atcaacatga gtacaagtac cctgccatca aagatttgaa 180
aaagccctgt ataaccctag gaaaggctcc cgatttaaat aaagcataca agtcagtttt 240
gtcaggcatg agcgccgcca aacttgatcc tgacgatgta tgttcctatt tggcagcggc 300
aatgcagttt tttgaggggga catgtccgga agactggacc agctatggaa tcgtgattgc 360
acgaaaagga gataagatca ccccaggttc tctggtggag ataaaacgta ctgatgtaga 420
agggaattgg gctctgacag gaggcatgga actgacaaga gaccccactg tccctgagca 480
tgcgtcctta gtcggtcttc tcttgagtct gtataggttg agcaaaatat ccgggcaaaa 540
cactggtaac tataagacaa acattgcaga caggatagag cagatttttg agacagcccc 600
ttttgttaaa atcgtggaac accatactct aatgacaact cacaaaatgt gtgctaattg 660
gagtactata ccaaacttca gatttttggc cggaacctat gacatgtttt tctcccggat 720
tgagcatcta tattcagcaa tcagagtggg cacagttgtc actgcttatg aagactgttc 780
aggactggta tcatttactg ggttcataaa acaaatcaat ctcaccgcta gagaggcaat 840
actatatttc ttccacaaga actttgagga agagataaga agaatgtttg agccagggca 900
ggagacagct gttcctcact cttatttcat ccacttccgt tcactaggct tgagtgggaa 960
atctccttat tcatcaaatg ctgttggtca cgtgttcaat ctcattcact ttgtaggatg 1020
ctatatgggt caagtcagat ccctaaatgc aacggttatt gctgcatgtg ctcctcatga 1080
aatgtctgtt ctaggggggct atctgggaga ggaattcttc gggaaaggga catttgaaag 1140
aagattcttc agagatgaga aagaacttca agaatacgag gcggctgaac tgacaaagac 1200
tgacgtagca ctggcagatg atggaactgt caactctgac gacgaggact acttctcagg 1260
tgaaaccaga agtccggagg ctgtttatac tcgaatcatg atgaatggag gtcgactaaa 1320
gagatctcac atacggagat atgtctcagt cagttccaat catcaagccc gtccaaactc 1380
attcgccgag tttctaaaca agacatattc gagtgactca taagaagttg aataacaaaa 1440
tgccggaaat ctacggattg tgtatatcca tcatgaaaaa aactaacacc cctcctttcg 1500
aaccatccca aacatgagca agatctttgt caatcctagt gctattagag ccggtctggc 1560
cgatcttgag atggctgaag aaactgttga tctgatcaat agaaatatcg aagacaatca 1620
ggctcatctc caaggggaac ccatagaagt ggacaatctc cctgaggata tggggcgact 1680
tcacctggat gatggaaaat cgcccaaccc tggtgagatg gccaaggtgg gagaaggcaa 1740
gtatcgagag gactttcaga tggatgaagg agaggatcct agcttcctgt tccagtcata 1800
cctggaaaat gttggagtcc aaatagtcag acaaatgagg tcaggagaga gatttctcaa 1860
gatatggtca cagaccgtag aagagattat atcctatgtc gcggtcaact ttcccaaccc 1920
tccaggaaag tcttcagagg ataaatcaac ccagactact ggccgagagc tcaagaagga 1980

-continued

```
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaaacaggc aacaccactg ataaaatgaa ctttctacgt aagatagtga   2520
aaaattgcag ggacgaggac actcaaaaac cctctcccgt gtcagcccct ctggatgacg   2580
atgacttgtg gcttccaccc cctgaatacg tcccgctgaa agaacttaca agcaagaaga   2640
acatgaggaa cttttgtatc aacggagggg ttaaagtgtg tagcccgaat ggttactcgt   2700
tcaggatcct gcggcacatt ctgaaatcat tcgacgagat atattctggg aatcatagga   2760
tgatcgggtt agtcaaagta gttattggac tggctttgtc aggatctcca gtccctgagg   2820
gcatgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagaatct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
agttgattac ctttacattt tgatcctctt ggatgtgaaa aaaactaaca cccctctgca   3300
gtttggtacc ttgaaaaaaa cctgggttca atagtcctcc ttgaactcca tgcaactggg   3360
tagattcaag agtcatgaga ttttcattaa tcctctcagt tgatcaagca agatcatgta   3420
gattctcata ataggggaga tcttctagca gtttcagtga ctaacggtac tttcattctc   3480
caggaactga caccaacagt tgtagacaaa ccacggggtg tctcgggtga ctctgtgctt   3540
gggcacagac aaaggtcatg gtgtgttcca tgatagcgga ctcaggatga gttaattgag   3600
agaggcagtc ttcctcccgt gaaggacata agcagtagct cacaatcatc tcgcgtctca   3660
gcaaagtgtg cataattata aagtgctggg tcatctaagc ttttcagtcg agaaaaaaac   3720
attagatcag aagaacaact ggcaacactt ctcaacctga gacctacttc aagatgctcg   3780
atcctggaga ggtctatgat gaccctattg acccaatcga gttagaggat gaacccagag   3840
gaacccccac tgtccccaac atcttgagga actctgacta caatctcaac tctcctttga   3900
tagaagatcc tgctagacta atgttagaat ggttaaaaac agggaataga ccttatcgga   3960
tgactctaac agacaattgc tccaggtctt tcagagtttt gaaagattat ttcaagaagg   4020
tagatttggg ttctctcaag gtgggcggaa tggctgcaca gtcaatgatt tctctctggt   4080
tatatggtgc ccactctgaa tccaacagga gccggagatg tataacagac ttggcccatt   4140
tctattccaa gtcgtccccc atagagaagc tgttgaatct cacgctagga aatagagggc   4200
tgagaatccc cccagaggga gtgttaagtt gccttgagag ggttgattat gataatgcat   4260
ttggaaggta tcttgccaac acgtattcct cttacttgtt cttccatgta atcaccttat   4320
```

-continued

```
acatgaacgc cctagactgg gatgaagaaa agaccatcct agcattatgg aaagatttaa   4380
cctcagtgga catcgggaag gacttggtaa agttcaaaga ccaaatatgg ggactgctga   4440
tcgtgacaaa ggactttgtt tactcccaaa gttccaattg tctttttgac agaaactaca   4500
cacttatgct aaaagatctt ttcttgtctc gcttcaactc cttaatggtc ttgctctctc   4560
ccccagagcc ccgatactca gatgacttga tatctcaact atgccagctg tacattgctg   4620
gggatcaagt cttgtctatg tgtggaaact ccggctatga agtcatcaaa atattggagc   4680
catatgtcgt gaatagttta gtccagagag cagaaaagtt taggcctctc attcattcct   4740
tgggagactt tcctgtattt ataaaagaca aggtaagtca acttgaagag acgttcggtc   4800
cctgtgcaag aaggttcttt agggctctgg atcaattcga caacatacat gacttggttt   4860
ttgtgtatgg ctgttacagg cattgggggc acccatatat agattatcga aagggtctgt   4920
caaaactata tgatcaggtt cacattaaaa aagtgataga taagtcctac caggagtgct   4980
tagcaagcga cctagccagg aggatcctta gatggggttt tgataagtac tccaagtggt   5040
atctggattc aagattccta gcccgagacc accccttgac tccttatatc aaaacccaaa   5100
catggccacc caaacatatt gtagacttgg tgggggatac atggcacaag ctcccgatca   5160
cgcagatctt tgagattcct gaatcaatgg atccgtcaga aatattggat gacaaatcac   5220
attctttcac cagaacgaga ctagcttctt ggctgtcaga aaaccgaggg ggacctgttc   5280
ctagcgaaaa agttattatc acggccctgt ctaagccgcc tgtcaatccc cgagagtttc   5340
tgaggtctat agacctcgga ggattgccag atgaagactt gataattggc ctcaagccaa   5400
aggaacggga attgaagatt gaaggtcgat tctttgctct aatgtcatgg aatctaagat   5460
tgtattttgt catcactgaa aaactcttgg ccaactacat cttgccactt tttgacgcgc   5520
tgactatgac agacaacctg aacaaggtgt ttaaaaagct gatcgacagg gtcaccgggc   5580
aagggctttt ggactattca agggtcacat atgcatttca cctggactat gaaaagtgga   5640
acaaccatca aagattagag tcaacagagg atgtattttc tgtcctagat caagtgtttg   5700
gattgaagag agtgttttct agaacacacg agtttttca aaaggcctgg atctattatt   5760
cagacagatc agacctcatc gggttacggg aggatcaaat atactgctta gatgcgtcca   5820
acggcccaac ctgttggaat ggccaggatg gcgggctaga aggcttacgg cagaagggct   5880
ggagtctagt cagcttattg atgatagata gagaatctca aatcaggaac acaagaacca   5940
aaatactagc tcaaggagac aaccaggttt tatgtccgac atatatgttg tcgccagggc   6000
tatctcaaga ggggctcctc tatgaattgg agagaatatc aaggaatgca ctttcgatat   6060
acagagccgt cgaggaaggg gcatctaagc tagggctgat catcaagaaa gaagagacca   6120
tgtgtagtta tgacttcctc atctatggaa aaaccccttt gtttagaggt aacatattgg   6180
tgcctgagtc caaaagatgg gccagagtct cttgcgtctc taatgaccaa atagtcaacc   6240
tcgccaatat aatgtcgaca gtgtccacca atgcgctaac agtggcacaa cactctcaat   6300
ctttgatcaa accgatgagg gattttctgc tcatgtcagt acaggcagtc tttcactacc   6360
tgctatttag cccaatctta aagggaagag tttacaagat tctgagcgct gaaggggata   6420
gctttctcct agccatgtca aggataatct atctagatcc ttctttggga ggggtatctg   6480
gaatgtccct cggaagattc catatacgac agttctcaga ccctgtctct gaagggttat   6540
ccttctggag agagatctgg ttaagctccc acgagtcctg gattcacgcg ttgtgtcaag   6600
aggctggaaa cccagatctt ggagagagaa cactcgagag cttcactcgc cttctagaag   6660
atcctaccac cttaaatatc agaggagggg ccagtcctac cattctactc aaggatgcaa   6720
```

```
tcagaaaggc tttatatgac gaggtggaca aggtggagaa ttcagagttt cgagaggcaa   6780
tcctgttgtc caagacccat agagataatt ttatactctt cttaacatct gttgagcctc   6840
tgtttcctcg atttctcagt gagctattca gttcgtcttt tttgggaatc cccgagtcaa   6900
tcattggatt gatacaaaac tcccgaacga taagaaggca gtttagaaag agtctctcaa   6960
aaactttaga agaatccttc tacaactcag agatccacgg gattagtcgg atgacccaga   7020
cacctcagag ggttgggggg gtgtggcctt gctcttcaga gagggcagat ctacttaggg   7080
agatctcttg gggaagaaaa gtggtaggca cgacagttcc tcacccttct gagatgttgg   7140
ggttacttcc caagtcctct atttcttgca cttgtggagc aacaggagga ggcaatccta   7200
gagtttctgt atcagtactc ccgtcctttg atcagtcatt tttttcacga ggccccctaa   7260
aggggtactt gggctcgtcc acctctatgt cgacccagct attccatgca tgggaaaaag   7320
tcactaatgt tcatgtggtg aagagagctc tatcgttaaa agaatctata aactggttca   7380
ttactagaga ttccaacttg gctcaagctc taattaggaa cattatgtct ctgacaggcc   7440
ctgatttccc tctagaggag gcccctgtct tcaaaaggac ggggtcagcc ttgcataggt   7500
tcaagtctgc cagatacagc gaaggagggt attcttctgt ctgcccgaac ctcctctctc   7560
atatttctgt tagtacagac accatgtctg atttgaccca agacgggaag aactacgatt   7620
tcatgttcca gccattgatg ctttatgcac agacatggac atcagagctg gtacagagag   7680
acacaaggct aagagactct acgtttcatt ggcacctccg atgcaacagg tgtgtgagac   7740
ccattgacga cgtgaccctg gagacctctc agatcttcga gtttccggat gtgtcgaaaa   7800
gaatatccag aatggtttct ggggctgtgc ctcacttcca gaggcttccc gatatccgtc   7860
tgagaccagg agattttgaa tctctaagcg gtagagaaaa gtctcaccat atcggatcag   7920
ctcaggggct cttatactca atcttagtgg caattcacga ctcaggatac aatgatggaa   7980
ccatcttccc tgtcaacata tacgacaagg tttcccctag agactatttg agagggctcg   8040
caaggggagt attgatagga tcctcgattt gcttcttgac aagaatgaca aatatcaata   8100
ttaatagacc tcttgaattg atctcagggg taatctcata tattctcctg aggctagata   8160
accatccctc cttgtacata atgctcagag aaccgtctct tagaggagag atattttcta   8220
tccctcagaa aatccccgcc gcttatccaa ccactatgaa agaaggcaac agatcaatct   8280
tgtgttatct ccaacatgtg ctacgctatg agcgagagat aatcacggcg tctccagaga   8340
atgactggct atggatcttt tcagacttta gaagtgccaa aatgacgtac ctaaccctca   8400
ttacttacca gtctcatctt ctactccaga gggttgagag aaacctatct aagagtatga   8460
gagataacct gcgacaattg agttccttga tgaggcaggt gctgggcggg cacggagaag   8520
ataccttaga gtcagacgac aacattcaac gactgctaaa agactcttta cgaaggacaa   8580
gatgggtgga tcaagaggtg cgccatgcag ctagaaccat gactggagat tacagcccca   8640
acaagaaggt gtcccgtaag gtaggatgtt cagaatgggt ctgctctgct caacaggttg   8700
cagtctctac ctcagcaaac ccggcccctg tctcggagct tgacataagg gccctctcta   8760
agaggttcca gaaccctttg atctcgggct tgagagtggt tcagtgggca accggtgctc   8820
attataagct taagcctatt ctagatgatc tcaatgtttt cccatctctc tgccttgtag   8880
ttggggacgg gtcagggggg atatcaaggg cagtcctcaa catgtttcca gatgccaagc   8940
ttgtgttcaa cagtctctta gaggtgaatg acctgatggc ttccggaaca catccactgc   9000
ctccttcagc aatcatgagg ggaggaaatg atatcgtctc cagagtgata gattttgact   9060
```

```
caatctggga aaaaccgtcc gacttgagaa acttggcaac ctggaaatac ttccagtcag   9120

tccaaaagca ggtcaacatg tcctatgacc tcattatttg cgatgcagaa gttactgaca   9180

ttgcatctat caaccggata accctgttaa tgtccgattt tgcattgtct atagatggac   9240

cactctattt ggtcttcaaa acttatggga ctatgctagt aaatccaaac tacaaggcta   9300

ttcaacacct gtcaagagcg ttcccctcgg tcacagggtt tatcacccaa gtaacttcgt   9360

ctttttcatc tgagctctac ctccgattct ccaaacgagg gaagtttttc agagatgctg   9420

agtacttgac ctcttccacc cttcgagaaa tgagccttgt gttattcaat tgtagcagcc   9480

ccaagagtga gatgcagaga gctcgttcct tgaactatca ggatcttgtg agaggatttc   9540

ctgaagaaat catatcaaat ccttacaatg agatgatcat aactctgatt gacagtgatg   9600

tagaatcttt tctagtccac aagatggttg atgatcttga gttacagagg ggaactctgt   9660

ctaaagtggc tatcattata gccatcatga tagttttctc caacagagtc ttcaacgttt   9720

ccaaacccct aactgacccc ttgttctatc caccgtctga tcccaaaatc ctgaggcact   9780

tcaacatatg ttgcagtact atgatgtatc tatctactgc tttaggtgac gtccctagct   9840

tcgcaagact tcacgacctg tataacagac ctataactta ttacttcaga aagcaattca   9900

ttcgagggaa cgtttatcta tcttggagtt ggtccaacga cacctcagtg ttcaaaaggg   9960

tagcctgtaa ttctagcctg agtctgtcat ctcactggat caggttgatt tacaagatag  10020

tgaagactac cagactcgtt ggcagcatca aggatctatc cagagaagtg gaaagacacc  10080

ttcataggta caacaggtgg atcaccctag aggatatcag atctagatca tccctactag  10140

actacagttg cctgtgatcc ggatactcct ggaagcctgc ccatgctaag actcttgtgt  10200

gatgtatctt gaaaaaaaca agatcctaaa tctgaacctt tggttgtttg attgtttttc  10260

tcatttttgt tgtttatttg ttaagcgt                                     10288
```

<210> SEQ ID NO 13
<211> LENGTH: 13150
<212> TYPE: DNA
<213> ORGANISM: artificial sequence
<220> FEATURE:
<223> OTHER INFORMATION: Recombinant ERA-2g3 rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (4988)..(6559)
<220> FEATURE:
<221> NAME/KEY: misc_feature
<222> LOCATION: (6636)..(13016)

<400> SEQUENCE: 13

```
acgcttaaca accagatcaa agaaaaaaca gacattgtca attgcaaagc aaaaatgtaa     60

cacccctaca atggatgccg acaagattgt attcaaagtc aataatcagg tggtctcttt    120

gaagcctgag attatcgtgg atcaacatga gtacaagtac cctgccatca aagatttgaa    180

aaagccctgt ataaccctag gaaaggctcc cgatttaaat aaagcataca agtcagtttt    240

gtcaggcatg agcgccgcca aacttgatcc tgacgatgta tgttcctatt tggcagcggc    300
```

-continued

```
aatgcagttt tttgagggga catgtccgga agactggacc agctatggaa tcgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagatttttg agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttctcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaagt ggacaatctc cctgaggata tggggcgact   1680
tcacctggat gatggaaaat cgcccaaccc tggtgagatg gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaaacaggc aacaccactg ataaaatgaa ctttctacgt aagatagtga   2520
aaaattgcag ggacgaggac actcaaaaac cctctcccgt gtcagcccct ctggatgacg   2580
atgacttgtg gcttccaccc cctgaatacg tcccgctgaa agaacttaca agcaagaaga   2640
```

-continued

```
acatgaggaa cttttgtatc aacggagggg ttaaagtgtg tagcccgaat ggttactcgt   2700
tcaggatcct gcggcacatt ctgaaatcat tcgacgagat atattctggg aatcatagga   2760
tgatcgggtt agtcaaagta gttattggac tggctttgtc aggatctcca gtccctgagg   2820
gcatgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagaatct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagactcaa ggaaagatgg ttcctcaggc tctcctgttt gtaccccttc tggtttttcc   3360
attgtgtttt gggaaattcc ctatttacac gataccagac aagcttggtc cctggagccc   3420
gattgacata catcacctca gctgcccaaa caatttggta gtggaggacg aaggatgcac   3480
caacctgtca gggttctcct acatggaact taaagttgga tacatcttag ccataaaaat   3540
gaacgggttc acttgcacag gcgttgtgac ggaggctgaa acctacacta acttcgttgg   3600
ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cactggcttc gaactgtaaa aaccaccaag gagtctctcg ttatcatatc   3780
tccaagtgtg gcagatttgg acccatatga cagatccctt cactcgaggg tcttccctag   3840
cgggaagtgc tcaggagtag cggtgtcttc tacctactgc tccactaacc acgattacac   3900
catttggatg cccgagaatc cgagactagg gatgtcttgt gacattttta ccaatagtag   3960
agggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtcgcga tgcaaacatc aaatgaaacc aaatggtgcc ctcccgatca   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtctcagtc atttaagaaa acttgtccct gggtttggaa aagcatatac   4320
catattcaac aagaccttga tggaagccga tgctcactac aagtcagtcg agacttggaa   4380
tgagatcctc ccttcaaaag ggtgtttaag agttgggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tccccctttgt   4560
gcaccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataatttt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgtg aggactggcc gtcctttcaa ctatccaagt   4920
cctgaagatc acctcccctt ggggggttca tcatgaaaaa aactaacacc cctcctttcg   4980
ctgcaggatg gttcctcagg ctctcctgtt tgtacccctt ctggtttttc cattgtgttt   5040
```

tgggaaattc cctatttaca cgataccaga caagcttggt ccctggagcc cgattgacat 5100
acatcacctc agctgcccaa acaatttggt agtggaggac gaaggatgca ccaacctgtc 5160
agggttctcc tacatggaac ttaaagttgg atacatctta gccataaaaa tgaacgggtt 5220
cacttgcaca ggcgttgtga cggaggctga aacctacact aacttcgttg gttatgtcac 5280
aaccacgttc aaaagaaagc atttccgccc aacaccagat gcatgtagag ccgcgtacaa 5340
ctggaagatg gccggtgacc ccagatatga agagtctcta cacaatccgt accctgacta 5400
ccactggctt cgaactgtaa aaaccaccaa ggagtctctc gttatcatat ctccaagtgt 5460
ggcagatttg gacccatatg acagatccct tcactcgagg gtcttcccta gcgggaagtg 5520
ctcaggagta gcggtgtctt ctacctactg ctccactaac cacgattaca ccatttggat 5580
gcccgagaat ccgagactag ggatgtcttg tgacattttt accaatagta gagggaagag 5640
agcatccaaa gggagtgaga cttgcggctt tgtagatgaa agaggcctat ataagtcttt 5700
aaaaggagca tgcaaactca agttatgtgg agttctagga cttagactta tggatggaac 5760
atgggtcgcg atgcaaacat caaatgaaac caaatggtgc cctcccgatc agttggtgaa 5820
cctgcacgac tttcgctcag acgaaattga gcaccttgtt gtagaggagt tggtcaggaa 5880
gagagaggag tgtctggatg cactagagtc catcatgaca accaagtcag tgagtttcag 5940
acgtctcagt catttaagaa aacttgtccc tgggtttgga aaagcatata ccatattcaa 6000
caagaccttg atggaagccg atgctcacta caagtcagtc gagacttgga atgagatcct 6060
cccttcaaaa gggtgtttaa gagttggggg gaggtgtcat cctcatgtga acggggtgtt 6120
tttcaatggt ataatattag gacctgacgg caatgtctta atcccagaga tgcaatcatc 6180
cctcctccag caacatatgg agttgttgga atcctcggtt atcccccttg tgcacccccct 6240
ggcagacccg tctaccgttt tcaaggacgg tgacgaggct gaggattttg ttgaagttca 6300
ccttcccgat gtgcacaatc aggtctcagg agttgacttg ggtctcccga actgggggaa 6360
gtatgtatta ctgagtgcag gggccctgac tgccttgatg ttgataattt tcctgatgac 6420
atgttgtaga agagtcaatc gatcagaacc tacgcaacac aatctcagag ggacagggag 6480
ggaggtgtca gtcactcccc aaagcgggaa gatcatatct tcatgggaat cacacaagag 6540
tgggggtgag accagactgt gaggtaccgt cgagaaaaaa acattagatc agaagaacaa 6600
ctggcaacac ttctcaacct gagacctact tcaagatgct cgatcctgga gaggtctatg 6660
atgaccctat tgacccaatc gagttagagg atgaacccag aggaaccccc actgtcccca 6720
acatcttgag gaactctgac tacaatctca actctccttt gatagaagat cctgctagac 6780
taatgttaga atggttaaaa acagggaata gaccttatcg gatgactcta acagacaatt 6840
gctccaggtc tttcagagtt ttgaaagatt atttcaagaa ggtagatttg ggttctctca 6900
aggtgggcgg aatggctgca cagtcaatga tttctctctg gttatatggt gcccactctg 6960
aatccaacag gagccggaga tgtataacag acttggccca tttctattcc aagtcgtccc 7020
ccatagagaa gctgttgaat ctcacgctag gaaatagagg gctgagaatc cccccagagg 7080
gagtgttaag ttgccttgag agggttgatt atgataatgc atttggaagg tatcttgcca 7140
acacgtattc ctcttacttg ttcttccatg taatcacctt atacatgaac gccctagact 7200
gggatgaaga aaagaccatc ctagcattat ggaaagattt aacctcagtg gacatcggga 7260
aggacttggt aaagttcaaa gaccaaatat ggggactgct gatcgtgaca aaggactttg 7320
tttactccca aagttccaat tgtctttttg acagaaacta cacacttatg ctaaaagatc 7380

-continued

```
ttttcttgtc tcgcttcaac tccttaatgg tcttgctctc tcccccagag ccccgatact   7440
cagatgactt gatatctcaa ctatgccagc tgtacattgc tggggatcaa gtcttgtcta   7500
tgtgtggaaa ctccggctat gaagtcatca aaatattgga gccatatgtc gtgaatagtt   7560
tagtccagag agcagaaaag tttaggcctc tcattcattc cttgggagac tttcctgtat   7620
ttataaaaga caaggtaagt caacttgaag agacgttcgg tccctgtgca agaaggttct   7680
ttagggctct ggatcaattc gacaacatac atgacttggt ttttgtgtat ggctgttaca   7740
ggcattgggg gcacccatat atagattatc gaaagggtct gtcaaaacta tatgatcagg   7800
ttcacattaa aaaagtgata gataagtcct accaggagtg cttagcaagc gacctagcca   7860
ggaggatcct tagatggggt tttgataagt actccaagtg gtatctggat tcaagattcc   7920
tagcccgaga ccaccccttg actccttata tcaaaaccca aacatggcca cccaaacata   7980
ttgtagactt ggtgggggat acatggcaca agctcccgat cacgcagatc tttgagattc   8040
ctgaatcaat ggatccgtca gaaatattgg atgacaaatc acattctttc accagaacga   8100
gactagcttc ttggctgtca gaaaaccgag gggacctgt tcctagcgaa aaagttatta    8160
tcacggccct gtctaagccg cctgtcaatc cccgagagtt tctgaggtct atagacctcg   8220
gaggattgcc agatgaagac ttgataattg gcctcaagcc aaaggaacgg gaattgaaga   8280
ttgaaggtcg attctttgct ctaatgtcat ggaatctaag attgtatttt gtcatcactg   8340
aaaaactctt ggccaactac atcttgccac tttttgacgc gctgactatg acagacaacc   8400
tgaacaaggt gtttaaaaag ctgatcgaca gggtcaccgg gcaagggctt ttggactatt   8460
caagggtcac atatgcattt cacctggact atgaaaagtg gaacaaccat caaagattag   8520
agtcaacaga ggatgtattt tctgtcctag atcaagtgtt tggattgaag agagtgtttt   8580
ctagaacaca cgagtttttt caaaaggcct ggatctatta ttcagacaga tcagacctca   8640
tcgggttacg ggaggatcaa atatactgct tagatgcgtc caacggccca acctgttgga   8700
atggccagga tggcgggcta gaaggcttac ggcagaaggg ctggagtcta gtcagcttat   8760
tgatgataga tagagaatct caaatcagga acacaagaac caaaatacta gctcaaggag   8820
acaaccaggt tttatgtccg acatatatgt tgtcgccagg gctatctcaa gaggggctcc   8880
tctatgaatt ggagagaata tcaaggaatg cactttcgat atacagagcc gtcgaggaag   8940
gggcatctaa gctagggctg atcatcaaga aagaagagac catgtgtagt tatgacttcc   9000
tcatctatgg aaaaacccct ttgtttagag gtaacatatt ggtgcctgag tccaaaagat   9060
gggccagagt ctcttgcgtc tctaatgacc aaatagtcaa cctcgccaat ataatgtcga   9120
cagtgtccac caatgcgcta acagtggcac aacactctca atctttgatc aaaccgatga   9180
gggattttct gctcatgtca gtacaggcag tctttcacta cctgctattt agcccaatct   9240
taaagggaag agtttacaag attctgagcg ctgaaggggga tagctttctc ctagccatgt  9300
caaggataat ctatctagat ccttctttgg gaggggtatc tggaatgtcc ctcggaagat   9360
tccatatacg acagttctca gaccctgtct ctgaagggtt atccttctgg agagagatct   9420
ggttaagctc ccacgagtcc tggattcacg cgttgtgtca agaggctgga aacccagatc   9480
ttggagagag aacactcgag agcttcactc gccttctaga agatcctacc accttaaata   9540
tcagaggagg ggccagtcct accattctac tcaaggatgc aatcagaaag gctttatatg   9600
acgaggtgga caaggtggag aattcagagt ttcgagaggc aatcctgttg tccaagaccc   9660
atagagataa ttttatactc ttcttaacat ctgttgagcc tctgtttcct cgatttctca   9720
gtgagctatt cagttcgtct tttttgggaa tccccgagtc aatcattgga ttgatacaaa   9780
```

```
actcccgaac gataagaagg cagtttagaa agagtctctc aaaaacttta gaagaatcct   9840
tctacaactc agagatccac gggattagtc ggatgaccca gacacctcag agggttgggg   9900
gggtgtggcc ttgctcttca gagagggcag atctacttag ggagatctct tggggaagaa   9960
aagtggtagg cacgacagtt cctcaccctt ctgagatgtt ggggttactt cccaagtcct  10020
ctatttcttg cacttgtgga gcaacaggag gaggcaatcc tagagtttct gtatcagtac  10080
tcccgtcctt tgatcagtca ttttttcac gaggccccct aaaggggtac ttgggctcgt  10140
ccacctctat gtcgacccag ctattccatg catgggaaaa agtcactaat gttcatgtgg  10200
tgaagagagc tctatcgtta aaagaatcta taaactggtt cattactaga gattccaact  10260
tggctcaagc tctaattagg aacattatgt ctctgacagg ccctgatttc cctctagagg  10320
aggcccctgt cttcaaaagg acggggtcag ccttgcatag gttcaagtct gccagataca  10380
gcgaaggagg gtattcttct gtctgcccga acctcctctc tcatatttct gttagtacag  10440
acaccatgtc tgatttgacc caagacggga agaactacga tttcatgttc cagccattga  10500
tgctttatgc acagacatgg acatcagagc tggtacagag agacacaagg ctaagagact  10560
ctacgtttca ttggcacctc cgatgcaaca ggtgtgtgag acccattgac gacgtgaccc  10620
tggagacctc tcagatcttc gagtttccgg atgtgtcgaa aagaatatcc agaatggttt  10680
ctggggctgt gcctcacttc cagaggcttc ccgatatccg tctgagacca ggagattttg  10740
aatctctaag cggtagagaa aagtctcacc atatcggatc agctcagggg ctcttatact  10800
caatcttagt ggcaattcac gactcaggat acaatgatgg aaccatcttc cctgtcaaca  10860
tatacgacaa ggtttcccct agagactatt tgagagggct cgcaagggga gtattgatag  10920
gatcctcgat ttgcttcttg acaagaatga caaatatcaa tattaataga cctcttgaat  10980
tgatctcagg ggtaatctca tatattctcc tgaggctaga taaccatccc tccttgtaca  11040
taatgctcag agaaccgtct cttagaggag agatattttc tatccctcag aaaatccccg  11100
ccgcttatcc aaccactatg aaagaaggca acagatcaat cttgtgttat ctccaacatg  11160
tgctacgcta tgagcgagag ataatcacgg cgtctccaga gaatgactgg ctatggatct  11220
tttcagactt tagaagtgcc aaaatgacgt acctaaccct cattacttac cagtctcatc  11280
ttctactcca gagggttgag agaaacctat ctaagagtat gagagataac ctgcgacaat  11340
tgagttcctt gatgaggcag gtgctgggcg ggcacggaga agatacctta gagtcagacg  11400
acaacattca acgactgcta aaagactctt tacgaaggac aagatgggtg gatcaagagg  11460
tgcgccatgc agctagaacc atgactggag attacagccc caacaagaag gtgtcccgta  11520
aggtaggatg ttcagaatgg gtctgctctg ctcaacaggt tgcagtctct acctcagcaa  11580
acccggcccc tgtctcggag cttgacataa gggccctctc taagaggttc cagaaccctt  11640
tgatctcggg cttgagagtg gttcagtggg caaccggtgc tcattataag cttaagccta  11700
ttctagatga tctcaatgtt ttcccatctc tctgccttgt agttggggac gggtcagggg  11760
ggatatcaag ggcagtcctc aacatgtttc cagatgccaa gcttgtgttc aacagtctct  11820
tagaggtgaa tgacctgatg gcttccggaa cacatccact gcctccttca gcaatcatga  11880
ggggaggaaa tgatatcgtc tccagagtga tagattttga ctcaatctgg gaaaaaccgt  11940
ccgacttgag aaacttggca acctggaaat acttccagtc agtccaaaag caggtcaaca  12000
tgtcctatga cctcattatt tgcgatgcag aagttactga cattgcatct atcaaccgga  12060
taaccctgtt aatgtccgat tttgcattgt ctatagatgg accactctat ttggtcttca  12120
```

aaacttatgg gactatgcta gtaaatccaa actacaaggc tattcaacac ctgtcaagag 12180
cgttcccctc ggtcacaggg tttatcaccc aagtaacttc gtctttttca tctgagctct 12240
acctccgatt ctccaaacga gggaagtttt tcagagatgc tgagtacttg acctcttcca 12300
cccttcgaga aatgagcctt gtgttattca attgtagcag ccccaagagt gagatgcaga 12360
gagctcgttc cttgaactat caggatcttg tgagaggatt tcctgaagaa atcatatcaa 12420
atccttacaa tgagatgatc ataactctga ttgacagtga tgtagaatct tttctagtcc 12480
acaagatggt tgatgatctt gagttacaga ggggaactct gtctaaagtg gctatcatta 12540
tagccatcat gatagttttc tccaacagag tcttcaacgt ttccaaaccc ctaactgacc 12600
ccttgttcta tccaccgtct gatcccaaaa tcctgaggca cttcaacata tgttgcagta 12660
ctatgatgta tctatctact gctttaggtg acgtccctag cttcgcaaga cttcacgacc 12720
tgtataacag acctataact tattacttca gaaagcaatt cattcgaggg aacgtttatc 12780
tatcttggag ttggtccaac gacacctcag tgttcaaaag ggtagcctgt aattctagcc 12840
tgagtctgtc atctcactgg atcaggttga tttacaagat agtgaagact accagactcg 12900
ttggcagcat caaggatcta tccagagaag tggaaagaca ccttcatagg tacaacaggt 12960
ggatcaccct agaggatatc agatctagat catccctact agactacagt tgcctgtgat 13020
ccggatactc ctggaagcct gcccatgcta agactcttgt gtgatgtatc ttgaaaaaaa 13080
caagatccta aatctgaacc tttggttgtt tgattgtttt tctcattttt gttgtttatt 13140
tgttaagcgt 13150

<210> SEQ ID NO 14
<211> LENGTH: 11976
<212> TYPE: DNA
<213> ORGANISM: artificial sequence
<220> FEATURE:
<223> OTHER INFORMATION: Recombinant ERA-pt rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2542)..(3147)
<220> FEATURE:
<221> NAME/KEY: misc_feature
<222> LOCATION: (3363)..(4934)
<220> FEATURE:
<221> NAME/KEY: misc_feature
<222> LOCATION: (5462)..(11842)

<400> SEQUENCE: 14
acgcttaaca accagatcaa agaaaaaaca gacattgtca attgcaaagc aaaaatgtaa 60
cacccctaca atggatgccg acaagattgt attcaaagtc aataatcagg tggtctcttt 120
gaagcctgag attatcgtgg atcaacatga gtacaagtac cctgccatca aagatttgaa 180
aaagccctgt ataaccctag gaaaggctcc cgatttaaat aaagcataca agtcagtttt 240
gtcaggcatg agcgccgcca aacttgatcc tgacgatgta tgttcctatt tggcagcggc 300
aatgcagttt tttgagggga catgtccgga agactggacc agctatggaa tcgtgattgc 360
acgaaaagga gataagatca ccccaggttc tctggtggag ataaaacgta ctgatgtaga 420
agggaattgg gctctgacag gaggcatgga actgacaaga gaccccactg tccctgagca 480
tgcgtcctta gtcggtcttc tcttgagtct gtataggttg agcaaaatat ccgggcaaaa 540

-continued

```
cactggtaac tataagacaa acattgcaga caggatagag cagattttttg agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttctcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaagt ggacaatctc cctgaggata tggggcgact   1680
tcacctggat gatggaaaat cgcccaaccc tggtgagatg gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaaactaac acccctcctt tcgctgcagt ttggtaccgt cgagaaaaaa   2520
acaggcaaca ccactgataa aatgaacttt ctacgtaaga tagtgaaaaa ttgcagggac   2580
gaggacactc aaaaaccctc tcccgtgtca gcccctctgg atgacgatga cttgtggctt   2640
ccacccccctg aatacgtccc gctgaaagaa cttacaagca agaagaacat gaggaacttt   2700
tgtatcaacg gaggggttaa agtgtgtagc ccgaatggtt actcgttcag gatcctgcgg   2760
cacattctga aatcattcga cgagatatat tctgggaatc ataggatgat cgggttagtc   2820
aaagtagtta ttggactggc tttgtcagga tctccagtcc ctgagggcat gaactgggta   2880
tacaaattga ggagaacctt tatcttccag tggctgatt ccaggggccc tcttgaaggg   2940
```

gaggagttgg aatactctca ggagatcact tgggatgatg atactgagtt cgtcggattg 3000
caaataagag tgattgcaaa acagtgtcat atccagggca gaatctggtg tatcaacatg 3060
aacccgagag catgtcaact atggtctgac atgtctcttc agacacaaag gtccgaagag 3120
gacaaagatt cctctctgct tctagaataa tcagattata tcccgcaaat ttatcacttg 3180
tttacctctg gaggagagaa catatgggct caactccaac ccttgggagc aatataacaa 3240
aaaacatgtt atggtgccat taaaccgctg catttcatca aagtcaagtt gattaccttt 3300
acattttgat cctcttggat gtgaaaaaaa ctattaacat ccctcaaaag actcaaggaa 3360
agatggttcc tcaggctctc ctgtttgtac cccttctggt tttccattg tgttttggga 3420
aattccctat ttacacgata ccagacaagc ttggtccctg gagcccgatt gacatacatc 3480
acctcagctg cccaaacaat ttggtagtgg aggacgaagg atgcaccaac ctgtcagggt 3540
tctcctacat ggaacttaaa gttggataca tcttagccat aaaaatgaac gggttcactt 3600
gcacaggcgt tgtgacggag gctgaaacct acactaactt cgttggttat gtcacaacca 3660
cgttcaaaag aaagcatttc cgcccaacac cagatgcatg tagagccgcg tacaactgga 3720
agatggccgg tgaccccaga tatgaagagt ctctacacaa tccgtaccct gactaccact 3780
ggcttcgaac tgtaaaaacc accaaggagt ctctcgttat catatctcca agtgtggcag 3840
atttggaccc atatgacaga tcccttcact cgagggtctt ccctagcggg aagtgctcag 3900
gagtagcggt gtcttctacc tactgctcca ctaaccacga ttacaccatt tggatgcccg 3960
agaatccgag actagggatg tcttgtgaca tttttaccaa tagtagaggg aagagagcat 4020
ccaaagggag tgagacttgc ggctttgtag atgaaagagg cctatataag tctttaaaag 4080
gagcatgcaa actcaagtta tgtggagttc taggacttag acttatggat ggaacatggg 4140
tcgcgatgca aacatcaaat gaaaccaaat ggtgccctcc cgatcagttg gtgaacctgc 4200
acgactttcg ctcagacgaa attgagcacc ttgttgtaga ggagttggtc aggaagagag 4260
aggagtgtct ggatgcacta gagtccatca tgacaaccaa gtcagtgagt ttcagacgtc 4320
tcagtcattt aagaaaactt gtccctgggt ttggaaaagc atataccata ttcaacaaga 4380
ccttgatgga agccgatgct cactacaagt cagtcgagac ttggaatgag atcctccctt 4440
caaaagggtg tttaagagtt ggggggaggt gtcatcctca tgtgaacggg gtgtttttca 4500
atggtataat attaggacct gacggcaatg tcttaatccc agagatgcaa tcatccctcc 4560
tccagcaaca tatggagttg ttggaatcct cggttatccc ccttgtgcac cccctggcag 4620
acccgtctac cgttttcaag gacggtgacg aggctgagga ttttgttgaa gttcaccttc 4680
ccgatgtgca caatcaggtc tcaggagttg acttgggtct cccgaactgg gggaagtatg 4740
tattactgag tgcaggggcc ctgactgcct tgatgttgat aattttcctg atgacatgtt 4800
gtagaagagt caatcgatca gaacctacgc aacacaatct cagagggaca gggagggagg 4860
tgtcagtcac tccccaaagc gggaagatca tatcttcatg ggaatcacac aagagtgggg 4920
gtgagaccag actgtgagga ctggccgtcc tttcaactat ccaagtcctg aagatcacct 4980
ccccttgggg ggttcttttt gaaaaaaacc tgggttcaat agtcctcctt gaactccatg 5040
caactgggta gattcaagag tcatgagatt ttcattaatc ctctcagttg atcaagcaag 5100
atcatgtaga ttctcataat aggggagatc ttctagcagt ttcagtgact aacggtactt 5160
tcattctcca ggaactgaca ccaacagttg tagacaaacc acggggtgtc tcgggtgact 5220
ctgtgcttgg gcacagacaa aggtcatggt gtgttccatg atagcggact caggatgagt 5280

-continued

```
taattgagag aggcagtctt cctcccgtga aggacataag cagtagctca caatcatctc   5340
gcgtctcagc aaagtgtgca taattataaa gtgctgggtc atctaagctt ttcagtcgag   5400
aaaaaaacat tagatcagaa gaacaactgg caacacttct caacctgaga cctacttcaa   5460
gatgctcgat cctggagagg tctatgatga ccctattgac ccaatcgagt tagaggatga   5520
acccagagga acccccactg tccccaacat cttgaggaac tctgactaca atctcaactc   5580
tcctttgata gaagatcctg ctagactaat gttagaatgg ttaaaaacag ggaatagacc   5640
ttatcggatg actctaacag acaattgctc caggtctttc agagttttga aagattattt   5700
caagaaggta gatttgggtt ctctcaaggt gggcggaatg gctgcacagt caatgatttc   5760
tctctggtta tatggtgccc actctgaatc caacaggagc cggagatgta taacagactt   5820
ggcccatttc tattccaagt cgtcccccat agagaagctg ttgaatctca cgctaggaaa   5880
tagagggctg agaatccccc cagagggagt gttaagttgc cttgagaggg ttgattatga   5940
taatgcattt ggaaggtatc ttgccaacac gtattcctct tacttgttct tccatgtaat   6000
caccttatac atgaacgccc tagactggga tgaagaaaag accatcctag cattatggaa   6060
agatttaacc tcagtggaca tcgggaagga cttggtaaag ttcaaagacc aaatatgggg   6120
actgctgatc gtgacaaagg actttgttta ctcccaaagt tccaattgtc tttttgacag   6180
aaactacaca cttatgctaa aagatctttt cttgtctcgc ttcaactcct taatggtctt   6240
gctctctccc ccagagcccc gatactcaga tgacttgata tctcaactat gccagctgta   6300
cattgctggg gatcaagtct tgtctatgtg tggaaactcc ggctatgaag tcatcaaaat   6360
attggagcca tatgtcgtga atagtttagt ccagagagca gaaaagttta ggcctctcat   6420
tcattccttg ggagactttc ctgtatttat aaaagacaag gtaagtcaac ttgaagagac   6480
gttcggtccc tgtgcaagaa ggttctttag ggctctggat caattcgaca acatacatga   6540
cttggttttt gtgtatggct gttacaggca ttgggggcac ccatatatag attatcgaaa   6600
gggtctgtca aaactatatg atcaggttca cattaaaaaa gtgatagata agtcctacca   6660
ggagtgctta gcaagcgacc tagccaggag gatccttaga tggggttttg ataagtactc   6720
caagtggtat ctggattcaa gattcctagc ccgagaccac cccttgactc cttatatcaa   6780
aacccaaaca tggccaccca aacatattgt agacttggtg ggggatacat ggcacaagct   6840
cccgatcacg cagatctttg agattcctga atcaatggat ccgtcagaaa tattggatga   6900
caaatcacat tctttcacca gaacgagact agcttcttgg ctgtcagaaa accgaggggg   6960
acctgttcct agcgaaaaag ttattatcac ggccctgtct aagccgcctg tcaatccccg   7020
agagtttctg aggtctatag acctcggagg attgccagat gaagacttga taattggcct   7080
caagccaaag gaacgggaat tgaagattga aggtcgattc tttgctctaa tgtcatggaa   7140
tctaagattg tattttgtca tcactgaaaa actcttggcc aactacatct tgccactttt   7200
tgacgcgctg actatgacag acaacctgaa caaggtgttt aaaaagctga tcgacagggt   7260
caccgggcaa gggcttttgg actattcaag ggtcacatat gcatttcacc tggactatga   7320
aaagtggaac aaccatcaaa gattagagtc aacagaggat gtattttctg tcctagatca   7380
agtgtttgga ttgaagagag tgttttctag aacacacgag ttttttcaaa aggcctggat   7440
ctattattca gacagatcag acctcatcgg gttacgggag gatcaaatat actgcttaga   7500
tgcgtccaac ggcccaacct gttggaatgg ccaggatggc gggctagaag gcttacggca   7560
gaagggctgg agtctagtca gcttattgat gatagataga gaatctcaaa tcaggaacac   7620
aagaaccaaa atactagctc aaggagacaa ccaggtttta tgtccgacat atatgttgtc   7680
```

```
gccagggcta tctcaagagg ggctcctcta tgaattggag agaatatcaa ggaatgcact   7740
ttcgatatac agagccgtcg aggaaggggc atctaagcta gggctgatca tcaagaaaga   7800
agagaccatg tgtagttatg acttcctcat ctatggaaaa accccttttgt ttagaggtaa   7860
catattggtg cctgagtcca aaagatgggc cagagtctct tgcgtctcta atgaccaaat   7920
agtcaacctc gccaatataa tgtcgacagt gtccaccaat gcgctaacag tggcacaaca   7980
ctctcaatct ttgatcaaac cgatgaggga ttttctgctc atgtcagtac aggcagtctt   8040
tcactacctg ctatttagcc caatcttaaa gggaagagtt tacaagattc tgagcgctga   8100
aggggatagc tttctcctag ccatgtcaag gataatctat ctagatcctt ctttgggagg   8160
ggtatctgga atgtccctcg gaagattcca tatacgacag ttctcagacc ctgtctctga   8220
agggttatcc ttctggagag agatctggtt aagctcccac gagtcctgga ttcacgcgtt   8280
gtgtcaagag gctggaaacc cagatcttgg agagagaaca ctcgagagct tcactcgcct   8340
tctagaagat cctaccacct taaatatcag aggaggggcc agtcctacca ttctactcaa   8400
ggatgcaatc agaaaggctt tatatgacga ggtggacaag gtggagaatt cagagtttcg   8460
agaggcaatc ctgttgtcca agacccatag agataatttt atactcttct taacatctgt   8520
tgagcctctg tttcctcgat ttctcagtga gctattcagt tcgtcttttt tgggaatccc   8580
cgagtcaatc attggattga tacaaaactc ccgaacgata agaaggcagt ttagaaagag   8640
tctctcaaaa actttagaag aatccttcta caactcagag atccacggga ttagtcggat   8700
gacccagaca cctcagaggg ttgggggggt gtggccttgc tcttcagaga gggcagatct   8760
acttagggag atctcttggg gaagaaaagt ggtaggcacg acagttcctc acccttctga   8820
gatgttgggg ttacttccca agtcctctat ttcttgcact tgtggagcaa caggaggagg   8880
caatcctaga gtttctgtat cagtactccc gtcctttgat cagtcatttt tttcacgagg   8940
cccccctaaag gggtacttgg gctcgtccac ctctatgtcg acccagctat tccatgcatg   9000
ggaaaaagtc actaatgttc atgtggtgaa gagagctcta tcgttaaaag aatctataaa   9060
ctggttcatt actagagatt ccaacttggc tcaagctcta attaggaaca ttatgtctct   9120
gacaggccct gatttccctc tagaggaggc ccctgtcttc aaaaggacgg ggtcagcctt   9180
gcataggttc aagtctgcca gatacagcga aggagggtat tcttctgtct gcccgaacct   9240
cctctctcat atttctgtta gtacagacac catgtctgat ttgacccaag acgggaagaa   9300
ctacgatttc atgttccagc cattgatgct ttatgcacag acatggacat cagagctggt   9360
acagagagac acaaggctaa gagactctac gtttcattgg cacctccgat gcaacaggtg   9420
tgtgagaccc attgacgacg tgaccctgga gacctctcag atcttcgagt ttccggatgt   9480
gtcgaaaaga atatccagaa tggtttctgg ggctgtgcct cacttccaga ggcttcccga   9540
tatccgtctg agaccaggag attttgaatc tctaagcggt agagaaaagt ctcaccatat   9600
cggatcagct caggggctct tatactcaat cttagtggca attcacgact caggatacaa   9660
tgatggaacc atcttccctg tcaacatata cgacaaggtt tcccctagag actatttgag   9720
agggctcgca aggggagtat tgataggatc ctcgatttgc ttcttgacaa gaatgacaaa   9780
tatcaatatt aatagacctc ttgaattgat ctcaggggta atctcatata ttctcctgag   9840
gctagataac catccctcct tgtacataat gctcagagaa ccgtctctta gaggagagat   9900
attttctatc cctcagaaaa tccccgccgc ttatccaacc actatgaaag aaggcaacag   9960
atcaatcttg tgttatctcc aacatgtgct acgctatgag cgagagataa tcacggcgtc  10020
```

```
tccagagaat gactggctat ggatcttttc agactttaga agtgccaaaa tgacgtacct  10080
aaccctcatt acttaccagt ctcatcttct actccagagg gttgagagaa acctatctaa  10140
gagtatgaga gataacctgc gacaattgag ttccttgatg aggcaggtgc tgggcgggca  10200
cggagaagat accttagagt cagacgacaa cattcaacga ctgctaaaag actctttacg  10260
aaggacaaga tgggtggatc aagaggtgcg ccatgcagct agaaccatga ctggagatta  10320
cagccccaac aagaaggtgt cccgtaaggt aggatgttca gaatgggtct gctctgctca  10380
acaggttgca gtctctacct cagcaaaccc ggcccctgtc tcggagcttg acataagggc  10440
cctctctaag aggttccaga accctttgat ctcgggcttg agagtggttc agtgggcaac  10500
cggtgctcat tataagctta agcctattct agatgatctc aatgttttcc catctctctg  10560
ccttgtagtt ggggacgggt caggggggat atcaagggca gtcctcaaca tgtttccaga  10620
tgccaagctt gtgttcaaca gtctcttaga ggtgaatgac ctgatggctt ccggaacaca  10680
tccactgcct ccttcagcaa tcatgagggg aggaaatgat atcgtctcca gagtgataga  10740
ttttgactca atctgggaaa aaccgtccga cttgagaaac ttggcaacct ggaaatactt  10800
ccagtcagtc caaaagcagg tcaacatgtc ctatgacctc attatttgcg atgcagaagt  10860
tactgacatt gcatctatca accggataac cctgttaatg tccgattttg cattgtctat  10920
agatggacca ctctatttgg tcttcaaaac ttatgggact atgctagtaa atccaaacta  10980
caaggctatt caacacctgt caagagcgtt cccctcggtc acagggttta tcacccaagt  11040
aacttcgtct tttcatctg agctctacct ccgattctcc aaacgaggga agtttttcag  11100
agatgctgag tacttgacct cttccaccct tcgagaaatg agccttgtgt tattcaattg  11160
tagcagcccc aagagtgaga tgcagagagc tcgttccttg aactatcagg atcttgtgag  11220
aggatttcct gaagaaatca tatcaaatcc ttacaatgag atgatcataa ctctgattga  11280
cagtgatgta gaatcttttc tagtccacaa gatggttgat gatcttgagt tacagagggg  11340
aactctgtct aaagtggcta tcattatagc catcatgata gttttctcca acagagtctt  11400
caacgtttcc aaacccctaa ctgacccctt gttctatcca ccgtctgatc ccaaaatcct  11460
gaggcacttc aacatatgtt gcagtactat gatgtatcta tctactgctt taggtgacgt  11520
ccctagcttc gcaagacttc acgacctgta taacagacct ataacttatt acttcagaaa  11580
gcaattcatt cgagggaacg tttatctatc ttggagttgg tccaacgaca cctcagtgtt  11640
caaaagggta gcctgtaatt ctagcctgag tctgtcatct cactggatca ggttgattta  11700
caagatagtg aagactacca gactcgttgg cagcatcaag gatctatcca gagaagtgga  11760
aagacacctt cataggtaca acaggtggat caccctagag gatatcagat ctagatcatc  11820
cctactagac tacagttgcc tgtgatccgg atactcctgg aagcctgccc atgctaagac  11880
tcttgtgtga tgtatcttga aaaaaacaag atcctaaatc tgaacctttg gttgtttgat  11940
tgtttttctc atttttgttg tttatttgtt aagcgt                            11976
```

<210> SEQ ID NO 15
<211> LENGTH: 12662
<212> TYPE: DNA
<213> ORGANISM: artificial sequence
<220> FEATURE:
<223> OTHER INFORMATION: Recombinant ERA-pt-GFP rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)

```
<220> FEATURE:
<221> NAME/KEY: misc_feature
<222> LOCATION: (2505)..(3185)
<220> FEATURE:
<221> NAME/KEY: misc_feature
<222> LOCATION: (3228)..(3833)
<220> FEATURE:
<221> NAME/KEY: misc_feature
<222> LOCATION: (4049)..(5620)
<220> FEATURE:
<221> NAME/KEY: misc_feature
<222> LOCATION: (6148)..(12528)

<400> SEQUENCE: 15

acgcttaaca accagatcaa agaaaaaaca gacattgtca attgcaaagc aaaaatgtaa     60

cacccctaca atggatgccg acaagattgt attcaaagtc aataatcagg tggtctcttt    120

gaagcctgag attatcgtgg atcaacatga gtacaagtac cctgccatca aagatttgaa    180

aaagccctgt ataaccctag gaaaggctcc cgatttaaat aaagcataca agtcagtttt    240

gtcaggcatg agcgccgcca aacttgatcc tgacgatgta tgttcctatt tggcagcggc    300

aatgcagttt tttgagggga catgtccgga agactggacc agctatggaa tcgtgattgc    360

acgaaaagga gataagatca ccccaggttc tctggtggag ataaaacgta ctgatgtaga    420

agggaattgg gctctgacag gaggcatgga actgacaaga gaccccactg tccctgagca    480

tgcgtcctta gtcggtcttc tcttgagtct gtataggttg agcaaaatat ccgggcaaaa    540

cactggtaac tataagacaa acattgcaga caggatagag cagatttttg agacagcccc    600

ttttgttaaa atcgtggaac accatactct aatgacaact cacaaaatgt gtgctaattg    660

gagtactata ccaaacttca gatttttggc cggaacctat gacatgtttt tctcccggat    720

tgagcatcta tattcagcaa tcagagtggg cacagttgtc actgcttatg aagactgttc    780

aggactggta tcatttactg ggttcataaa acaaatcaat ctcaccgcta gagaggcaat    840

actatatttc ttccacaaga actttgagga agagataaga agaatgtttg agccagggca    900

ggagacagct gttcctcact cttatttcat ccacttccgt tcactaggct tgagtgggaa    960

atctccttat tcatcaaatg ctgttggtca cgtgttcaat ctcattcact ttgtaggatg   1020

ctatatgggt caagtcagat ccctaaatgc aacggttatt gctgcatgtg ctcctcatga   1080

aatgtctgtt ctagggggct atctgggaga ggaattcttc gggaaaggga catttgaaag   1140

aagattcttc agagatgaga aagaacttca agaatacgag gcggctgaac tgacaaagac   1200

tgacgtagca ctggcagatg atggaactgt caactctgac gacgaggact acttctcagg   1260

tgaaaccaga agtccggagg ctgtttatac tcgaatcatg atgaatggag gtcgactaaa   1320

gagatctcac atacggagat atgtctcagt cagttccaat catcaagccc gtccaaactc   1380

attcgccgag tttctaaaca agacatattc gagtgactca taagaagttg aataacaaaa   1440

tgccggaaat ctacggattg tgtatatcca tcatgaaaaa aactaacacc cctcctttcg   1500

aaccatccca aacatgagca agatctttgt caatcctagt gctattagag ccggtctggc   1560

cgatcttgag atggctgaag aaactgttga tctgatcaat agaaatatcg aagacaatca   1620

ggctcatctc caaggggaac ccatagaagt ggacaatctc cctgaggata tggggcgact   1680

tcacctggat gatggaaaat cgcccaaccc tggtgagatg gccaaggtgg gagaaggcaa   1740

gtatcgagag gactttcaga tggatgaagg agaggatcct agcttcctgt tccagtcata   1800

cctggaaaat gttggagtcc aaatagtcag acaaatgagg tcaggagaga gatttctcaa   1860

gatatggtca cagaccgtag aagagattat atcctatgtc gcggtcaact ttcccaaccc   1920
```

-continued

```
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaaactaac acccctcctt tcgctgcagc caccatgggc gtgatcaagc   2520
ccgacatgaa gatcaagctg cggatggagg gcgccgtgaa cggccacaaa ttcgtgatcg   2580
agggcgacgg gaaaggcaag ccctttgagg gtaagcagac tatggacctg accgtgatcg   2640
agggcgcccc cctgcccttc gcttatgaca ttctcaccac cgtgttcgac tacggtaacc   2700
gtgtcttcgc caagtacccc aaggacatcc ctgactactt caagcagacc ttccccgagg   2760
gctactcgtg ggagcgaagc atgacatacg aggaccaggg aatctgtatc gctacaaacg   2820
acatcaccat gatgaagggt gtggacgact gcttcgtgta caaaatccgc ttcgacgggg   2880
tcaacttccc tgctaatggc ccggtgatgc agcgcaagac cctaaagtgg gagcccagta   2940
ccgagaagat gtacgtgcgg gacggcgtac tgaagggcga tgttaatatg gcactgctct   3000
tggagggagg cggccactac cgctgcgact tcaagaccac ctacaaagcc aagaaggtgg   3060
tgcagcttcc cgactaccac ttcgtggacc accgcatcga gatcgtgagc cacgacaagg   3120
actacaacaa agtcaagctg tacgagcacg ccgaagccca cagcggacta ccccgccagg   3180
ccggctaagg taccgtcgag aaaaaaacag gcaacaccac tgataaaatg aactttctac   3240
gtaagatagt gaaaaattgc agggacgagg acactcaaaa accctctccc gtgtcagccc   3300
ctctggatga cgatgacttg tggcttccac cccctgaata cgtcccgctg aaagaactta   3360
caagcaagaa gaacatgagg aacttttgta tcaacggagg ggttaaagtg tgtagcccga   3420
atggttactc gttcaggatc ctgcggcaca ttctgaaatc attcgacgag atatattctg   3480
ggaatcatag gatgatcggg ttagtcaaag tagttattgg actggctttg tcaggatctc   3540
cagtccctga gggcatgaac tgggtataca aattgaggag aacctttatc ttccagtggg   3600
ctgattccag gggccctctt gaaggggagg agttggaata ctctcaggag atcacttggg   3660
atgatgatac tgagttcgtc ggattgcaaa taagagtgat tgcaaaacag tgtcatatcc   3720
agggcagaat ctggtgtatc aacatgaacc cgagagcatg tcaactatgg tctgacatgt   3780
ctcttcagac acaaaggtcc gaagaggaca aagattcctc tctgcttcta gaataatcag   3840
attatatccc gcaaatttat cacttgttta cctctggagg agagaacata tgggctcaac   3900
tccaaccctt gggagcaata taacaaaaaa catgttatgg tgccattaaa ccgctgcatt   3960
tcatcaaagt caagttgatt acctttacat tttgatcctc ttggatgtga aaaaaactat   4020
taacatccct caaaagactc aaggaaagat ggttcctcag gctctcctgt ttgtacccct   4080
tctggttttt ccattgtgtt ttgggaaatt ccctatttac acgataccag acaagcttgg   4140
tccctggagc ccgattgaca tacatcacct cagctgccca aacaatttgg tagtggagga   4200
cgaaggatgc accaacctgt cagggttctc ctacatggaa cttaaagttg gatacatctt   4260
agccataaaa atgaacgggt tcacttgcac aggcgttgtg acggaggctg aaacctacac   4320
```

```
taacttcgtt ggttatgtca caaccacgtt caaaagaaag catttccgcc caacaccaga   4380
tgcatgtaga gccgcgtaca actggaagat ggccggtgac cccagatatg aagagtctct   4440
acacaatccg taccctgact accactggct tcgaactgta aaaaccacca aggagtctct   4500
cgttatcata tctccaagtg tggcagattt ggacccatat gacagatccc ttcactcgag   4560
ggtcttccct agcgggaagt gctcaggagt agcggtgtct tctacctact gctccactaa   4620
ccacgattac accatttgga tgcccgagaa tccgagacta gggatgtctt gtgacatttt   4680
taccaatagt agagggaaga gagcatccaa agggagtgag acttgcggct ttgtagatga   4740
aagaggccta tataagtctt taaaaggagc atgcaaactc aagttatgtg gagttctagg   4800
acttagactt atggatggaa catgggtcgc gatgcaaaca tcaaatgaaa ccaaatggtg   4860
ccctcccgat cagttggtga acctgcacga ctttcgctca gacgaaattg agcaccttgt   4920
tgtagaggag ttggtcagga agagagagga gtgtctggat gcactagagt ccatcatgac   4980
aaccaagtca gtgagtttca gacgtctcag tcatttaaga aaacttgtcc ctgggtttgg   5040
aaaagcatat accatattca acaagacctt gatggaagcc gatgctcact acaagtcagt   5100
cgagacttgg aatgagatcc tcccttcaaa agggtgttta agagttgggg ggaggtgtca   5160
tcctcatgtg aacggggtgt ttttcaatgg tataatatta ggacctgacg gcaatgtctt   5220
aatcccagag atgcaatcat ccctcctcca gcaacatatg gagttgttgg aatcctcggt   5280
tatccccctt gtgcaccccc tggcagaccc gtctaccgtt ttcaaggacg gtgacgaggc   5340
tgaggatttt gttgaagttc accttcccga tgtgcacaat caggtctcag gagttgactt   5400
gggtctcccg aactggggga agtatgtatt actgagtgca ggggccctga ctgccttgat   5460
gttgataatt ttcctgatga catgttgtag aagagtcaat cgatcagaac ctacgcaaca   5520
caatctcaga gggacaggga gggaggtgtc agtcactccc caaagcggga agatcatatc   5580
ttcatgggaa tcacacaaga gtgggggtga gaccagactg tgaggactgg ccgtcctttc   5640
aactatccaa gtcctgaaga tcacctcccc ttgggggggtt ctttttgaaa aaaacctggg   5700
ttcaatagtc ctccttgaac tccatgcaac tgggtagatt caagagtcat gagattttca   5760
ttaatcctct cagttgatca agcaagatca tgtagattct cataataggg gagatcttct   5820
agcagtttca gtgactaacg gtactttcat tctccaggaa ctgacaccaa cagttgtaga   5880
caaaccacgg ggtgtctcgg gtgactctgt gcttgggcac agacaaaggt catggtgtgt   5940
tccatgatag cggactcagg atgagttaat tgagagaggc agtcttcctc ccgtgaagga   6000
cataagcagt agctcacaat catctcgcgt ctcagcaaag tgtgcataat tataaagtgc   6060
tgggtcatct aagcttttca gtcgagaaaa aaacattaga tcagaagaac aactggcaac   6120
acttctcaac ctgagaccta cttcaagatg ctcgatcctg gagaggtcta tgatgaccct   6180
attgacccaa tcgagttaga ggatgaaccc agaggaaccc ccactgtccc caacatcttg   6240
aggaactctg actacaatct caactctcct ttgatagaag atcctgctag actaatgtta   6300
gaatggttaa aaacagggaa tagaccttat cggatgactc taacagacaa ttgctccagg   6360
tctttcagag ttttgaaaga ttatttcaag aaggtagatt tgggttctct caaggtgggc   6420
ggaatggctg cacagtcaat gatttctctc tggttatatg gtgcccactc tgaatccaac   6480
aggagccgga gatgtataac agacttggcc catttctatt ccaagtcgtc ccccatagag   6540
aagctgttga atctcacgct aggaaataga gggctgagaa tccccccaga gggagtgtta   6600
agttgccttg agagggttga ttatgataat gcatttggaa ggtatcttgc caacacgtat   6660
```

-continued

```
tcctcttact tgttcttcca tgtaatcacc ttatacatga acgccctaga ctgggatgaa   6720
gaaaagacca tcctagcatt atggaaagat ttaacctcag tggacatcgg gaaggacttg   6780
gtaaagttca aagaccaaat atggggactg ctgatcgtga caaaggactt tgtttactcc   6840
caaagttcca attgtctttt tgacagaaac tacacactta tgctaaaaga tcttttcttg   6900
tctcgcttca actccttaat ggtcttgctc tctcccccag agccccgata ctcagatgac   6960
ttgatatctc aactatgcca gctgtacatt gctggggatc aagtcttgtc tatgtgtgga   7020
aactccggct atgaagtcat caaaatattg gagccatatg tcgtgaatag tttagtccag   7080
agagcagaaa agtttaggcc tctcattcat tccttgggag actttcctgt atttataaaa   7140
gacaaggtaa gtcaacttga agagacgttc ggtccctgtg caagaaggtt ctttagggct   7200
ctggatcaat tcgacaacat acatgacttg gtttttgtgt atggctgtta caggcattgg   7260
gggcacccat atatagatta tcgaaagggt ctgtcaaaac tatatgatca ggttcacatt   7320
aaaaaagtga tagataagtc ctaccaggag tgcttagcaa gcgacctagc caggaggatc   7380
cttagatggg gttttgataa gtactccaag tggtatctgg attcaagatt cctagcccga   7440
gaccacccct tgactcctta tatcaaaacc caaacatggc cacccaaaca tattgtagac   7500
ttggtggggg atacatggca caagctcccg atcacgcaga tctttgagat tcctgaatca   7560
atggatccgt cagaaatatt ggatgacaaa tcacattctt tcaccagaac gagactagct   7620
tcttggctgt cagaaaaccg aggggggacct gttcctagcg aaaaagttat tatcacggcc   7680
ctgtctaagc cgcctgtcaa tccccgagag tttctgaggt ctatagacct cggaggattg   7740
ccagatgaag acttgataat tggcctcaag ccaaaggaac gggaattgaa gattgaaggt   7800
cgattctttg ctctaatgtc atggaatcta agattgtatt ttgtcatcac tgaaaaactc   7860
ttggccaact acatcttgcc actttttgac gcgctgacta tgacagacaa cctgaacaag   7920
gtgtttaaaa agctgatcga cagggtcacc gggcaagggc ttttggacta ttcaagggtc   7980
acatatgcat ttcacctgga ctatgaaaag tggaacaacc atcaaagatt agagtcaaca   8040
gaggatgtat tttctgtcct agatcaagtg tttggattga agagagtgtt ttctagaaca   8100
cacgagtttt ttcaaaaggc ctggatctat tattcagaca gatcagacct catcgggtta   8160
cgggaggatc aaatatactg cttagatgcg tccaacggcc caacctgttg gaatggccag   8220
gatggcgggc tagaaggctt acggcagaag ggctggagtc tagtcagctt attgatgata   8280
gatagagaat ctcaaatcag gaacacaaga accaaaatac tagctcaagg agacaaccag   8340
gttttatgtc cgacatatat gttgtcgcca gggctatctc aagaggggct cctctatgaa   8400
ttggagagaa tatcaaggaa tgcactttcg atatacagag ccgtcgagga aggggcatct   8460
aagctagggc tgatcatcaa gaaagaagag accatgtgta gttatgactt cctcatctat   8520
ggaaaaaccc ctttgtttag aggtaacata ttggtgcctg agtccaaaag atgggccaga   8580
gtctcttgcg tctctaatga ccaaatagtc aacctcgcca atataatgtc gacagtgtcc   8640
accaatgcgc taacagtggc acaacactct caatctttga tcaaaccgat gagggatttt   8700
ctgctcatgt cagtacaggc agtctttcac tacctgctat ttagcccaat cttaaaggga   8760
agagtttaca agattctgag cgctgaaggg gatagctttc tcctagccat gtcaaggata   8820
atctatctag atccttcttt gggaggggta tctggaatgt ccctcggaag attccatata   8880
cgacagttct cagaccctgt ctctgaaggg ttatccttct ggagagagat ctggttaagc   8940
tcccacgagt cctggattca cgcgttgtgt caagaggctg gaaacccaga tcttggagag   9000
agaacactcg agagcttcac tcgccttcta gaagatccta ccaccttaaa tatcagagga   9060
```

-continued

```
gggggccagtc ctaccattct actcaaggat gcaatcagaa aggctttata tgacgaggtg   9120
gacaaggtgg agaattcaga gtttcgagag gcaatcctgt tgtccaagac ccatagagat   9180
aattttatac tcttcttaac atctgttgag cctctgtttc ctcgatttct cagtgagcta   9240
ttcagttcgt cttttttggg aatccccgag tcaatcattg gattgataca aaactcccga   9300
acgataagaa ggcagtttag aaagagtctc tcaaaaactt tagaagaatc cttctacaac   9360
tcagagatcc acgggattag tcggatgacc cagacacctc agagggttgg gggggtgtgg   9420
ccttgctctt cagagagggc agatctactt agggagatct cttggggaag aaaagtggta   9480
ggcacgacag ttcctcaccc ttctgagatg ttggggttac ttcccaagtc ctctatttct   9540
tgcacttgtg gagcaacagg aggaggcaat cctagagttt ctgtatcagt actcccgtcc   9600
tttgatcagt catttttttc acgaggcccc ctaaaggggt acttgggctc gtccacctct   9660
atgtcgaccc agctattcca tgcatgggaa aaagtcacta atgttcatgt ggtgaagaga   9720
gctctatcgt taaaagaatc tataaactgg ttcattacta gagattccaa cttggctcaa   9780
gctctaatta ggaacattat gtctctgaca ggccctgatt tccctctaga ggaggcccct   9840
gtcttcaaaa ggacggggtc agccttgcat aggttcaagt ctgccagata cagcgaagga   9900
gggtattctt ctgtctgccc gaacctcctc tctcatattt ctgttagtac agacaccatg   9960
tctgatttga cccaagacgg gaagaactac gatttcatgt tccagccatt gatgctttat  10020
gcacagacat ggacatcaga gctggtacag agagacacaa ggctaagaga ctctacgttt  10080
cattggcacc tccgatgcaa caggtgtgtg agacccattg acgacgtgac cctggagacc  10140
tctcagatct tcgagtttcc ggatgtgtcg aaaagaatat ccagaatggt ttctggggct  10200
gtgcctcact tccagaggct tcccgatatc cgtctgagac caggagattt tgaatctcta  10260
agcggtagag aaaagtctca ccatatcgga tcagctcagg ggctcttata ctcaatctta  10320
gtggcaattc acgactcagg atacaatgat ggaaccatct tccctgtcaa catatacgac  10380
aaggtttccc ctagagacta tttgagaggg ctcgcaaggg gagtattgat aggatcctcg  10440
atttgcttct tgacaagaat gacaaatatc aatattaata gacctcttga attgatctca  10500
ggggtaatct catatattct cctgaggcta gataaccatc cctccttgta cataatgctc  10560
agagaaccgt ctcttagagg agagatattt tctatccctc agaaaatccc cgccgcttat  10620
ccaaccacta tgaaagaagg caacagatca atcttgtgtt atctccaaca tgtgctacgc  10680
tatgagcgag agataatcac ggcgtctcca gagaatgact ggctatggat cttttcagac  10740
tttagaagtg ccaaaatgac gtacctaacc ctcattactt accagtctca tcttctactc  10800
cagagggttg agagaaacct atctaagagt atgagagata acctgcgaca attgagttcc  10860
ttgatgaggc aggtgctggg cgggcacgga gaagatacct tagagtcaga cgacaacatt  10920
caacgactgc taaaagactc tttacgaagg acaagatggg tggatcaaga ggtgcgccat  10980
gcagctagaa ccatgactgg agattacagc cccaacaaga aggtgtcccg taaggtagga  11040
tgttcagaat gggtctgctc tgctcaacag gttgcagtct ctacctcagc aaacccggcc  11100
cctgtctcgg agcttgacat aagggccctc tctaagaggt tccagaaccc tttgatctcg  11160
ggcttgagag tggttcagtg ggcaaccggt gctcattata agcttaagcc tattctagat  11220
gatctcaatg ttttcccatc tctctgcctt gtagttgggg acgggtcagg ggggatatca  11280
agggcagtcc tcaacatgtt tccagatgcc aagcttgtgt tcaacagtct cttagaggtg  11340
aatgacctga tggcttccgg aacacatcca ctgcctcctt cagcaatcat gaggggagga  11400
```

aatgatatcg tctccagagt gatagatttt gactcaatct gggaaaaacc gtccgacttg 11460
agaaacttgg caacctggaa atacttccag tcagtccaaa agcaggtcaa catgtcctat 11520
gacctcatta tttgcgatgc agaagttact gacattgcat ctatcaaccg gataaccctg 11580
ttaatgtccg attttgcatt gtctatagat ggaccactct atttggtctt caaaacttat 11640
gggactatgc tagtaaatcc aaactacaag gctattcaac acctgtcaag agcgttcccc 11700
tcggtcacag ggtttatcac ccaagtaact tcgtcttttt catctgagct ctacctccga 11760
ttctccaaac gagggaagtt tttcagagat gctgagtact tgacctcttc cacccttcga 11820
gaaatgagcc ttgtgttatt caattgtagc agccccaaga gtgagatgca gagagctcgt 11880
tccttgaact atcaggatct tgtgagagga tttcctgaag aaatcatatc aaatccttac 11940
aatgagatga tcataactct gattgacagt gatgtagaat cttttctagt ccacaagatg 12000
gttgatgatc ttgagttaca gaggggaact ctgtctaaag tggctatcat tatagccatc 12060
atgatagttt tctccaacag agtcttcaac gtttccaaac ccctaactga ccccttgttc 12120
tatccaccgt ctgatcccaa aatcctgagg cacttcaaca tatgttgcag tactatgatg 12180
tatctatcta ctgctttagg tgacgtccct agcttcgcaa gacttcacga cctgtataac 12240
agacctataa cttattactt cagaaagcaa ttcattcgag ggaacgttta tctatcttgg 12300
agttggtcca acgacacctc agtgttcaaa agggtagcct gtaattctag cctgagtctg 12360
tcatctcact ggatcaggtt gatttacaag atagtgaaga ctaccagact cgttggcagc 12420
atcaaggatc tatccagaga agtggaaaga caccttcata ggtacaacag gtggatcacc 12480
ctagaggata tcagatctag atcatcccta ctagactaca gttgcctgtg atccggatac 12540
tcctggaagc ctgcccatgc taagactctt gtgtgatgta tcttgaaaaa aacaagatcc 12600
taaatctgaa cctttggttg tttgattgtt tttctcattt ttgttgttta tttgttaagc 12660
gt 12662

<210> SEQ ID NO 16
<211> LENGTH: 11914
<212> TYPE: DNA
<213> ORGANISM: artificial sequence
<220> FEATURE:
<223> OTHER INFORMATION: Recombinant ERAgm rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2505)..(4076)
<220> FEATURE:
<221> NAME/KEY: misc_feature
<222> LOCATION: (4122)..(4727)
<220> FEATURE:
<221> NAME/KEY: misc_feature
<222> LOCATION: (5400)..(11780)

<400> SEQUENCE: 16
acgcttaaca accagatcaa agaaaaaaca gacattgtca attgcaaagc aaaaatgtaa 60
cacccctaca atggatgccg acaagattgt attcaaagtc aataatcagg tggtctcttt 120
gaagcctgag attatcgtgg atcaacatga gtacaagtac cctgccatca aagatttgaa 180
aaagccctgt ataaccctag gaaaggctcc cgatttaaat aaagcataca agtcagtttt 240
gtcaggcatg agcgccgcca aacttgatcc tgacgatgta tgttcctatt tggcagcggc 300

-continued

```
aatgcagttt tttgagggga catgtccgga agactggacc agctatggaa tcgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagatttttg agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttctcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaagt ggacaatctc cctgaggata tggggcgact   1680
tcacctggat gatggaaaat cgcccaaccc tggtgagatg gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaaactaac acccctcctt tcgctgcagc caccatggtt cctcaggctc   2520
tcctgtttgt accccttctg gtttttccat tgtgttttgg gaaattccct atttacacga   2580
taccagacaa gcttggtccc tggagcccga ttgacataca tcacctcagc tgcccaaaca   2640
atttggtagt ggaggacgaa ggatgcacca acctgtcagg gttctcctac atggaactta   2700
```

-continued

```
aagttggata catcttagcc ataaaaatga acgggttcac ttgcacaggc gttgtgacgg   2760
aggctgaaac ctacactaac ttcgttggtt atgtcacaac cacgttcaaa agaaagcatt   2820
tccgcccaac accagatgca tgtagagccg cgtacaactg gaagatggcc ggtgacccca   2880
gatatgaaga gtctctacac aatccgtacc ctgactacca ctggcttcga actgtaaaaa   2940
ccaccaagga gtctctcgtt atcatatctc caagtgtggc agatttggac ccatatgaca   3000
gatcccttca ctcgagggtc ttccctagcg ggaagtgctc aggagtagcg gtgtcttcta   3060
cctactgctc cactaaccac gattacacca tttggatgcc cgagaatccg agactaggga   3120
tgtcttgtga catttttacc aatagtagag ggaagagagc atccaaaggg agtgagactt   3180
gcggctttgt agatgaaaga ggcctatata agtctttaaa aggagcatgc aaactcaagt   3240
tatgtggagt tctaggactt agacttatgg atggaacatg ggtcgcgatg caaacatcaa   3300
atgaaaccaa atggtgccct cccgatcagt tggtgaacct gcacgacttt cgctcagacg   3360
aaattgagca ccttgttgta gaggagttgg tcaggaagag agaggagtgt ctggatgcac   3420
tagagtccat catgacaacc aagtcagtga gtttcagacg tctcagtcat ttaagaaaac   3480
ttgtccctgg gtttggaaaa gcatatacca tattcaacaa gaccttgatg gaagccgatg   3540
ctcactacaa gtcagtcaga acttggaatg agatcctccc ttcaaaaggg tgtttaagag   3600
ttgggggggag gtgtcatcct catgtgaacg gggtgttttt caatggtata atattaggac   3660
ctgacggcaa tgtcttaatc ccagagatgc aatcatccct cctccagcaa catatggagt   3720
tgttggaatc ctcggttatc ccccttgtgc acccccctggc agacccgtct accgttttca   3780
aggacggtga cgaggctgag gattttgttg aagttcacct tcccgatgtg cacaatcagg   3840
tctcaggagt tgacttgggt ctcccgaact gggggaagta tgtattactg agtgcagggg   3900
ccctgactgc cttgatgttg ataattttcc tgatgacatg ttgtagaaga gtcaatcgat   3960
cagaacctac gcaacacaat ctcagaggga cagggaggga ggtgtcagtc actccccaaa   4020
gcgggaagat catatcttca tgggaatcac acaagagtgg gggtgagacc agactgtgat   4080
ttggtaccgt cgagaaaaaa acaggcaaca ccactgataa aatgaacttt ctacgtaaga   4140
tagtgaaaaa ttgcagggac gaggacactc aaaaaccctc tcccgtgtca gcccctctgg   4200
atgacgatga cttgtggctt ccacccccctg aatacgtccc gctgaaagaa cttacaagca   4260
agaagaacat gaggaacttt tgtatcaacg gagggggttaa agtgtgtagc ccgaatggtt   4320
actcgttcag gatcctgcgg cacattctga aatcattcga cgagatatat tctgggaatc   4380
ataggatgat cgggttagtc aaagtagtta ttggactggc tttgtcagga tctccagtcc   4440
ctgagggcat gaactgggta tacaaattga ggagaacctt tatcttccag tgggctgatt   4500
ccaggggccc tcttgaaggg gaggagttgg aatactctca ggagatcact tgggatgatg   4560
atactgagtt cgtcggattg caaataagag tgattgcaaa acagtgtcat atccagggca   4620
gaatctggtg tatcaacatg aacccgagag catgtcaact atggtctgac atgtctcttc   4680
agacacaaag gtccgaagag gacaaagatt cctctctgct tctagaataa tcagattata   4740
tcccgcaaat ttatcacttg tttacctctg gaggagagaa catatgggct caactccaac   4800
ccttgggagc aatataacaa aaaacatgtt atggtgccat taaaccgctg catttcatca   4860
aagtcaagtt gattaccttt acattttgat cctcttggat gtgaaaaaaa ctaacacccc   4920
tctgcagttt ggtaccttga aaaaaacctg ggttcaatag tcctccttga actccatgca   4980
actgggtaga ttcaagagtc atgagatttt cattaatcct ctcagttgat caagcaagat   5040
```

-continued

```
catgtagatt ctcataatag gggagatctt ctagcagttt cagtgactaa cggtactttc   5100
attctccagg aactgacacc aacagttgta gacaaaccac ggggtgtctc gggtgactct   5160
gtgcttgggc acagacaaag gtcatggtgt gttccatgat agcggactca ggatgagtta   5220
attgagagag gcagtcttcc tcccgtgaag gacataagca gtagctcaca atcatctcgc   5280
gtctcagcaa agtgtgcata attataaagt gctgggtcat ctaagctttt cagtcgagaa   5340
aaaaacatta gatcagaaga acaactggca acacttctca acctgagacc tacttcaaga   5400
tgctcgatcc tggagaggtc tatgatgacc ctattgaccc aatcgagtta gaggatgaac   5460
ccagaggaac ccccactgtc cccaacatct tgaggaactc tgactacaat ctcaactctc   5520
ctttgataga agatcctgct agactaatgt tagaatggtt aaaaacaggg aatagacctt   5580
atcggatgac tctaacagac aattgctcca ggtctttcag agttttgaaa gattatttca   5640
agaaggtaga tttgggttct ctcaaggtgg gcggaatggc tgcacagtca atgatttctc   5700
tctggttata tggtgcccac tctgaatcca acaggagccg gagatgtata acagacttgg   5760
cccatttcta ttccaagtcg tcccccatag agaagctgtt gaatctcacg ctaggaaata   5820
gagggctgag aatcccccca gagggagtgt taagttgcct tgagagggtt gattatgata   5880
atgcatttgg aaggtatctt gccaacacgt attcctctta cttgttcttc catgtaatca   5940
ccttatacat gaacgcccta gactgggatg aagaaaagac catcctagca ttatggaaag   6000
atttaacctc agtggacatc gggaaggact tggtaaagtt caaagaccaa atatggggac   6060
tgctgatcgt gacaaaggac tttgtttact cccaaagttc caattgtctt tttgacagaa   6120
actacacact tatgctaaaa gatcttttct tgtctcgctt caactcctta atggtcttgc   6180
tctctccccc agagccccga tactcagatg acttgatatc tcaactatgc cagctgtaca   6240
ttgctgggga tcaagtcttg tctatgtgtg gaaactccgg ctatgaagtc atcaaaatat   6300
tggagccata tgtcgtgaat agtttagtcc agagagcaga aaagtttagg cctctcattc   6360
attccttggg agactttcct gtatttataa aagacaaggt aagtcaactt gaagagacgt   6420
tcggtccctg tgcaagaagg ttctttaggg ctctggatca attcgacaac atacatgact   6480
tggtttttgt gtatggctgt tacaggcatt gggggcaccc atatatagat tatcgaaagg   6540
gtctgtcaaa actatatgat caggttcaca ttaaaaaagt gatagataag tcctaccagg   6600
agtgcttagc aagcgaccta gccaggagga tccttagatg ggttttgat aagtactcca    6660
agtggtatct ggattcaaga ttcctagccc gagaccaccc cttgactcct tatatcaaaa   6720
cccaaacatg gccacccaaa catattgtag acttggtggg ggatacatgg cacaagctcc   6780
cgatcacgca gatctttgag attcctgaat caatggatcc gtcagaaata ttggatgaca   6840
aatcacattc tttcaccaga acgagactag cttcttggct gtcagaaaac cgagggggac   6900
ctgttcctag cgaaaaagtt attatcacgg ccctgtctaa gccgcctgtc aatccccgag   6960
agtttctgag gtctatagac ctcggaggat tgccagatga agacttgata attggcctca   7020
agccaaagga acgggaattg aagattgaag gtcgattctt tgctctaatg tcatggaatc   7080
taagattgta ttttgtcatc actgaaaaac tcttggccaa ctacatcttg ccactttttg   7140
acgcgctgac tatgacagac aacctgaaca aggtgtttaa aaagctgatc gacagggtca   7200
ccgggcaagg gcttttggac tattcaaggg tcacatatgc atttcacctg gactatgaaa   7260
agtggaacaa ccatcaaaga ttagagtcaa cagaggatgt attttctgtc ctagatcaag   7320
tgtttggatt gaagagagtg ttttctagaa cacacgagtt ttttcaaaag gcctggatct   7380
attattcaga cagatcagac ctcatcgggt tacgggagga tcaaatatac tgcttagatg   7440
```

-continued cgtccaacgg cccaacctgt tggaatggcc aggatggcgg gctagaaggc ttacggcaga 7500
agggctggag tctagtcagc ttattgatga tagatagaga atctcaaatc aggaacacaa 7560
gaaccaaaat actagctcaa ggagacaacc aggttttatg tccgacatat atgttgtcgc 7620
cagggctatc tcaagagggg ctcctctatg aattggagag aatatcaagg aatgcacttt 7680
cgatatacag agccgtcgag gaaggggcat ctaagctagg gctgatcatc aagaaagaag 7740
agaccatgtg tagttatgac ttcctcatct atggaaaaac ccctttgttt agaggtaaca 7800
tattggtgcc tgagtccaaa agatgggcca gagtctcttg cgtctctaat gaccaaatag 7860
tcaacctcgc caatataatg tcgacagtgt ccaccaatgc gctaacagtg gcacaacact 7920
ctcaatcttt gatcaaaccg atgagggatt ttctgctcat gtcagtacag gcagtctttc 7980
actacctgct atttagccca atcttaaagg gaagagttta caagattctg agcgctgaag 8040
gggatagctt tctcctagcc atgtcaagga taatctatct agatccttct ttgggagggg 8100
tatctggaat gtccctcgga agattccata tacgacagtt ctcagaccct gtctctgaag 8160
ggttatcctt ctggagagag atctggttaa gctcccacga gtcctggatt cacgcgttgt 8220
gtcaagaggc tggaaaccca gatcttggag agagaacact cgagagcttc actcgccttc 8280
tagaagatcc taccacctta aatatcagag gaggggccag tcctaccatt ctactcaagg 8340
atgcaatcag aaaggcttta tatgacgagg tggacaaggt ggagaattca gagtttcgag 8400
aggcaatcct gttgtccaag acccatagag ataattttat actcttctta acatctgttg 8460
agcctctgtt tcctcgattt ctcagtgagc tattcagttc gtctttttg ggaatccccg 8520 agtcaatcat tggattgata caaaactccc gaacgataag aaggcagttt agaaagagtc 8580
tctcaaaaac tttagaagaa tccttctaca actcagagat ccacgggatt agtcggatga 8640
cccagacacc tcagagggtt gggggggtgt ggccttgctc ttcagagagg gcagatctac 8700
ttagggagat ctcttgggga agaaaagtgg taggcacgac agttcctcac ccttctgaga 8760
tgttggggtt acttcccaag tcctctattt cttgcacttg tggagcaaca ggaggaggca 8820
atcctagagt ttctgtatca gtactcccgt cctttgatca gtcatttttt tcacgaggcc 8880
ccctaaaggg gtacttgggc tcgtccacct ctatgtcgac ccagctattc catgcatggg 8940
aaaaagtcac taatgttcat gtggtgaaga gagctctatc gttaaaagaa tctataaact 9000
ggttcattac tagagattcc aacttggctc aagctctaat taggaacatt atgtctctga 9060
caggccctga tttccctcta gaggaggccc ctgtcttcaa aaggacgggg tcagccttgc 9120
ataggttcaa gtctgccaga tacagcgaag gagggtattc ttctgtctgc ccgaacctcc 9180
tctctcatat ttctgttagt acagacacca tgtctgattt gacccaagac gggaagaact 9240
acgatttcat gttccagcca ttgatgcttt atgcacagac atggacatca gagctggtac 9300
agagagacac aaggctaaga gactctacgt ttcattggca cctccgatgc aacaggtgtg 9360
tgagacccat tgacgacgtg accctggaga cctctcagat cttcgagttt ccggatgtgt 9420
cgaaaagaat atccagaatg gtttctgggg ctgtgcctca cttccagagg cttcccgata 9480
tccgtctgag accaggagat tttgaatctc taagcggtag agaaaagtct caccatatcg 9540
gatcagctca ggggctctta tactcaatct tagtggcaat tcacgactca ggatacaatg 9600
atggaaccat cttccctgtc aacatatacg acaaggtttc ccctagagac tatttgagag 9660
ggctcgcaag gggagtattg ataggatcct cgatttgctt cttgacaaga atgacaaata 9720
tcaatattaa tagacctctt gaattgatct caggggtaat ctcatatatt ctcctgaggc 9780

-continued

```
tagataacca tccctccttg tacataatgc tcagagaacc gtctcttaga ggagagatat   9840
tttctatccc tcagaaaatc cccgccgctt atccaaccac tatgaaagaa ggcaacagat   9900
caatcttgtg ttatctccaa catgtgctac gctatgagcg agagataatc acggcgtctc   9960
cagagaatga ctggctatgg atcttttcag actttagaag tgccaaaatg acgtacctaa  10020
ccctcattac ttaccagtct catcttctac tccagagggt tgagagaaac ctatctaaga  10080
gtatgagaga taacctgcga caattgagtt ccttgatgag gcaggtgctg ggcgggcacg  10140
gagaagatac cttagagtca gacgacaaca ttcaacgact gctaaaagac tctttacgaa  10200
ggacaagatg ggtggatcaa gaggtgcgcc atgcagctag aaccatgact ggagattaca  10260
gccccaacaa gaaggtgtcc cgtaaggtag gatgttcaga atgggtctgc tctgctcaac  10320
aggttgcagt ctctacctca gcaaacccgg cccctgtctc ggagcttgac ataagggccc  10380
tctctaagag gttccagaac cctttgatct cgggcttgag agtggttcag tgggcaaccg  10440
gtgctcatta taagcttaag cctattctag atgatctcaa tgttttccca tctctctgcc  10500
ttgtagttgg ggacgggtca ggggggatat caagggcagt cctcaacatg tttccagatg  10560
ccaagcttgt gttcaacagt ctcttagagg tgaatgacct gatggcttcc ggaacacatc  10620
cactgcctcc ttcagcaatc atgaggggag gaaatgatat cgtctccaga gtgatagatt  10680
ttgactcaat ctgggaaaaa ccgtccgact tgagaaactt ggcaacctgg aaatacttcc  10740
agtcagtcca aaagcaggtc aacatgtcct atgacctcat tatttgcgat gcagaagtta  10800
ctgacattgc atctatcaac cggataaccc tgttaatgtc cgattttgca ttgtctatag  10860
atggaccact ctatttggtc ttcaaaactt atgggactat gctagtaaat ccaaactaca  10920
aggctattca acacctgtca agagcgttcc cctcggtcac agggtttatc acccaagtaa  10980
cttcgtcttt ttcatctgag ctctacctcc gattctccaa acgagggaag tttttcagag  11040
atgctgagta cttgacctct tccacccttc gagaaatgag ccttgtgtta ttcaattgta  11100
gcagccccaa gagtgagatg cagagagctc gttccttgaa ctatcaggat cttgtgagag  11160
gatttcctga agaaatcata tcaaatcctt acaatgagat gatcataact ctgattgaca  11220
gtgatgtaga atcttttcta gtccacaaga tggttgatga tcttgagtta cagaggggaa  11280
ctctgtctaa agtggctatc attatagcca tcatgatagt tttctccaac agagtcttca  11340
acgtttccaa acccctaact gaccccttgt tctatccacc gtctgatccc aaaatcctga  11400
ggcacttcaa catatgttgc agtactatga tgtatctatc tactgcttta ggtgacgtcc  11460
ctagcttcgc aagacttcac gacctgtata acagacctat aacttattac ttcagaaagc  11520
aattcattcg agggaacgtt tatctatctt ggagttggtc caacgacacc tcagtgttca  11580
aaagggtagc ctgtaattct agcctgagtc tgtcatctca ctggatcagg ttgatttaca  11640
agatagtgaa gactaccaga ctcgttggca gcatcaagga tctatccaga gaagtggaaa  11700
gacaccttca taggtacaac aggtggatca ccctagagga tatcagatct agatcatccc  11760
tactagacta cagttgcctg tgatccggat actcctggaa gcctgcccat gctaagactc  11820
ttgtgtgatg tatcttgaaa aaaacaagat cctaaatctg aacctttggt tgtttgattg  11880
tttttctcat tttgttgtt tatttgttaa gcgt                             11914
```

<210> SEQ ID NO 17
<211> LENGTH: 11914
<212> TYPE: DNA
<213> ORGANISM: artificial seuqence
<220> FEATURE:
<223> OTHER INFORMATION: Recombinant ERAg3m rabies virus genome

```
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2505)..(4076)
<220> FEATURE:
<221> NAME/KEY: misc_feature
<222> LOCATION: (4122)..(4727)
<220> FEATURE:
<221> NAME/KEY: misc_feature
<222> LOCATION: (5400)..(11780)

<400> SEQUENCE: 17

acgcttaaca accagatcaa agaaaaaaca gacattgtca attgcaaagc aaaaatgtaa     60

caccccctaca atggatgccg acaagattgt attcaaagtc aataatcagg tggtctcttt    120

gaagcctgag attatcgtgg atcaacatga gtacaagtac cctgccatca aagatttgaa    180

aaagccctgt ataaccctag gaaaggctcc cgatttaaat aaagcataca agtcagtttt    240

gtcaggcatg agcgccgcca aacttgatcc tgacgatgta tgttcctatt tggcagcggc    300

aatgcagttt tttgagggga catgtccgga agactggacc agctatggaa tcgtgattgc    360

acgaaaagga gataagatca ccccaggttc tctggtggag ataaaacgta ctgatgtaga    420

agggaattgg gctctgacag gaggcatgga actgacaaga gaccccactg tccctgagca    480

tgcgtcctta gtcggtcttc tcttgagtct gtataggttg agcaaaatat ccgggcaaaa    540

cactggtaac tataagacaa acattgcaga caggatagag cagatttttg agacagcccc    600

ttttgttaaa atcgtggaac accatactct aatgacaact cacaaaatgt gtgctaattg    660

gagtactata ccaaacttca gatttttggc cggaacctat gacatgtttt tctcccggat    720

tgagcatcta tattcagcaa tcagagtggg cacagttgtc actgcttatg aagactgttc    780

aggactggta tcatttactg ggttcataaa acaaatcaat ctcaccgcta gagaggcaat    840

actatatttc ttccacaaga actttgagga agagataaga agaatgtttg agccagggca    900

ggagacagct gttcctcact cttatttcat ccacttccgt tcactaggct tgagtgggaa    960

atctccttat tcatcaaatg ctgttggtca cgtgttcaat ctcattcact ttgtaggatg   1020

ctatatgggt caagtcagat ccctaaatgc aacggttatt gctgcatgtg ctcctcatga   1080

aatgtctgtt ctagggggct atctgggaga ggaattcttc gggaaaggga catttgaaag   1140

aagattcttc agagatgaga aagaacttca agaatacgag gcggctgaac tgacaaagac   1200

tgacgtagca ctggcagatg atggaactgt caactctgac gacgaggact acttctcagg   1260

tgaaaccaga agtccggagg ctgtttatac tcgaatcatg atgaatggag gtcgactaaa   1320

gagatctcac atacggagat atgtctcagt cagttccaat catcaagccc gtccaaactc   1380

attcgccgag tttctaaaca agacatattc gagtgactca taagaagttg aataacaaaa   1440

tgccggaaat ctacggattg tgtatatcca tcatgaaaaa aactaacacc cctcctttcg   1500

aaccatccca aacatgagca agatctttgt caatcctagt gctattagag ccggtctggc   1560

cgatcttgag atggctgaag aaactgttga tctgatcaat agaaatatcg aagacaatca   1620

ggctcatctc caaggggaac ccatagaagt ggacaatctc cctgaggata tggggcgact   1680

tcacctggat gatggaaaat cgcccaaccc tggtgagatg gccaaggtgg gagaaggcaa   1740

gtatcgagag gactttcaga tggatgaagg agaggatcct agcttcctgt tccagtcata   1800

cctggaaaat gttggagtcc aaatagtcag acaaatgagg tcaggagaga gatttctcaa   1860
```

```
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaaactaac acccctcctt tcgctgcagc caccatggtt cctcaggctc   2520
tcctgtttgt accccttctg gtttttccat tgtgttttgg gaaattccct atttacacga   2580
taccagacaa gcttggtccc tggagtccga ttgacataca tcacctcagc tgcccaaaca   2640
atttggtagt ggaggacgaa ggatgcacca acctgtcagg gttctcctac atggaactta   2700
aagttggata catcttagcc ataaaagtga acgggttcac ttgcacaggc gttgtgacgg   2760
aggctgaaac ctacactaac ttcgttggtt atgtcacaac cacgttcaaa agaaagcatt   2820
tccgcccaac accagatgca tgtagagccg cgtacaactg gaagatggcc ggtgacccca   2880
gatatgaaga gtctctacac aatccgtacc ctgactaccg ctggcttcga actgtaaaaa   2940
ccaccaagga gtctctcgtt atcatatctc caagtgtggc agatttggac ccatatgaca   3000
gatcccttca ctcgagggtc ttccctagcg ggaagtgctc aggagtagcg gtgtcttcta   3060
cctactgctc cactaaccac gattacacca tttggatgcc cgagaatccg agactaggga   3120
tgtcttgtga catttttacc aatagtagag ggaagagagc atccaaaggg agtgagactt   3180
gcggctttgt agatgaaaga ggcctatata agtctttaaa aggagcatgc aaactcaagt   3240
tatgtggagt tctaggactt agacttatgg atggaacatg ggtctcgatg caaacatcaa   3300
atgaaaccaa atggtgccct cccgataagt tggtgaacct gcacgacttt cgctcagacg   3360
aaattgagca ccttgttgta gaggagttgg tcaggaagag agaggagtgt ctggatgcac   3420
tagagtccat catgacaacc aagtcagtga gtttcagacg tctcagtcat ttaagaaaac   3480
ttgtccctgg gtttggaaaa gcatatacca tattcaacaa gaccttgatg gaagccgatg   3540
ctcactacaa gtcagtcgag acttggaatg agatcctccc ttcaaaaggg tgtttaagag   3600
ttgggggggag gtgtcatcct catgtgaacg gggtgttttt caatggtata atattaggac   3660
ctgacggcaa tgtcttaatc ccagagatgc aatcatccct cctccagcaa catatggagt   3720
tgttggaatc ctcggttatc ccccttgtgc accccctggc agacccgtct accgttttca   3780
aggacggtga cgaggctgag gattttgttg aagttcacct tcccgatgtg cacaatcagg   3840
tctcaggagt tgacttgggt ctcccgaact gggggaagta tgtattactg agtgcagggg   3900
ccctgactgc cttgatgttg ataattttcc tgatgacatg ttgtagaaga gtcaatcgat   3960
cagaacctac gcaacacaat ctcagaggga cagggaggga ggtgtcagtc actccccaaa   4020
gcgggaagat catatcttca tgggaatcac acaagagtgg gggtgagacc agactgtaat   4080
ttggtaccgt cgagaaaaaa acaggcaaca ccactgataa aatgaacttt ctacgtaaga   4140
tagtgaaaaa ttgcagggac gaggacactc aaaaaccctc tcccgtgtca gcccctctgg   4200
```

-continued atgacgatga cttgtggctt ccaccccctg aatacgtccc gctgaaagaa cttacaagca 4260
agaagaacat gaggaacttt tgtatcaacg gaggggttaa agtgtgtagc ccgaatggtt 4320
actcgttcag gatcctgcgg cacattctga aatcattcga cgagatatat tctgggaatc 4380
ataggatgat cgggttagtc aaagtagtta ttggactggc tttgtcagga tctccagtcc 4440
ctgagggcat gaactgggta tacaaattga ggagaacctt tatcttccag tgggctgatt 4500
ccaggggccc tcttgaaggg gaggagttgg aatactctca ggagatcact tgggatgatg 4560
atactgagtt cgtcggattg caaataagag tgattgcaaa acagtgtcat atccagggca 4620
gaatctggtg tatcaacatg aacccgagag catgtcaact atggtctgac atgtctcttc 4680
agacacaaag gtccgaagag gacaaagatt cctctctgct tctagaataa tcagattata 4740
tcccgcaaat ttatcacttg tttacctctg gaggagagaa catatgggct caactccaac 4800
ccttgggagc aatataacaa aaaacatgtt atggtgccat taaaccgctg catttcatca 4860
aagtcaagtt gattaccttt acattttgat cctcttggat gtgaaaaaaa ctaacacccc 4920
tctgcagttt ggtaccttga aaaaaacctg ggttcaatag tcctccttga actccatgca 4980
actgggtaga ttcaagagtc atgagatttt cattaatcct ctcagttgat caagcaagat 5040
catgtagatt ctcataatag gggagatctt ctagcagttt cagtgactaa cggtactttc 5100
attctccagg aactgacacc aacagttgta gacaaaccac ggggtgtctc gggtgactct 5160
gtgcttgggc acagacaaag gtcatggtgt gttccatgat agcggactca ggatgagtta 5220
attgagagag gcagtcttcc tcccgtgaag gacataagca gtagctcaca atcatctcgc 5280
gtctcagcaa agtgtgcata attataaagt gctgggtcat ctaagctttt cagtcgagaa 5340
aaaaacatta gatcagaaga acaactggca acacttctca acctgagacc tacttcaaga 5400
tgctcgatcc tggagaggtc tatgatgacc ctattgaccc aatcgagtta gaggatgaac 5460
ccagaggaac ccccactgtc cccaacatct tgaggaactc tgactacaat ctcaactctc 5520
ctttgataga agatcctgct agactaatgt tagaatggtt aaaaacaggg aatagacctt 5580
atcggatgac tctaacagac aattgctcca ggtctttcag agttttgaaa gattatttca 5640
agaaggtaga tttgggttct ctcaaggtgg gcggaatggc tgcacagtca atgatttctc 5700
tctggttata tggtgcccac tctgaatcca acaggagccg gagatgtata acagacttgg 5760
cccatttcta ttccaagtcg tcccccatag agaagctgtt gaatctcacg ctaggaaata 5820
gagggctgag aatcccccca gagggagtgt taagttgcct tgagagggtt gattatgata 5880
atgcatttgg aaggtatctt gccaacacgt attcctctta cttgttcttc catgtaatca 5940
ccttatacat gaacgcccta gactgggatg aagaaaagac catcctagca ttatggaaag 6000
atttaacctc agtggacatc gggaaggact tggtaaagtt caaagaccaa atatggggac 6060
tgctgatcgt gacaaaggac tttgtttact cccaaagttc caattgtctt tttgacagaa 6120
actacacact tatgctaaaa gatcttttct tgtctcgctt caactcctta atggtcttgc 6180
tctctccccc agagccccga tactcagatg acttgatatc tcaactatgc cagctgtaca 6240
ttgctgggga tcaagtcttg tctatgtgtg gaaactccgg ctatgaagtc atcaaaatat 6300
tggagccata tgtcgtgaat agtttagtcc agagagcaga aaagtttagg cctctcattc 6360
attccttggg agactttcct gtatttataa aagacaaggt aagtcaactt gaagagacgt 6420
tcggtccctg tgcaagaagg ttctttaggg ctctggatca attcgacaac atacatgact 6480
tggtttttgt gtatggctgt tacaggcatt gggggcaccc atatatagat tatcgaaagg 6540
gtctgtcaaa actatatgat caggttcaca ttaaaaaagt gatagataag tcctaccagg 6600

```
agtgcttagc aagcgaccta gccaggagga tccttagatg gggttttgat aagtactcca   6660
agtggtatct ggattcaaga ttcctagccc gagaccaccc cttgactcct tatatcaaaa   6720
cccaaacatg gccacccaaa catattgtag acttggtggg ggatacatgg cacaagctcc   6780
cgatcacgca gatctttgag attcctgaat caatggatcc gtcagaaata ttggatgaca   6840
aatcacattc tttcaccaga acgagactag cttcttggct gtcagaaaac cgagggggac   6900
ctgttcctag cgaaaaagtt attatcacgg ccctgtctaa gccgcctgtc aatccccgag   6960
agtttctgag gtctatagac ctcggaggat tgccagatga agacttgata attggcctca   7020
agccaaagga acgggaattg aagattgaag gtcgattctt tgctctaatg tcatggaatc   7080
taagattgta ttttgtcatc actgaaaaac tcttggccaa ctacatcttg ccactttttg   7140
acgcgctgac tatgacagac aacctgaaca aggtgtttaa aaagctgatc gacagggtca   7200
ccgggcaagg gcttttggac tattcaaggg tcacatatgc atttcacctg gactatgaaa   7260
agtggaacaa ccatcaaaga ttagagtcaa cagaggatgt attttctgtc ctagatcaag   7320
tgtttggatt gaagagagtg ttttctagaa cacacgagtt ttttcaaaag gcctggatct   7380
attattcaga cagatcagac ctcatcgggt tacgggagga tcaaatatac tgcttagatg   7440
cgtccaacgg cccaacctgt tggaatggcc aggatggcgg gctagaaggc ttacggcaga   7500
agggctggag tctagtcagc ttattgatga tagatagaga atctcaaatc aggaacacaa   7560
gaaccaaaat actagctcaa ggagacaacc aggttttatg tccgacatat atgttgtcgc   7620
cagggctatc tcaagagggg ctcctctatg aattggagag aatatcaagg aatgcacttt   7680
cgatatacag agccgtcgag gaaggggcat ctaagctagg gctgatcatc aagaaagaag   7740
agaccatgtg tagttatgac ttcctcatct atggaaaaac ccctttgttt agaggtaaca   7800
tattggtgcc tgagtccaaa agatgggcca gagtctcttg cgtctctaat gaccaaatag   7860
tcaacctcgc caatataatg tcgacagtgt ccaccaatgc gctaacagtg gcacaacact   7920
ctcaatcttt gatcaaaccg atgagggatt ttctgctcat gtcagtacag gcagtctttc   7980
actacctgct atttagccca atcttaaagg gaagagttta caagattctg agcgctgaag   8040
gggatagctt tctcctagcc atgtcaagga taatctatct agatccttct ttgggagggg   8100
tatctggaat gtccctcgga agattccata tacgacagtt ctcagaccct gtctctgaag   8160
ggttatcctt ctggagagag atctggttaa gctcccacga gtcctggatt cacgcgttgt   8220
gtcaagaggc tggaaaccca gatcttggag agagaacact cgagagcttc actcgccttc   8280
tagaagatcc taccacctta aatatcagag gaggggccag tcctaccatt ctactcaagg   8340
atgcaatcag aaaggcttta tatgacgagg tggacaaggt ggagaattca gagtttcgag   8400
aggcaatcct gttgtccaag acccatagag ataattttat actcttctta acatctgttg   8460
agcctctgtt tcctcgattt ctcagtgagc tattcagttc gtctttttttg ggaatccccg   8520
agtcaatcat tggattgata caaaactccc gaacgataag aaggcagttt agaaagagtc   8580
tctcaaaaac tttagaagaa tccttctaca actcagagat ccacgggatt agtcggatga   8640
cccagacacc tcagagggtt gggggggtgt ggccttgctc ttcagagagg gcagatctac   8700
ttagggagat ctcttgggga agaaaagtgg taggcacgac agttcctcac ccttctgaga   8760
tgttggggtt acttcccaag tcctctattt cttgcacttg tggagcaaca ggaggaggca   8820
atcctagagt ttctgtatca gtactcccgt cctttgatca gtcatttttt tcacgaggcc   8880
ccctaaaggg gtacttgggc tcgtccacct ctatgtcgac ccagctattc catgcatggg   8940
```

-continued

```
aaaaagtcac taatgttcat gtggtgaaga gagctctatc gttaaaagaa tctataaact   9000
ggttcattac tagagattcc aacttggctc aagctctaat taggaacatt atgtctctga   9060
caggccctga tttccctcta gaggaggccc ctgtcttcaa aaggacgggg tcagccttgc   9120
ataggttcaa gtctgccaga tacagcgaag gagggtattc ttctgtctgc ccgaacctcc   9180
tctctcatat ttctgttagt acagacacca tgtctgattt gacccaagac gggaagaact   9240
acgatttcat gttccagcca ttgatgcttt atgcacagac atggacatca gagctggtac   9300
agagagacac aaggctaaga gactctacgt ttcattggca cctccgatgc aacaggtgtg   9360
tgagacccat tgacgacgtg accctggaga cctctcagat cttcgagttt ccggatgtgt   9420
cgaaaagaat atccagaatg gtttctgggg ctgtgcctca cttccagagg cttcccgata   9480
tccgtctgag accaggagat tttgaatctc taagcggtag agaaaagtct caccatatcg   9540
gatcagctca ggggctctta tactcaatct tagtggcaat tcacgactca ggatacaatg   9600
atggaaccat cttccctgtc aacatatacg acaaggtttc ccctagagac tatttgagag   9660
ggctcgcaag ggagtattg ataggatcct cgatttgctt cttgacaaga atgacaaata   9720
tcaatattaa tagacctctt gaattgatct caggggtaat ctcatatatt ctcctgaggc   9780
tagataacca tccctccttg tacataatgc tcagagaacc gtctcttaga ggagagatat   9840
tttctatccc tcagaaaatc cccgccgctt atccaaccac tatgaaagaa ggcaacagat   9900
caatcttgtg ttatctccaa catgtgctac gctatgagcg agagataatc acggcgtctc   9960
cagagaatga ctggctatgg atcttttcag actttagaag tgccaaaatg acgtacctaa  10020
ccctcattac ttaccagtct catcttctac tccagagggt tgagagaaac ctatctaaga  10080
gtatgagaga taacctgcga caattgagtt ccttgatgag gcaggtgctg ggcgggcacg  10140
gagaagatac cttagagtca gacgacaaca ttcaacgact gctaaaagac tctttacgaa  10200
ggacaagatg ggtggatcaa gaggtgcgcc atgcagctag aaccatgact ggagattaca  10260
gccccaacaa gaaggtgtcc cgtaaggtag gatgttcaga atgggtctgc tctgctcaac  10320
aggttgcagt ctctacctca gcaaacccgg cccctgtctc ggagcttgac ataagggccc  10380
tctctaagag gttccagaac cctttgatct cgggcttgag agtggttcag tgggcaaccg  10440
gtgctcatta taagcttaag cctattctag atgatctcaa tgttttccca tctctctgcc  10500
ttgtagttgg ggacgggtca ggggggatat caagggcagt cctcaacatg tttccagatg  10560
ccaagcttgt gttcaacagt ctcttagagg tgaatgacct gatggcttcc ggaacacatc  10620
cactgcctcc ttcagcaatc atgaggggag gaaatgatat cgtctccaga gtgatagatt  10680
ttgactcaat ctgggaaaaa ccgtccgact tgagaaactt ggcaacctgg aaatacttcc  10740
agtcagtcca aaagcaggtc aacatgtcct atgacctcat tatttgcgat gcagaagtta  10800
ctgacattgc atctatcaac cggataaccc tgttaatgtc cgattttgca ttgtctatag  10860
atggaccact ctatttggtc ttcaaaactt atgggactat gctagtaaat ccaaactaca  10920
aggctattca acacctgtca agagcgttcc cctcggtcac agggtttatc acccaagtaa  10980
cttcgtcttt ttcatctgag ctctacctcc gattctccaa acgagggaag tttttcagag  11040
atgctgagta cttgacctct tccacccttc gagaaatgag ccttgtgtta ttcaattgta  11100
gcagccccaa gagtgagatg cagagagctc gttccttgaa ctatcaggat cttgtgagag  11160
gatttcctga agaaatcata tcaaatcctt acaatgagat gatcataact ctgattgaca  11220
gtgatgtaga atcttttcta gtccacaaga tggttgatga tcttgagtta cagaggggaa  11280
ctctgtctaa agtggctatc attatagcca tcatgatagt tttctccaac agagtcttca  11340
```

acgtttccaa acccctaact gaccccttgt tctatccacc gtctgatccc aaaatcctga 11400
ggcacttcaa catatgttgc agtactatga tgtatctatc tactgcttta ggtgacgtcc 11460
ctagcttcgc aagacttcac gacctgtata acagacctat aacttattac ttcagaaagc 11520
aattcattcg agggaacgtt tatctatctt ggagttggtc caacgacacc tcagtgttca 11580
aaagggtagc ctgtaattct agcctgagtc tgtcatctca ctggatcagg ttgatttaca 11640
agatagtgaa gactaccaga ctcgttggca gcatcaagga tctatccaga gaagtggaaa 11700
gacaccttca taggtacaac aggtggatca ccctagagga tatcagatct agatcatccc 11760
tactagacta cagttgcctg tgatccggat actcctggaa gcctgcccat gctaagactc 11820
ttgtgtgatg tatcttgaaa aaaacaagat cctaaatctg aacctttggt tgtttgattg 11880
tttttctcat ttttgttgtt tatttgttaa gcgt 11914

<210> SEQ ID NO 18
<211> LENGTH: 13556
<212> TYPE: DNA
<213> ORGANISM: artificial sequence
<220> FEATURE:
<223> OTHER INFORMATION: Recombinant ERAgmg rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2505)..(4076)
<220> FEATURE:
<221> NAME/KEY: misc_feature
<222> LOCATION: (4122)..(4727)
<220> FEATURE:
<221> NAME/KEY: misc_feature
<222> LOCATION: (4943)..(6514)
<220> FEATURE:
<221> NAME/KEY: misc_feature
<222> LOCATION: (7042)..(13422)

<400> SEQUENCE: 18
acgcttaaca accagatcaa agaaaaaaca gacattgtca attgcaaagc aaaaatgtaa 60
cacccctaca atggatgccg acaagattgt attcaaagtc aataatcagg tggtctcttt 120
gaagcctgag attatcgtgg atcaacatga gtacaagtac cctgccatca aagatttgaa 180
aaagccctgt ataaccctag gaaaggctcc cgatttaaat aaagcataca agtcagtttt 240
gtcaggcatg agcgccgcca aacttgatcc tgacgatgta tgttcctatt tggcagcggc 300
aatgcagttt tttgagggga catgtccgga agactggacc agctatggaa tcgtgattgc 360
acgaaaagga gataagatca ccccaggttc tctggtggag ataaaacgta ctgatgtaga 420
agggaattgg gctctgacag gaggcatgga actgacaaga gaccccactg tccctgagca 480
tgcgtcctta gtcggtcttc tcttgagtct gtataggttg agcaaaatat ccgggcaaaa 540
cactggtaac tataagacaa acattgcaga caggatagag cagatttttg agacagcccc 600
ttttgttaaa atcgtggaac accatactct aatgacaact cacaaaatgt gtgctaattg 660
gagtactata ccaaacttca gatttttggc cggaacctat gacatgtttt tctcccggat 720
tgagcatcta tattcagcaa tcagagtggg cacagttgtc actgcttatg aagactgttc 780
aggactggta tcatttactg ggttcataaa acaaatcaat ctcaccgcta gagaggcaat 840
actatatttc ttccacaaga actttgagga agagataaga agaatgtttg agccagggca 900
ggagacagct gttcctcact cttatttcat ccacttccgt tcactaggct tgagtgggaa 960
atctccttat tcatcaaatg ctgttggtca cgtgttcaat ctcattcact ttgtaggatg 1020
ctatatgggt caagtcagat ccctaaatgc aacggttatt gctgcatgtg ctcctcatga 1080
aatgtctgtt ctagggggct atctgggaga ggaattcttc gggaaaggga catttgaaag 1140
aagattcttc agagatgaga aagaacttca agaatacgag gcggctgaac tgacaaagac 1200
tgacgtagca ctggcagatg atggaactgt caactctgac gacgaggact acttctcagg 1260
tgaaaccaga agtccggagg ctgtttatac tcgaatcatg atgaatggag gtcgactaaa 1320
gagatctcac atacggagat atgtctcagt cagttccaat catcaagccc gtccaaactc 1380
attcgccgag tttctaaaca agacatattc gagtgactca taagaagttg aataacaaaa 1440
tgccggaaat ctacggattg tgtatatcca tcatgaaaaa aactaacacc cctcctttcg 1500
aaccatccca aacatgagca agatctttgt caatcctagt gctattagag ccggtctggc 1560
cgatcttgag atggctgaag aaactgttga tctgatcaat agaaatatcg aagacaatca 1620
ggctcatctc caaggggaac ccatagaagt ggacaatctc cctgaggata tggggcgact 1680
tcacctggat gatggaaaat cgcccaaccc tggtgagatg gccaaggtgg gagaaggcaa 1740
gtatcgagag gactttcaga tggatgaagg agaggatcct agcttcctgt tccagtcata 1800
cctggaaaat gttggagtcc aaatagtcag acaaatgagg tcaggagaga gatttctcaa 1860
gatatggtca cagaccgtag aagagattat atcctatgtc gcggtcaact ttcccaaccc 1920
tccaggaaag tcttcagagg ataaatcaac ccagactact ggccgagagc tcaagaagga 1980
gacaacaccc actccttctc agagagaaag ccaatcatcg aaagccagga tggcggctca 2040
aattgcttct ggccctccag cccttgaatg gtcggccacc aatgaagagg atgatctatc 2100
agtggaggct gagatcgctc accagattgc agaaagtttc tccaaaaaat ataagtttcc 2160
ctctcgatcc tcagggatac tcttgtataa ttttgagcaa ttgaaaatga accttgatga 2220
tatagttaaa gaggcaaaaa atgtaccagg tgtgacccgt ttagcccatg acgggtccaa 2280
actcccccta agatgtgtac tgggatgggt cgctttggcc aactctaaga aattccagtt 2340
gttagtcgaa tccgacaagc tgagtaaaat catgcaagat gacttgaatc gctatacatc 2400
ttgctaaccg aacctctcca ctcagtccct ctagacaata aagtccgaga tgtcctaaag 2460
tcaacatgaa aaaaactaac acccctcctt tcgctgcagc caccatggtt cctcaggctc 2520
tcctgtttgt accccttctg gtttttccat tgtgttttgg gaaattccct atttacacga 2580
taccagacaa gcttggtccc tggagcccga ttgacataca tcacctcagc tgcccaaaca 2640
atttggtagt ggaggacgaa ggatgcacca acctgtcagg gttctcctac atggaactta 2700
aagttggata catcttagcc ataaaaatga acgggttcac ttgcacaggc gttgtgacgg 2760
aggctgaaac ctacactaac ttcgttggtt atgtcacaac cacgttcaaa agaaagcatt 2820
tccgcccaac accagatgca tgtagagccg cgtacaactg gaagatggcc ggtgacccca 2880
gatatgaaga gtctctacac aatccgtacc ctgactacca ctggcttcga actgtaaaaa 2940
ccaccaagga gtctctcgtt atcatatctc caagtgtggc agatttggac ccatatgaca 3000
gatcccttca ctcgagggtc ttccctagcg ggaagtgctc aggagtagcg gtgtcttcta 3060
cctactgctc cactaaccac gattacacca tttggatgcc cgagaatccg agactaggga 3120
tgtcttgtga catttttacc aatagtagag ggaagagagc atccaaaggg agtgagactt 3180
gcggctttgt agatgaaaga ggcctatata agtctttaaa aggagcatgc aaactcaagt 3240
tatgtggagt tctaggactt agacttatgg atggaacatg ggtcgcgatg caaacatcaa 3300

-continued atgaaaccaa atggtgccct cccgatcagt tggtgaacct gcacgacttt cgctcagacg 3360
aaattgagca ccttgttgta gaggagttgg tcaggaagag agaggagtgt ctggatgcac 3420
tagagtccat catgacaacc aagtcagtga gtttcagacg tctcagtcat ttaagaaaac 3480
ttgtccctgg gtttggaaaa gcatatacca tattcaacaa gaccttgatg gaagccgatg 3540
ctcactacaa gtcagtcaga acttggaatg agatcctccc ttcaaaaggg tgtttaagag 3600
ttggggggag gtgtcatcct catgtgaacg gggtgttttt caatggtata atattaggac 3660
ctgacggcaa tgtcttaatc ccagagatgc aatcatccct cctccagcaa catatggagt 3720
tgttggaatc ctcggttatc cccttgtgc accccctggc agacccgtct accgttttca 3780
aggacggtga cgaggctgag gattttgttg aagttcacct tcccgatgtg cacaatcagg 3840
tctcaggagt tgacttgggt ctcccgaact gggggaagta tgtattactg agtgcagggg 3900
ccctgactgc cttgatgttg ataattttcc tgatgacatg ttgtagaaga gtcaatcgat 3960
cagaacctac gcaacacaat ctcagaggga cagggaggga ggtgtcagtc actccccaaa 4020
gcgggaagat catatcttca tgggaatcac acaagagtgg gggtgagacc agactgtgat 4080
ttggtaccgt cgagaaaaaa acaggcaaca ccactgataa aatgaacttt ctacgtaaga 4140
tagtgaaaaa ttgcagggac gaggacactc aaaaaccctc tcccgtgtca gcccctctgg 4200
atgacgatga cttgtggctt ccaccccctg aatacgtccc gctgaaagaa cttacaagca 4260
agaagaacat gaggaacttt tgtatcaacg gaggggttaa agtgtgtagc ccgaatggtt 4320
actcgttcag gatcctgcgg cacattctga aatcattcga cgagatatat tctgggaatc 4380
ataggatgat cgggttagtc aaagtagtta ttggactggc tttgtcagga tctccagtcc 4440
ctgagggcat gaactgggta tacaaattga ggagaacctt tatcttccag tgggctgatt 4500
ccaggggccc tcttgaaggg gaggagttgg aatactctca ggagatcact tgggatgatg 4560
atactgagtt cgtcggattg caaataagag tgattgcaaa acagtgtcat atccagggca 4620
gaatctggtg tatcaacatg aacccgagag catgtcaact atggtctgac atgtctcttc 4680
agacacaaag gtccgaagag gacaaagatt cctctctgct tctagaataa tcagattata 4740
tcccgcaaat ttatcacttg tttacctctg gaggagagaa catatgggct caactccaac 4800
ccttgggagc aatataacaa aaaacatgtt atggtgccat taaaccgctg catttcatca 4860
aagtcaagtt gattaccttt acattttgat cctcttggat gtgaaaaaaa ctattaacat 4920
ccctcaaaag actcaaggaa agatggttcc tcaggctctc ctgtttgtac cccttctggt 4980
ttttccattg tgttttggga aattccctat ttacacgata ccagacaagc ttggtccctg 5040
gagcccgatt gacatacatc acctcagctg cccaaacaat ttggtagtgg aggacgaagg 5100
atgcaccaac ctgtcagggt tctcctacat ggaacttaaa gttggataca tcttagccat 5160
aaaaatgaac gggttcactt gcacaggcgt tgtgacggag gctgaaacct acactaactt 5220
cgttggttat gtcacaacca cgttcaaaag aaagcatttc cgcccaacac cagatgcatg 5280
tagagccgcg tacaactgga agatggccgg tgaccccaga tatgaagagt ctctacacaa 5340
tccgtaccct gactaccact ggcttcgaac tgtaaaaacc accaaggagt ctctcgttat 5400
catatctcca agtgtggcag atttggaccc atatgacaga tcccttcact cgagggtctt 5460
ccctagcggg aagtgctcag gagtagcggt gtcttctacc tactgctcca ctaaccacga 5520
ttacaccatt tggatgcccg agaatccgag actagggatg tcttgtgaca tttttaccaa 5580
tagtagaggg aagagagcat ccaaagggag tgagacttgc ggctttgtag atgaaagagg 5640

-continued

```
cctatataag tctttaaaag gagcatgcaa actcaagtta tgtggagttc taggacttag   5700
acttatggat ggaacatggg tcgcgatgca aacatcaaat gaaaccaaat ggtgccctcc   5760
cgatcagttg gtgaacctgc acgactttcg ctcagacgaa attgagcacc ttgttgtaga   5820
ggagttggtc aggaagagag aggagtgtct ggatgcacta gagtccatca tgacaaccaa   5880
gtcagtgagt ttcagacgtc tcagtcattt aagaaaactt gtccctgggt ttggaaaagc   5940
atataccata ttcaacaaga ccttgatgga agccgatgct cactacaagt cagtcagaac   6000
ttggaatgag atcctccctt caaaagggtg tttaagagtt ggggggaggt gtcatcctca   6060
tgtgaacggg gtgtttttca atggtataat attaggacct gacggcaatg tcttaatccc   6120
agagatgcaa tcatccctcc tccagcaaca tatggagttg ttggaatcct cggttatccc   6180
ccttgtgcac cccctggcag acccgtctac cgttttcaag gacggtgacg aggctgagga   6240
ttttgttgaa gttcaccttc ccgatgtgca caatcaggtc tcaggagttg acttgggtct   6300
cccgaactgg gggaagtatg tattactgag tgcaggggcc ctgactgcct tgatgttgat   6360
aattttcctg atgacatgtt gtagaagagt caatcgatca gaacctacgc aacacaatct   6420
cagagggaca gggagggagg tgtcagtcac tccccaaagc gggaagatca tatcttcatg   6480
ggaatcacac aagagtgggg gtgagaccag actgtgagga ctggccgtcc tttcaactat   6540
ccaagtcctg aagatcacct ccccttgggg ggttcttttt gaaaaaaacc tgggttcaat   6600
agtcctcctt gaactccatg caactgggta gattcaagag tcatgagatt ttcattaatc   6660
ctctcagttg atcaagcaag atcatgtaga ttctcataat aggggagatc ttctagcagt   6720
ttcagtgact aacggtactt tcattctcca ggaactgaca ccaacagttg tagacaaacc   6780
acggggtgtc tcgggtgact ctgtgcttgg gcacagacaa aggtcatggt gtgttccatg   6840
atagcggact caggatgagt taattgagag aggcagtctt cctcccgtga aggacataag   6900
cagtagctca caatcatctc gcgtctcagc aaagtgtgca taattataaa gtgctgggtc   6960
atctaagctt ttcagtcgag aaaaaaacat tagatcagaa gaacaactgg caacacttct   7020
caacctgaga cctacttcaa gatgctcgat cctggagagg tctatgatga ccctattgac   7080
ccaatcgagt tagaggatga acccagagga acccccactg tccccaacat cttgaggaac   7140
tctgactaca atctcaactc tcctttgata gaagatcctg ctagactaat gttagaatgg   7200
ttaaaaacag ggaatagacc ttatcggatg actctaacag acaattgctc caggtctttc   7260
agagttttga aagattattt caagaaggta gatttgggtt ctctcaaggt gggcggaatg   7320
gctgcacagt caatgatttc tctctggtta tatggtgccc actctgaatc caacaggagc   7380
cggagatgta taacagactt ggcccatttc tattccaagt cgtcccccat agagaagctg   7440
ttgaatctca cgctaggaaa tagagggctg agaatccccc cagagggagt gttaagttgc   7500
cttgagaggg ttgattatga taatgcattt ggaaggtatc ttgccaacac gtattcctct   7560
tacttgttct tccatgtaat caccttatac atgaacgccc tagactggga tgaagaaaag   7620
accatcctag cattatggaa agatttaacc tcagtggaca tcgggaagga cttggtaaag   7680
ttcaaagacc aaatatgggg actgctgatc gtgacaaagg actttgttta ctcccaaagt   7740
tccaattgtc tttttgacag aaactacaca cttatgctaa aagatctttt cttgtctcgc   7800
ttcaactcct taatggtctt gctctctccc ccagagcccc gatactcaga tgacttgata   7860
tctcaactat gccagctgta cattgctggg gatcaagtct tgtctatgtg tggaaactcc   7920
ggctatgaag tcatcaaaat attggagcca tatgtcgtga atagtttagt ccagagagca   7980
gaaaagttta ggcctctcat tcattccttg ggagactttc ctgtatttat aaaagacaag   8040
```

-continued

```
gtaagtcaac ttgaagagac gttcggtccc tgtgcaagaa ggttctttag ggctctggat   8100
caattcgaca acatacatga cttggttttt gtgtatggct gttacaggca ttgggggcac   8160
ccatatatag attatcgaaa gggtctgtca aaactatatg atcaggttca cattaaaaaa   8220
gtgatagata agtcctacca ggagtgctta gcaagcgacc tagccaggag gatccttaga   8280
tggggttttg ataagtactc caagtggtat ctggattcaa gattcctagc ccgagaccac   8340
cccttgactc cttatatcaa aacccaaaca tggccaccca aacatattgt agacttggtg   8400
ggggatacat ggcacaagct cccgatcacg cagatctttg agattcctga atcaatggat   8460
ccgtcagaaa tattggatga caaatcacat tctttcacca gaacgagact agcttcttgg   8520
ctgtcagaaa accgaggggg acctgttcct agcgaaaaag ttattatcac ggccctgtct   8580
aagccgcctg tcaatccccg agagtttctg aggtctatag acctcggagg attgccagat   8640
gaagacttga taattggcct caagccaaag gaacgggaat tgaagattga aggtcgattc   8700
tttgctctaa tgtcatggaa tctaagattg tattttgtca tcactgaaaa actcttggcc   8760
aactacatct tgccactttt tgacgcgctg actatgacag acaacctgaa caaggtgttt   8820
aaaaagctga tcgacagggt caccgggcaa gggcttttgg actattcaag ggtcacatat   8880
gcatttcacc tggactatga aaagtggaac aaccatcaaa gattagagtc aacagaggat   8940
gtattttctg tcctagatca agtgtttgga ttgaagagag tgttttctag aacacacgag   9000
tttttcaaa aggcctggat ctattattca gacagatcag acctcatcgg gttacgggag   9060
gatcaaatat actgcttaga tgcgtccaac ggcccaacct gttggaatgg ccaggatggc   9120
gggctagaag gcttacggca gaagggctgg agtctagtca gcttattgat gatagataga   9180
gaatctcaaa tcaggaacac aagaaccaaa atactagctc aaggagacaa ccaggtttta   9240
tgtccgacat atatgttgtc gccagggcta tctcaagagg ggctcctcta tgaattggag   9300
agaatatcaa ggaatgcact ttcgatatac agagccgtcg aggaaggggc atctaagcta   9360
gggctgatca tcaagaaaga agagaccatg tgtagttatg acttcctcat ctatggaaaa   9420
accccttgt ttagaggtaa catattggtg cctgagtcca aaagatgggc cagagtctct   9480
tgcgtctcta atgaccaaat agtcaacctc gccaatataa tgtcgacagt gtccaccaat   9540
gcgctaacag tggcacaaca ctctcaatct ttgatcaaac cgatgaggga ttttctgctc   9600
atgtcagtac aggcagtctt tcactacctg ctatttagcc caatcttaaa gggaagagtt   9660
tacaagattc tgagcgctga aggggatagc tttctcctag ccatgtcaag gataatctat   9720
ctagatcctt ctttgggagg ggtatctgga atgtccctcg gaagattcca tatacgacag   9780
ttctcagacc ctgtctctga agggttatcc ttctggagag agatctggtt aagctcccac   9840
gagtcctgga ttcacgcgtt gtgtcaagag gctggaaacc cagatcttgg agagagaaca   9900
ctcgagagct tcactcgcct tctagaagat cctaccacct taaatatcag aggagggggcc   9960
agtcctacca ttctactcaa ggatgcaatc agaaaggctt tatatgacga ggtggacaag  10020
gtggagaatt cagagtttcg agaggcaatc ctgttgtcca agacccatag agataatttt  10080
atactcttct taacatctgt tgagcctctg tttcctcgat ttctcagtga gctattcagt  10140
tcgtcttttt tgggaatccc cgagtcaatc attggattga tacaaaactc ccgaacgata  10200
agaaggcagt ttagaaagag tctctcaaaa actttagaag aatccttcta caactcagag  10260
atccacggga ttagtcggat gacccagaca cctcagaggg ttggggggt gtggccttgc  10320
tcttcagaga gggcagatct acttagggag atctcttggg gaagaaaagt ggtaggcacg  10380
```

acagttcctc accttctga gatgttgggg ttacttccca agtcctctat ttcttgcact 10440
tgtggagcaa caggaggagg caatcctaga gtttctgtat cagtactccc gtcctttgat 10500
cagtcatttt tttcacgagg ccccctaaag gggtacttgg gctcgtccac ctctatgtcg 10560
acccagctat tccatgcatg ggaaaaagtc actaatgttc atgtggtgaa gagagctcta 10620
tcgttaaaag aatctataaa ctggttcatt actagagatt ccaacttggc tcaagctcta 10680
attaggaaca ttatgtctct gacaggccct gatttccctc tagaggaggc ccctgtcttc 10740
aaaaggacgg ggtcagcctt gcataggttc aagtctgcca gatacagcga aggagggtat 10800
tcttctgtct gcccgaacct cctctctcat atttctgtta gtacagacac catgtctgat 10860
ttgacccaag acgggaagaa ctacgatttc atgttccagc cattgatgct ttatgcacag 10920
acatggacat cagagctggt acagagagac acaaggctaa gagactctac gtttcattgg 10980
cacctccgat gcaacaggtg tgtgagaccc attgacgacg tgaccctgga gacctctcag 11040
atcttcgagt ttccggatgt gtcgaaaaga atatccagaa tggtttctgg ggctgtgcct 11100
cacttccaga ggcttcccga tatccgtctg agaccaggag attttgaatc tctaagcggt 11160
agagaaaagt ctcaccatat cggatcagct caggggctct tatactcaat cttagtggca 11220
attcacgact caggatacaa tgatggaacc atcttccctg tcaacatata cgacaaggtt 11280
tcccctagag actatttgag agggctcgca aggggagtat tgataggatc ctcgatttgc 11340
ttcttgacaa gaatgacaaa tatcaatatt aatagacctc ttgaattgat ctcaggggta 11400
atctcatata ttctcctgag gctagataac catccctcct tgtacataat gctcagagaa 11460
ccgtctctta gaggagagat atttctatc cctcagaaaa tccccgccgc ttatccaacc 11520
actatgaaag aaggcaacag atcaatcttg tgttatctcc aacatgtgct acgctatgag 11580
cgagagataa tcacggcgtc tccagagaat gactggctat ggatcttttc agactttaga 11640
agtgccaaaa tgacgtacct aaccctcatt acttaccagt ctcatcttct actccagagg 11700
gttgagagaa acctatctaa gagtatgaga gataacctgc gacaattgag ttccttgatg 11760
aggcaggtgc tgggcgggca cggagaagat accttagagt cagacgacaa cattcaacga 11820
ctgctaaaag actctttacg aaggacaaga tgggtggatc aagaggtgcg ccatgcagct 11880
agaaccatga ctggagatta cagccccaac aagaaggtgt cccgtaaggt aggatgttca 11940
gaatgggtct gctctgctca acaggttgca gtctctacct cagcaaaccc ggcccctgtc 12000
tcggagcttg acataagggc cctctctaag aggttccaga accctttgat ctcgggcttg 12060
agagtggttc agtgggcaac cggtgctcat tataagctta agcctattct agatgatctc 12120
aatgttttcc catctctctg ccttgtagtt ggggacgggt caggggggat atcaagggca 12180
gtcctcaaca tgtttccaga tgccaagctt gtgttcaaca gtctcttaga ggtgaatgac 12240
ctgatggctt ccggaacaca tccactgcct ccttcagcaa tcatgagggg aggaaatgat 12300
atcgtctcca gagtgataga ttttgactca atctgggaaa aaccgtccga cttgagaaac 12360
ttggcaacct ggaaatactt ccagtcagtc caaaagcagg tcaacatgtc ctatgacctc 12420
attatttgcg atgcagaagt tactgacatt gcatctatca accggataac cctgttaatg 12480
tccgattttg cattgtctat agatggacca ctctatttgg tcttcaaaac ttatgggact 12540
atgctagtaa atccaaacta caaggctatt caacacctgt caagagcgtt cccctcggtc 12600
acagggttta tcacccaagt aacttcgtct tttcatctg agctctacct ccgattctcc 12660
aaacgaggga agtttttcag agatgctgag tacttgacct cttccaccct tcgagaaatg 12720
agccttgtgt tattcaattg tagcagcccc aagagtgaga tgcagagagc tcgttccttg 12780
aactatcagg atcttgtgag aggatttcct gaagaaatca tatcaaatcc ttacaatgag 12840
atgatcataa ctctgattga cagtgatgta gaatcttttc tagtccacaa gatggttgat 12900
gatcttgagt tacagagggg aactctgtct aaagtggcta tcattatagc catcatgata 12960
gttttctcca acagagtctt caacgtttcc aaacccctaa ctgacccctt gttctatcca 13020
ccgtctgatc ccaaaatcct gaggcacttc aacatatgtt gcagtactat gatgtatcta 13080
tctactgctt taggtgacgt ccctagcttc gcaagacttc acgacctgta taacagacct 13140
ataacttatt acttcagaaa gcaattcatt cgagggaacg tttatctatc ttggagttgg 13200
tccaacgaca cctcagtgtt caaaagggta gcctgtaatt ctagcctgag tctgtcatct 13260
cactggatca ggttgattta caagatagtg aagactacca gactcgttgg cagcatcaag 13320
gatctatcca gagaagtgga aagacacctt cataggtaca acaggtggat caccctagag 13380
gatatcagat ctagatcatc cctactagac tacagttgcc tgtgatccgg atactcctgg 13440
aagcctgccc atgctaagac tcttgtgtga tgtatcttga aaaaaacaag atcctaaatc 13500
tgaacctttg gttgtttgat tgtttttctc atttttgttg tttatttgtt aagcgt 13556

<210> SEQ ID NO 19
<211> LENGTH: 10
<212> TYPE: DNA
<213> ORGANISM: artificial sequence
<220> FEATURE:
<223> OTHER INFORMATION: hammerhead terminus

<400> SEQUENCE: 19
tgttaagcgt 10

<210> SEQ ID NO 20
<211> LENGTH: 27
<212> TYPE: DNA
<213> ORGANISM: artificial sequence
<220> FEATURE:
<223> OTHER INFORMATION: synthetic oligonucleotide encoding SV40 nuclear localization signal

<400> SEQUENCE: 20
atgccaaaaa agaagagaaa ggtagaa 27

<210> SEQ ID NO 21
<211> LENGTH: 10
<212> TYPE: DNA
<213> ORGANISM: artificial sequence
<220> FEATURE:
<223> OTHER INFORMATION: Artificial Kozak sequence

<400> SEQUENCE: 21
accaccatgg 10

<210> SEQ ID NO 22
<211> LENGTH: 10
<212> TYPE: DNA
<213> ORGANISM: artificial sequence
<220> FEATURE:
<223> OTHER INFORMATION: Artificial Kozak sequence

<400> SEQUENCE: 22
accaccatga 10

<210> SEQ ID NO 23
<211> LENGTH: 10

<212> TYPE: DNA
<213> ORGANISM: artificial sequence
<220> FEATURE:
<223> OTHER INFORMATION: Artificial Kozak sequence

<400> SEQUENCE: 23
accaccatgc 10

<210> SEQ ID NO 24
<211> LENGTH: 11
<212> TYPE: DNA
<213> ORGANISM: artificial sequence
<220> FEATURE:
<223> OTHER INFORMATION: oligonucleotide primer Le5

<400> SEQUENCE: 24
acgcttaaca a 11

<210> SEQ ID NO 25
<211> LENGTH: 24
<212> TYPE: DNA
<213> ORGANISM: artificial sequence
<220> FEATURE:
<223> OTHER INFORMATION: oligonucleotide primer Blp5

<400> SEQUENCE: 25
gtcgcttgct aagcactcct ggta 24

<210> SEQ ID NO 26
<211> LENGTH: 11
<212> TYPE: DNA
<213> ORGANISM: artificial sequence
<220> FEATURE:
<223> OTHER INFORMATION: oligonucleotide primer Le3

<400> SEQUENCE: 26
tgcgaattgt t 11

<210> SEQ ID NO 27
<211> LENGTH: 24
<212> TYPE: DNA
<213> ORGANISM: artificial sequence
<220> FEATURE:
<223> OTHER INFORMATION: oligonucleotide primer Blp5

<400> SEQUENCE: 27
ccaggagtgc ttagcaagcg acct 24

<210> SEQ ID NO 28
<211> LENGTH: 32
<212> TYPE: DNA
<213> ORGANISM: artificial sequence
<220> FEATURE:
<223> OTHER INFORMATION: oligonucleotide primer Le5-Kpn

<400> SEQUENCE: 28
ccgggtacca cgcttaacaa ccagatcaaa ga 32

<210> SEQ ID NO 29
<211> LENGTH: 31
<212> TYPE: DNA
<213> ORGANISM: artificial sequence
<220> FEATURE:
<223> OTHER INFORMATION: oligonucleotide primer Le3-Blp

<400> SEQUENCE: 29

-continued taggtcgctt gctaagcact cctggtagga c 31

<210> SEQ ID NO 30
<211> LENGTH: 31
<212> TYPE: DNA
<213> ORGANISM: artificial sequence
<220> FEATURE:
<223> OTHER INFORMATION: oligonucleotide primer Tr5-Blp

<400> SEQUENCE: 30
gtcctaccag gagtgcttag caagcgacct a 31

<210> SEQ ID NO 31
<211> LENGTH: 34
<212> TYPE: DNA
<213> ORGANISM: artificial sequence
<220> FEATURE:
<223> OTHER INFORMATION: oligonucleotide primer Tr3-Pst

<400> SEQUENCE: 31
aaaactgcag acgcttaaca aataaacaac aaaa 34

<210> SEQ ID NO 32
<211> LENGTH: 79
<212> TYPE: DNA
<213> ORGANISM: artificial sequence
<220> FEATURE:
<223> OTHER INFORMATION: oligonucleotide primer HH1

<400> SEQUENCE: 32
caaggctagc tgttaagcgt ctgatgagtc cgtgaggacg aaactatagg aaaggaattc 60
ctatagtcgg taccacgct 79

<210> SEQ ID NO 33
<211> LENGTH: 79
<212> TYPE: DNA
<213> ORGANISM: artificial sequence
<220> FEATURE:
<223> OTHER INFORMATION: oligonucleotide primer HH2

<400> SEQUENCE: 33
agcgtggtac cgactatagg aattcctttc ctatagtttc gtcctcacgg actcatcaga 60
cgcttaacag ctagccttg 79

<210> SEQ ID NO 34
<211> LENGTH: 108
<212> TYPE: DNA
<213> ORGANISM: artificial sequence
<220> FEATURE:
<223> OTHER INFORMATION: oligonucleotide primer HDV3

<400> SEQUENCE: 34
gacctgcagg ggtcggcatg gcatctccac ctcctcgcgg tccgacctgg gcatccgaag 60
gaggacgcac gtccactcgg atggctaagg gagggcgcgg ccgcactc 108

<210> SEQ ID NO 35
<211> LENGTH: 108
<212> TYPE: DNA
<213> ORGANISM: artificial sequence
<220> FEATURE:
<223> OTHER INFORMATION: oligonucleotide primer HDV 4

<400> SEQUENCE: 35
gagtgcggcc gcgccctccc ttagccatcc gagtggacgt gcgtcctcct tcggatgccc 60
aggtcggacc gcgaggaggt ggagatgcca tgccgacccc tgcaggtc 108

<210> SEQ ID NO 36
<211> LENGTH: 25
<212> TYPE: DNA
<213> ORGANISM: artificial sequence
<220> FEATURE:
<223> OTHER INFORMATION: oligonucleotide primer 5N

<400> SEQUENCE: 36
accaccatgg atgccgacaa gattg 25

<210> SEQ ID NO 37
<211> LENGTH: 33
<212> TYPE: DNA
<213> ORGANISM: artificial sequence
<220> FEATURE:
<223> OTHER INFORMATION: oligonucleotide primer 3N

<400> SEQUENCE: 37
ggcccatggt tatgagtcac tcgaatatgt ctt 33

<210> SEQ ID NO 38
<211> LENGTH: 33
<212> TYPE: DNA
<213> ORGANISM: artificial sequence
<220> FEATURE:
<223> OTHER INFORMATION: oligonucleotide primer 5P

<400> SEQUENCE: 38
ttggtaccac catgagcaag atctttgtca atc 33

<210> SEQ ID NO 39
<211> LENGTH: 34
<212> TYPE: DNA
<213> ORGANISM: artificial sequence
<220> FEATURE:
<223> OTHER INFORMATION: oligonucleotide primer 3P

<400> SEQUENCE: 39
ggagaggaat tcttagcaag atgtatagcg attc 34

<210> SEQ ID NO 40
<211> LENGTH: 32
<212> TYPE: DNA
<213> ORGANISM: artificial sequence
<220> FEATURE:
<223> OTHER INFORMATION: oligonucleotide primer 5G

<400> SEQUENCE: 40
ttggtaccac catggttcct caggctctcc tg 32

<210> SEQ ID NO 41
<211> LENGTH: 33
<212> TYPE: DNA
<213> ORGANISM: artificial sequence
<220> FEATURE:
<223> OTHER INFORMATION: oligonucleotide primer 3G

<400> SEQUENCE: 41
aaaactgcag tcacagtctg gtctcacccc cac 33

<210> SEQ ID NO 42
<211> LENGTH: 36
<212> TYPE: DNA

<213> ORGANISM: artificial sequence
<220> FEATURE:
<223> OTHER INFORMATION: oligonucleotide primer 5L

<400> SEQUENCE: 42
accgctagca ccaccatgct cgatcctgga gaggtc 36

<210> SEQ ID NO 43
<211> LENGTH: 34
<212> TYPE: DNA
<213> ORGANISM: artificial sequence
<220> FEATURE:
<223> OTHER INFORMATION: oligonucleotide primer 3L

<400> SEQUENCE: 43
aaaactgcag tcacaggcaa ctgtagtcta gtag 34

<210> SEQ ID NO 44
<211> LENGTH: 38
<212> TYPE: DNA
<213> ORGANISM: artificial sequence
<220> FEATURE:
<223> OTHER INFORMATION: oligonucleotide primer 5T7

<400> SEQUENCE: 44
tcgctagcac caccatgaac acgattaaca tcgctaag 38

<210> SEQ ID NO 45
<211> LENGTH: 33
<212> TYPE: DNA
<213> ORGANISM: artificial sequence
<220> FEATURE:
<223> OTHER INFORMATION: oligonucleotide primer 3T7

<400> SEQUENCE: 45
gatgaattct tacgcgaacg cgaagtccga ctc 33

<210> SEQ ID NO 46
<211> LENGTH: 63
<212> TYPE: DNA
<213> ORGANISM: artificial sequence
<220> FEATURE:
<223> OTHER INFORMATION: oligonucleotide primer 5T7NLS

<400> SEQUENCE: 46
tcgctagcca ccatgccaaa aaagaagaga aaggtagaaa acacgattaa catcgctaag 60
aac 63

<210> SEQ ID NO 47
<211> LENGTH: 31
<212> TYPE: DNA
<213> ORGANISM: artificial sequence
<220> FEATURE:
<223> OTHER INFORMATION: oligonucleotide primer GFP5

<400> SEQUENCE: 47
aaaactgcag gccaccatgg gcgtgatcaa g 31

<210> SEQ ID NO 48
<211> LENGTH: 31
<212> TYPE: DNA
<213> ORGANISM: artificial sequence
<220> FEATURE:
<223> OTHER INFORMATION: oligonucleotide primer GFP3

<400> SEQUENCE: 48
ccgctcggta cctattagcc ggcctggcgg g 31

<210> SEQ ID NO 49
<211> LENGTH: 25
<212> TYPE: DNA
<213> ORGANISM: artificial sequence
<220> FEATURE:
<223> OTHER INFORMATION: oligonucleotide primer EF5G5

<400> SEQUENCE: 49
caccatggtt cctcaggctc tcctg 25

<210> SEQ ID NO 50
<211> LENGTH: 23
<212> TYPE: DNA
<213> ORGANISM: artificial sequence
<220> FEATURE:
<223> OTHER INFORMATION: oligonucleotide primer EF5G3

<400> SEQUENCE: 50
tcacagtctg gtctcacccc cac 23

<210> SEQ ID NO 51
<211> LENGTH: 46
<212> TYPE: DNA
<213> ORGANISM: artificial sequence
<220> FEATURE:
<223> OTHER INFORMATION: oligonucleotide primer 5delpsi

<400> SEQUENCE: 51
ccctctgcag tttggtaccg tcgagaaaaa aacattagat cagaag 46

<210> SEQ ID NO 52
<211> LENGTH: 24
<212> TYPE: DNA
<213> ORGANISM: artificial sequence
<220> FEATURE:
<223> OTHER INFORMATION: oligonucleotide primer SnaB5

<400> SEQUENCE: 52
atgaactttc tacgtaagat agtg 24

<210> SEQ ID NO 53
<211> LENGTH: 46
<212> TYPE: DNA
<213> ORGANISM: artificial sequence
<220> FEATURE:
<223> OTHER INFORMATION: oligonucleotide primer 3delpsi

<400> SEQUENCE: 53
caaactgcag aggggtgtta gtttttttca aaaagaaccc cccaag 46

<210> SEQ ID NO 54
<211> LENGTH: 44
<212> TYPE: DNA
<213> ORGANISM: artificial sequence
<220> FEATURE:
<223> OTHER INFORMATION: oligonucleotide primer 3deltag

<400> SEQUENCE: 54
caaactgcag aggggtgtta gtttttttca catccaagag gatc 44

<210> SEQ ID NO 55
<211> LENGTH: 42
<212> TYPE: DNA

-continued

<213> ORGANISM: artificial sequence
<220> FEATURE:
<223> OTHER INFORMATION: oligonucleotide primer 5deltag

<400> SEQUENCE: 55
cctctgcagt ttggtacctt gaaaaaaacc tgggttcaat ag 42

<210> SEQ ID NO 56
<211> LENGTH: 35
<212> TYPE: DNA
<213> ORGANISM: artificial sequence
<220> FEATURE:
<223> OTHER INFORMATION: oligonucleotide primer M5G

<400> SEQUENCE: 56
ctcactacaa gtcagtcgag acttggaatg agatc 35

<210> SEQ ID NO 57
<211> LENGTH: 35
<212> TYPE: DNA
<213> ORGANISM: artificial sequence
<220> FEATURE:
<223> OTHER INFORMATION: oligonucleotide primer M3G

<400> SEQUENCE: 57
gactgacttt gagtgagcat cggcttccat caagg 35

<210> SEQ ID NO 58
<211> LENGTH: 524
<212> TYPE: PRT
<213> ORGANISM: artificial sequence
<220> FEATURE:
<223> OTHER INFORMATION: Mutated G protein Aa333

<400> SEQUENCE: 58

```
Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
```

-continued

```
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Pro
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Glu
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520
```

<210> SEQ ID NO 59
<211> LENGTH: 60
<212> TYPE: DNA
<213> ORGANISM: artificial sequence
<220> FEATURE:
<223> OTHER INFORMATION: oligonucleotide primer 3psicis

<400> SEQUENCE: 59
ccaaactgca gcgaaaggag gggtgttagt ttttttcatg atgaaccccc caaggggagg 60

<210> SEQ ID NO 60
<211> LENGTH: 39
<212> TYPE: DNA
<213> ORGANISM: artificial sequence
<220> FEATURE:
<223> OTHER INFORMATION: oligonucleotide primer cis55

<400> SEQUENCE: 60
gactcactat agggagaccc aagctggcta gctgttaag 39

<210> SEQ ID NO 61
<211> LENGTH: 60
<212> TYPE: DNA
<213> ORGANISM: artificial sequence
<220> FEATURE:
<223> OTHER INFORMATION: oligonucleotide primer cis53

<400> SEQUENCE: 61
ccaaactgca gcgaaaggag gggtgttagt ttttttcatg ttgactttag gacatctcgg 60

<210> SEQ ID NO 62
<211> LENGTH: 61
<212> TYPE: DNA
<213> ORGANISM: artificial sequence
<220> FEATURE:
<223> OTHER INFORMATION: oligonucleotide primer cis35

<400> SEQUENCE: 62
cctttcgctg cagtttggta ccgtcgagaa aaaaacaggc aacaccactg ataaaatgaa 60
c 61

<210> SEQ ID NO 63
<211> LENGTH: 30
<212> TYPE: DNA
<213> ORGANISM: artificial sequence
<220> FEATURE:
<223> OTHER INFORMATION: cis33

<400> SEQUENCE: 63
cctccccttc aagagggccc ctggaatcag 30

<210> SEQ ID NO 64
<211> LENGTH: 46
<212> TYPE: DNA
<213> ORGANISM: artificial sequence
<220> FEATURE:
<223> OTHER INFORMATION: oligonucleotide primer TU1

<400> SEQUENCE: 64
ctaacacccc tcctttcgct gcagtttggt accgtcgaga aaaaaa 46

<210> SEQ ID NO 65
<211> LENGTH: 53
<212> TYPE: DNA
<213> ORGANISM: artificial sequence
<220> FEATURE:
<223> OTHER INFORMATION: TU2

<400> SEQUENCE: 65
tttttttgat tgtggggagg aaagcgacgt caaaccatgg cagctctttt ttt 53